US011718679B2

(12) United States Patent
Eskiocak et al.

(10) Patent No.: US 11,718,679 B2
(45) Date of Patent: *Aug. 8, 2023

(54) CD137 ANTIBODIES AND PD-1 ANTAGONISTS AND USES THEREOF

(71) Applicant: Compass Therapeutics LLC, Brighton, MA (US)

(72) Inventors: Ugur Eskiocak, Somerville, MA (US); Robert V. Tighe, III, North Reading, MA (US)

(73) Assignee: Compass Therapeutics LLC, Cambridge, MA (US)

( * ) Notice: Subject to any disclaimer, the term of this patent is extended or adjusted under 35 U.S.C. 154(b) by 215 days.

This patent is subject to a terminal disclaimer.

(21) Appl. No.: 16/760,600

(22) PCT Filed: Oct. 31, 2018

(86) PCT No.: PCT/US2018/058451
§ 371 (c)(1),
(2) Date: Apr. 30, 2020

(87) PCT Pub. No.: WO2019/089753
PCT Pub. Date: May 9, 2019

(65) Prior Publication Data
US 2021/0221902 A1    Jul. 22, 2021

Related U.S. Application Data

(60) Provisional application No. 62/579,337, filed on Oct. 31, 2017.

(51) Int. Cl.
*A61K 39/395* (2006.01)
*C07K 16/28* (2006.01)
(Continued)

(52) U.S. Cl.
CPC ... *C07K 16/2878* (2013.01); *A61K 39/001111* (2018.08); *A61K 39/001117* (2018.08);
(Continued)

(58) Field of Classification Search
None
See application file for complete search history.

(56) References Cited

U.S. PATENT DOCUMENTS 3,710,795 A    1/1973    Higuchi
3,773,919 A    11/1973   Boswell
(Continued)

FOREIGN PATENT DOCUMENTS

CA    2108401    3/1995
EP    0036676    7/1984
(Continued)

OTHER PUBLICATIONS

ClinicalTrials.gov, Study NCT02179918(v25), A Study of 4-1 BB Agonist PF-05082566 Plus PD-1 Inhibitor MK-3475 in Patients With Solid Tumors, Retrieved from <URL: https://clinicaltrials.gov/ct2/history/NCT02179918?V_25=View#StudyPageTop>), retrieved on May 16, 2022. May 2, 2016.*

(Continued)

*Primary Examiner* — Claire Kaufman
(74) *Attorney, Agent, or Firm* — Crowell & Moring LLP

(57) ABSTRACT

The present disclosure relates to combinations of antibodies, or antigen-binding fragments thereof, that bind to CD137, and PD-1 antagonists. The disclosure also relates to methods for treating or ameliorating one or more symptoms of a disease, such as cancer, by administering the combination.

28 Claims, 60 Drawing Sheets

Specification includes a Sequence Listing.

(51) Int. Cl.
  *A61P 35/00* (2006.01)
  *A61K 39/00* (2006.01)
(52) U.S. Cl.
  CPC ........ *A61P 35/00* (2018.01); *A61K 2039/507* (2013.01); *C07K 2317/565* (2013.01); *C07K 2317/75* (2013.01); *C07K 2317/92* (2013.01)

(56) References Cited

U.S. PATENT DOCUMENTS

| | | |
|---|---|---|
| 4,433,059 A | 2/1984 | Chang |
| 4,444,878 A | 4/1984 | Paulus |
| 4,496,654 A | 1/1985 | Katz |
| 4,863,457 A | 9/1989 | Lee |
| 5,026,773 A | 6/1991 | Steel |
| 5,071,909 A | 12/1991 | Pappin |
| 5,122,458 A | 6/1992 | Post |
| 5,168,062 A | 12/1992 | Stinski |
| 5,223,409 A | 6/1993 | Ladner |
| 5,273,743 A | 12/1993 | Ahlem |
| 5,342,585 A | 8/1994 | Lebl |
| 5,403,484 A | 4/1995 | Ladner |
| 5,427,908 A | 6/1995 | Dower |
| 5,501,856 A | 3/1996 | Ohtori |
| 5,516,637 A | 5/1996 | Huang |
| 5,534,254 A | 7/1996 | Huston |
| 5,571,698 A | 11/1996 | Ladner |
| 5,580,717 A | 12/1996 | Dower |
| 5,582,996 A | 12/1996 | Curtis |
| 5,591,828 A | 1/1997 | Bosslet |
| 5,624,821 A | 4/1997 | Winter |
| 5,635,602 A | 6/1997 | Cantor |
| 5,637,481 A | 6/1997 | Ledbetter |
| 5,648,260 A | 7/1997 | Winter |
| 5,658,727 A | 8/1997 | Barbas |
| 5,698,426 A | 12/1997 | Huse |
| 5,733,743 A | 3/1998 | Johnson |
| 5,750,753 A | 5/1998 | Kimae |
| 5,759,808 A | 6/1998 | Casterman |
| 5,780,225 A | 7/1998 | Wigler |
| 5,821,047 A | 10/1998 | Garrard |
| 5,837,242 A | 11/1998 | Holliger |
| 5,837,821 A | 11/1998 | Wu |
| 5,844,094 A | 12/1998 | Hudson |
| 5,864,019 A | 1/1999 | King |
| 5,869,620 A | 2/1999 | Whitlow |
| 5,874,240 A | 2/1999 | Ni |
| 5,885,793 A | 3/1999 | Griffiths |
| 5,928,893 A | 7/1999 | Kang |
| 5,932,448 A | 8/1999 | Tso |
| 5,959,083 A | 9/1999 | Bosslet |
| 5,969,108 A | 10/1999 | McCafferty |
| 5,989,830 A | 11/1999 | Davis |
| 6,001,329 A | 12/1999 | Buchsbaum |
| 6,005,079 A | 12/1999 | Casterman |
| 6,172,197 B1 | 1/2001 | McCafferty |
| 6,180,370 B1 | 1/2001 | Queen |
| 6,194,551 B1 | 2/2001 | Idusogie |
| 6,210,669 B1 | 4/2001 | Aruffo |
| 6,239,259 B1 | 5/2001 | Davis |
| 6,248,516 B1 | 6/2001 | Winter |
| 6,291,158 B1 | 9/2001 | Winter |
| 6,291,159 B1 | 9/2001 | Winter |
| 6,294,353 B1 | 9/2001 | Pack |
| 6,300,064 B1 | 10/2001 | Knappik |
| 6,303,121 B1 | 10/2001 | Kwon |
| 6,319,690 B1 | 11/2001 | Little |
| 6,333,396 B1 | 12/2001 | Filpula |
| 6,476,198 B1 | 11/2002 | Kang |
| 6,482,591 B2 | 11/2002 | Lockhart |
| 6,511,663 B1 | 1/2003 | King |
| 6,548,640 B1 | 4/2003 | Winter |
| 6,569,997 B1 | 5/2003 | Kwon |
| 6,670,453 B2 | 12/2003 | Frenken |
| 6,743,896 B2 | 6/2004 | Filpula |
| 6,809,185 B1 | 10/2004 | Schoonjans |
| 6,818,749 B1 | 11/2004 | Kashmiri |
| 6,833,441 B2 | 12/2004 | Wang |
| 6,887,673 B2 | 5/2005 | Kunkel |
| 6,905,685 B2 | 6/2005 | Kwon |
| 6,933,368 B2 | 8/2005 | Co |
| 6,946,292 B2 | 9/2005 | Kanda |
| 6,974,863 B2 | 12/2005 | Kwon |
| 6,995,259 B1 | 2/2006 | Vargeese |
| 7,083,785 B2 | 8/2006 | Browning |
| 7,129,330 B1 | 10/2006 | Little |
| 7,138,500 B1 | 11/2006 | Goodwin |
| 7,183,076 B2 | 2/2007 | Arathoon |
| 7,211,259 B1 | 5/2007 | Goodwin |
| 7,214,775 B2 | 5/2007 | Hanai |
| 7,288,638 B2 | 10/2007 | Jure-Kunkel |
| 7,387,271 B2 | 6/2008 | Noelle |
| 7,425,446 B2 | 9/2008 | Kanda |
| 7,521,056 B2 | 4/2009 | Chang |
| 7,527,787 B2 | 5/2009 | Chang |
| 7,534,866 B2 | 5/2009 | Chang |
| 7,566,771 B1 | 7/2009 | Adair |
| 7,651,686 B2 | 1/2010 | Chen |
| 7,708,992 B2 | 5/2010 | Hanai |
| 7,737,325 B2 | 6/2010 | Kanda |
| 7,790,655 B2 | 9/2010 | Gao |
| 7,829,088 B2 | 11/2010 | Kwon |
| 7,947,495 B2 | 5/2011 | Dubridge |
| 7,972,993 B2 | 7/2011 | Slootstra |
| 8,026,353 B2 | 9/2011 | Kwon |
| 8,258,082 B2 | 9/2012 | Ladner |
| 8,288,322 B2 | 10/2012 | Ladner |
| 8,337,850 B2 | 12/2012 | Ahrens |
| 8,399,645 B2 | 3/2013 | Campana |
| 8,475,790 B2 | 7/2013 | Jure-Kunkel |
| 8,551,920 B2 | 10/2013 | Hoet |
| 8,679,490 B2 | 3/2014 | Dennis |
| 8,697,359 B1 | 4/2014 | Zhang |
| 8,716,452 B2 | 5/2014 | Jure-Kunkel |
| 8,735,331 B2 | 5/2014 | Villa |
| 8,772,026 B2 | 7/2014 | Chen |
| 8,821,867 B2 | 9/2014 | Ahrens |
| 8,877,688 B2 | 11/2014 | Vasquez |
| 9,005,619 B2 | 4/2015 | Kohrt |
| 9,181,327 B2 | 11/2015 | Dimitrov |
| 9,300,829 B2 | 3/2016 | Sohara |
| 9,354,228 B2 | 5/2016 | Vasquez |
| 9,388,510 B2 | 7/2016 | Ladner |
| 9,758,589 B2 | 9/2017 | Kohrt |
| 9,845,356 B2 | 12/2017 | Freeman |
| 9,861,621 B2 | 1/2018 | Saha |
| 10,279,038 B2 | 5/2019 | Bobrowicz |
| 10,279,039 B2 | 5/2019 | Bobrowicz |
| 10,279,040 B1 | 5/2019 | Bobrowicz |
| 10,350,292 B1 | 7/2019 | Bobrowicz |
| 10,434,175 B2 | 10/2019 | Bobrowicz |
| 10,899,842 B2 * | 1/2021 | Wang ............... A61P 35/00 |
| 11,008,396 B2 * | 5/2021 | Ellmark ............ A61P 35/00 |
| 2002/0004587 A1 | 1/2002 | Miller |
| 2002/0076406 A1 | 6/2002 | Leung |
| 2002/0103345 A1 | 8/2002 | Zhu |
| 2003/0118588 A1 | 6/2003 | Diehl |
| 2003/0207346 A1 | 11/2003 | Arathoon |
| 2003/0211078 A1 | 11/2003 | Heavner |
| 2003/0232410 A1 | 12/2003 | Liljedahl |
| 2004/0109847 A1 | 6/2004 | Chen |
| 2004/0219643 A1 | 11/2004 | Winter |
| 2004/0220388 A1 | 11/2004 | Mertens |
| 2004/0242847 A1 | 12/2004 | Fukushima |
| 2005/0003403 A1 | 1/2005 | Rossi |
| 2005/0004352 A1 | 1/2005 | Kontermann |
| 2005/0026157 A1 | 2/2005 | Baltimore |
| 2005/0064474 A1 | 3/2005 | Urnov |
| 2005/0069552 A1 | 3/2005 | Bleck |
| 2005/0079170 A1 | 4/2005 | Le Gall |
| 2005/0100543 A1 | 5/2005 | Hansen |
| 2005/0136049 A1 | 6/2005 | Ledbetter |
| 2005/0136051 A1 | 6/2005 | Scallon |
| 2005/0163782 A1 | 7/2005 | Glaser |
| 2005/0208489 A1 | 9/2005 | Carroll |

(56) References Cited

U.S. PATENT DOCUMENTS

| | | |
|---|---|---|
| 2005/0266425 A1 | 12/2005 | Zauderer |
| 2006/0029595 A1 | 2/2006 | Kwon |
| 2006/0040354 A1 | 2/2006 | O'Keefe |
| 2006/0083747 A1 | 4/2006 | Winter |
| 2006/0120960 A1 | 6/2006 | Deyev |
| 2006/0121030 A1 | 6/2006 | Schwarz |
| 2006/0188987 A1 | 8/2006 | Guschin |
| 2006/0204493 A1 | 9/2006 | Huang |
| 2006/0263367 A1 | 11/2006 | Fey |
| 2007/0004909 A1 | 1/2007 | Johnson |
| 2007/0087381 A1 | 4/2007 | Kojima |
| 2007/0128150 A1 | 6/2007 | Norman |
| 2007/0141049 A1 | 6/2007 | Bredehorst |
| 2007/0154901 A1 | 7/2007 | Thogersen |
| 2007/0274985 A1 | 11/2007 | Dubel |
| 2008/0008716 A1 | 1/2008 | Kwon |
| 2008/0050370 A1 | 2/2008 | Glaser |
| 2008/0069820 A1 | 3/2008 | Fuh |
| 2008/0152645 A1 | 6/2008 | Pardridge |
| 2008/0152655 A1 | 6/2008 | Liu |
| 2008/0171855 A1 | 7/2008 | Rossi |
| 2008/0241223 A1 | 10/2008 | Nivaggioli |
| 2008/0241884 A1 | 10/2008 | Shitara |
| 2008/0254512 A1 | 10/2008 | Capon |
| 2008/0260738 A1 | 10/2008 | Moore |
| 2009/0130106 A1 | 5/2009 | Christopherson |
| 2009/0148905 A1 | 6/2009 | Ashman |
| 2009/0155275 A1 | 6/2009 | Wu |
| 2009/0162359 A1 | 6/2009 | Klein |
| 2009/0162360 A1 | 6/2009 | Klein |
| 2009/0175851 A1 | 7/2009 | Klein |
| 2009/0175867 A1 | 7/2009 | Thompson |
| 2009/0196877 A1 | 8/2009 | Chen |
| 2009/0232811 A1 | 9/2009 | Klein |
| 2009/0234105 A1 | 9/2009 | Gervay-Hague |
| 2009/0263392 A1 | 10/2009 | Igawa |
| 2009/0274649 A1 | 11/2009 | Qu |
| 2011/0104049 A1 | 5/2011 | Strome |
| 2012/0045414 A1 | 2/2012 | Delucia |
| 2012/0076722 A1 | 3/2012 | Strome |
| 2012/0165201 A1 | 6/2012 | Short |
| 2014/0017836 A1 | 1/2014 | Wei |
| 2014/0178368 A1 | 6/2014 | Sharp |
| 2015/0313965 A1 | 11/2015 | Pogue |
| 2016/0152722 A1 | 6/2016 | Sharp |
| 2016/0264670 A1 | 9/2016 | Graziano |
| 2016/0304607 A1 | 10/2016 | Sadineni |
| 2017/0088627 A1 | 3/2017 | Lin |
| 2017/0174773 A1 | 6/2017 | Davis |
| 2017/0247467 A1 | 8/2017 | Amann |
| 2018/0251548 A1 | 9/2018 | Sabzevari |
| 2018/0318417 A1 | 11/2018 | Schuetz |
| 2019/0015508 A1 | 1/2019 | Bobrowicz |
| 2019/0031785 A1 | 1/2019 | Schuetz |
| 2019/0055314 A1 | 2/2019 | Luo |
| 2019/0060454 A1 | 2/2019 | Bobrowicz |
| 2019/0099488 A1 | 4/2019 | Bobrowicz |
| 2019/0125866 A1 | 5/2019 | Bobrowicz |
| 2019/0224315 A1 | 7/2019 | Bobrowicz |
| 2019/0269776 A1 | 9/2019 | Bobrowicz |

FOREIGN PATENT DOCUMENTS

| | | |
|---|---|---|
| EP | 0088046 | 12/1987 |
| EP | 0143949 | 10/1988 |
| EP | 0346087 | 12/1989 |
| EP | 0430539 | 6/1991 |
| EP | 488401 | 6/1992 |
| EP | 2330120 | 6/2011 |
| EP | 2522727 | 11/2012 |
| WO | 1984003564 | 9/1984 |
| WO | 1990002809 | 3/1990 |
| WO | 1991010737 | 7/1991 |
| WO | 1992001047 | 1/1992 |
| WO | 1992018619 | 10/1992 |
| WO | 1993009872 | 5/1993 |
| WO | 1993011162 | 6/1993 |
| WO | 1993011236 | 6/1993 |
| WO | 1993023537 | 11/1993 |
| WO | 1994001875 | 1/1994 |
| WO | 1994004678 | 3/1994 |
| WO | 1994009131 | 4/1994 |
| WO | 1994012625 | 6/1994 |
| WO | 1994025591 | 11/1994 |
| WO | 1994029351 | 12/1994 |
| WO | 1995009917 | 4/1995 |
| WO | 1995015982 | 6/1995 |
| WO | 1995020401 | 8/1995 |
| WO | 1996027011 | 9/1996 |
| WO | 1996037621 | 11/1996 |
| WO | 1999051642 | 10/1999 |
| WO | 1999064460 | 12/1999 |
| WO | 2000061739 | 10/2000 |
| WO | 2002083872 | 4/2002 |
| WO | 2002072635 | 9/2002 |
| WO | 2003104415 | 12/2003 |
| WO | 2004081051 | 9/2004 |
| WO | 2005035584 | 4/2005 |
| WO | 2005073384 | 8/2005 |
| WO | 2005118629 | 12/2005 |
| WO | 2006012414 | 2/2006 |
| WO | 2006020258 | 2/2006 |
| WO | 2006106905 | 10/2006 |
| WO | 2007014275 | 2/2007 |
| WO | 2007024715 | 3/2007 |
| WO | 2007044887 | 4/2007 |
| WO | 2007095338 | 8/2007 |
| WO | 2007110205 | 10/2007 |
| WO | 2007137760 | 12/2007 |
| WO | 2008024188 | 2/2008 |
| WO | 2008119353 | 10/2008 |
| WO | 2009021754 | 2/2009 |
| WO | 2009036379 | 3/2009 |
| WO | 2009068630 | 6/2009 |
| WO | 2009089004 | 7/2009 |
| WO | 2009103493 | 8/2009 |
| WO | 2010105256 | 9/2010 |
| WO | 2010129304 | 11/2010 |
| WO | 2011034605 | 3/2011 |
| WO | 2011131746 | 10/2011 |
| WO | 2012009568 | 1/2012 |
| WO | 2012032433 | 3/2012 |
| WO | 2013060867 | 5/2013 |
| WO | 2014134165 | 9/2014 |
| WO | 2015103072 | 7/2015 |
| WO | 2015104406 | 7/2015 |
| WO | 2015119923 | 8/2015 |
| WO | 2015179236 | 11/2015 |
| WO | 2015188047 | 12/2015 |
| WO | 2016029073 | 2/2016 |
| WO | 2016134358 | 8/2016 |
| WO | 2016177802 | 11/2016 |
| WO | 2016185016 | 11/2016 |
| WO | 2017005845 | 1/2017 |
| WO | 2017130076 | 8/2017 |
| WO | 2017174329 | 10/2017 |
| WO | 2017181034 | 10/2017 |
| WO | 2017205745 | 11/2017 |
| WO | 2018127787 | 7/2018 |
| WO | 2018191502 | 10/2018 |
| WO | 2019014328 | 1/2019 |
| WO | 2019027754 | 2/2019 |
| WO | 2019089753 A3 | 5/2019 |
| WO | 2020006605 | 1/2020 |

OTHER PUBLICATIONS

Kranz et al., Restricted reassociation of heavy and light chains from hapten-specific monoclonal antibodies, Proc. Natl. Acad. Sci. USA, 78(9):5807-5811, Spet. 1981.*

Nezlin, RS, Biochemistry of Antibodies, Plenum Press:New York, p. 160, 1970.*

(56) References Cited

OTHER PUBLICATIONS

Lamminmaki et al., Crystal structure of a recombinant anti-estradiol Fab fragment in compelxtwith 17B-estradiol, J. Biol. Chem. 276 (39):36687-94, 2001.*

Chen et al.,Enhancement and destruction of antibody function by somatic mutation: unequal occurrence is controlled by V gene combinatorial associationsEMBO J. 14 (12): 2784-2794, 1995.*

Yan et al., Construction of a synthetic phage-displayed Nanobody library with CDR3 regions randomized by trinucleotide cassettes for diagnostic applications, J. Translational Med. 12:343, 12 pages, 2014.*

Thommen et al., Progression of Lung Cancer Is Associated with Increased Dysfunction of T Cells Defined by Coexpression of Multiple Inhibitory Receptors Cancer Immunology Research; 3(12) Dec. 2015.

Ngiow et al., A Threshold Level of Intratumor CD8b T-cell PD1 Expression Dictates Therapeutic Response to Anti-PD1, Cancer Research; 75(18) Sep. 15, 2015.

Duraiswamy et al., Therapeutic PD-1 Pathway Blockade Augments with Other Modalities of Immunotherapy T-Cell Function to Prevent Immune Decline in Ovarian Cancer Cancer Res; 73(23) Dec. 1, 2013: 6900-6912.

Dubrot et al., Treatment with anti-CD137 mAbs causes intense accumulations of liver T cells without selective antitumor immunotherapeutic effects in this organ Cancer Immunology, Immunotherapy, vol. 59(8):1223-1233 (2010).

Fisher, T. S. et al., Targeting of 4-1 BB by monoclonal antibody PF-05082566 enhances T-cell function and promotes anti tumor activity Cancer Immunol Immunother (2012) 61: 1721-1733.

Gauttier, V. et al., Agonistic anti-CD137 antibody treatment leads to antitumor response in mice with liver cancer International Journal of Cancer: 135, 2857-2867 (2014).

Gilbreth, R. N., et al., Crystal structure of the human 4-1 BB/4-1 BBL complex J Biol Chem., (2018), 30 pages.

Houot, R., et al., Therapeutic effect of CD137 immunomodulation in lymphoma and its enhancement by Treg depletion Blood, Oct. 15, 2009; vol. 114 (16): 3431-3438.

Kohrt, H. E., et al., CD137 stimulation enhances the antilymphoma activity of anti-CD20 antibodies Blood, Feb. 24, 2011; vol. 117 (8): 2423-2432.

Kohrt, H. E., et al., Stimulation of natural killer cells with a CD137-specific antibody enhances trastuzumab efficacy in xenotransplant models of breast cancer the Journal of Clinical Investigation, Mar. 2012; vol. 122 (3): 1066-1075.

Kohrt, H. E., et al., Targeting CD137 enhances the efficacy of cetuximab the Journal of Clinical Investigation, Jun. 2014; vol. 124 (6):2668-2682.

Kroon, P. et al., Concomitant targeting of programmed death-1 (PD-1) and CD137 improves the efficacy of radiotherapy in a mouse model of human BRAFV600-mutant melanoma Cancer Immunol Immunother (2016) 65:753-763.

Madireddi, S. et al., Galectin-9 controls the therapeutic activity of 4-1 BB-targeting antibodies J. Exp Med. 2014: vol. 211 (7); 1433-1448.

Melero, I. et al., Monoclonal antibodies against the 4-1 BB T-cell activation molecule eradicate established tumors, Nature Medicine, vol. 3(6):682-685 (1997).

Mittler, R. S. et al., Anti-4-1 BB Monoclonal Antibodies Abrogate T Cell-dependent Humeral Immune Responses In Vivo through the Induction of Helper T Cell Anergy J. Exp. Med., Nov. 15, 1999; vol. 190 (10): 1535-1540.

Qian, Y. et al., CD137 ligand-mediated reverse signaling inhibits proliferation and induces apoptosis in non-small cell lung cancer Med. Oneal. (2015) 32:44.

Sanchez-Paulete A. R. et al., Cancer Immunotherapy with Immunomodulatory Anti-CD137 and Anti-PD-1 Monoclonal Antibodies Requires BATF3-Dependent Dendritic Cells Jan. 2016; Cancer Discovery: 71-79.

Shi, W. et al., Augmented Antitumor Effects of Radiation Therapy by 4-1 BB Antibody (BMS-469492) Treatment Anticancer Research 26: 3445-3454 (2006).

Shindo, Y. et al., Combination Immunotherapy with 4-1 BB Activation and PD-1 Blockade Enhances Antitumor Efficacy in a Mouse Model of Subcutaneous Tumor Anticancer Research 35: 129-136 (2015).

Shuford W. W. et al., 4-1 BB Costimulatory Signals Preferentially Induce CDS+ T Cell Proliferation and Lead to the Amplification In Vivo of Cytotoxic T Cell Responses J. Exp. Med Jul. 7, 1997: vol. 186 (1 ): 47-55.

Souza-Fonseca-Guimaraes, F. et al., Anti-CD137 enhances anti-CD20 therapy of systemic B-cell lymphoma with altered immune homeostasis but negligible toxicity OncoImmunology: Jun. 2016.

Almagro, J. C. et al. Humanization of Antibodies Frontiers in Bioscience 2008; 13:1619-33.

Srivastava, R. M. et al., CD137 stimulation enhances cetuximab induced natural killer (NK): dendritic cell (DC) priming of anti-tumor T cell immunity in head and neck cancer patients Clin Cancer Res. Feb. 1, 2017; 23(3): 707-716.

Stagg, J. et al., Anti-ErbB-2 mAb therapy requires type I and II interferons and synergizes with anti-PD-1 or anti-CD137 mAb therapy 7142-7147: PNAS: Apr. 26, 2011: vol. 108 (17).

Tolcher, A. et al., Phase lb Study of Utomilumab (PF-05082566), a 4-1BB/CD137 Agonist, in Combination with Pembrolizumab (MK-3475) in Patients with Advanced Solid Tumors, Clin Cancer Res., vol. 23(18): 5349-5357 (2017).

Uno, T. et al., Eradication of established tumors in mice by a combination antibody-based therapy, Nature Medicine, vol. 12(6):693-698 (2006).

Ye, Q. et al., CD137 accurately identifies and enriches for naturally occurring tumor-reactive T cells in tumor., Clin Cancer Res., vol. 20(1):44-55 (2014).

Wei, H. et al., Combinatorial PD-1 Blockade and CD137 Activation Has Therapeutic Efficacy in Murine Cancer Models and Synergizes with Cisplatin PLOS One: Dec. 2013: vol. 8 (12).

Wei, H. et al., Dual targeting of CD137 co-stimulatory and PD-1 co-inhibitory molecules for ovarian cancer immunotherapy OncoImmunology (3); Mar. 2014.

Wilcox, R. et al., Provision of antigen and CD137 signaling breaks immunological ignorance, promoting regression of poorly immunogenic tumors the Journal of Clinical Investigation: Mar. 2002: vol. 109 (5): 651-659.

International Search Report and Written Opinion, PCT/US2018/041612, dated Jan. 15, 2019, 20 pages.

Chester, C. et al. Biomarker Characterization Using Mass Cytometry in a Pase 1 Trial of Urelumab (BMS-663513) in Subjects with Advanced Solid Tumors and Relapsed/Refractory B-cell non-Hodgkin Lymphoma J Clin. Oneal. 2014, 32 (15 suppl), p. 3017.

Invitation to Pay Additional Fees, and where applicable, Protest Fee, PCT/US2018/041612, dated Nov. 19, 2018, 16 pages.

Bartkowiak, T. et al., Activation of 4-1BB on Liver Myeloid Cells Triggers Hepatitis via an Interieukin-27-Dependent Pathway Clin Cancer Res., vol. 24(5):1138-1151 (2018).

Bitra, A. et al., Crystal structures of the human 4-1 BB receptor bound to its ligand 4-1 BBL reveal covalent receptor dimerization as a potential signaling amplifier J Biol Chem., vol. 293(26):9958-9969 (2018).

Bitra, A. et al., Crystal structures of murine 4-1 BB and its interaction with 4-1 BBL support a role for galectin-9 in 4-1 BB signaling J Biol Chem., (2017).

Chen, S. et al. Combination of 4-1 BB Agonist and PD-1 Antagonist Promotes Antitumor Effector/Memory CDS T Cells in a Poorly Immunogenic Tumor Model Cancer Immunology Research: Nov. 11, 2014: 149-161.

Tjio et al., Genetics of somatic mammalian cells. II. Chromosomal constitution of cells in tissue culture, J Exp. Med. 108:259-271, 1958.

Spiess et al., Alternative molecular formats and therapeutic applications for bispecific antibodies, Mol. Jmmunol. 67:95-106, 2015.

Kipriyanov et al., Generation of bispecific and tandem diabodies, Methods Mal. Biol. 317-331, 2002.

(56) References Cited

OTHER PUBLICATIONS

Coloma and Morrison, Design and production of novel tetravalent bispecific antibodies, Nature Biotechnol. 15:159-163, 1997.
Vaughan et al., Of minibody, camel and bacteriophage, Combinatorial Chem. High Throughput Screening 4:417-430, 2001.
Baeuerle et al., BiTE: Teaching antibodies to engage T-cells for cancer therapy, Curr. Opin. Mal. Ther. 11:22-30, 2009.
Forbes et al., The Catalogue of Somatic Mutations in Cancer (COSMIC), Curr. Protoc. Hum. Genet. 2008.
DiGiammarino et al., Design and generation of DVD-Ig™ molecules for dual-specific targeting, Methods Mal. Biol. 899:145-156, 2012.
Intlekofer and Thompson, at the Bench: Preclinical rationale for CTLA-4 and PD-1 blockade as cancer immunotherapy, J. Leukoc. Biol. 94(1):25-39, 2013.
Garber, Bispecific antibodies rise again, Nature Rev. Druz Discov. 13:799-801, 2014.
Segal, N.H. et al., Results from an Integrated Safety Analysis of Urelumab, an Agonist Anti-CD 137 Monoclonal Antibody., Clin Cancer Res., vol. 23(8):1929-1936(2016).
Wolf et al., BiTEs: bispecific antibody constructs with unique anti-tumor activity, Drug Discovery Today 10:1237-1244, 2005.
Kontermann et al., Bispecific Antibodies. Drug Discovery Today 20:838-847, 2015.
Ishida et al., Induced expression of PD-1, a novel member of the immunoglobulin gene superfamily, upon programmed cell death. The EMBO journal. Nov. 1992;11(11):3887-3895.
Iwai et al., Involvement of PD-L1 on tumor cells in the escape from host immune system and tumor immunotherapy by PD-L1 blockade. Proceedings of the National Academy of Sciences. Sep. 17, 2002;99(19):12293-12297.
Jacob et al., Peptide-polymer biotherapeutic synthesis on novel cross-linked beads with "spatially tunable" and "isolated" functional sites. Biopolymers 90(4):512-525, 2008.
Jiang et al., RNA-guided editing of bacterial genomes using CRISPR-Cas systems, Nature Biotechnol. 31(3):233-239, 2013.
Jinek et al., A programmable dual-RNA-guided DNA endonuclease in adaptive bacterial immunity, Science 337 (6096):816-821, 2012.
Johnson et al., 3-O-Desacyl monophosphoryl lipid A derivatives: synthesis and immunostimulant activities. Journal of Medicinal Chemistry. Nov. 4, 1999;42(22):4640-4649.
Jones et al., Replacing the complementarity-determining regions in a human antibody with those from a mouse. Nature. May 1986;321(6069):522-525.
Jones, MHC class I and class II structures, Curr. Opinion Immunol. 9(1):75-79, 1997.
Ju and Jung, "A glycosylated full-length IgG antibodies: steps toward next generation immunotherapeutics," Curr. Opin. Biotechnol. 30:128-139, 2014.
Juarez et al., Monoclonal antibodies for the identification and purification of vNAR domains and IgNAR immunoglobulins from the horn shark Heterodontus francisci, Hybridoma (Larchmt), 30(4):323-329, 2011.
Kaszubska et al., Expression, purification, and characterization of human recombinant thrombopoietin in Chinese hamster ovary cells. Protein Expression and Purification. Mar. 1, 2000;18(2):213-220.
Kawabe et al., Production of scFv-Fc fusion protein using genetically manipulated quails, J. Biosci. Bioeng. 102(4): 297-303, 2006.
Kessler, The digoxigenin: anti-digoxigenin (DIG) technology—a survey on the concept and realization of a novel bioanalytical indicator system. Mol. Cell. Probes 5(3):161-205, 1991.
Kieke et al., Isolation of anti-T cell receptor scFv mutants by yeast surface display. Protein Engineering. Nov. 1, 1997;10 (11):1303-1310.
Kijanka et al., Nanobody-based cancer therapy of solid tumors, Nanomedicine 10:161-174, 2015.
Kim et al., Genome editing with modularly assembled zinc-finger nucleases, Nature Methods 7(2):91; Author Reply 91-2, 2010.
Kinstler et al., Mono-N-terminal poly (ethylene glycol)-protein conjugates. Advanced Drug Delivery Reviews. Jun. 17, 2002;54(4):477-485.
Klein et al., Progress in overcoming the chain association issue in bispecific heterodimeric IgG antibodies. MAbs. Nov. 1, 2012;4(6):653-663.
Klemm et al., Fimbrial surface display systems in bacteria: from vaccines to random libraries. Microbiology. Dec. 1, 2000;146(12):3025-3032.
Knappik et al., Fully synthetic human combinatorial antibody libraries (HuCAL) based on modular consensus frameworks and CDRs randomized with trinucleotides, J. Mol. Biol. 296(1):57-86, 2000.
Kochupurakkal et al., Nourseothricin N-acetyl transferase: a positive selection marker for mammalian cells, PLoS ONE 8(7):e68509, 2013.
Kohrt et al., Stimulation of natural killer cells with a CD137-specific antibody enhances trastuzumab efficacy in xenotransplant models of breast cancer. J Clin Investigation. Mar. 1, 2012; 122(3):1066-1075.
Konishi et al., B7-H1 expression on non-small cell lung cancer cells and its relationship with tumor-infiltrating lymphocytes and their PD-1 expression. Clinical Cancer Research. Aug. 1, 2004;10(15):5094-5100.
Konning et al., Camelid and shark single domain antibodies: structural features and therapeutic potential, Curr. Opin. Struct. Biol. 45:10-16, 2017.
Kovaleva et al., Shark variable new antigen receptor biologies—a novel technology platform for therapeutic drug development, Exvert. Ovin. Biol. Ther. 14:1527-1539, 2014.
Krah et al., Single-domain antibodies for biomedical applications, Immunopharmacol. Immunotoxicol. 38:21-28, 2016.
Langer et al., Biocompatibility of polymeric delivery systems for macromolecules. Journal of Biomedical Materials Research. Mar. 1981;15(2):267-277.
Lazar-Molnar et al., Crystal structure of the complex between programmed death-1 (PD-1) and its ligand PD-L2. Proceedings of the National Academy of Sciences. Jul. 29, 2008; 105(30):10483-10488.
Lee et al., High-affinity human antibodies from phage-displayed synthetic Fab libraries with a single framework scaffold, J. Mol. Biol. 340(5):1073-1093, 2004.
Levitt et al., Definition of an efficient synthetic poly(A) site, Genes Dev. 3(7): 1019-1025, 1989.
Li et al., Reduction of kidney uptake in radiometal labeled peptide linkers conjugated to recombinant antibody fragments. Site-specific conjugation of DOT A—peptides to a Cys-diabody, Bioconiuzate Chem. 13:985-995, 2002.
Lo, B. K. (2004). Antibody engineering: Methods and protocols. Totowa, NJ: Humana Press.
Loughran et al., Evidence of efficient stop codon readthrough in four mammalian genes, Nucleic Acids Res. 42 (14):8928-8938, 2014.
Lusky & Botchan., Inhibition of SV40 replication in simian cells by specific pBR322 DNA sequences. Nature. Sep. 3, 1981;293(5827):79-81.
MacCallum et al., Antibody-antigen interactions: contact analysis and binding site topography. Journal of Molecular Biology. Oct. 11, 1996;262(5):732-745.
Macke et al., RNA Motif, an RNA secondary structure definition and search algorithm, Nucleic Acids Res. 29 (22):4724-4735, 2001.
Mali et al., RNA-Guided Human Genome Engineering via Cas9, Science 339:823-826, 2013.
Martins et al., Evaluation of a Multiplex Fluorescent Microsphere Immunoassay for the Determination of Epstein-Barr Virus Serologic Status. Am. J. Clin. Pathol. 129(1):34-41, 2008.
Mcconville et al., The structure, biosynthesis and function of glycosylated phosphatidylinositols in the parasitic protozoa and higher eukaryotes, Biochem. J. 294(Pt 2):305-324, 1993.
McHugh et al., Simultaneous detection of antibodies to cytomegalovirus and herpes simplex virus by using flow cytometry and a microsphere-based fluorescence immunoassay. J. Clin. Microbiol. 26(10):1957-1961, 1988.
Merchant et al., An efficient route to human bispecific IgG. Nature Biotechnology. Jul. 1998;16(7):677-681.

(56) References Cited

OTHER PUBLICATIONS

Merz & Drapeau. Generating a phage display antibody library against an indentified neuron. J Neurosci Methods Nov. 1995,62(1-2):213-9.
Michael et al., Addition of a short peptide ligand to the adenovirus fiber protein. Gene Therapy. Nov. 1995;2(9):660-668.
Miller et al., A TALE nuclease architecture for efficient genome editing, Nature Biotechnol. 29(2):143-148, 2011.
Milstein and Cuello, Hybrid hybridomas and their use in immunohistochemistry, Nature 305(5934):537-540, 1983.
Mueller et al., Homing endonucleases, in Nucleases 2nd Edition, S. M. Linn, R. S. Lloyd, and R. J. Roberts (Eds) Cold Spring Harbor Laboratory Press:1993, DD. 111-143.
Mujic-Delic et al., GPCR-targeting nanobodies: attractive research tools, diagnostics, and therapeutics, Trends Pharmacol. Sci. 35:247-255, 2014.
Mulligan and Berg, Selection for animal cells that express the *Escherichia coli* gene coding for xanthine-guanine phosphoribosyltransferase, Proc. Natl. Acad. Sci. U.S.A. 78(4):2072-2076, 1981.
Muyldermans et al., Recognition of antigens by single-domain antibody fragments: the superfluous luxury of paired domains, Trends Biochem. Sci. 26:230-235, 2001.
Muyldermans, Nanobodies: natural single-domain antibodies, Ann. Rev. Biochem. 82:775-797, 2013.
Cromie et al., Nanobodies and their Use in GPCR Drug Discovery, Curr. Top. Med. Chem. 15:2543-2557,2016.
Davis et al., SEEDbodies: fusion proteins based on strand-exchange engineered domain (Seed) CH3 heterodimers in an Fc analogue platform for asymmetric binders or immunofusions and bispecific antibodies. Protein Engineering, Design & Selection. Apr. 1, 2010;23(4):195-202.
De Genst et al., Antibody repertoire development in camelids, Dev. Comp. Immunol. 30: 187-198, 2006.
De Meyer et al., Nanobody-based products as research and diagnostic tools, Trends Biotechnol. 32:263-270, 2014.
Deans et al., Expression of an immunoglobulin heavy chain gene transfected into lymphocytes. Proceedings of the National Academy of Sciences. Mar. 1, 1984;81(5):1292-1296.
Dharmadhikari et al., CD137 and CD137L signals are main drivers of type 1, cell-mediated immune responses. Oncoimmunology. Apr. 2, 2016;5(4):e1113367.
Di Niro et al., Characterizing monoclonal antibody epitopes by filtered gene fragment phage display. The Biochemical Journal. Jun. 7, 2005;388(Pt 3):889-894.
Doering et al., Biosynthesis of glycosyl phosphatidylinositol membrane anchors, J. Biol. Chem. 265(2):611-614, 1990.
Dong et al., B7-H1 pathway and its role in the evasion of tumor immunity. Journal of Molecular Medicine. May 1, 2003;81(5):281-287.
Dooley et al., Antibody repertoire development in cartilaginous fish, Dev. Comp. Immunol. 30:43-56,2006.
Dumoulin et al., A camelid antibody fragment inhibits the formation of amyloid fibrils by human lysozyme, Nature 424 (6950):783-788, 2003.
Eisenhaber et al., Automated annotation of GPI anchor sites: case study C. elegans, Trends Biochem. Sci. 25 (7):340-341, 2000.
Eisenhaber et al., Post-translational GPI lipid anchor modification of proteins in kingdoms of life: analysis of protein sequence data from complete genomes, Protein Engineering 14( 1): 17-25, 2001.
Eisenhaber et al., Prediction of lipid posttranslational modifications and localization signals from protein sequences: big-Pi, NMT and PTSI, Nucleic Acids Res. 31(13):3631-3634, 2003.
Eisenhaber et al., Prediction of potential GPI-modification sites in proprotein sequences, J. Mol. Biol. 292(3):741-758, 1999.
Eisenhaber et al., Sequence properties of GPI-anchored proteins near the omega-site: constraints for the polypeptide binding site of the putative transamidase, Protein Engineering 11(12):1155-1161, 1998.

Engberg et al., Phage-display libraries of murine and human antibody Fab fragments. Antibody Engineering Protocols. 1995;(pp. 355-376). Humana Press.
Estep et al., High throughput solution-based measurement of antibody-antigen affinity and epitope binning. Mabs. Mar. 1, 2013; 5(2):270-278.
Etz et al., Bacterial phage receptors, versatile tools for display of polypeptides on the cell surface. Journal of Bacteriology. Dec. 1, 2001;183(23):6924-6935.
Fatima et al., Development of VHH antibodies against dengue virus type 2 NSI and comparison with monoclonal antibodies for use in immunological diagnosis, PLOS One 9(4):e95263, 2014.
Firth et al., Stimulation of stop codon readthrough: frequent presence of an extended 3' RNA structural element, Nucleic Acids Res. 39(15):6679-6691, 2011.
Freeman et al., Engagement of the PD-1 immunoinhibitory receptor by a novel B7 family member leads to negative regulation of lymphocyte activation. The Journal of Experimental Medicine. Oct. 2, 2000;192(7):1027-1034.
Freeman G., Structures of PD-1 with its ligands: Sideways and dancing cheek to cheek. Proceedings of the National Academy of Sciences. Jul. 29, 2008;105(30):10275-10276.
Fulton et al., Advanced multiplexed analysis with the FlowMetrixTM system. Clin. Chem. 43(9):1749-1756, 1997.
Gautheret and Lambert, Direct RNA motif definition and identification from multiple sequence alignments using secondary structure profiles, J. Mol. Biol. 313(5):1003-1011, 2001.
George et al., An analysis of protein domain linkers: their classification and role in protein folding, Protein Eng Des. Sel. 15(11):871-879, 2002.
Ghiotto et al., PD-L1 and PD-L2 differ in their molecular mechanisms of interaction with PD-1. International Immunology. Aug. 1, 2010;22(8):651-660.
Grabher et al., The baculovirus expression system as a tool for generating diversity by viral surface display. Combinatorial Chemistry & High Throughput Screening. Apr. 1, 2001;4(2):185-192.
Gronwald et al., Cloning and expression of a cDNA coding for the human platelet-derived growth factor receptor: evidence for more than one receptor class. Proc. Natl. Acad. Sci. U.S.A. 85(10):3435-3439, 1988.
Gunasekaran et al., Enhancing antibody Fc heterodimer formation through electrostatic steering effects: applications to bispecific molecules and monovalent IgG. Journal of Biological Chemistry. Jun. 18, 2010;285(25):19637-19646.
Hanes et al., Picomolar affinity antibodies from a fully synthetic naive library selected and evolved by ribosome display. Nature Biotechnology. Dec. 2000;18(12):1287-1292.
Harlow, E., & Lane, D. (1988). Antibodies: A laboratory manual. Cold Spring Harbor, NY, NY: Cold Spring Harbor Laboratory, Title page only.
Harmer & Samuel, The FITC-anti-FITC System Is a Sensitive Alternative to Biotin-Streptavidin in ELISA. J. Immunol. Methods 122(1):115-121, 1989.
Hasler et al., VNAR single-domain antibodies specific for BAFF inhibit B cell development by molecular mimicry, Mol. Immunol. 75:28-37, 2016.
Haynie, Physics of polypeptide multilayer films. J. Biomed. Mater. Res. B Appl. Biomater. 78(2):243-252, Abtract only, 2006.
Hedhammar et al., Chromatographic methods for protein purification. Stockholm: Royal Institute of Technology, 2006.
Hellen et al., Internal ribosome entry sites in eukaryotic mRNA molecules, Genes Dev. 15(13):1593-612, 2001.
Hey et al., Artificial, non-antibody binding proteins for pharmaceutical and industrial applications, TRENDS Biotechnol. 23(10):514-522, 2005.
Hilpert et al., Cellulose-bound peptide arrays: preparation and applications. Biotechnol. Genet. Engin. Rev. 24:31-106, 2007.
Hollinger et al., 'Diabodies': small bivalent and bispecific antibody fragments, Proc. Natl. Acad. Sci. U.S.A. 90:6444-6448, 1993.
Holmes et al., Murine hematopoietic cells with pre-B or pre-B/myeloid characteristics are generated by in vitro transformation with retroviruses containing fes, ras, abl, and src oncogenes, J. Exp. Med. 164(2):443-457, 1986.

(56) References Cited

OTHER PUBLICATIONS

Hoogenboom., Designing and optimizing library selection strategies for generating high-affinity antibodies. Trends in Biotechnology. Feb. 1, 1997;15(2):62-70.
Horan & Wheeless, Quantitative Single Cell Analysis and Sorting. Science 198(4313):149-157, 1977.
Houdebine., Antibody manufacture in transgenic animals and comparisons with other systems. Current Opinion in Biotechnology. Dec. 1, 2002;13(6):625-629.
Houot et al., Boosting antibody-dependant cellular cytotoxicity against tumor cells with a CD137 stimulatory antibody. Oncoimmunology. Sep. 1, 2012;1(6):957-8.
Houseman & Mrksich, Towards quantitative assays with peptide chips: a surface engineering approach. Trends Biotechnol. 20(7):279-281, 2002.
Hudson et al., High avidity scFv multimers; diabodies and triabodies, J. Immunol. Methods 231:177-189, 1999.
Huston et al., Protein engineering of antibody binding sites: recovery of specific activity in an anti-digoxin single-chain Fv analogue produced in *Escherichia coli*. Proceedings of the National Academy of Sciences. Aug. 1, 1988;85(16):5879-5883.
Hwang et al., Efficient genome editing in zebrafish using a CRISPR-Cas system, Nature Biotechnol. 31(3):227-229, 2013.
Jakob et al., Structure reveals function of the dual variable domain immunoglobulin (DVD-Ig™) molecule, MABs 5:358-363, 2013.
Huehls et al., Bispecific T-cell engagers for cancer immunotherapy, Immunol. Cell Biol. 93:290-296,2015.
Brennan et al., Preparation of bispecific antibodies by chemical recombination of monoclonal immunoglobulin GI fragments, Science 229(4708):81-83, 1985.
Gruber et al., Efficient tumor cell lysis mediated by a bispecific single chain antibody expressed in *Escherichia coli*, J. Immunol. 152(11):5368-5374, 1994.
Holt et al., Domain antibodies: proteins for therapy, Trends Biotechnol. 21(11):484-490, 2003.
Huston et al., Engineered antibodies take center stage, Hum. Antibodies 10(3-4):127-142, 2001.
Kipriyanov et al., Bispecific tandem diabody for tumor therapy with improved antigen binding and pharmacokinetics, J. Mol. Biol. 293(1):41-56, Oct. 1999.
Kostelny et al., Formation of a bispecific antibody by the use of leucine zippers, J. Immunol. 148(5):1547-1553, 1992.
Suresh et al., Bispecific monoclonal antibodies from hybrid hybridomas, Methods Enzymol. 121:210-228, 1986.
Takemura et al., Construction of a diabody (small recombinant bispecific antibody) using a refolding system, Protein Enz. 13(8):583-588, 2000.
Todorovska et al., Design and application of diabodies, triabodies and tetrabodies for cancer targeting, J Immunol. Methods 248(1-2):47-66, 2001.
Xu et al., Production of bispecific antibodies in knobs-into-holes using a cell-free expression system, mAbs7 (1):231-242, 2015.
Zhu et al., High Level Secretion of a Humanized Bispecific Diabody from *Escherichia coli*, Nature Biotech. 14:192-196, 1996.
Stephen et al., "SATB1 Expression Governs Epigenetic Repression of PD-1 in Tumor-Reactive T Cells," Immunity. 46:51-64, 2017.
Zhu et al., "BET Bromodomain Inhibition Promotes Anti-Tumor Immunity by Suppressing PD-LI Expression," Cell Rep. 16:2829-2837, 2016.
Pluckthun, Antibodies from *E. coli*. in Rosenberg M. & Moore G.P. (Eds.), The Pharmacology of Monoclonal Antibodies, vol. 113, pp. 269-315, Spinger-Verlag, New York, 1994.
Abdel-Motal et al., Anti-gpl20 minibody gene transfer to female genital epithelial cells protects against HIV-1 vims challenge in vitro, PLoS ONE 6:e26473, 2011.
Agata et al., Expression of the PD-1 antigen on the surface of stimulated mouse T and B lymphocytes. International Immunology. May 1, 1996;8(5):765-772.
Alderson et al., Molecular and biological characterization of human 4-1BB and its ligand. Eur J Immunol. Sep. 1994;24 (9):2219-27.

Ali et al., Transferrin Trojan Horses as a Rational Approach for the Biological Delivery of Therapeutic Peptide Domains, J Biol. Chem. 274:24066-24073, 1999.
Ames et al., Conversion of murine Fabs isolated from a combinatorial phage display library to full length immunoglobulins. Journal of Immunological Methods. Aug. 18, 1995;184(2):177-186.
Amet et al., Insertion of the designed helical linker led to increased expression of tf-based fusion proteins, Pharm. Res. 26:523-528, 2009.
Anderson et al., Intercellular transfer of a glycosylphosphatidylinositol (GPI)-linked protein: release and uptake of CD4-GPI from recombinant adeno-associated virus-transduced HeLa cells, Proc. Natl. Acad. Sci. U.S.A. 93(12):5894-5898, 1996.
Arnau et al., Current strategies for the use of affinity tags and tag removal for the purification of recombinant proteins, Protein Express. Purification 48(1):1-13, 2006.
Ayoglu et al., Antigen arrays for profiling autoantibody repertoires. Bioanalysis 8(10):1105-1126, 2016.
Ayoglu et al., Autoantibody Profiling in Multiple Sclerosis Using Arrays of Human Protein Fragments. Mol. Cell. Proteomics 12(9):2657-2672, 2013.
Baldridge et al., Monophosphoryl Lipid A (MPL) Formulations for the Next Generation of Vaccines. Methods. Sep. 1999;19(1):103-107.
Batt et al., Characterization of the polyomavirus late polyadenylation signal, Mol. Cell Biol. 15(9):4783-4790, 1995.
Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses. The Journal of Immunology. Jan. 15, 2003;170(2):711-718.
Berg, J. M., Tymoczko, J. L., & Stryer, L. (2002). Biochemistry (5th ed.). New York, NY: W.H. Freeman.
Bever et al., Development and utilization of camelid VHH antibodies from alpaca for 2,2',4,4'-tetrabrominated diphenvl ether detection, Analytical Chem. 86(15):7875-7882, 2014.
Bever et al., VHH antibodies: emerging reagents for the analysis of environmental chemicals, Anal. Bioanal. Chem. 408(22):5985-6002, 2016.
Binz et al., Engineering novel binding proteins from nonimmunoglobulin domains. Nature biotechnology. Oct. 6, 2005,23 (10):1257-1268.
Bird et al., Single-chain antigen-binding proteins, Science 242:423-426, 1989.
Blank et al., Interaction of PD-L1 on tumor cells with PD-1 on tumor-specific T cells as a mechanism of immune evasion: implications for tumor immunotherapy. Cancer Immunology, Immunotherapy Apr. 1, 2005;54(4):307-314.
Blank, C et al., Contribution of the PD-L1/PD-1 pathway to T-cell exhaustion: an update on implications for chronic infections and tumor evasion. Cancer immunology, immunotherapy. May 1, 2007;56(5):739-745.
Boder et al., Yeast surface display for directed evolution of protein expression, affinity, and stability. Methods in Enzymology. Jan. 1, 2000; 328:430-444.
Bonocora and Shub, A novel group I intron-encoded endonuclease specific for the anticodon region of tRNA(fMet) genes, Mol. Microbial. 39(5): 1299-1306, 2001.
Borrebaeck, C. A. (1995). Antibody engineering. New York, NY: Oxford University Press, Abstract only.
Braeckmans et al., Encoding microcarriers: present and future technologies. Nat. Rev. Drug Discov. 1:447-456, 2002.
Brinkman et al., Phage display of disulfide-stabilized Fv fragments. Journal of Immunological Methods. Jan. 1, 1995;182 (1):41-50.
Brown et al., Blockade of programmed death-1 ligands on dendritic cells enhances T cell activation and cytokine production. The Journal of Immunology. Feb. 1, 2003;170(3):1257-1266.
Brunschwig et al., Protein transfer of glycosyl-phosphatidylinositol (GPI)-modified murine B7-I and B7-2 costimulators, J Immunother. 22(5):390-400, 1999.
Burton et al., Human antibodies from combinatorial libraries. Advances in Immunology. Jan. 1, 1994; 57:191-280.

(56) References Cited

OTHER PUBLICATIONS

Burton, D.R., & Woof J.M. (1992). Human Antibody Effector Function. In F.J. (Ed), Advances in Immunology (pp. 1-2, 2a, 2b, 3084) ScienceDirect.

Canfield et al., The binding affinity of human IgG for its high affinity Fc receptor is determined by multiple amino acids in the CH2 domain and is modulated by the hinge region. The Journal of Experimental Medicine. Jun. 1, 1991;173 (6):1483-1491.

Caras et al., Signal for attachment of a phospholipid membrane anchor in decay accelerating factor, Science 238 (4831):1280-1283, 1987.

Caras et al., Signal peptide for protein secretion directing glycophospholipid membrane anchor attachment, Science 243(4895):1196-1198, 1989.

Carter et al., PD-1: PD-L inhibitory pathway affects both CD4+ and CD8+ T cells and is overcome by IL-2. European Journal of Immunology. Mar. 2002;32(3):634-643.

Chasteen et al., Eliminating helper phage from phage display. Nucleic Acids Research. Dec. 1, 2006;34(21):e145.

Chester et al., 4-1BB agonism: adding the accelerator to cancer immunotherapy. Cancer Immunol Immunother. Oct. 1, 2016;65(10):1243-8.

Chestnut et al., Selective isolation of transiently transfected cells from a mammalian cell population with vectors expressing a membrane anchored single-chain antibody, J Immunol. Methods 193(1):17-27, 1996.

Chevalier and Stoddard, Homing endonucleases: structural and functional insight into the catalysts of intron/intein mobility, Nucleic Acids Res. 29(18):3757-3774, 2001.

Cho et al., Targeted genome engineering in human cells with the Cas9 RNA-guided endonuclease, Nature Biotechnol. 31(3):230-232, 2013.

Chothia et al., Canonical structures for the hypervariable regions of immunoglobulins. Journal of Molecular Biology. Aug. 20, 1987;196(4):901-917.

Chothia et al., Conformations of immunoglobulin hypervariable regions. Nature. Dec. 1989;342(6252):877-883.

Chou et al., Expression of chimeric monomer and dimer proteins on the plasma membrane of mammalian cells, Biotechnol. Bioeng 65(2):160-169, 1999.

Christian et al., Targeting DNA double-strand breaks with TAL effector nucleases, Genetics 186(2):757-761, 2010.

Chu et al., Increasing the efficiency of homology-directed repair for CRISPR-Cas9-induced precise gene editing in mammalian cells, Nature Biotechnol. 33(5):543-548, 2015.

Cong et al., Multiplex Genome Engineering Using CRISPR/Cas Systems, Science 339(6121):819-823, 2013.

Conti et al., Differential distribution of ryanodine receptor type 3 (RyR3) gene product in mammalian skeletal muscles. Biochem J. 316(1):19-23, 1996.

Cornelis., Expressing genes in different *Escherichia coli* compartments. Current Opinion in Biotechnology. Oct. 1, 2000;11(5):450-454.

Tashiro et al., Signal sequence trap: a cloning strategy for secreted proteins and type I membrane proteins, Science 261(5121):600-603, 1993.

Thein et al., The polyadenylation site mutation in the alpha-globin gene cluster, Blood 71(2):313-319, 1988.

Tutt et al., Trispecific F (ab') 3 derivatives that use cooperative signaling via the TCR/CD3 complex and CD2 to activate and redirect resting cytotoxic T cells. The Journal of Immunology. Jul. 1, 1991;147(1):60-9.

Urnov et al., Genome editing with engineered zinc finger nucleases, Nature Reviews Genetics 11(9):636-656, 2010.

Vagner et al., Rigid linkers for bioactive peptides, Bioconjug. Chem. 17(6): 1545-1550, 2006.

Van Audenhove et al., Nanobodies as Versatile Tools to Understand, Diagnose, Visualize and Treat Cancer, EBioMedicine 8:40-48, 2016.

Van Bockstaele et al., The development of nano bodies for therapeutic applications, Curr. Opin. Investig Drugs 10: 1212-1224, 2009.

Van Kuik-Romeijn et al., Expression of a functional mouse-human chimeric anti-CD19 antibody in the milk of transgenic mice. Transgenic Research. Apr. 1, 2000;9(2):155-159.

Vincke et al., Introduction to heavy chain antibodies and derived Nanobodies, Methods Mal. Biol. 911: 15-26, 2012.

Watts TH. TNF/TNFR family members in costimulation of T cell responses. Annu. Rev. Immunol. Apr. 23, 2005;23:23-68.

Welch, Michael J & Redvanly, Carol S (2003). Handbook of radiopharmaceuticals : radiochemistry and applications. J. Wiley, New York. ISBN 0471495603, Abstract only.

Wesolowski et al., Single domain antibodies: promising experimental and therapeutic tools in infection and immunity, Med. Microbiol. Jmmunol. 198:157-174, 2009.

Wheeler et al., Intrabody and intrakine strategies for molecular therapy, Mol. Ther. 8(3):355-366, 2003.

Wigler et al., Transformation of mammalian cells with genes from procaryotes and eucaryotes. Cell. Apr. 1, 1979;16 (4):777-785.

Won et al., The structure of the trimer of human 4-1 BB ligand is unique among members of the tumor necrosis factor superfamily. Journal of Biological Chemistry. Mar. 19, 2010;285(12):9202-10.

Woychik et al., Requirement for the 3' flanking region of the bovine growth hormone gene for accurate polyadenylation, Proc. Natl. Acad Sci. U.S.A. 81(13):3944-3948, 1984.

Wranik et al., LUZ-Y, a novel platform for the mammalian cell production of full-length IgG-bispecific antibodies. Journal of Biological Chemistry. Dec. 21, 2012;287(52):43331-43339.

Wright et al., Antibody variable region glycosylation: position effects on antigen binding and carbohydrate structure. The EMBO journal. Oct. 1991;10(10):2717-2723.

Wu et al. Antibody array analysis with label-based detection and resolution of protein size Proteomics. Mol. Cell. Proteomics. 8(2):245-257, 2009.

Wu et al., Simultaneous targeting of multiple disease mediators by a dual-variable-domain immunoglobulin, Nat. Biotechnol. 25(11):1290-1297, 2007.

Wu, Diabodies: molecular engineering and therapeutic applications, Drug News Perspect. 22:453-458,2009.

Yang et al., ELISA microplate: a viable immunocapture platform over magnetic beads for immunoaffinity-LC-MS/MS quantitation of protein therapeutics? Bioanalysis 7(3):307-318, 2015.

Yazaki et al., Tumor targeting of radiometal labeled anti-CEA recombinant T84.66 diabody and t84.66 minibody: comparison to radioiodinated fragments. Bioconjugate Chemistry 12:220-228, 2001.

Ye et al., CD137 accurately identifies and enriches for naturally occurring tumor-reactive T cells in tumor. Clinical Cancer Research. Jan. 1, 2014;20(1):44-55.

Yeung et al., Quantitative screening of yeast surface-displayed polypeptide libraries by magnetic bead capture. Biotechnology Progress. 2002;18(2):212-220.

Yokoyama-Kobayashi et al., A signal sequence detection system using secreted protease activity as an indicator, Gene 163(2):193-196, 1995.

Zak, K., et al., Structure of the Complex of Human Programmed Death 1, PD-1, and Its Ligand PD-L1. Structure. Dec. 1, 2015;23(12):2341-2348.

Zapata et al., Engineering linear F(ab')2 fragments for efficient production in *Escherichia coli* and enhanced antiproliferative activity, Protein Ensz. 8(10):1057-1062, 1995.

Zhang et al., Programmable Sequence-Specific Transcriptional Regulation of Mammalian Genome Using Designer TAL Effectors, Nat. Biotechnol. 29(2):149-153, 2011.

Zhao et al., The restriction fold turns to the dark side: a bacterial homing endonuclease with a PD-(D/E)-XK motif, EMBO J. 26(9):2432-42, 2007.

Zhou et al., Photocleavable peptide-conjugated magnetic beads for protein kinase assays by MALDI-TOF MS. Bioconjug. Chem. 21(10):1917-1924, 2010.

Chen et al., Characterization of germline antibody libraries from human umbilical cord blood and selection of monoclonal antibodies to viral envelope glycoproteins: implications for mechanisms of

(56) References Cited

OTHER PUBLICATIONS immune evasion and design of vaccine immunogents, Biochem Biophys Res Commun. 417(4): 1164-1169, 2012.
Gabibov et al., Combinatorial antibody library from multiple sclerosis patients reveals antibodies that cross-react with myelin basic protein and EBV antigen, FASEB Journ. 25:4211-4221, 2011.
Prabakaran et al., Expressed antibody repertoires in human cord blood cells: 454 sequencing and IMGT/HighV-QUEST analysis of germline gene usage, junctional diversity, and somatic mutations, Immunogenetics 64:337-350 (2012).
Muyldermans, Single domain camel antibodies: current status, J. Biotechnol. 74:277-302, 2001.
Nam et al., The therapeutic potential of 4-1BB (CD137) in cancer. Current cancer drug targets. Aug. 1, 2005;5 (5):357-63.
Needleman & Wunsch., A General Method Applicable to the Search for Similarities in the Amino Acid Sequences of Two Proteins. Journal of Molecular Biology. Mar. 28, 1970;48(2)443-453.
Nuttall, Overview and discovery of IgNARs and generation of VNARs, Methods Mal. Biol. 911:27-36, 2012.
Okazaki et al., New regulatory co-receptors: inducible co-stimulator and PD-1. Curr Opin Immunol. Dec. 2002;14 (6):779-782.
Oke et al., The Scottish Structural Proteomics Facility: targets, methods and outputs, J. Struct. Funct. Genomics 11(2): 167-180, 2010.
Orkin et al., Thalassemia due to a mutation in the cleavage-polyadenylation signal of the human beta-globin gene, EMBO J 4(2):453-456, 1985.
Papapetrou et al., Gene Insertion Into Genomic Safe Harbors for Human Gene Therapy, Mol. Theravv 24(4):678-684, 2016.
Pearson & Lipman., Improved tools for biological sequence comparison. Proceedings of the National Academy of Sciences. Apr. 1, 1988;85(8):1444-2448.
Pelletier et al., Cap-independent translation of poliovirus mRNA is conferred by sequence elements within the 5' noncoding region, Mol. Cell. Biol. 8(3): 1103-1112, 1988.
Pereboev et al., Phage display of adenovirus type 5 fiber knob as a tool for specific ligand selection and validation. Journal of Virology. Aug. 1, 2001;75(15):7107-7113.
Persic et al., An integrated vector system for the eukaryotic expression of antibodies or their fragments after selection from phage display libraries. Gene. Mar. 10, 1997;187(1):9-18.
Pleschberger et al., Generation of a functional monomolecular protein lattice consisting of an s-layer fusion protein comprising the variable domain of a camel heavy chain antibody, Bioconjugate Chem. 14(2):440-448, 2003.
Pogson et al., Immunogenomic engineering of a plug-and-(dis)play hybridoma platform, Nature Comm. 7:12535, 2016.
Poljak, Production and structure of diabodies, Structure 2:1121-1123, 1994.
Pollock et al., Transgenic milk as a method for the production of recombinant antibodies. Journal of Immunological Methods. Dec. 10, 1999;231(1-2):147-157.
Presta., Antibody engineering. Current Opinion in Structural Biology. Aug. 1, 1992;2(4):593-596.
Proudfoot et al., Integrating mRNA processing with transcription, Cell 108(4):501-512, 2002.
Rabu et al., Production of recombinant human trimeric CD137L (4-1BBL) cross-linking is essential to its t cell co-stimulation activity. Journal of Biological Chemistry. Dec. 16, 2005;280(50):41472-81.
Rahbarizadeh et al., Nanobody; an old concept and new vehicle for immunotargeting, Immunol. Invest. 40:299-338, 2011.
Repp et al., Combined Fc-protein- and Fc-glyco-engineering of scFv-Fc fusion proteins synergistically enhances CD 16a binding but does not further enhance NK-cell mediated ADCC, J. Immunol. Methods 373(1-2):67-78, 2011.
Reuter & Matthews, RNAstructure: software for RNA secondary structure prediction and analysis, BMC Bioinformatics 11:129, 2010.
Ridgway et al., Knobs-into-holes' engineering of antibody CH3 domains for heavy chain heterodimerization. Protein Engineering, Design and Selection. Jul. 1, 1996;9(7):617-621.
Riechmann et al., Reshaping human antibodies for therapy. Nature. Mar. 1988;332(6162):323-327.
Roberts et al., Chemistry for peptide and protein PEGylation. Advanced Drug Delivery Reviews. Jun. 17, 2002;54 (4):459-476.
Sadelain et al., Safe harbours for the integration of new DNA in the human genome, Nature Reviews 12(1):51-58, 2012.
Sambrook, J., Fritsch, E., & Maniatis, T. (1989). Molecular Cloning: A Laboratory Manual (2nd ed.). NY: Cold Spring Harbor Laboratory Press, Taple of Contents only.
Sarver et al., Transformation and replication in mouse cells of a bovine papillomavirus—pML2 plasmid vector that can be rescued in bacteria. Proceedings of the National Academy of Sciences Dec. 1, 1982;79(23):7147-7151.
Schaffitzel et al., Ribosome display: an in vitro method for selection and evolution of antibodies from libraries. Journal of Immunological Methods. Dec. 10, 1999;231(1-2):119-135.
Schek et al., Definition of the upstream efficiency element of the simian vims 40 late polyadenylation signal by using in vitro analyses, Mol. Cell Biol. 12(12):5386-5393, 1992.
Schoonbroodt et al., Oligonucleotide-assisted cleavage and ligation: a novel directional DNA cloning technology to capture cDNAs. Application in the construction of a human immune antibody phage-display library. Nucleic Acids Research. Jan. 1, 2005;33(9):e81.
Schoonooghe et al., Efficient production of human bivalent and trivalent anti-MU CI Fab-scFv antibodies in Pichia vastoris, BMC Biotechnol. 9:70, 2009.
Schroeder, H.W., et al. "Structure and Function of Immunoglobulins" J Allergy Clin Immunol. Feb. 2010; 125(2 0 2): S41-S52. doi:10.1016/j.jaci.2009.09.046.
Schueren et al., Peroxisomal lactate dehydrogenase is generated by translational readthrough in mammals, eLife 3: e03640, 2014.
Schwarz et al., A receptor induced by lymphocyte activation (ILA): a new member of the human nerve-growth-factor/tumor-necrosis-factor receptor family. Gene. Dec. 8, 1993;134(2):295-8.
Scopes, R. (1994). Protein Purification (3rd ed.) (C. R. Cantor, Ed.). New York City, NY: Springer-Verlag, Abstract only.
Sedivy and Sharp, Positive genetic selection for gene disruption in mammalian cells by homologous recombination, Proc. Natl. Acad. Sci. U.S.A. 86(1):227-231, 1989.
Semmler et al., De novo sequencing of peptides on single resin beads by MALDI-FTICR tandem mass spectrometry. J. Am. Soc. Mass Spec. 21(2):215-219, 2010.
Shiraishi et al., Short-step chemical synthesis of DNA by use of MMTrS group for protection of 5'-hydroxyl group. Nucleic Acids Symposium Series. Nov. 1, 2007;51(1):129-130.
Sidman et al., Controlled release of macromolecules and pharmaceuticals from synthetic polypeptides based on glutamic acid. Biopolymers: Original Research on Biomolecules. Jan. 1983;22(1):547-556.
Smith & Waterman., Comparison of biosequences. Advances in Applied Mathematics. Dec. 1981;2(4):482-489.
Smith and Berg, Homologous recombination between defective neo genes in mouse 3T6 cells, Cold Spring Harbor Symp. Quant. Biol. 49:171-181, 1984.
Southern and Berg, Transformation of mammalian cells to antibiotic resistance with a bacterial gene under control of the SV40 eariy region promoter, J Mol. Appl. Genet. 1(4):327-341, 1982.
Spiess et al., Sequence of Human Asialoglycoprotein Receptor cDNA, J Biol. Chem. 260( 4): 1979-1982, 1985.
Stijlemans et al., Efficient targeting of conserved cryptic epitopes of infectious agents by single domain antibodies. African trypanosomes as paradigm, J Biol. Chem. 279(2):1256-1261, 2004.
Stocks Intrabodies: production and promise, Drug Discov. Today 9(22):960-966, 2004.
Stoddard, Homing endonuclease structure and function, Q Rev. Biophys. 38(1):49-95, 2005.
Sutandy et al. Overview of Protein Microarrays. Curr.Protoc. Protein Sci. 27(1):27.1.1-27.1.16, 2013.

(56) References Cited

OTHER PUBLICATIONS

Szymanski et al., Development and validation of a robust and versatile one-plasmid regulated gene expression system. Mol. Therapy 15(7):1340-1347, 2007.

International Search Report and Written Opinion for correspondence PCT Application No. PCT/US2018/058451entitled "CD137 Antibodies and PD-1 Antagonists and Uses Thereof" dated Jun. 18, 2019.

Huafeng Wei et al: "Combinatorial PD-1 Blockade and CD137 Activation Has Therapeutic Efficacy in Murine Cancer Models and Synergizes with Cisplatin1" Plos One, vol. 8, No. 12, Dec. 19, 2013.

* cited by examiner

| Position | 95 | 96 | 97 | 98 | 99 | 100 | 100A | 100B | 100C | 100D | 100E | 100F | 100G | 100H | 100I |
|---|---|---|---|---|---|---|---|---|---|---|---|---|---|---|---|
| Amino Acid | | | | | | | | | | | | | | | |
| huCD137 | D | S | P | F | L | L | D | D | Y | Y | Y | Y | Y | Y | I |
| mCD137 | | | | | | | | | | | | | | | M |

FIG. 2

Retained Binding / Weak Binding / No Binding

LQDPCSNCPAGTFCDNNRNQIC
SPCPPNSFSSAGGQRTCDICRQCKGVFRTRKECSSTSNAEC
DCTPGFHCLGAGCSMCEQDCKQGQELTKKGCK
DCCFGTFNDQKRGICRPWTNCSLDGKSVLVNGTKERDVVCG mAb1

LQDPCSNCPAGTFCDNNRNQIC
SPCPPNSFSSAGGQRTCDICRQCKGVFRTRKECSSTSNAEC
DCTPGFHCLGAGCSMCEQDCKQGQELTKKGCK
DCCFGTFNDQKRGICRPWTNCSLDGKSVLVNGTKERDVVCG mAb4

LQDPCSNCPAGTFCDNNRNQIC
SPCPPNSFSSAGGQRTCDICRQCKGVFRTRKECSSTSNAEC
DCTPGFHCLGAGCSMCEQDCKQGQELTKKGCK
DCCFGTFNDQKRGICRPWTNCSLDGKSVLVNGTKERDVVCG mAb5

FIG.3A

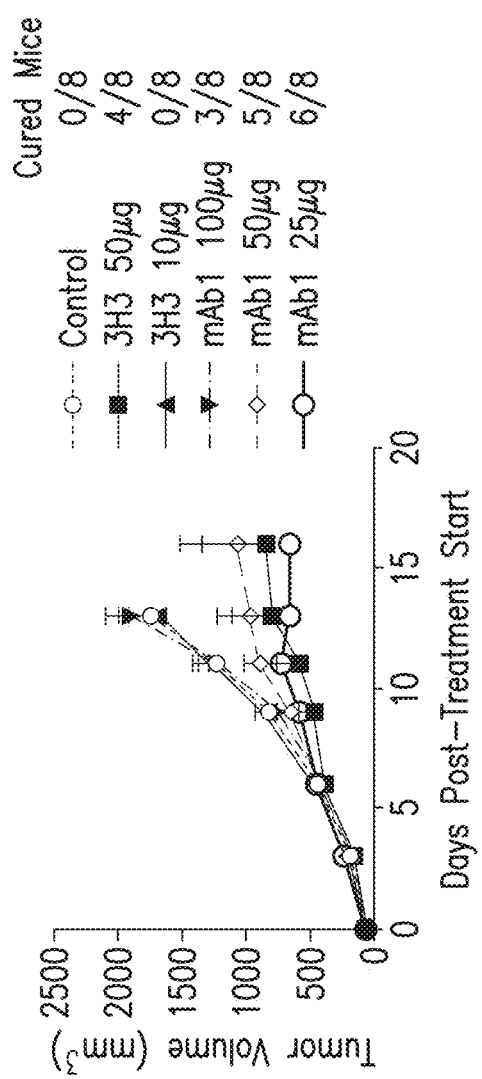
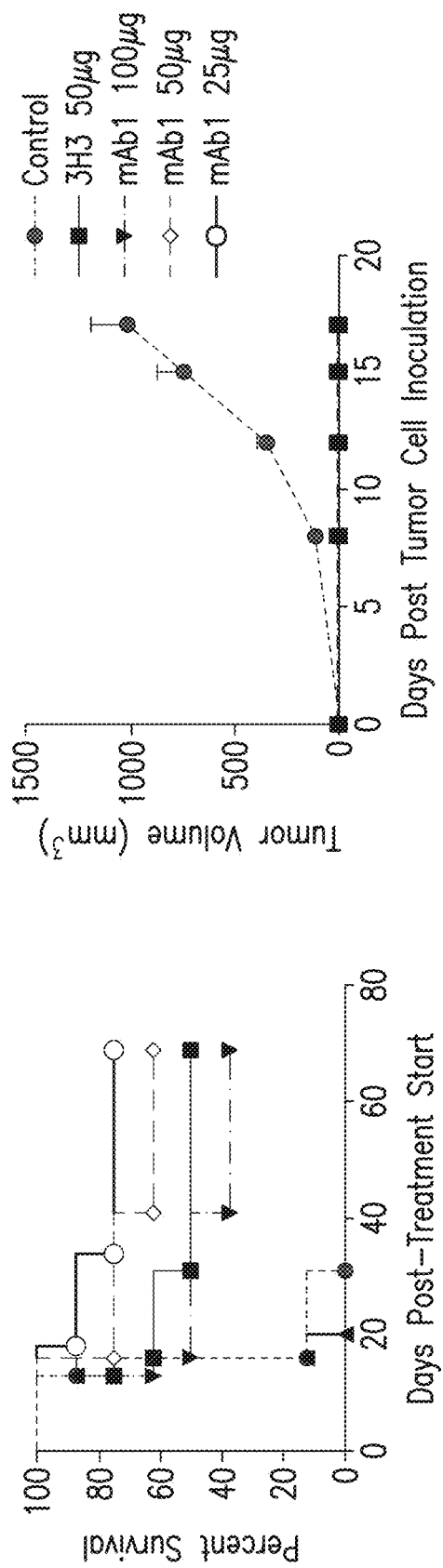

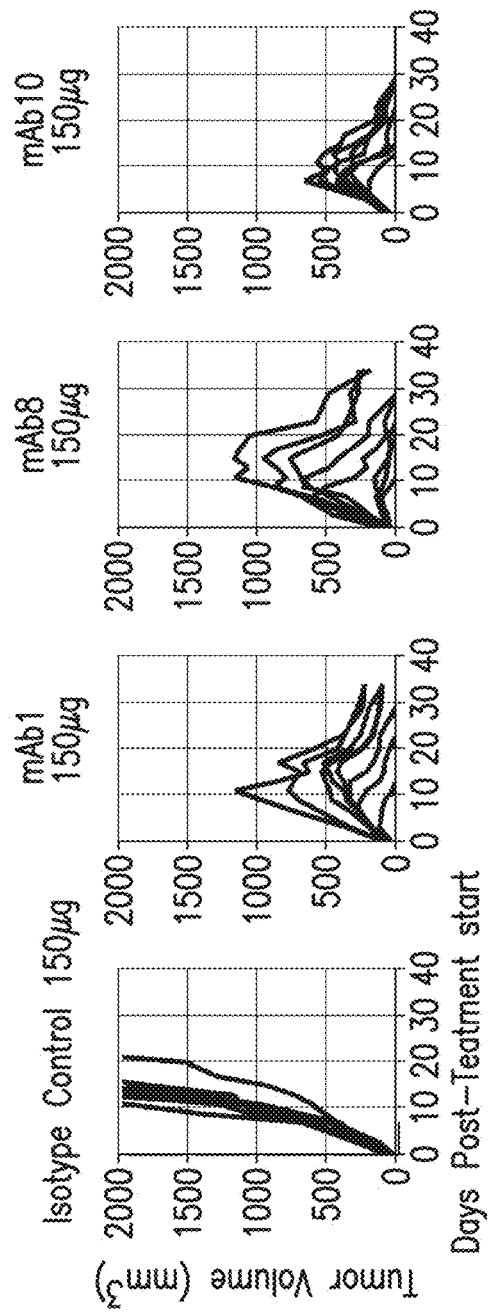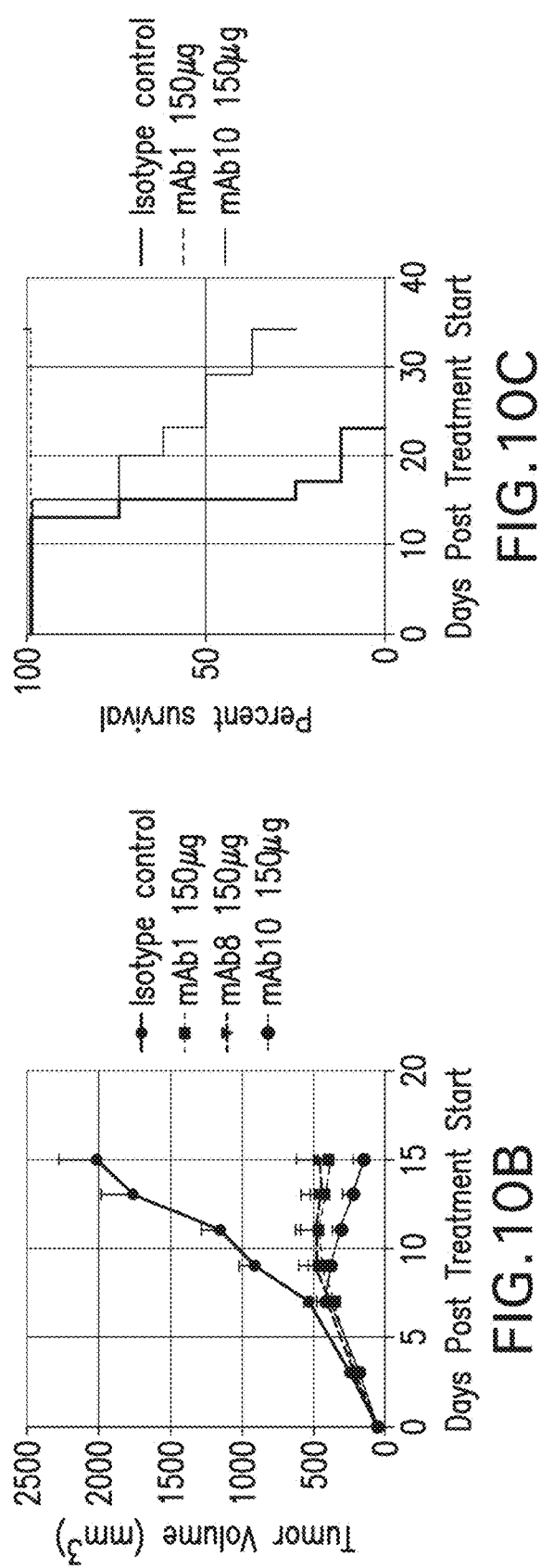
FIG. 10A
FIG. 10B
FIG. 10C

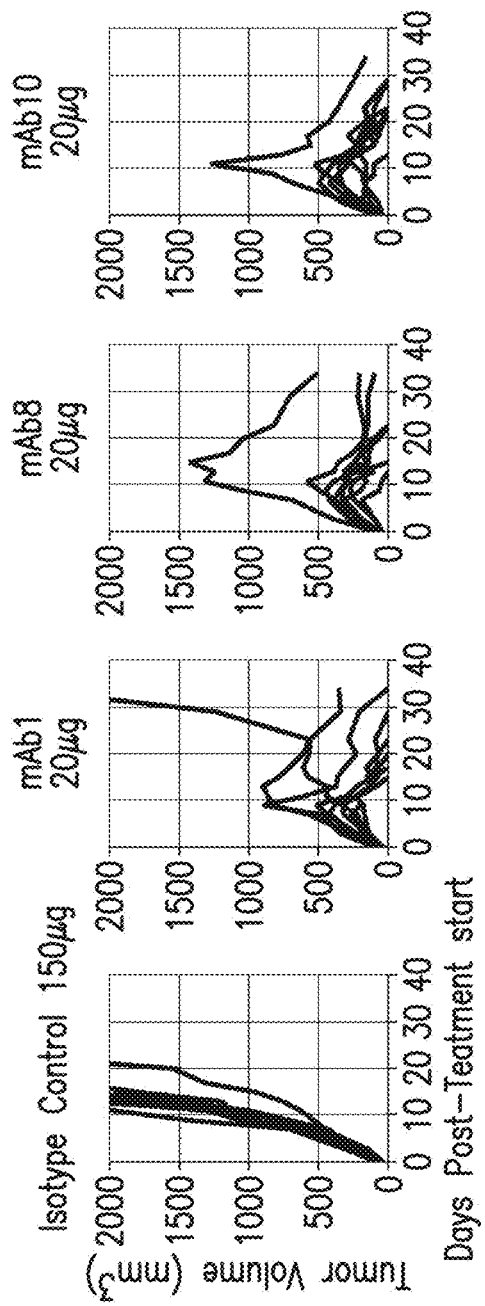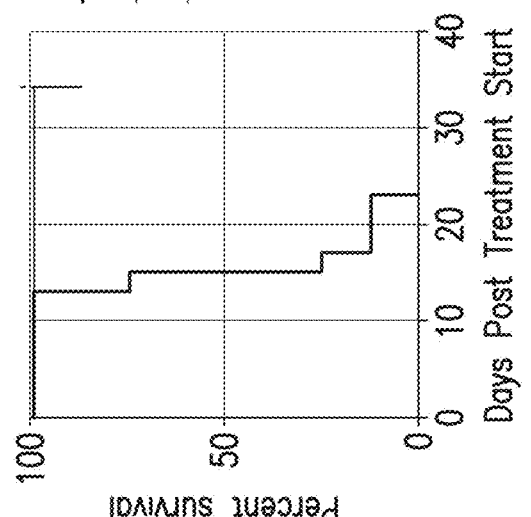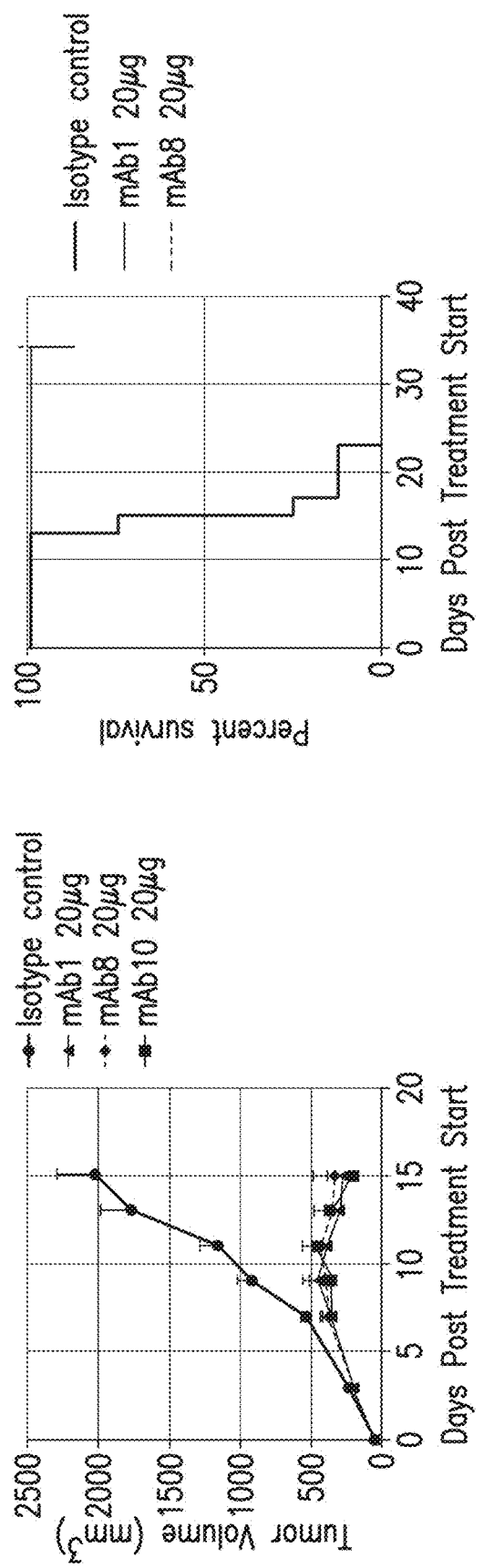
FIG. 11A
FIG. 11B
FIG. 11C

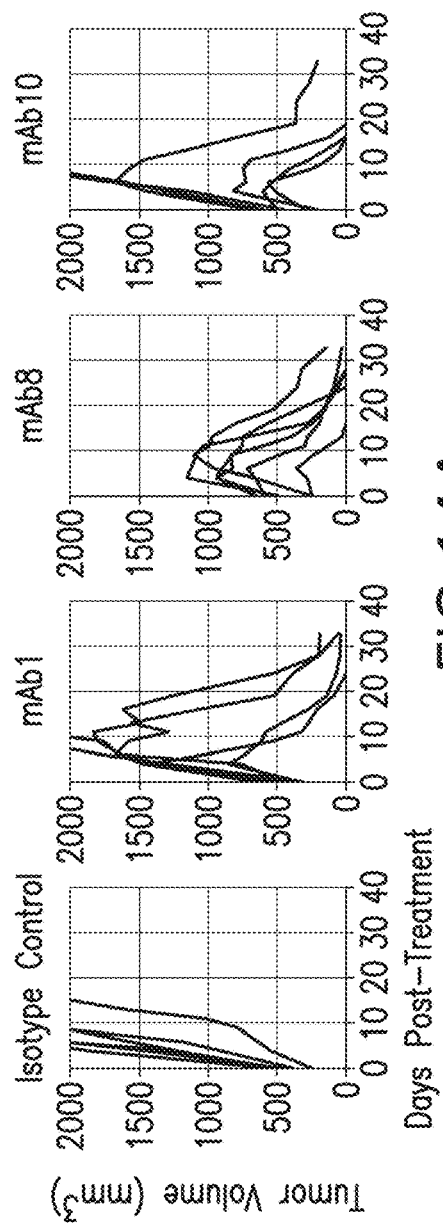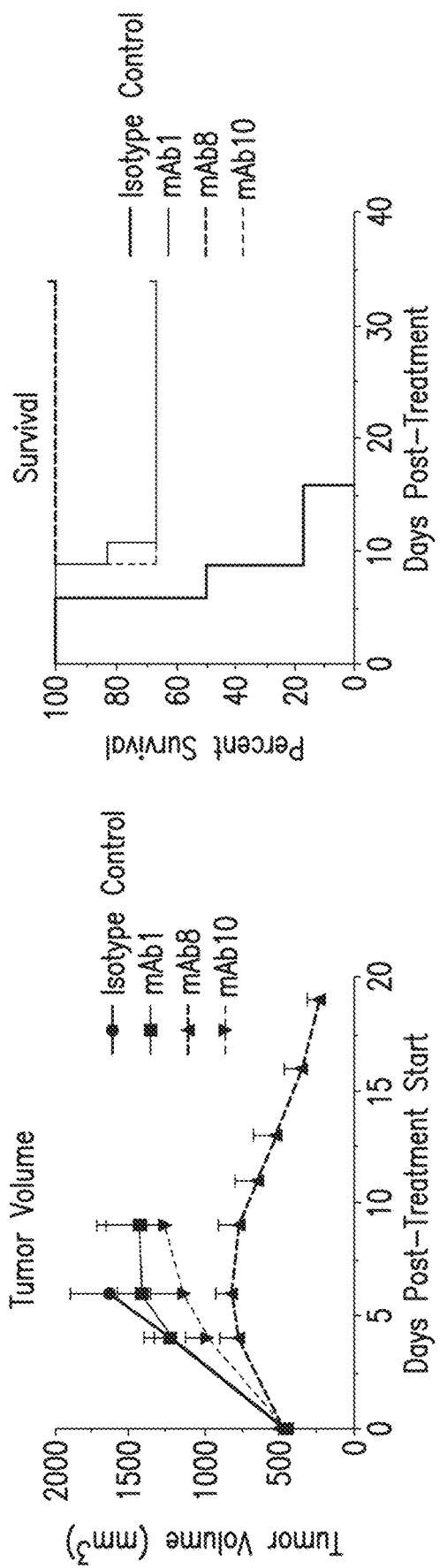
FIG. 14A
FIG. 14B
FIG. 14C

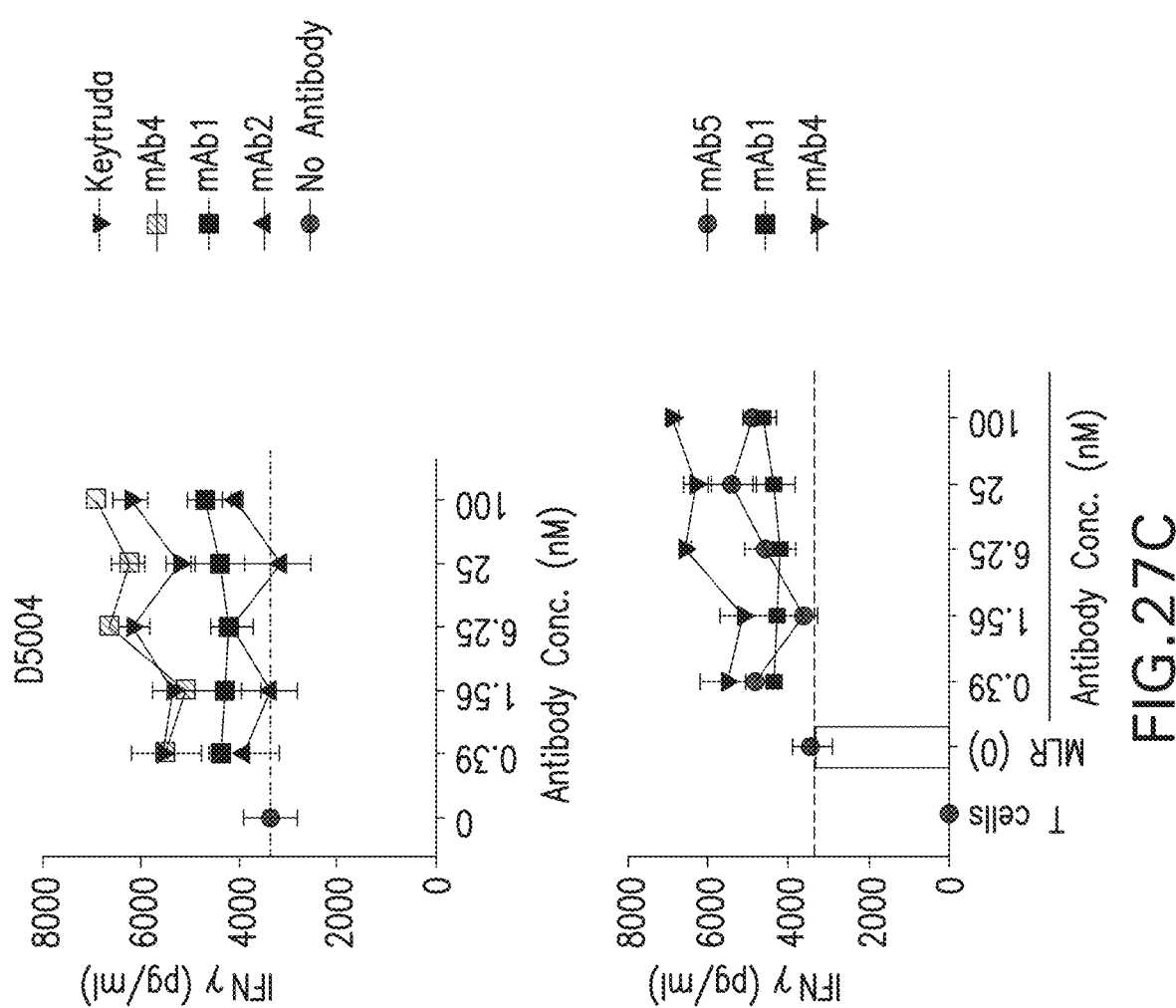

SEQUENCE LISTING

<160> NUMBER OF SEQ ID NOS: 136

<210> SEQ ID NO 1
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: Human IgG4 mutant (S228P/C-terminal K
      truncation)

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

-continued

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 3
<211> LENGTH: 255
<212> TYPE: PRT
<213> ORGANISM: Homo sapiens
<220> FEATURE:
<221> NAME/KEY: misc_feature
<222> LOCATION: (1)..(255)
<223> OTHER INFORMATION: Human CD137

<400> SEQUENCE: 3

Met Gly Asn Ser Cys Tyr Asn Ile Val Ala Thr Leu Leu Leu Val Leu
 1                   5                  10                  15

Asn Phe Glu Arg Thr Arg Ser Leu Gln Asp Pro Cys Ser Asn Cys Pro
                 20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60
```

```
Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
             85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130             135                 140

Ser Val Leu Val Asn Gly Thr Lys Glu Arg Asp Val Val Cys Gly Pro
145             150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
210             215                 220

Lys Gln Pro Phe Met Arg Pro Val Gln Thr Thr Gln Glu Glu Asp Gly
225             230                 235                 240

Cys Ser Cys Arg Phe Pro Glu Glu Glu Glu Gly Gly Cys Glu Leu
                245                 250                 255

<210> SEQ ID NO 4
<211> LENGTH: 126
<212> TYPE: PRT
<213> ORGANISM: Artificial Sequence
<220> FEATURE:
<223> OTHER INFORMATION: Synthetic: VH1 amino acid sequence

<400> SEQUENCE: 4

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
            115                 120                 125

<210> SEQ ID NO 5
<211> LENGTH: 384
<212> TYPE: DNA
<213> ORGANISM: Artificial Sequence
<220> FEATURE:
<223> OTHER INFORMATION: Synthetic: VH1 nucleic acid sequence
```

-continued

```
<400> SEQUENCE: 5
gaagtgcaat tattggaatc cggcggcggt ttagttcagc caggtggctc tttgaggctg      60
agttgcgcag cctctggatt cacttttagt tcgtatgcaa tgtcgtgggt tcgccaggcg     120
cccggtaagg gtctggagtg ggtgagtgct atttccggct ctggcggatc tacctattac     180
gccgactctg tgaaaggtcg ttttaccata agccgcgaca attctaagaa tactttatat     240
cttcaaatga attcgctgcg ggcagaagac acggccgtct attactgcgc aaaggactca     300
ccttttctat agacgactac tactactac tactacatgg acgtatgggg caagggtaca     360
actgtcaccg tctcctcagc tagc                                            384

<210> SEQ ID NO 6
<211> LENGTH: 107
<212> TYPE: PRT
<213> ORGANISM: Artificial Sequence
<220> FEATURE:
<223> OTHER INFORMATION: Synthetic: VL1 amino acid sequence

<400> SEQUENCE: 6

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Leu Phe Pro Ile
                85                  90                  95

Thr Phe Gly Gly Gly Thr Lys Val Glu Ile Lys
            100                 105

<210> SEQ ID NO 7
<211> LENGTH: 327
<212> TYPE: DNA
<213> ORGANISM: Artificial Sequence
<220> FEATURE:
<223> OTHER INFORMATION: Synthetic: VL1 nucleic acid sequence

<400> SEQUENCE: 7
gatattcaga tgacacagag cccgtcatca gtaagtgcaa gcgtcggaga tcgggttaca      60
ataacatgtc gtgcctcgca aggaatttcc tcctggttgg cctggtatca gcagaaacct     120
ggcaaagccc ccaaattact aatttatgcc gcaagctctc tgcaatcggg tgttccttcg     180
cggttttctg gctctggaag tggcaccgac ttcacgctta ctatctctag ccttcagccg     240
gaggattttg ctacctacta ctgccaacaa ggccatttat ccctattac ctttgggggc     300 ggtacaaaag tcgagatcaa gcgtacg                                         327

<210> SEQ ID NO 8
<211> LENGTH: 126
<212> TYPE: PRT
<213> ORGANISM: Artificial Sequence
<220> FEATURE:
<223> OTHER INFORMATION: Synthetic: VH2 amino acid sequence

<400> SEQUENCE: 8
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Tyr Tyr
            20                  25                  30

Ala Met Ser Trp Val Arg Gln Ala Pro Gly Lys Gly Leu Glu Trp Val
        35                  40                  45

Ser Ala Ile Asp Gly Ser Gly Asp Asn Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
        115                 120                 125

<210> SEQ ID NO 9
<211> LENGTH: 384
<212> TYPE: DNA
<213> ORGANISM: Artificial Sequence
<220> FEATURE:
<223> OTHER INFORMATION: Synthetic: VH2 nucleic acid sequence

<400> SEQUENCE: 9
gaagtgcaat tattggaatc cggcggcggt ttagttcagc caggtggctc tttgaggctg      60
agttgcgcag cctctggatt cacctttaac tattacgcaa tgtcttgggt tcgccaggcg     120
cccggtaagg gtctggagtg ggtgtctgca atcgatggtt ctggtgataa cactacttac     180
gccgactctg tgaaaggtcg ttttaccata agccgcgaca attctaagaa tactttatat     240
cttcaaatga attcgctgcg ggcagaagac acggccgtct attactgcgc aaaggactca     300
ccttttctat agacgactac tactactac tactacatgg acgtatgggg caagggtaca     360
actgtcaccg tctcctcagc tagc                                            384

<210> SEQ ID NO 10
<211> LENGTH: 126
<212> TYPE: PRT
<213> ORGANISM: Artificial Sequence
<220> FEATURE:
<223> OTHER INFORMATION: Synthetic: VH3 amino acid sequence

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Tyr Tyr
            20                  25                  30

Ala Met Ser Trp Val Arg Gln Ala Pro Gly Lys Gly Leu Glu Trp Val
        35                  40                  45

Ala Ala Ile Ser Gly Ser Gly Asp Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr
            100                 105                 110

```
Met Asp Val Trp Gly Lys Gly Thr Thr Val Thr Val Ser Ser
        115                 120                 125
```

<210> SEQ ID NO 11
<211> LENGTH: 384
<212> TYPE: DNA
<213> ORGANISM: Artificial Sequence
<220> FEATURE:
<223> OTHER INFORMATION: Synthetic: VH3 nucleic acid sequence

<400> SEQUENCE: 11

```
gaagtgcaat tattggaatc cggcggcggt ttagttcagc caggtggctc tttgaggctg    60
agttgcgcag cctctggatt cacctttaac tattacgcaa tgtcttgggt tcgccaggcg   120
cccggtaagg gtctggagtg ggtggcagca atctctggtt ctggtgatgg tacttactac   180
gccgactctg tgaaaggtcg ttttaccata agccgcgaca attctaagaa tactttatat   240
cttcaaatga attcgctgcg ggcagaagac acggccgtct attactgcgc aaaggactca   300
ccttttctat tagacgacta ctactactac tactacatgg acgtatgggg caagggtaca   360
actgtcaccg tctcctcagc tagc                                          384
```

<210> SEQ ID NO 12
<211> LENGTH: 126
<212> TYPE: PRT
<213> ORGANISM: Artificial Sequence
<220> FEATURE:
<223> OTHER INFORMATION: Synthetic: VH4 amino acid sequence

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Tyr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
        115                 120                 125
```

<210> SEQ ID NO 13
<211> LENGTH: 384
<212> TYPE: DNA
<213> ORGANISM: Artificial Sequence
<220> FEATURE:
<223> OTHER INFORMATION: Synthetic: VH4 nucleic acid sequence

<400> SEQUENCE: 13

```
gaagtgcaat tattggaatc cggcggcggt ttagttcagc caggtggctc tttgaggctg    60
agttgcgcag cctctggatt cacctttaac tattacgcaa tgtcttgggt tcgccaggcg   120
cccggtaagg gtctggagtg ggtgtctgca atctctggtt ctggtgattc tacttactac   180
gccgactctg tgaaaggtcg ttttaccata agccgcgaca attctaagaa tactttatat   240
```

```
cttcaaatga attcgctgcg ggcagaagac acggccgtct attactgcgc aaaggactca   300
ccttttctat tagacgacta ctactactac tactacatgg acgtatgggg caagggtaca   360
actgtcaccg tctcctcagc tagc                                          384
```

<210> SEQ ID NO 14
<211> LENGTH: 126
<212> TYPE: PRT
<213> ORGANISM: Artificial Sequence
<220> FEATURE:
<223> OTHER INFORMATION: Synthetic: VH5 amino acid sequence

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Tyr Tyr
            20                  25                  30

Ala Met Ser Trp Val Arg Gln Ala Pro Gly Lys Gly Leu Glu Trp Val
        35                  40                  45

Ala Ala Ile Ser Gly Gly Gly Asp Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
        115                 120                 125
```

<210> SEQ ID NO 15
<211> LENGTH: 384
<212> TYPE: DNA
<213> ORGANISM: Artificial Sequence
<220> FEATURE:
<223> OTHER INFORMATION: Synthetic: VH5 nucleic acid sequence

<400> SEQUENCE: 15

```
gaagtgcaat tattggaatc cggcggcggt ttagttcagc caggtggctc tttgaggctg   60
agttgcgcag cctctggatt cacctttaac tattacgcaa tgtcttgggt tcgccaggcg   120
cccggtaagg gtctggagtg ggtggcagca atctctggtg gtggtgatgc aacttactac   180
gccgactctg tgaaaggtcg ttttaccata agccgcgaca attctaagaa tactttatat   240
cttcaaatga attcgctgcg ggcagaagac acggccgtct attactgcgc aaaggactca   300
ccttttctat tagacgacta ctactactac tactacatgg acgtatgggg caagggtaca   360
actgtcaccg tctcctcagc tagc                                          384
```

<210> SEQ ID NO 16
<211> LENGTH: 126
<212> TYPE: PRT
<213> ORGANISM: Artificial Sequence
<220> FEATURE:
<223> OTHER INFORMATION: Synthetic: VH6 amino acid sequence

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Gly Tyr
            20                  25                  30
```

Ala Met Ser Trp Val Arg Gln Ala Pro Gly Lys Gly Leu Glu Trp Val
            35                  40                  45

Ser Ser Ile Ser Gly Ser Gly Asp Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
            115                 120                 125

<210> SEQ ID NO 17
<211> LENGTH: 384
<212> TYPE: DNA
<213> ORGANISM: Artificial Sequence
<220> FEATURE:
<223> OTHER INFORMATION: Synthetic: VH6 nucleic acid sequence

<400> SEQUENCE: 17
gaagtgcaat tattggaatc cggcggcggt ttagttcagc caggtggctc tttgaggctg      60
agttgcgcag cctctggatt caccttttat ggttacgcaa tgtcttgggt tcgccaggcg     120
cccggtaagg gtctggagtg ggtgtcttct atctctggtt ctggtgatgt tacttactac     180
gccgactctg tgaaaggtcg ttttaccata agccgcgaca attctaagaa tactttatat     240
cttcaaatga attcgctgcg ggcagaagac acggccgtct attactgcgc aaaggactca     300
ccttttctat tagacgacta ctactactac tactacatgg acgtatgggg caagggtaca     360
actgtcaccg tctcctcagc tagc                                            384

<210> SEQ ID NO 18
<211> LENGTH: 126
<212> TYPE: PRT
<213> ORGANISM: Artificial Sequence
<220> FEATURE:
<223> OTHER INFORMATION: Synthetic: VH7 amino acid sequence

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Gly Tyr
            20                  25                  30

Ala Met Ser Trp Val Arg Gln Ala Pro Gly Lys Gly Leu Glu Trp Val
            35                  40                  45

Ala Ala Ile Ser Gly Ser Gly Asp Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
            115                 120                 125

<210> SEQ ID NO 19

```
<211> LENGTH: 384
<212> TYPE: DNA
<213> ORGANISM: Artificial Sequence
<220> FEATURE:
<223> OTHER INFORMATION: Synthetic: VH7 nucleic acid sequence

<400> SEQUENCE: 19
gaagtgcaat tattggaatc cggcggcggt ttagttcagc caggtggctc tttgaggctg      60
agttgcgcag cctctggatt cacctttat ggttacgcaa tgtcttgggt tcgccaggcg      120
cccggtaagg gtctggagtg ggtggcagca atctctggtt ctggtgatgg tacttactac     180
gccgactctg tgaaaggtcg ttttaccata agccgcgaca attctaagaa tactttatat      240
cttcaaatga attcgctgcg ggcagaagac acggccgtct attactgcgc aaaggactca     300
ccttttctat tagacgacta ctactactac tactacatgg acgtatgggg caagggtaca     360
actgtcaccg tctcctcagc tagc                                           384

<210> SEQ ID NO 20
<211> LENGTH: 126
<212> TYPE: PRT
<213> ORGANISM: Artificial Sequence
<220> FEATURE:
<223> OTHER INFORMATION: Synthetic: VH8 amino acid sequence

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ser Gly Phe Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
        115                 120                 125

<210> SEQ ID NO 21
<211> LENGTH: 384
<212> TYPE: DNA
<213> ORGANISM: Artificial Sequence
<220> FEATURE:
<223> OTHER INFORMATION: Synthetic: VH8 nucleic acid sequence

<400> SEQUENCE: 21
gaagtgcaat tattggaatc cggcggcggt ttagttcagc caggtggctc tttgaggctg      60
agttgcgcag cctctggatt cacctttaga aactacgcaa tgtcttgggt tcgccaggcg     120
cccggtaagg gtctggagtg ggtgtctgca atctctggtt ttggtgaatc tacttactac     180
gccgactctg tgaaaggtcg ttttaccata agccgcgaca attctaagaa tactttatat     240
cttcaaatga attcgctgcg ggcagaagac acggccgtct attactgcgc aaaggactca     300
ccttttctat tagacgacta ctactactac tactacatgg acgtatgggg caagggtaca     360
actgtcaccg tctcctcagc tagc                                           384
```

<210> SEQ ID NO 22
<211> LENGTH: 126
<212> TYPE: PRT
<213> ORGANISM: Artificial Sequence
<220> FEATURE:
<223> OTHER INFORMATION: Synthetic: VH9 amino acid sequence

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Tyr Tyr
            20                  25                  30

Ala Met Asn Trp Val Arg Gln Ala Pro Gly Lys Gly Leu Glu Trp Val
        35                  40                  45

Ala Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
        115                 120                 125

<210> SEQ ID NO 23
<211> LENGTH: 384
<212> TYPE: DNA
<213> ORGANISM: Artificial Sequence
<220> FEATURE:
<223> OTHER INFORMATION: Synthetic: VH9 nucleic acid sequence

<400> SEQUENCE: 23
gaagtgcaat tattggaatc cggcggcggt ttagttcagc caggtggctc tttgaggctg      60
agttgcgcag cctctggatt cacctttaac tattacgcaa tgaactgggt tcgccaggcg     120
cccggtaagg gtctggagtg ggtggcagca atctctggtt ctggtggtag aacttactac     180
gccgactctg tgaaaggtcg ttttaccata agccgcgaca attctaagaa tactttatat     240
cttcaaatga attcgctgcg ggcagaagac acggccgtct attactgcgc aaaggactca     300 cctttttctat tagacgacta ctactactac tactacatgg acgtatgggg caagggtaca     360
actgtcaccg tctcctcagc tagc                                            384

<210> SEQ ID NO 24
<211> LENGTH: 126
<212> TYPE: PRT
<213> ORGANISM: Artificial Sequence
<220> FEATURE:
<223> OTHER INFORMATION: Synthetic: VH10 amino acid sequence

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Gly Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Asn Thr Ser Tyr Ala Asp Ser Val

```
                  50                    55                    60
Lys Gly Arg Phe Thr Ile Ser Arg Asp Asn Ser Lys Asn Thr Leu Tyr
 65                      70                      75                      80

Leu Gln Met Asn Ser Leu Arg Ala Glu Asp Thr Ala Val Tyr Tyr Cys
                     85                      90                      95

Ala Lys Asp Ser Pro Phe Leu Leu Asp Asp Tyr Tyr Tyr Tyr Tyr
                    100                     105                     110

Met Asp Val Trp Gly Lys Gly Thr Thr Val Thr Val Ser Ser
            115                     120                     125

<210> SEQ ID NO 25
<211> LENGTH: 384
<212> TYPE: DNA
<213> ORGANISM: Artificial Sequence
<220> FEATURE:
<223> OTHER INFORMATION: Synthetic: VH10 nucleic acid sequence

<400> SEQUENCE: 25
gaagtgcaat tattggaatc cggcggcggt ttagttcagc caggtggctc tttgaggctg      60
agttgcgcag cctctggatt cacctttat ggttacgcaa tgtcttgggt tcgccaggcg     120
cccggtaagg gtctggagtg gtgtctgca atctctggtt ctggtggtaa cacttcttac     180
gccgactctg tgaaaggtcg ttttaccata agccgcgaca attctaagaa tactttatat     240
cttcaaatga attcgctgcg ggcagaagac acggccgtct attactgcgc aaaggactca     300
ccttttctat tagacgacta ctactactac tactacatgg acgtatgggg caagggtaca     360
actgtcaccg tctcctcagc tagc                                             384

<210> SEQ ID NO 26
<211> LENGTH: 126
<212> TYPE: PRT
<213> ORGANISM: Artificial Sequence
<220> FEATURE:
<223> OTHER INFORMATION: Synthetic: VH11 amino acid sequence

<400> SEQUENCE: 26

Glu Val Gln Leu Leu Glu Ser Gly Gly Gly Leu Val Gln Pro Gly Gly
 1               5                      10                      15

Ser Leu Arg Leu Ser Cys Ala Ala Ser Gly Phe Thr Phe Tyr Gly Tyr
                20                      25                      30

Ala Met Ser Trp Val Arg Gln Ala Pro Gly Lys Gly Leu Glu Trp Val
            35                      40                      45

Ala Ala Ile Ser Gly Ser Gly Asp Ser Thr Tyr Tyr Ala Asp Ser Val
 50                      55                      60

Lys Gly Arg Phe Thr Ile Ser Arg Asp Asn Ser Lys Asn Thr Leu Tyr
 65                      70                      75                      80

Leu Gln Met Asn Ser Leu Arg Ala Glu Asp Thr Ala Val Tyr Tyr Cys
                85                      90                      95

Ala Lys Asp Ser Pro Phe Leu Leu Asp Asp Tyr Tyr Tyr Tyr Tyr
                    100                     105                     110

Met Asp Val Trp Gly Lys Gly Thr Thr Val Thr Val Ser Ser
            115                     120                     125

<210> SEQ ID NO 27
<211> LENGTH: 384
<212> TYPE: DNA
<213> ORGANISM: Artificial Sequence
<220> FEATURE:
<223> OTHER INFORMATION: Synthetic: VH11 nucleic acid sequence
```

<400> SEQUENCE: 27

```
gaagtgcaat tattggaatc cggcggcggt ttagttcagc caggtggctc tttgaggctg      60
agttgcgcag cctctggatt cacctttat ggttacgcaa tgtcttgggt tcgccaggcg     120
cccggtaagg gtctggagtg ggtggcagca atctctggtt ctggtgattc tacttactac    180
gccgactctg tgaaaggtcg ttttaccata agccgcgaca attctaagaa tactttatat    240
cttcaaatga attcgctgcg ggcagaagac acggccgtct attactgcgc aaaggactca    300
ccttttctat tagacgacta ctactactac tactacatgg acgtatgggg caagggtaca    360
actgtcaccg tctcctcagc tagc                                           384
```

<210> SEQ ID NO 28
<211> LENGTH: 107
<212> TYPE: PRT
<213> ORGANISM: Artificial Sequence
<220> FEATURE:
<223> OTHER INFORMATION: Synthetic: VL2 amino acid sequence

<400> SEQUENCE: 28

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile His Asn Trp
            20                  25                  30

Leu Ala Trp Tyr Gln Gln Lys Pro Gly Lys Ala Pro Lys Leu Leu Ile
        35                  40                  45

Tyr Lys Ala Ser Gly Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Asp Arg Phe Pro Leu
                85                  90                  95

Thr Phe Gly Gly Gly Thr Lys Val Glu Ile Lys
            100                 105
```

<210> SEQ ID NO 29
<211> LENGTH: 327
<212> TYPE: DNA
<213> ORGANISM: Artificial Sequence
<220> FEATURE:
<223> OTHER INFORMATION: Synthetic: VL2 nucleic acid sequence

<400> SEQUENCE: 29

```
gacatccaga tgacccagtc tccttccacc ctgtctgcat ctgtaggaga cagagtcacc      60
atcacttgcc gggccagtca gaatattcat aactggttgg cctggtatca gcaaaaacca    120
gggaaagccc ctaagctcct gatctataag gcgtctggtt tggaaagtgg ggtcccatca    180
agattcagcg gcagtggatc tgggacagag ttcactctca ccatcagcag cctgcaacct    240
gatgattttg caacttacta ctgtcaacag ggtgacagat tccctctcac tttcggcgga    300
gggaccaagg tggagatcaa acgtacg                                        327
```

<210> SEQ ID NO 30
<211> LENGTH: 107
<212> TYPE: PRT
<213> ORGANISM: Artificial Sequence
<220> FEATURE:
<223> OTHER INFORMATION: Synthetic: VL3 amino acid sequence

<400> SEQUENCE: 30

```
Asp Ile Gln Met Thr Gln Ser Pro Ser Ile Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Lys Pro Gly Lys Pro Pro Lys Leu Leu Ile
        35                  40                  45

Phe Lys Ala Ser Ala Leu Glu Ser Gly Val Pro Ser Arg Phe Ser Gly
    50                  55                  60

Ser Gly Tyr Gly Thr Asp Phe Thr Leu Thr Ile Ser Asn Leu Gln Pro
65              70                  75                  80

Glu Asp Phe Ala Thr Tyr Phe Cys Gln Gln Gly Asn Ser Phe Pro Leu
                85                  90                  95

Thr Phe Gly Gly Gly Thr Lys Val Asp Ile Lys
            100                 105
```

<210> SEQ ID NO 31
<211> LENGTH: 327
<212> TYPE: DNA
<213> ORGANISM: Artificial Sequence
<220> FEATURE:
<223> OTHER INFORMATION: Synthetic: VL3 nucleic acid sequence

<400> SEQUENCE: 31

```
gacatccaga tgacccagtc tccttccatc ctgtctgcat ctgtaggaga cagagtcact    60
atcacttgcc gggccagtca gagtatcagt aggtggttgg cctggtatca gcagaagcca   120
gggaaacccc ctaaactcct gatctttaag gcgtctgctt tagaaagtgg ggtcccatcg   180
aggttcagcg gcagtggata tgggacagat ttcactctca ccatcagcaa cctgcagcct   240
gaagactttg caacttactt ctgtcaacag ggtaatagtt tccctctcac tttcggcgga   300
gggaccaaag tggatatcaa acgtacg                                      327
```

<210> SEQ ID NO 32
<211> LENGTH: 107
<212> TYPE: PRT
<213> ORGANISM: Artificial Sequence
<220> FEATURE:
<223> OTHER INFORMATION: Synthetic: VL4 amino acid sequence

<400> SEQUENCE: 32

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asp Ile Trp
            20                  25                  30

Leu Ala Trp Tyr Gln Trp Lys Pro Gly Lys Ala Pro Lys Leu Leu Ile
        35                  40                  45

Tyr Lys Ala Ser Gly Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Gly Asn Gln Phe Pro Leu
                85                  90                  95

Thr Phe Gly Gln Gly Thr Arg Leu Glu Ile Lys
            100                 105
```

<210> SEQ ID NO 33
<211> LENGTH: 327
<212> TYPE: DNA

-continued

```
<213> ORGANISM: Artificial Sequence
<220> FEATURE:
<223> OTHER INFORMATION: Synthetic: VL4 nucleic acid sequence

<400> SEQUENCE: 33
gacatccaga tgacccagtc tccttccacc ctgtctgcat ctgtaggaga cagagtcacc      60
atcacttgcc gggccagtca gaatattgat atctggttgg cctggtatca gtggaaacca     120
gggaaggccc ctaaactcct gatctataag gcgtctggtt tagaaactgg ggtcccttca     180
aggttcagcg gcagtggatc tgggacagaa ttcactctca ctatcagcag cctgcagcca     240
gaggattttg cgacttacta ttgtcaacag ggtaaccagt tcccgctcac cttcggccaa     300
gggacacgac tggagattaa acgtacg                                         327

<210> SEQ ID NO 34
<211> LENGTH: 107
<212> TYPE: PRT
<213> ORGANISM: Artificial Sequence
<220> FEATURE:
<223> OTHER INFORMATION: Synthetic: VL5 amino acid sequence

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Trp
            20                  25                  30

Leu Ala Trp Tyr Gln Gln Lys Pro Gly Lys Ala Pro Lys Leu Leu Ile
        35                  40                  45

Phe Lys Ala Ser Ala Leu Glu Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Leu
                85                  90                  95

Thr Phe Gly Gly Gly Thr Lys Val Asp Ile Lys
            100                 105

<210> SEQ ID NO 35
<211> LENGTH: 327
<212> TYPE: DNA
<213> ORGANISM: Artificial Sequence
<220> FEATURE:
<223> OTHER INFORMATION: Synthetic: VL5 nucleic acid sequence

<400> SEQUENCE: 35
gacatccaga tgacccagtc tccttcctcc ctgtctgcat ctgtaggaga cagagtcacc      60
atcacttgcc gggccagtca gagtatcggt aggtggttgg cctggtatca gcagaaacca     120
gggaaagccc ctaaactcct gatctttaag gcgtctgctt tagaagttgg ggtcccatca     180
aggttcagcg gcagtgggtc tgggacagat ttcactctca ccatcagcag cctgcagcct     240
gaagattttg caacttacta ttgtcaacag ggtaacagtt tcccgctcac tttcggcgga     300
gggaccaaag tggatatcaa acgtacg                                         327

<210> SEQ ID NO 36
<211> LENGTH: 107
<212> TYPE: PRT
<213> ORGANISM: Artificial Sequence
<220> FEATURE:
<223> OTHER INFORMATION: Synthetic: VL6 amino acid sequence
```

<400> SEQUENCE: 36

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Phe Pro Leu
                85                  90                  95

Thr Phe Gly Gly Gly Thr Lys Val Glu Ile Lys
            100                 105

<210> SEQ ID NO 37
<211> LENGTH: 327
<212> TYPE: DNA
<213> ORGANISM: Artificial Sequence
<220> FEATURE:
<223> OTHER INFORMATION: Synthetic: VL6 nucleic acid sequence

<400> SEQUENCE: 37

```
gacatccagt tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaaactcct gatctatgct gcatccgctt tgcaaagtgg ggtcccatca     180
aggttcagcg gcagcggatc tgggacagat tcactctca  ctatcagcag cctgcagccc     240
gaagattttg caacttacta ttgtcaacag ggtgacagtt tccctctcac tttcggcgga     300
gggaccaagg tggagatcaa acgtacg                                         327
```

<210> SEQ ID NO 38
<211> LENGTH: 107
<212> TYPE: PRT
<213> ORGANISM: Artificial Sequence
<220> FEATURE:
<223> OTHER INFORMATION: Synthetic: VL7 amino acid sequence

<400> SEQUENCE: 38

Asp Ile Gln Met Thr Gln Ser Pro Ser Thr Leu Ser Ala Ser Val Gly
1               5                   10                  15

Asp Thr Val Thr Phe Ser Cys Arg Ala Ser Gln Ser Ile Asn Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ala Leu Glu Asn Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Leu
                85                  90                  95

Thr Phe Gly Gly Gly Thr Lys Val Glu Ile Lys
            100                 105

<210> SEQ ID NO 39
<211> LENGTH: 327

```
<212> TYPE: DNA
<213> ORGANISM: Artificial Sequence
<220> FEATURE:
<223> OTHER INFORMATION: Synthetic: VL7 nucleic acid sequence

<400> SEQUENCE: 39
gacatccaga tgacccagtc tccttccacc ctgtctgcat ctgtaggaga cacagtcacc    60
ttcagttgcc gggccagtca gagtattaac acctggttgg cctggtatca gcaaaagcca   120
gggaaagccc ctaaactcct tatctataag gcgtctgctt tagaaaatgg ggtcccatca   180
aggttcagcg gcagtggatc tgggacagag ttcactctca caatcagcag cctgcagcct   240
gaagattttg caacttacta ttgtcaacag gggaacagtt ccctctcac tttcggcgga    300 gggaccaagg tggagatcaa acgtacg                                       327

<210> SEQ ID NO 40
<211> LENGTH: 107
<212> TYPE: PRT
<213> ORGANISM: Artificial Sequence
<220> FEATURE:
<223> OTHER INFORMATION: Synthetic: VL8 amino acid sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ala Leu Glu Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly His Ser Phe Pro Leu
                85                  90                  95

Thr Phe Gly Gly Gly Thr Lys Leu Glu Ile Lys
            100                 105

<210> SEQ ID NO 41
<211> LENGTH: 327
<212> TYPE: DNA
<213> ORGANISM: Artificial Sequence
<220> FEATURE:
<223> OTHER INFORMATION: Synthetic: VL8 nucleic acid sequence

<400> SEQUENCE: 41
gacatccaga tgacccagtc tccatcctcc ctgtctgcat ctgtaggaga cagagtcacc    60
atcacttgcc gggccagtca gagtattagt agctggttgg cctggtatca gcagaaacca   120
gggaaagccc ctaaactcct catctataag gcgtctgctt tagaaagtgg ggtcccatca   180
aggttcagcg gcggtggatc tgggacagaa ttcactctca ccatcagcag cctgcagcct   240
gaagattttg caacttacta ttgtcaacag ggtcacagtt ccctctcac tttcggcgga    300 gggaccaagc tggagatcaa acgtacg                                       327

<210> SEQ ID NO 42
<211> LENGTH: 107
<212> TYPE: PRT
<213> ORGANISM: Artificial Sequence
<220> FEATURE:
<223> OTHER INFORMATION: Synthetic: VL9 amino acid sequence
```

<400> SEQUENCE: 42

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Phe Lys Ala Ser Ala Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Ile
                85                  90                  95

Thr Phe Gly Gln Gly Thr Arg Leu Glu Ile Lys
            100                 105

<210> SEQ ID NO 43
<211> LENGTH: 327
<212> TYPE: DNA
<213> ORGANISM: Artificial Sequence
<220> FEATURE:
<223> OTHER INFORMATION: Synthetic: VL9 nucleic acid sequence

<400> SEQUENCE: 43

```
gacatccagt tgacccagtc tccatcctcc ctgtctgcat ctgtaggaga cagagtcacc    60
atcacttgcc gggccagtca gagtattagt gactggttgg cctggtatca gcagaagcca   120
ggtaaagccc ctaaactcct gatctttaag gcttctgctt tagaaggtgg ggtcccatca   180
aggttcagcg gcagtggatc tgggacagat ttcactctca ccatcagcag cctgcagcct   240
gaagattttg caacttacta ttgtcaacag ggtaacagtt tcccgatcac cttcggccaa   300
gggacacgac tggagattaa acgtacg                                       327
```

<210> SEQ ID NO 44
<211> LENGTH: 107
<212> TYPE: PRT
<213> ORGANISM: Artificial Sequence
<220> FEATURE:
<223> OTHER INFORMATION: Synthetic: VL10 amino acid sequence

<400> SEQUENCE: 44

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Val Asp Arg Trp
            20                  25                  30

Leu Ala Trp Tyr Gln Gln Lys Pro Gly Lys Ala Pro Asn Leu Leu Ile
        35                  40                  45

Tyr Glu Ala Ser Ala Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Phe Pro Leu
                85                  90                  95

Thr Phe Gly Gly Gly Thr Lys Val Glu Ile Lys
            100                 105

<210> SEQ ID NO 45

<211> LENGTH: 327
<212> TYPE: DNA
<213> ORGANISM: Artificial Sequence
<220> FEATURE:
<223> OTHER INFORMATION: Synthetic: VL10 nucleic acid sequence

<400> SEQUENCE: 45

| | | |
|---|---|---|
| gacatccaga tgacccagtc tccagccacc ctgtctgcat ctgttggaga cagggtcacc | 60 |
| atcacttgcc gggccagtca gagtgttgat aggtggttgg cctggtacca gcagaaacca | 120 |
| gggaaagccc ctaacctcct aatctatgag gcgtctgcct tacaaggtgg ggtcccgtca | 180 |
| aggttcagcg gcagtggatc tgggacagat ttcactctca ccatcagcag cctgcagcct | 240 |
| gaagattttg caacttacta ttgtcaacag ggtgatagtt tccctctcac tttcggcgga | 300 |
| gggaccaagg tggagatcaa acgtacg | 327 |

<210> SEQ ID NO 46
<211> LENGTH: 107
<212> TYPE: PRT
<213> ORGANISM: Artificial Sequence
<220> FEATURE:
<223> OTHER INFORMATION: Synthetic: VL11 amino acid sequence

<400> SEQUENCE: 46

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Gly Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Arg Phe Pro Leu
                85                  90                  95

Thr Phe Gly Gly Gly Thr Lys Val Glu Ile Lys
            100                 105

<210> SEQ ID NO 47
<211> LENGTH: 327
<212> TYPE: DNA
<213> ORGANISM: Artificial Sequence
<220> FEATURE:
<223> OTHER INFORMATION: Synthetic: VL11 nucleic acid sequence

<400> SEQUENCE: 47

| | | |
|---|---|---|
| gacatccagt tgacccagtc tccatcttcc gtgtctgcat ctgtaggaga cagagtcacc | 60 |
| atcacttgtc gggcgagtca gggtattagc agctggttag cctggtatca gcagaaacca | 120 |
| gggaaagccc ctaagctcct gatctatgct gcatccggtt tgcaaaatgg ggtcccatca | 180 |
| aggttcagcg gcagtggatc tgggacagat ttcactctca ccatcagcag cctgcagcct | 240 |
| gaagattttg caacttacta ttgtcaacag ggtgacaggt tcccgctcac tttcggcgga | 300 |
| gggaccaagg tggagatcaa acgtacg | 327 |

<210> SEQ ID NO 48
<211> LENGTH: 9
<212> TYPE: PRT
<213> ORGANISM: Artificial Sequence
<220> FEATURE:

```
<223> OTHER INFORMATION: Synthetic: VH CDR1

<400> SEQUENCE: 48

Phe Thr Phe Ser Ser Tyr Ala Met Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic: VH CDR1.1

<400> SEQUENCE: 49

Phe Thr Phe Asn Tyr Tyr Ala Met Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic: VH CDR1.2

<400> SEQUENCE: 50

Phe Thr Phe Tyr Gly Tyr Ala Met Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic: VH CDR1.3

<400> SEQUENCE: 51

Phe Thr Phe Arg Asn Tyr Ala Met Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic: VH CDR1.4

<400> SEQUENCE: 52

Phe Thr Phe Asn Tyr Tyr Ala Met Asn
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic: VH CDR1.5
<220> FEATURE:
<221> NAME/KEY: misc_feature
<222> LOCATION: (9)..(9)
<223> OTHER INFORMATION: X = S or N

<400> SEQUENCE: 53

Phe Thr Phe Asn Tyr Tyr Ala Met Xaa
1               5

<210> SEQ ID NO 54
<211> LENGTH: 9
```

```
<212> TYPE: PRT
<213> ORGANISM: Artificial Sequence
<220> FEATURE:
<223> OTHER INFORMATION: Synthetic: VH CDR1.6
<220> FEATURE:
<221> NAME/KEY: misc_feature
<222> LOCATION: (4)..(4)
<223> OTHER INFORMATION: X = S, N, Y, or R
<220> FEATURE:
<221> NAME/KEY: misc_feature
<222> LOCATION: (5)..(5)
<223> OTHER INFORMATION: X = S, N, Y, or G

<400> SEQUENCE: 54

Phe Thr Phe Xaa Xaa Tyr Ala Met Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic: VH CDR1.7
<220> FEATURE:
<221> NAME/KEY: misc_feature
<222> LOCATION: (4)..(4)
<223> OTHER INFORMATION: X = S, N, Y, or R X = S or N
<220> FEATURE:
<221> NAME/KEY: misc_feature
<222> LOCATION: (5)..(5)
<223> OTHER INFORMATION: X = S, N, Y, or G
<220> FEATURE:
<221> NAME/KEY: misc_feature
<222> LOCATION: (9)..(9)
<223> OTHER INFORMATION: X = S or N

<400> SEQUENCE: 55

Phe Thr Phe Xaa Xaa Tyr Ala Met Xaa
1               5

<210> SEQ ID NO 56
<211> LENGTH: 12
<212> TYPE: PRT
<213> ORGANISM: Artificial Sequence
<220> FEATURE:
<223> OTHER INFORMATION: Synthetic: VH CDR2

<400> SEQUENCE: 56

Ser Ala Ile Ser Gly Ser Gly Gly Ser Thr Tyr Tyr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic: VH CDR2.1

<400> SEQUENCE: 57

Ser Ala Ile Asp Gly Ser Gly Asp Asn Thr Thr Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic: VH CDR2.2

<400> SEQUENCE: 58
```

Ala Ala Ile Ser Gly Ser Gly Asp Gly Thr Tyr Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic: VH CDR2.3

<400> SEQUENCE: 59

Ser Ala Ile Ser Gly Ser Gly Asp Ser Thr Tyr Tyr
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic: VH CDR2.4

<400> SEQUENCE: 60

Ala Ala Ile Ser Gly Gly Gly Asp Ala Thr Tyr Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic: VH CDR2.5

<400> SEQUENCE: 61

Ser Ser Ile Ser Gly Ser Gly Asp Val Thr Tyr Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic: VH CDR2.6

<400> SEQUENCE: 62

Ser Ala Ile Ser Gly Phe Gly Glu Ser Thr Tyr Tyr
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic: VH CDR2.7

<400> SEQUENCE: 63

Ala Ala Ile Ser Gly Ser Gly Gly Arg Thr Tyr Tyr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic: VH CDR2.8

<400> SEQUENCE: 64

Ser Ala Ile Ser Gly Ser Gly Gly Asn Thr Ser Tyr 1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic: VH CDR2.9

<400> SEQUENCE: 65

Ala Ala Ile Ser Gly Ser Gly Asp Ser Thr Tyr Tyr
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic: VH CDR2.10
<220> FEATURE:
<221> NAME/KEY: misc_feature
<222> LOCATION: (6)..(6)
<223> OTHER INFORMATION: X = S or G
<220> FEATURE:
<221> NAME/KEY: misc_feature
<222> LOCATION: (8)..(8)
<223> OTHER INFORMATION: X = D or G
<220> FEATURE:
<221> NAME/KEY: misc_feature
<222> LOCATION: (9)..(9)
<223> OTHER INFORMATION: X = S, R, G, or A

<400> SEQUENCE: 66

Ala Ala Ile Ser Gly Xaa Gly Xaa Xaa Thr Tyr Tyr
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic: VH CDR2.11
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 67

Xaa Xaa Ile Xaa Gly Xaa Gly Xaa Xaa Thr Xaa Tyr
1               5                   10

<210> SEQ ID NO 68
<211> LENGTH: 18
<212> TYPE: PRT
<213> ORGANISM: Artificial Sequence
<220> FEATURE:

```
<223> OTHER INFORMATION: Synthetic: VH CDR3

<400> SEQUENCE: 68

Ala Lys Asp Ser Pro Phe Leu Leu Asp Asp Tyr Tyr Tyr Tyr Tyr
1               5                   10                  15

Met Asp

<210> SEQ ID NO 69
<211> LENGTH: 12
<212> TYPE: PRT
<213> ORGANISM: Artificial Sequence
<220> FEATURE:
<223> OTHER INFORMATION: Synthetic: VL CDR1

<400> SEQUENCE: 69

Arg Ala Ser Gln Gly Ile Ser Ser Trp Leu Ala Trp
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic: VL CDR1.1

<400> SEQUENCE: 70

Arg Ala Ser Gln Asn Ile His Asn Trp Leu Ala Trp
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic: VL CDR1.2

<400> SEQUENCE: 71

Arg Ala Ser Gln Ser Ile Ser Arg Trp Leu Ala Trp
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic: VL CDR1.3

<400> SEQUENCE: 72

Arg Ala Ser Gln Asn Ile Asp Ile Trp Leu Ala Trp
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic: VL CDR1.4

<400> SEQUENCE: 73

Arg Ala Ser Gln Ser Ile Gly Arg Trp Leu Ala Trp
1               5                   10

<210> SEQ ID NO 74
<211> LENGTH: 12
<212> TYPE: PRT
<213> ORGANISM: Artificial Sequence
```

```
<220> FEATURE:
<223> OTHER INFORMATION: Synthetic: VL CDR1.5

<400> SEQUENCE: 74

Arg Ala Ser Gln Ser Ile Ser Ser Trp Leu Ala Trp
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic: VL CDR1.6

<400> SEQUENCE: 75

Arg Ala Ser Gln Ser Ile Asn Thr Trp Leu Ala Trp
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic: VL CDR1.7

<400> SEQUENCE: 76

Arg Ala Ser Gln Ser Ile Ser Asp Trp Leu Ala Trp
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic: VL CDR1.8

<400> SEQUENCE: 77

Arg Ala Ser Gln Ser Val Asp Arg Trp Leu Ala Trp
1               5                   10

<210> SEQ ID NO 78
<211> LENGTH: 8
<212> TYPE: PRT
<213> ORGANISM: Artificial Sequence
<220> FEATURE:
<223> OTHER INFORMATION: Synthetic: VL CDR2

<400> SEQUENCE: 78

Tyr Ala Ala Ser Ser Leu Gln Ser
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic: VL CDR2.1

<400> SEQUENCE: 79

Tyr Lys Ala Ser Gly Leu Glu Ser
1               5

<210> SEQ ID NO 80
<211> LENGTH: 8
<212> TYPE: PRT
<213> ORGANISM: Artificial Sequence
<220> FEATURE:
```

```
<223> OTHER INFORMATION: Synthetic: VL CDR2.2

<400> SEQUENCE: 80

Phe Lys Ala Ser Ala Leu Glu Ser
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic: VL CDR2.3

<400> SEQUENCE: 81

Tyr Lys Ala Ser Gly Leu Glu Thr
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic: VL CDR2.4

<400> SEQUENCE: 82

Phe Lys Ala Ser Ala Leu Glu Val
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic: VL CDR2.5

<400> SEQUENCE: 83

Tyr Ala Ala Ser Ala Leu Gln Ser
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic: VL CDR2.6

<400> SEQUENCE: 84

Tyr Lys Ala Ser Ala Leu Glu Asn
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic: VL CDR2.7

<400> SEQUENCE: 85

Tyr Lys Ala Ser Ala Leu Glu Ser
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic: VL CDR2.8
```

<400> SEQUENCE: 86

Phe Lys Ala Ser Ala Leu Glu Gly
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic: VL CDR2.9

<400> SEQUENCE: 87

Tyr Glu Ala Ser Ala Leu Gln Gly
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic: VL CDR2.10

<400> SEQUENCE: 88

Tyr Ala Ala Ser Gly Leu Gln Asn
1               5

<210> SEQ ID NO 89
<211> LENGTH: 10
<212> TYPE: PRT
<213> ORGANISM: Artificial Sequence
<220> FEATURE:
<223> OTHER INFORMATION: Synthetic: VL CDR3

<400> SEQUENCE: 89

Gln Gln Gly His Leu Phe Pro Ile Thr Phe
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic: VL CDR3.1

<400> SEQUENCE: 90

Gln Gln Gly Asp Arg Phe Pro Leu Thr Phe
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic: VL CDR3.2

<400> SEQUENCE: 91

Gln Gln Gly Asn Ser Phe Pro Leu Thr Phe
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic: VL CDR3.3

```
<400> SEQUENCE: 92

Gln Gln Gly Asn Gln Phe Pro Leu Thr Phe
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic: VL CDR3.4

<400> SEQUENCE: 93

Gln Gln Gly Asp Ser Phe Pro Leu Thr Phe
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic: VL CDR3.5

<400> SEQUENCE: 94

Gln Gln Gly His Ser Phe Pro Leu Thr Phe
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic: VL CDR3.6

<400> SEQUENCE: 95

Gln Gln Gly Asn Ser Phe Pro Ile Thr Phe
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic: VL CDR3.7
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 96

Gln Gln Gly Xaa Xaa Phe Pro Xaa Thr Phe
1               5                   10

<210> SEQ ID NO 97
<211> LENGTH: 254
<212> TYPE: PRT
<213> ORGANISM: Homo sapiens
<220> FEATURE:
<221> NAME/KEY: misc_feature
<222> LOCATION: (1)..(254)
<223> OTHER INFORMATION: Human CD137L

<400> SEQUENCE: 97

Met Glu Tyr Ala Ser Asp Ala Ser Leu Asp Pro Glu Ala Pro Trp Pro
1               5                   10                  15
```

```
Pro Ala Pro Arg Ala Arg Ala Cys Arg Val Leu Pro Trp Ala Leu Val
            20                  25                  30
Ala Gly Leu Leu Leu Leu Leu Ala Ala Cys Ala Val Phe
        35                  40                  45
Leu Ala Cys Pro Trp Ala Val Ser Gly Ala Arg Ala Ser Pro Gly Ser
 50              55                  60
Ala Ala Ser Pro Arg Leu Arg Glu Gly Pro Glu Leu Ser Pro Asp Asp
 65                  70                  75                  80
Pro Ala Gly Leu Leu Asp Leu Arg Gln Gly Met Phe Ala Gln Leu Val
                 85                  90                  95
Ala Gln Asn Val Leu Leu Ile Asp Gly Pro Leu Ser Trp Tyr Ser Asp
            100                 105                 110
Pro Gly Leu Ala Gly Val Ser Leu Thr Gly Gly Leu Ser Tyr Lys Glu
            115                 120                 125
Asp Thr Lys Glu Leu Val Val Ala Lys Ala Gly Val Tyr Tyr Val Phe
        130                 135                 140
Phe Gln Leu Glu Leu Arg Arg Val Val Ala Gly Glu Gly Ser Gly Ser
145                 150                 155                 160
Val Ser Leu Ala Leu His Leu Gln Pro Leu Arg Ser Ala Ala Gly Ala
                165                 170                 175
Ala Ala Leu Ala Leu Thr Val Asp Leu Pro Pro Ala Ser Ser Glu Ala
            180                 185                 190
Arg Asn Ser Ala Phe Gly Phe Gln Gly Arg Leu Leu His Leu Ser Ala
            195                 200                 205
Gly Gln Arg Leu Gly Val His Leu His Thr Glu Ala Arg Ala Arg His
        210                 215                 220
Ala Trp Gln Leu Thr Gln Gly Ala Thr Val Leu Gly Leu Phe Arg Val
225                 230                 235                 240
Thr Pro Glu Ile Pro Ala Gly Leu Pro Ser Pro Arg Ser Glu
                245                 250
```

<210> SEQ ID NO 98
<211> LENGTH: 8
<212> TYPE: PRT
<213> ORGANISM: Artificial Sequence
<220> FEATURE:
<223> OTHER INFORMATION: Synthetic: FLAG

<400> SEQUENCE: 98

```
Asp Tyr Lys Asp Asp Asp Asp Lys
1               5
```

<210> SEQ ID NO 99
<211> LENGTH: 6
<212> TYPE: PRT
<213> ORGANISM: Artificial Sequence
<220> FEATURE:
<223> OTHER INFORMATION: Synthetic: 6-His

<400> SEQUENCE: 99

```
His His His His His His
1               5
```

<210> SEQ ID NO 100
<211> LENGTH: 9
<212> TYPE: PRT
<213> ORGANISM: Artificial Sequence
<220> FEATURE:
<223> OTHER INFORMATION: Synthetic: HA

<400> SEQUENCE: 100

Tyr Pro Tyr Asp Val Pro Asp Tyr Ala
1               5

<210> SEQ ID NO 101
<211> LENGTH: 126
<212> TYPE: PRT
<213> ORGANISM: Artificial Sequence
<220> FEATURE:
<223> OTHER INFORMATION: Synthetic: VH12 amino acid sequence

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
        115                 120                 125

<210> SEQ ID NO 102
<211> LENGTH: 384
<212> TYPE: DNA
<213> ORGANISM: Artificial Sequence
<220> FEATURE:
<223> OTHER INFORMATION: Synthetic: VH12 nucleic acid sequence

<400> SEQUENCE: 102
gaagtgcaat tattggaatc cggcggcggt ttagttcagc caggtggctc tttgaggctg      60
agttgcgcag cctctggatt cacctttaga aactacgcaa tgtcttgggt tcgccaggcg     120
cccggtaagg gtctggagtg ggtgtctgca atctctggtt ctggtgatac tacttactac     180
gccgactctg tgaaaggtcg ttttaccata agccgcgaca attctaagaa tactttatat     240
cttcaaatga attcgctgcg ggcagaagac acggccgtct attactgcgc aaaggactca     300
ccttttctat tagacgacta ctactactac tactacatgg acgtatgggg caagggtaca     360
actgtcaccg tctcctcagc tagc                                            384

<210> SEQ ID NO 103
<211> LENGTH: 126
<212> TYPE: PRT
<213> ORGANISM: Artificial Sequence
<220> FEATURE:
<223> OTHER INFORMATION: Synthetic: VH13 amino acid sequence

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser
            115                 120                 125

<210> SEQ ID NO 104
<211> LENGTH: 384
<212> TYPE: DNA
<213> ORGANISM: Artificial Sequence
<220> FEATURE:
<223> OTHER INFORMATION: Synthetic: VH13 nucleic acid sequence

<400> SEQUENCE: 104
gaagtgcaat tattggaatc cggcggcggt ttagttcagc caggtggctc tttgaggctg      60
agttgcgcag cctctggatt cacctttggt tcttacgcaa tgtcttgggt tcgccaggcg     120
cccggtaagg gtctggagtg ggtgtctgca atctctggtt ctggtggttc tacttactac     180
gccgactctg tgaaaggtcg ttttaccata agccgcgaca attctaagaa tactttatat     240
cttcaaatga attcgctgcg ggcagaagac acggccgtct attactgcgc aaaggactca     300
ccttttctat tagacgacta ctactactac tactacatgg acgtatgggg caagggtaca     360
actgtcaccg tctcctcagc tagc                                            384

<210> SEQ ID NO 105
<211> LENGTH: 105
<212> TYPE: PRT
<213> ORGANISM: Artificial Sequence
<220> FEATURE:
<223> OTHER INFORMATION: Synthetic: VL12 amino acid sequence

<400> SEQUENCE: 105

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asp Trp
             20                  25                  30

Leu Ala Trp Tyr Gln Gln Lys Pro Gly Lys Ala Pro Lys Leu Leu Ile
            35                  40                  45

Tyr Lys Ala Ser Gly Leu Gln Ser Gly Val Pro Ser Arg Phe Ser Gly
 50                  55                  60

Ser Gly Ser Gly Thr Glu Phe Thr Leu Thr Ile Ser Asn Leu Gln Pro
 65                  70                  75                  80

Glu Asp Phe Ala Thr Tyr Tyr Cys Gln Gln Gly Asn Gln Phe Pro Leu
                 85                  90                  95

Thr Phe Gly Gln Gly Thr Arg Leu Glu
            100                 105

<210> SEQ ID NO 106
<211> LENGTH: 315
<212> TYPE: DNA
<213> ORGANISM: Artificial Sequence
<220> FEATURE:
<223> OTHER INFORMATION: Synthetic: VL12 nucleic acid sequence

<400> SEQUENCE: 106
gacatccagt tgacccagtc tccatcctcc ctgtctgcat ctgtaggaga cagagtaacc    60
atcacttgcc gggcaagtca ggatattggt gactggttgg cctggtatca gcagaagcct   120
gggaaagccc ctaagctcct gatctataag gcgtctggtt tacaaagtgg ggtcccatca   180
agattcagtg gcagtggatc tgggacagaa ttcactctca ctatcagcaa cctgcagcca   240
gaggattttg cgacttacta ttgtcaacag ggtaaccagt tcccgctcac cttcggccaa   300
gggacacgac tggag                                                    315

<210> SEQ ID NO 107
<211> LENGTH: 9
<212> TYPE: PRT
<213> ORGANISM: Artificial Sequence
<220> FEATURE:
<223> OTHER INFORMATION: Synthetic: VH CDR1.8

<400> SEQUENCE: 107

Phe Thr Phe Gly Trp Tyr Ala Met Ser
1               5

<210> SEQ ID NO 108
<211> LENGTH: 12
<212> TYPE: PRT
<213> ORGANISM: Artificial Sequence
<220> FEATURE:
<223> OTHER INFORMATION: Synthetic: VH CDR2.12

<400> SEQUENCE: 108

Ser Ala Ile Ser Gly Ser Gly Asp Thr Thr Tyr Tyr
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic: VL CDR1.9

<400> SEQUENCE: 109

Arg Ala Ser Gln Asp Ile Gly Asp Trp Leu Ala Trp
1               5                   10

<210> SEQ ID NO 110
<211> LENGTH: 8
<212> TYPE: PRT
<213> ORGANISM: Artificial Sequence
<220> FEATURE:
<223> OTHER INFORMATION: Synthetic: VL CDR2.11

<400> SEQUENCE: 110

Tyr Lys Ala Ser Gly Leu Gln Ser
1               5

<210> SEQ ID NO 111
<211> LENGTH: 18
<212> TYPE: PRT
<213> ORGANISM: Artificial Sequence
<220> FEATURE:
<223> OTHER INFORMATION: Synthetic: VH CDR3.1

<400> SEQUENCE: 111

```
Ala Lys Ala Ser Pro Phe Leu Leu Asp Asp Tyr Tyr Tyr Tyr Tyr
1               5                   10                  15

Met Asp

<210> SEQ ID NO 112
<211> LENGTH: 18
<212> TYPE: PRT
<213> ORGANISM: Artificial Sequence
<220> FEATURE:
<223> OTHER INFORMATION: Synthetic: VH CDR3.2

<400> SEQUENCE: 112

Ala Lys Asp Ala Pro Phe Leu Leu Asp Asp Tyr Tyr Tyr Tyr Tyr
1               5                   10                  15

Met Asp

<210> SEQ ID NO 113
<211> LENGTH: 18
<212> TYPE: PRT
<213> ORGANISM: Artificial Sequence
<220> FEATURE:
<223> OTHER INFORMATION: Synthetic: VH CDR3.3

<400> SEQUENCE: 113

Ala Lys Asp Ser Ala Phe Leu Leu Asp Asp Tyr Tyr Tyr Tyr Tyr
1               5                   10                  15

Met Asp

<210> SEQ ID NO 114
<211> LENGTH: 18
<212> TYPE: PRT
<213> ORGANISM: Artificial Sequence
<220> FEATURE:
<223> OTHER INFORMATION: Synthetic: VH CDR3.4

<400> SEQUENCE: 114

Ala Lys Asp Ser Pro Ala Leu Leu Asp Asp Tyr Tyr Tyr Tyr Tyr
1               5                   10                  15

Met Asp

<210> SEQ ID NO 115
<211> LENGTH: 18
<212> TYPE: PRT
<213> ORGANISM: Artificial Sequence
<220> FEATURE:
<223> OTHER INFORMATION: Synthetic: VH CDR3.5

<400> SEQUENCE: 115

Ala Lys Asp Ser Pro Phe Ala Leu Asp Asp Tyr Tyr Tyr Tyr Tyr
1               5                   10                  15

Met Asp

<210> SEQ ID NO 116
<211> LENGTH: 18
<212> TYPE: PRT
<213> ORGANISM: Artificial Sequence
<220> FEATURE:
<223> OTHER INFORMATION: Synthetic: VH CDR3.6

<400> SEQUENCE: 116

Ala Lys Asp Ser Pro Phe Leu Ala Asp Asp Tyr Tyr Tyr Tyr Tyr
1               5                   10                  15

Met Asp
```

<210> SEQ ID NO 117
<211> LENGTH: 18
<212> TYPE: PRT
<213> ORGANISM: Artificial Sequence
<220> FEATURE:
<223> OTHER INFORMATION: Synthetic: VH CDR3.7

<400> SEQUENCE: 117

Ala Lys Asp Ser Pro Phe Leu Leu Ala Asp Tyr Tyr Tyr Tyr Tyr
1               5                   10                  15
Met Asp

<210> SEQ ID NO 118
<211> LENGTH: 18
<212> TYPE: PRT
<213> ORGANISM: Artificial Sequence
<220> FEATURE:
<223> OTHER INFORMATION: Synthetic: VH CDR3.8

<400> SEQUENCE: 118

Ala Lys Asp Ser Pro Phe Leu Leu Asp Ala Tyr Tyr Tyr Tyr Tyr
1               5                   10                  15
Met Asp

<210> SEQ ID NO 119
<211> LENGTH: 18
<212> TYPE: PRT
<213> ORGANISM: Artificial Sequence
<220> FEATURE:
<223> OTHER INFORMATION: Synthetic: VH CDR3.9

<400> SEQUENCE: 119

Ala Lys Asp Ser Pro Phe Leu Leu Asp Asp Ala Tyr Tyr Tyr Tyr
1               5                   10                  15
Met Asp

<210> SEQ ID NO 120
<211> LENGTH: 18
<212> TYPE: PRT
<213> ORGANISM: Artificial Sequence
<220> FEATURE:
<223> OTHER INFORMATION: Synthetic: VH CDR3.10

<400> SEQUENCE: 120

Ala Lys Asp Ser Pro Phe Leu Leu Asp Asp Tyr Ala Tyr Tyr Tyr
1               5                   10                  15
Met Asp

<210> SEQ ID NO 121
<211> LENGTH: 18
<212> TYPE: PRT
<213> ORGANISM: Artificial Sequence
<220> FEATURE:
<223> OTHER INFORMATION: Synthetic: VH CDR3.11

<400> SEQUENCE: 121

Ala Lys Asp Ser Pro Phe Leu Leu Asp Asp Tyr Tyr Ala Tyr Tyr
1               5                   10                  15
Met Asp

<210> SEQ ID NO 122
<211> LENGTH: 18

```
<212> TYPE: PRT
<213> ORGANISM: Artificial Sequence
<220> FEATURE:
<223> OTHER INFORMATION: Synthetic: VH CDR3.12

<400> SEQUENCE: 122

Ala Lys Asp Ser Pro Phe Leu Leu Asp Asp Tyr Tyr Tyr Ala Tyr Tyr
1               5                   10                  15

Met Asp

<210> SEQ ID NO 123
<211> LENGTH: 18
<212> TYPE: PRT
<213> ORGANISM: Artificial Sequence
<220> FEATURE:
<223> OTHER INFORMATION: Synthetic: VH CDR3.13

<400> SEQUENCE: 123

Ala Lys Asp Ser Pro Phe Leu Leu Asp Asp Tyr Tyr Tyr Tyr Ala Tyr
1               5                   10                  15

Met Asp

<210> SEQ ID NO 124
<211> LENGTH: 18
<212> TYPE: PRT
<213> ORGANISM: Artificial Sequence
<220> FEATURE:
<223> OTHER INFORMATION: Synthetic: VH CDR3.14

<400> SEQUENCE: 124

Ala Lys Asp Ser Pro Phe Leu Leu Asp Asp Tyr Tyr Tyr Tyr Tyr Ala
1               5                   10                  15

Met Asp

<210> SEQ ID NO 125
<211> LENGTH: 18
<212> TYPE: PRT
<213> ORGANISM: Artificial Sequence
<220> FEATURE:
<223> OTHER INFORMATION: Synthetic: VH CDR3.15

<400> SEQUENCE: 125

Ala Lys Asp Ser Pro Phe Leu Leu Asp Asp Tyr Tyr Tyr Tyr Tyr Tyr
1               5                   10                  15

Ala Asp

<210> SEQ ID NO 126
<211> LENGTH: 15
<212> TYPE: PRT
<213> ORGANISM: Artificial Sequence
<220> FEATURE:
<223> OTHER INFORMATION: Synthetic: VH CDR3.16
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
```

```
<223> OTHER INFORMATION: Xaa can be any naturally occurring amino acid

<400> SEQUENCE: 126

Asp Xaa Xaa Xaa Xaa Leu Xaa Xaa Xaa Xaa Tyr Xaa Tyr Tyr Xaa
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthetic: VH CDR3.17
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 127

Asp Xaa Pro Phe Xaa Leu Asp Xaa Xaa Tyr Tyr Tyr Tyr Tyr Xaa
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic: VH CDR3.18
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 128

Asp Xaa Xaa Xaa Xaa Leu Xaa Xaa Xaa Xaa Tyr Xaa Tyr Tyr Xaa
1               5                   10                  15

<210> SEQ ID NO 129
<211> LENGTH: 452
<212> TYPE: PRT
<213> ORGANISM: Artificial Sequence
<220> FEATURE:
<223> OTHER INFORMATION: Synthetic: mAb1 heavy chain

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20              25              30
Ala Met Ser Trp Val Arg Gln Ala Pro Gly Lys Gly Leu Glu Trp Val
        35              40              45
Ser Ala Ile Ser Gly Ser Gly Gly Ser Thr Tyr Tyr Ala Asp Ser Val
    50              55              60
Lys Gly Arg Phe Thr Ile Ser Arg Asp Asn Ser Lys Asn Thr Leu Tyr
65              70              75              80
Leu Gln Met Asn Ser Leu Arg Ala Glu Asp Thr Ala Val Tyr Tyr Cys
                85              90              95
Ala Lys Asp Ser Pro Phe Leu Leu Asp Asp Tyr Tyr Tyr Tyr Tyr Tyr
            100             105             110
Met Asp Val Trp Gly Lys Gly Thr Thr Val Thr Val Ser Ser Ala Ser
            115             120             125
Thr Lys Gly Pro Ser Val Phe Pro Leu Ala Pro Cys Ser Arg Ser Thr
        130             135             140
Ser Glu Ser Thr Ala Ala Leu Gly Cys Leu Val Lys Asp Tyr Phe Pro
145             150             155             160
Glu Pro Val Thr Val Ser Trp Asn Ser Gly Ala Leu Thr Ser Gly Val
            165             170             175
His Thr Phe Pro Ala Val Leu Gln Ser Ser Gly Leu Tyr Ser Leu Ser
            180             185             190
Ser Val Val Thr Val Pro Ser Ser Ser Leu Gly Thr Lys Thr Tyr Thr
            195             200             205
Cys Asn Val Asp His Lys Pro Ser Asn Thr Lys Val Asp Lys Arg Val
    210             215             220
Glu Ser Lys Tyr Gly Pro Pro Cys Pro Pro Cys Pro Ala Pro Glu Phe
225             230             235             240
Leu Gly Gly Pro Ser Val Phe Leu Phe Pro Pro Lys Pro Lys Asp Thr
            245             250             255
Leu Met Ile Ser Arg Thr Pro Glu Val Thr Cys Val Val Val Asp Val
            260             265             270
Ser Gln Glu Asp Pro Glu Val Gln Phe Asn Trp Tyr Val Asp Gly Val
        275             280             285
Glu Val His Asn Ala Lys Thr Lys Pro Arg Glu Glu Gln Phe Asn Ser
    290             295             300
Thr Tyr Arg Val Val Ser Val Leu Thr Val Leu His Gln Asp Trp Leu
305             310             315             320
Asn Gly Lys Glu Tyr Lys Cys Lys Val Ser Asn Lys Gly Leu Pro Ser
            325             330             335
Ser Ile Glu Lys Thr Ile Ser Lys Ala Lys Gly Gln Pro Arg Glu Pro
        340             345             350
Gln Val Tyr Thr Leu Pro Pro Ser Gln Glu Glu Met Thr Lys Asn Gln
        355             360             365
Val Ser Leu Thr Cys Leu Val Lys Gly Phe Tyr Pro Ser Asp Ile Ala
        370             375             380
Val Glu Trp Glu Ser Asn Gly Gln Pro Glu Asn Asn Tyr Lys Thr Thr
385             390             395             400
Pro Pro Val Leu Asp Ser Asp Gly Ser Phe Phe Leu Tyr Ser Arg Leu
            405             410             415
Thr Val Asp Lys Ser Arg Trp Gln Glu Gly Asn Val Phe Ser Cys Ser
            420             425             430
Val Met His Glu Ala Leu His Asn His Tyr Thr Gln Lys Ser Leu Ser
            435             440             445
```

Leu Ser Leu Gly
        450

<210> SEQ ID NO 130
<211> LENGTH: 454
<212> TYPE: PRT
<213> ORGANISM: Artificial Sequence
<220> FEATURE:
<223> OTHER INFORMATION: Synthetic: mAb8 heavy chain V1

<400> SEQUENCE: 130

Gly Thr Glu Val Gln Leu Leu Glu Ser Gly Gly Leu Val Gln Pro
1               5                   10                  15

Gly Gly Ser Leu Arg Leu Ser Cys Ala Ala Ser Gly Phe Thr Phe Arg
            20                  25                  30

Asn Tyr Ala Met Ser Trp Val Arg Gln Ala Pro Gly Lys Gly Leu Glu
        35                  40                  45

Trp Val Ser Ala Ile Ser Gly Ser Gly Asp Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Pro Phe Leu Leu Asp Tyr Tyr Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Met Thr Lys
            355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
            435                 440                 445

Leu Ser Leu Ser Leu Gly
    450

<210> SEQ ID NO 131
<211> LENGTH: 452
<212> TYPE: PRT
<213> ORGANISM: Artificial Sequence
<220> FEATURE:
<223> OTHER INFORMATION: Synthetic: mAb8 heavy chain V2

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly
    450

<210> SEQ ID NO 132
<211> LENGTH: 452
<212> TYPE: PRT
<213> ORGANISM: Artificial Sequence
<220> FEATURE:
<223> OTHER INFORMATION: Synthetic: mAb10 heavy chain

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Gly Tyr
            20                  25                  30

Ala Met Ser Trp Val Arg Gln Ala Pro Gly Lys Gly Leu Glu Trp Val
        35                  40                  45

Ala Ala Ile Ser Gly Ser Gly Asp Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr
            100                 105                 110

Met Asp Val Trp Gly Lys Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

```
Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450

<210> SEQ ID NO 133
<211> LENGTH: 214
<212> TYPE: PRT
<213> ORGANISM: Artificial Sequence
<220> FEATURE:
<223> OTHER INFORMATION: Synthetic: mAb1, mAb8 and mAb10 light chain

<400> SEQUENCE: 133

Asp Ile Gln Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Leu Phe Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 134
<211> LENGTH: 288
<212> TYPE: PRT
<213> ORGANISM: Homo sapiens
<220> FEATURE:
<221> NAME/KEY: misc_feature
<222> LOCATION: (1)..(288)
<223> OTHER INFORMATION: Human PD-1 Amino Acid Sequence

<400> SEQUENCE: 134

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Phe Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

```
Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285
```

<210> SEQ ID NO 135
<211> LENGTH: 290
<212> TYPE: PRT
<213> ORGANISM: Homo sapiens
<220> FEATURE:
<221> NAME/KEY: misc_feature
<222> LOCATION: (1)..(290)
<223> OTHER INFORMATION: Human PD-L1 Amino Acid Sequence

<400> SEQUENCE: 135

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
```

```
                    260                 265                 270
Gly Ile Gln Asp Thr Asn Ser Lys Lys Gln Ser Asp Thr His Leu Glu
            275                 280                 285

Glu Thr
    290

<210> SEQ ID NO 136
<211> LENGTH: 327
<212> TYPE: PRT
<213> ORGANISM: Homo sapiens
<220> FEATURE:
<221> NAME/KEY: misc_feature
<222> LOCATION: (1)..(327)
<223> OTHER INFORMATION: Human IgG4

<400> SEQUENCE: 136

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325
```

CD137 ANTIBODIES AND PD-1 ANTAGONISTS AND USES THEREOF

CROSS REFERENCE TO RELATED APPLICATIONS

This application is a 35 U.S.C. § 371 U.S. National Stage Entry of International Application No. PCT/US2018/058451 filed Oct. 31, 2018, entitled "CD137 ANTIBODIES AND PD-I ANTAGONISTS AND USES THEREOF", which claims the benefit of priority U.S. Provisional Patent Application No. 62/579,337, filed Oct. 31, 2017, entitled "CD137 ANTIBODIES AND PD-I ANTAGONISTS AND USES THEREOF", the contents of which are herein incorporated by reference in their entirety.

SEQUENCE LISTING

The present application is being filed along with a Sequence Listing in electronic format. The Sequence Listing file, entitled 21831010 US371 SEQLST.txt, was created on Apr. 30, 2020, and is 100,019 bytes in size. The information in electronic format of the Sequence Listing is incorporated herein by reference in its entirety.

BACKGROUND

Combinatorial therapy has become an important development in cancer treatment. However, determining which therapies are more effective when combined is not intuitive.

In recent years, an increasing body of evidence suggests that the immune system operates as a significant barrier to tumor formation and progression. The principle that naturally-occurring T cells with anti-tumor potential or activity exist in a patient with cancer has rationalized the development of immunotherapeutic approaches in oncology. Immune cells, such as T cells, macrophages, and natural killer cells, can exhibit anti-tumor activity and effectively control the occurrence and growth of malignant tumors. Tumor-specific or -associated antigens can induce immune cells to recognize and eliminate malignancies (Chen & Mellman, (2013) *Immunity* 39(1):1-10). In spite of the existence of tumor-specific immune responses, malignant tumors often evade or avoid immune attack through a variety of immunomodulatory mechanisms resulting in the failure to control tumor occurrence and progression (Motz & Coukos, (2013) *Immunity* 39(1):61-730). Indeed, an emerging hallmark of cancer is the exploitation of these immunomodulatory mechanisms and the disablement of anti-tumor immune responses, resulting in tumor evasion and escape from immunological killing (Hanahan and Weinberg (2011) *Cell* 144(5):646-674).

Novel approaches in the immunotherapy of cancer involve counteracting these immune evasion and escape mechanisms and inducing the endogenous immune system to reject tumors. Antibody blockade of T cell co-inhibitory molecules, also known as immune checkpoints, has recently emerged as a frontline treatment for cancer. Antibodies targeting CTLA-4, PD-1, and PD-L1 have shown therapeutic benefit in human clinical trials. Specifically, the anti-CTLA-4 antibody ipilimumab (YERVOY®) and the anti-PD-1 antibodies nivolumab (OPDIVO®) and pembrolizumab (KEYTRUDA®), are currently approved for treating cancer patients.

Moreover, therapies targeting CD137 have recently been explored. CD137 (alternatively known as "tumor necrosis factor receptor superfamily member 9" (TNFRSF9), 4-1BB, and "induced by lymphocyte activation" (ILA)) is a transmembrane co-stimulatory receptor protein belonging to the tumor necrosis factor superfamily. CD137 is a T cell co-stimulatory receptor induced upon TCR activation (Nam et al., (2005) *Curr Cancer Drug Targets* 5:357-363; Watts et al., (2005) *Annu Rev Immunol* 23:23-68). In addition to its expression on activated CD4+ and CD8+ T cells, CD137 is also expressed on CD4+CD25+ regulatory T cells, activated natural killer (NK) and NK-T cells, monocytes, neutrophils, and dendritic cells.

Under physiological conditions, CD137 is ligated by CD137 ligand (CD137L), an agonist membrane molecule present on antigen-presenting cells including B cells, monocytes, macrophages, and dendritic cells (Watts et al., (2005) *Annu Rev Immunol* 23:23-68). Upon interaction with its ligand, CD137 leads to increased TCR-induced T-cell proliferation, cytokine production, functional maturation, and prolonged CD8+ T-cell survival. The potential of CD137 co-stimulation using various agonists (e.g. agonistic antibodies, recombinant CD137L protein, and CD137-specific aptamers) in enabling the immune system to attack tumors has been documented in numerous models (Dharmadhikari et al., (2016) *Oncoimmunology* 5(4):e1113367 and references therein). A recent report on the clinical evaluation of an agonistic CD137 antibody (Urelumab, BMS-663513; Bristol-Myers Squibb) documented the observation of treatment-related adverse events in human subjects, including indications of severe hepatotoxicity (transaminitis) correlating with antibody dose (Segal et al., (2016) *Clin Cancer Res* 23(8):1929-1936). In contrast, a different agonistic CD137 antibody (Utomilumab, PF-05082566; Pfizer) tested in combination with an anti-PD-1 antibody (pembrolizumab), though not resulting in any dose-limiting toxicities, showed comparable results to anti-PD-1 antibody therapy alone (Tolcher, A. et al., (2017) *Clin Cancer Res* 23(18): 5349-5357). These results highlight that for patients with various diseases and conditions, including cancer, that are amenable to treatment with a CD137 agonist, there continues to be an unmet need for novel agonistic antibodies that bind to human CD137 and exhibit characteristics sufficient for the development of a safe and efficacious therapeutic.

These various therapies have shown promising results. However, as noted above, the effectiveness of a given combination, let alone potential synergies, of therapies in treating cancer is not predictable. The effectiveness of these therapies together has not been fully characterized. Novel combination therapies and therapeutic regimens are needed to more effectively combat various cancers.

SUMMARY OF THE DISCLOSURE

The present disclosure is based, in part, on the discovery that blockade of the PD-1/PD-L1/PD-L2 signaling pathway in combination with agonism of CD137 synergistically induces cytokine production in vitro and anti-tumor immunity in vivo. Tumor cells often evade the immune response, which allows for the establishment of cancer.

Unexpectedly, the anti-CD137 monoclonal antibodies of the disclosure were found to agonize CD137 and induce protective anti-tumor immunity in vivo with a concomitant reduction in the potential for toxicity-related events. Notably, the anti-CD137 antibodies described herein are efficacious against diverse tumor types, and over a wide dose range. The anti-CD137 agonist antibodies of the disclosure were also found to induce and/or enhance cytokine production, expansion of CD8+ T cells, and protective anti-tumor immunity and thus are particularly effective in treating cancer. Moreover, the anti-CD137 agonist antibodies of the disclosure were found to bind a unique epitope on human CD137. In addition the disclosure also features agonist anti-CD137 antibodies having an affinity ($K_D$) that is optimal for maximizing anti-tumor immunity while avoiding toxicity-related events associated with CD137 agonism. Moreover, as exemplified in the working examples, the antibodies described herein are therapeutically effective against very large tumors. For example, treatment of tumor-bearing mice with agonist anti-CD137 antibodies described herein resulted in complete regression of tumors as large as 1,800 $mm^3$. As set forth in FIG. 15, treatment of such mice also resulted in protective immunity. And coincident with the observed efficacy were positive immunophenotypic changes in the tumor microenvironment, such as increased immune cell infiltration with concomitant reductions in regulatory T cell and exhausted T cell populations (see, e.g., FIGS. 22A-22D).

As described above, agonism of CD137 has been associated with certain adverse events, including hepatotoxicity-related deaths in humans (see, e.g., Segal et al. (2017) Clin Cancer Res 23(8): 1929-1935). Similar toxicities resulting from treatment with agonist anti-CD137 antibodies (such as the 3H3 antibody) have also been observed in animal models (see, e.g., Bartkowiak et al. (2018) Clin Cancer Res 24(5): 1138-1151). Yet, the agonist anti-CD137 antibodies described herein have minimal effects on the liver, as determined by, e.g., plasma levels of liver enzymes (e.g., alanine aminotransferase (ALT)) and immune cell infiltration. For example, there was no evidence of increased intrahepatic or intrasplenic immune cell infiltration in mice treated with the antibodies. Thus, the CD137 binding antibodies described herein are not only highly efficacious, but also sparing of certain toxicities associated with CD137 agonism.

While the disclosure is not bound by any particular theory or mechanism of action, the superior therapeutic and toxicity-sparing properties of the CD137 binding antibodies described herein are believed to derive in part from one or both of their affinity and the novel epitope to which they bind. That is, the antibodies described herein share a common, novel epitope that is distinct from that of other agonist anti-CD137 antibodies. And, as exemplified in the working examples, engagement of this epitope by the antibodies described herein gives rise to differentiated in vitro activity, such as effects on regulatory T cell proliferation, cytokine production by CD8+ T cells and macrophages, and intracellular signaling, as compared to agonist antibodies that bind to different epitopes of CD137. Furthermore, it has been demonstrated that an affinity range (a "sweet spot") for CD137 binding antibodies is particularly optimal for anti-tumor activity. For example, antibodies of intermediate affinity were shown to be more efficacious against large tumors as compared to antibodies with higher or lower affinity.

Further, the disclosure provides combinations of agonist anti-CD137 antibodies and PD-1 antagonists that function in a synergistic manner to induce cytokine production and anti-tumor immunity. In particular, the disclosure features treatment regimens in which an agonist anti-CD137 antibody is administered first in time and a PD-1 antagonist is administered second in time, the result of which is a synergistic enhancement of anti-tumor efficacy in vivo, as well as increases in cytokine production by peripheral blood mononuclear cells in vitro.

Accordingly, in some aspects, the disclosure relates to methods for treating cancer or enhancing a cancer-specific immune response in a subject in need thereof with an isolated agonistic monoclonal antibody that specifically binds human CD137 in combination with a PD-1 antagonist, thereby treating the subject.

In some aspects, the disclosure provides a method for treating cancer in a subject, the method comprising administering to the subject an effective amount of an isolated agonistic monoclonal antibody that specifically binds to human CD137 with an affinity ($K_D$) of about 30-100 nM, or that binds to an epitope on human CD137 comprising K114 of SEQ ID NO: 3, or both, or an antigen-binding fragment thereof, and a PD-1 antagonist, wherein the agonistic monoclonal antibody or antigen-binding fragment thereof is administered to the subject prior to administration of the PD-1 antagonist, thereby treating the subject.

In some aspects, the disclosure provides a method for enhancing a cancer-specific immune response in a subject in need thereof, the method comprising administering to the subject an effective amount of an isolated agonistic monoclonal antibody that specifically binds to human CD137 with an affinity ($K_D$) of about 30-100 nM, or that binds to an epitope on human CD137 comprising K114 of SEQ ID NO: 3, or both, or an antigen-binding fragment thereof, and a PD-1 antagonist, wherein the agonistic monoclonal antibody or antigen-binding fragment thereof is administered to the subject prior to administration of the PD-1 antagonist, thereby enhancing a cancer-specific immune response in the subject as compared to the cancer-specific immune response in the subject following administration of either the PD-1 antagonist or the isolated agonistic monoclonal antibody, or antigen-binding fragment thereof, alone.

In some aspects, the disclosure provides a method for treating cancer in a subject in need thereof who has received or is receiving treatment with an isolated agonistic monoclonal antibody that specifically binds to human CD137 with an affinity (KD) of about 30-100 nM, or that binds to an epitope on human CD137 comprising K114 of SEQ ID NO: 3, or both, or an antigen-binding fragment thereof, the method comprising administering to the subject an effective amount of a PD-1 antagonist, thereby treating the subject.

In some aspects, the disclosure provides a method for enhancing a cancer-specific immune response in a subject in need thereof who has received or is receiving treatment with an isolated agonistic monoclonal antibody that specifically binds to human CD137 with an affinity (KD) of about 30-100 nM, or that binds to an epitope on human CD137 comprising K114 of SEQ ID NO: 3, or both, or an antigen-binding fragment thereof, the method comprising administering to the subject an effective amount of a PD-1 antagonist, thereby enhancing a cancer-specific immune response in the subject as compared to the cancer-specific immune response in the subject following administration of the isolated agonistic monoclonal antibody, or antigen-binding fragment thereof, alone.

In some aspects, the disclosure provides compositions comprising isolated agonistic monoclonal antibodies, or antigen-binding fragments thereof, that specifically bind human CD137 for use in combination with a PD-1 antagonist.

In some aspects, the disclosure provides a composition comprising an isolated agonistic monoclonal antibody that specifically binds CD137 with an affinity (KD) of about 30-100 nM, or that binds to an epitope on human CD137 comprising K114 of SEQ ID NO: 3, or both, or an antigen-binding fragment thereof, and an optional pharmaceutically acceptable carrier, for use in treating cancer, delaying cancer progression, or enhancing a cancer-specific immune response in a subject in need thereof, wherein the agonistic monoclonal antibody, or antigen-binding fragment thereof, is administered in combination with a second composition comprising a PD-1 antagonist, and optionally a pharmaceutically acceptable carrier.

In any of the foregoing or related embodiments, the isolated agonistic monoclonal antibody specifically binds to human CD137 with an affinity ($K_D$) of about 30-100 nM and binds to an epitope on human CD137 comprising K114 of SEQ ID NO: 3.

In any of the foregoing or related embodiments, administration of the PD-1 antagonist occurs after at least one or more doses of the isolated agonistic monoclonal antibody, or antigen-binding fragment thereof, and prior to a subsequent dose of the isolated agonistic monoclonal antibody, or antigen-binding fragment thereof.

In any of the foregoing or related embodiments, administration of the PD-1 antagonist occurs after at least 2 doses, at least 3 doses, at least 4 doses, at least 5 doses, at least 6 doses, at least 7 doses, at least 8 doses, at least 9 doses, at least 10 doses of the isolated agonistic monoclonal antibody, or antigen-binding fragment thereof. In some embodiments, administration of the PD-1 antagonist occurs after at least 2 doses of the isolated agonistic monoclonal antibody, or antigen-binding fragment thereof. In some embodiments, administration of the PD-1 antagonist occurs after at least 3 doses of the isolated agonistic monoclonal antibody, or antigen-binding fragment thereof. In some embodiments, administration of the PD-1 antagonist occurs after at least 4 doses of the isolated agonistic monoclonal antibody, or antigen-binding fragment thereof. In some embodiments, administration of the PD-1 antagonist occurs after at least 5 doses of the isolated agonistic monoclonal antibody, or antigen-binding fragment thereof. In some embodiments, administration of the PD-1 antagonist occurs after at least 6 doses of the isolated agonistic monoclonal antibody, or antigen-binding fragment thereof. In some embodiments, administration of the PD-1 antagonist occurs after least 7 doses of the isolated agonistic monoclonal antibody, or antigen-binding fragment thereof. In some embodiments, administration of the PD-1 antagonist occurs after at least 8 doses of the isolated agonistic monoclonal antibody, or antigen-binding fragment thereof. In some embodiments, administration of the PD-1 antagonist occurs after at least 9 doses of the isolated agonistic monoclonal antibody, or antigen-binding fragment thereof. In some embodiments, administration of the PD-1 antagonist occurs after at least 10 doses of the isolated agonistic monoclonal antibody, or antigen-binding fragment thereof.

In any of the foregoing or related embodiments, the isolated agonistic monoclonal antibody, or antigen-binding fragment thereof, is administered at least 4 days, at least 5 days, at least 6 days, at least 7 days, at least 8 days, at least 9 days, or at least 10 days prior to administration of the PD-1 antagonist. In some embodiments, the isolated agonistic monoclonal antibody, or antigen-binding fragment thereof, is administered at least 4 days prior to administration of the PD-1 antagonist. In some embodiments, the isolated agonistic monoclonal antibody, or antigen-binding fragment thereof, is administered at least 5 days prior to administration of the PD-1 antagonist. In some embodiments, the isolated agonistic monoclonal antibody, or antigen-binding fragment thereof, is administered at least 6 days prior to administration of the PD-1 antagonist. In some embodiments, the isolated agonistic monoclonal antibody, or antigen-binding fragment thereof, is administered at least 7 days prior to administration of the PD-1 antagonist. In some embodiments, the isolated agonistic monoclonal antibody, or antigen-binding fragment thereof, is administered at least 8 days prior to administration of the PD-1 antagonist. In some embodiments, the isolated agonistic monoclonal antibody, or antigen-binding fragment thereof, is administered at least 9 days prior to administration of the PD-1 antagonist. In some embodiments, the isolated agonistic monoclonal antibody, or antigen-binding fragment thereof, is administered at least 10 days prior to administration of the PD-1 antagonist.

In any of the foregoing or related embodiments, the PD-1 antagonist is administered at least 4 days, at least 5 days, at least 6 days, at least 7 days, at least 8 days, at least 9 days, or at least 10 days after beginning treatment with the isolated agonistic monoclonal antibody, or antigen-binding fragment thereof. In some embodiments, the PD-1 antagonist is administered at least 4 days after beginning treatment with the isolated agonistic monoclonal antibody, or antigen-binding fragment thereof. In some embodiments, the PD-1 antagonist is administered at least 5 days after beginning treatment with the isolated agonistic monoclonal antibody, or antigen-binding fragment thereof. In some embodiments, the PD-1 antagonist is administered at least 6 days after beginning treatment with the isolated agonistic monoclonal antibody, or antigen-binding fragment thereof. In some embodiments, the PD-1 antagonist is administered at least 7 days after beginning treatment with the isolated agonistic monoclonal antibody, or antigen-binding fragment thereof. In some embodiments, the PD-1 antagonist is administered at least 8 days after beginning treatment with the isolated agonistic monoclonal antibody, or antigen-binding fragment thereof. In some embodiments, the PD-1 antagonist is administered at least 9 days after beginning treatment with the isolated agonistic monoclonal antibody, or antigen-binding fragment thereof. In some embodiments, the PD-1 antagonist is administered at least 10 days after beginning treatment with the isolated agonistic monoclonal antibody, or antigen-binding fragment thereof.

In any of the foregoing or related embodiments, treatment comprises delaying cancer progression in the subject.

In any of the foregoing or related embodiments, treatment comprises enhancing a cancer-specific immune response in the subject. In some embodiments, the cancer-specific immune response is a T cell response. In some embodiments, the T cell response comprises the production of IFNγ by one or both of $CD4^+$ T cells and CD8+ T cells. In some embodiments, the T cell response comprises the production of IFNγ by one or both of $CD4^+$ T cells. In some embodiments, the T cell response comprises the production of IFNγ by $CD8^+$ T cells. In some embodiments, the T cell response comprises the production of IFNγ by both of CD4+ T cells and CD8+ T cells. In some embodiments, the T cell response comprises the production of IL-2 by one or both of CD4+ T cells and CD8+ T cells. In some embodiments, the T cell response comprises the production of IL-2 by CD4+ T cells. In some embodiments, the T cell response comprises the production of IL-2 by CD8+ T cells. In some embodiments, the T cell response comprises the production of IL-2 by both of CD4+ T cells and $CD8^+$ T cells. In some embodiments, the T cell response comprises proliferation of one or both of CD4+ T cells and $CD8^+$ T cells. In some embodiments, the T cell response comprises proliferation of CD4+ T cells. In some embodiments, the T cell response comprises proliferation of CD8+ T cells. In some embodiments, the T cell response comprises proliferation of both of CD4+ T cells and CD8+ T cells.

In any of the foregoing or related embodiments, the subject comprises a tumor expressing or overexpressing PD-L1. In some embodiments, the tumor expresses more PD-L1 following administration of the isolated agonistic monoclonal antibody or antigen-binding fragment thereof.

In any of the foregoing or related embodiments, the PD-1 antagonist is an isolated monoclonal antibody that specifically binds to human PD-L1, or an antigen-binding fragment thereof. In some embodiments, the PD-1 antagonist is avelumab, durvalumab, or atezolizumab.

In any of the foregoing or related embodiments, the PD-1 antagonist is an isolated monoclonal antibody that specifically binds to human PD-1, or an antigen-binding fragment thereof. In some embodiments, the PD-1 antagonist is pembrolizumab or nivolumab.

In any of the foregoing or related embodiments, the epitope on human CD137 comprises residues E111, T113, and K114 of SEQ ID NO: 3. In some embodiments, the epitope comprises E111, T113, K114 and P135 of SEQ ID NO: 3. In some embodiments, the epitope comprises residues E111, T113, K114, N126 and I132 of SEQ ID NO: 3. In some embodiments, the epitope comprises residues E111, T113, K114, N126, I132 and P135 of SEQ ID NO: 3. In any of the foregoing or related embodiments, the epitope comprises one or more of residues E111, T113, K114, N126, I132 and P135 of SEQ ID NO: 3.

In any of the foregoing or related embodiments, the epitope on human CD137 comprises a sequence of one or more amino acid residues corresponding to amino acid positions 111 to 135 of SEQ ID NO: 3. In some embodiments, the epitope comprises 2, 3, 4, 5, 6, 7, 8, 9, 10, 11, 12, 13, 14, 15, 16, 17, 18, 19, 20, 21, 22, 23, 24, or 25 amino acid residues corresponding to amino acid positions 111 to 135 of SEQ ID NO: 3.

In any of the foregoing or related embodiments, the epitope on human CD137 comprises the amino acid residues ELTK (corresponding to amino acid residues 111-114 of SEQ ID NO: 3). In some embodiments, the epitope further comprises one or more residues N126, I132 and P135 of SEQ ID NO: 3. In some embodiments, the epitope further comprises residues N126, I132 and P135 of SEQ ID NO: 3.

In any of the foregoing or related embodiments, the epitope is a non-linear epitope. In any of the foregoing aspects, mutation of residue K114 of SEQ ID NO: 3 abrogates binding of the antibody or antigen binding portion thereof to human CD137.

In any of the foregoing or related embodiments, the isolated agonistic monoclonal antibody or antigen-binding fragment binds human CD137 with an affinity ($K_D$) of about: 45-95 nM, 50-90 nM, 55-85 nM, 60-80 nM, 65-75 nM, 55-75 nM, 40-70 nM, 50-80 nM, or 60-90 nM. In any of the foregoing or related embodiments, the isolated agonistic monoclonal antibody or antigen-binding fragment binds to a non-ligand binding region of the extracellular domain of human CD137. In some embodiments, the non-ligand binding region spans cysteine rich domain (CRD) III and CRD IV. In any of the foregoing or related embodiments, the isolated agonistic monoclonal antibody or antigen-binding fragment does not inhibit the interaction between CD137 and CD137L. In any of the foregoing or related embodiments, the antibody or antigen binding portion does not inhibit the formation of a trimer of CD137: CD137L monomers.

In any of the foregoing or related embodiments, the isolated agonistic monoclonal antibody or antigen-binding fragment comprises a heavy chain CDR3 comprising the amino acid sequence DXXXXLXXXXYXYYX (SEQ ID NO: 126), wherein X is any amino acid. In some embodiments, the isolated agonistic monoclonal antibody or antigen-binding fragment comprises a heavy chain CDR3 comprising the amino acid sequence DXPFXLDXXYYYYYX (SEQ ID NO: 127), wherein X is any amino acid. In some embodiments, mutation of residues D95, L100, Y100E, Y100G, Y100H, or combinations thereof, of the heavy chain CDR3, to alanine, results in loss of binding to human CD137. In some embodiments, mutation of residues P97, F98, D100A, Y100D, Y100F, or combinations thereof, of the heavy chain CDR3, to alanine, results in reduction of binding to human CD137.

In any of the foregoing or related embodiments, the isolated agonistic monoclonal antibody or antigen-binding fragment comprises heavy and light chain CDRs, wherein heavy chain CDR3 comprises the amino acid sequence set forth in SEQ ID NO: 68.

In any of the foregoing or related embodiments, the isolated agonistic monoclonal antibody or antigen-binding fragment thereof comprises heavy and light chain CDRs selected from the group consisting of:
 (a) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively; and
 (b) heavy chain CDR1, CDR2 and CDR3 sequences set forth in SEQ ID NOs: 51, 108 and 68, respectively, and light chain CDR1, CDR2 and CDR3 sequences set forth in SEQ ID NOs: 69, 78 and 89, respectively.

In any of the foregoing or related embodiments, the isolated agonistic monoclonal antibody or antigen-binding fragment thereof comprises heavy and light chain variable regions, wherein the heavy chain variable region comprises an amino acid sequence selected from the group consisting of SEQ ID NOs: 4 and 101; and wherein the light chain variable region comprises an amino acid sequence of SEQ ID NO: 6.

In any of the foregoing or related embodiments, the isolated agonistic monoclonal antibody or antigen-binding fragment thereof comprises heavy and light chain variable regions comprising amino acid sequences selected from the group consisting of:
 (a) SEQ ID NOs: 4 and 6, respectively; and
 (b) SEQ ID NOs: 101 and 6, respectively.

In any of the foregoing or related embodiments, the isolated agonistic monoclonal antibody or antigen-binding fragment thereof comprises heavy and light chain variable regions, wherein the heavy chain variable region comprises an amino acid sequence which is at least 90% identical to the amino acid sequence selected from the group consisting of SEQ ID NOs: 4 and 101; and wherein the light chain variable region comprises an amino acid sequence which is at least 90% identical to the amino acid sequence of SEQ ID NO: 6.

In any of the foregoing or related embodiments, the isolated agonistic monoclonal antibody or antigen-binding fragment thereof comprises heavy and light chain variable regions comprising amino acid sequences at least 90% identical to the amino acid sequences selected from the group consisting of:
 (a) SEQ ID NOs: 4 and 6, respectively; and
 (b) SEQ ID NOs: 101 and 6, respectively.

In any of the foregoing or related embodiments, the isolated agonistic monoclonal antibody or antigen-binding fragment thereof comprises heavy and light chain CDRs selected from the group consisting of:

(a) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively;

(b) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 70, 79 and 90, respectively;

(c) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 71, 80 and 91, respectively;

(d) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 72, 81 and 92, respectively;

(e) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 73, 82 and 91, respectively;

(f) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 74, 83 and 93, respectively;

(g) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 75, 84 and 91, respectively;

(h) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 74, 85 and 94, respectively;

(i) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 76, 86 and 95, respectively;

(j) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 77, 87 and 93, respectively;

(k) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 88 and 90, respectively;

(l) heavy chain CDR1, CDR2 and CDR3 sequences set forth in SEQ ID NOs: 49, 57 and 68, respectively, and light chain CDR1, CDR2 and CDR3 sequences set forth in SEQ ID NOs: 69, 78 and 89, respectively;

(m) heavy chain CDR1, CDR2 and CDR3 sequences set forth in SEQ ID NOs: 49, 58 and 68, respectively, and light chain CDR1, CDR2 and CDR3 sequences set forth in SEQ ID NOs: 69, 78 and 89, respectively;

(n) heavy chain CDR1, CDR2 and CDR3 sequences set forth in SEQ ID NOs: 49, 59 and 68, respectively, and light chain CDR1, CDR2 and CDR3 sequences set forth in SEQ ID NOs: 69, 78 and 89, respectively;

(o) heavy chain CDR1, CDR2 and CDR3 sequences set forth in SEQ ID NOs: 49, 60 and 68, respectively, and light chain CDR1, CDR2 and CDR3 sequences set forth in SEQ ID NOs: 69, 78 and 89, respectively;

(p) heavy chain CDR1, CDR2 and CDR3 sequences set forth in SEQ ID NOs: 50, 61 and 68, respectively, and light chain CDR1, CDR2 and CDR3 sequences set forth in SEQ ID NOs: 69, 78 and 89, respectively;

(q) heavy chain CDR1, CDR2 and CDR3 sequences set forth in SEQ ID NOs: 50, 58 and 68, respectively, and light chain CDR1, CDR2 and CDR3 sequences set forth in SEQ ID NOs: 69, 78 and 89, respectively;

(r) heavy chain CDR1, CDR2 and CDR3 sequences set forth in SEQ ID NOs: 51, 62 and 68, respectively, and light chain CDR1, CDR2 and CDR3 sequences set forth in SEQ ID NOs: 69, 78 and 89, respectively;

(s) heavy chain CDR1, CDR2 and CDR3 sequences set forth in SEQ ID NOs: 52, 63 and 68, respectively, and light chain CDR1, CDR2 and CDR3 sequences set forth in SEQ ID NOs: 69, 78 and 89, respectively;

(t) heavy chain CDR1, CDR2 and CDR3 sequences set forth in SEQ ID NOs: 50, 64 and 68, respectively, and light chain CDR1, CDR2 and CDR3 sequences set forth in SEQ ID NOs: 69, 78 and 89, respectively;

(u) heavy chain CDR1, CDR2 and CDR3 sequences set forth in SEQ ID NOs: 50, 65 and 68, respectively, and light chain CDR1, CDR2 and CDR3 sequences set forth in SEQ ID NOs: 69, 78 and 89, respectively;

(v) heavy chain CDR1, CDR2 and CDR3 sequences set forth in SEQ ID NOs: 51, 108 and 68, respectively, and light chain CDR1, CDR2 and CDR3 sequences set forth in SEQ ID NOs: 69, 78 and 89, respectively;

(w) heavy chain CDR1, CDR2 and CDR3 sequences set forth in SEQ ID NOs: 107, 56 and 68, respectively, and light chain CDR1, CDR2 and CDR3 sequences set forth in SEQ ID NOs: 69, 78 and 89, respectively; and (x) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 109, 110 and 92, respectively.

In any of the foregoing or related embodiments, the isolated agonistic monoclonal antibody or antigen-binding fragment thereof comprises heavy and light chain variable regions, wherein the heavy chain variable region comprises an amino acid sequence selected from the group consisting of SEQ ID NOs: 4, 8, 10, 12, 14, 16, 18, 20, 22, 24, 26, 101 and 103; and wherein the light chain variable region comprises an amino acid sequence selected from the group consisting of SEQ ID NOs: 6, 28, 30, 32, 34, 36, 38, 40, 42, 44, 46 and 105.

In any of the foregoing or related embodiments, the isolated agonistic monoclonal antibody or antigen-binding fragment thereof comprises heavy and light chain variable regions encoded by nucleotide sequences selected from the group consisting of:

(a) SEQ ID NOs: 5 and 7, respectively; and (b) SEQ ID NOs: 102 and 7, respectively.

In any of the foregoing or related embodiments, the isolated agonistic monoclonal antibody or antigen-binding fragment thereof comprises heavy and light chain variable regions encoded by nucleotide sequences having at least 90% identity to the nucleotide sequences selected from the group consisting of:

(a) SEQ ID NOs: 5 and 7, respectively; and (b) SEQ ID NOs: 102 and 7, respectively.

In any of the foregoing or related embodiments, the isolated agonistic monoclonal antibody or antigen-binding fragment thereof comprises heavy and light chain variable regions encoded by nucleotide sequences having at least 90% identity to SEQ ID NOs: 5 and 7, respectively.

In any of the foregoing or related embodiments, the isolated agonistic monoclonal antibody or antigen-binding portion thereof comprises heavy and light chain variable regions encoded by nucleotide sequences selected from the group consisting of:

(a) SEQ ID NO: 5 and 7, respectively;

(b) SEQ ID NO: 5 and 29, respectively;

(c) SEQ ID NO: 5 and 31, respectively;
(d) SEQ ID NO: 5 and 33, respectively;
(e) SEQ ID NO: 5 and 35, respectively;
(f) SEQ ID NO: 5 and 37, respectively;
(g) SEQ ID NO: 5 and 39, respectively;
(h) SEQ ID NO: 5 and 41, respectively;
(i) SEQ ID NO: 5 and 43, respectively;
(j) SEQ ID NO: 5 and 45, respectively;
(k) SEQ ID NO: 5 and 47, respectively;
(l) SEQ ID NO: 9 and 7, respectively;
(m) SEQ ID NO: 11 and 7, respectively;
(n) SEQ ID NO: 13 and 7, respectively;
(o) SEQ ID NO: 15 and 7, respectively;
(p) SEQ ID NO: 17 and 7, respectively;
(q) SEQ ID NO: 19 and 7, respectively;
(r) SEQ ID NO: 21 and 7, respectively;
(s) SEQ ID NO: 23 and 7, respectively;
(t) SEQ ID NO: 25 and 7, respectively;
(u) SEQ ID NO: 27 and 7, respectively;
(v) SEQ ID NO: 102 and 7, respectively;
(w) SEQ ID NO: 104 and 7, respectively; and
(x) SEQ ID NO: 5 and 106, respectively.

In any of the foregoing or related embodiments, the isolated agonistic monoclonal antibody or antigen-binding fragment thereof comprises heavy and light chain variable regions comprising amino acid sequences selected from the group consisting of:
(a) SEQ ID NO: 4 and 6, respectively;
(b) SEQ ID NO: 4 and 28, respectively;
(c) SEQ ID NO: 4 and 30, respectively;
(d) SEQ ID NO: 4 and 32, respectively;
(e) SEQ ID NO: 4 and 34, respectively;
(f) SEQ ID NO: 4 and 36, respectively;
(g) SEQ ID NO: 4 and 38, respectively;
(h) SEQ ID NO: 4 and 40, respectively;
(i) SEQ ID NO: 4 and 42, respectively;
(j) SEQ ID NO: 4 and 44, respectively;
(k) SEQ ID NO: 4 and 46, respectively;
(l) SEQ ID NO: 8 and 6, respectively;
(m) SEQ ID NO: 10 and 6, respectively;
(n) SEQ ID NO: 12 and 6, respectively;
(o) SEQ ID NO: 14 and 6, respectively;
(p) SEQ ID NO: 16 and 6, respectively;
(q) SEQ ID NO: 18 and 6, respectively;
(r) SEQ ID NO: 20 and 6, respectively;
(s) SEQ ID NO: 22 and 6, respectively;
(t) SEQ ID NO: 24 and 6, respectively;
(u) SEQ ID NO: 26 and 6, respectively;
(v) SEQ ID NO: 101 and 6, respectively;
(w) SEQ ID NO: 103 and 6, respectively; and
(x) SEQ ID NO: 4 and 105, respectively.

In any of the foregoing or related embodiments, the isolated agonistic monoclonal antibody or antigen-binding fragment thereof comprises heavy and light chain variable regions, wherein the heavy chain variable region comprises an amino acid sequence which is at least 90% identical to the amino acid sequence selected from the group consisting of SEQ ID NOs: 4, 8, 10, 12, 14, 16, 18, 20, 22, 24, 26, 101 and 103; and wherein the light chain variable region comprises an amino acid sequence which is at least 90% identical to the amino acid sequence selected from the group consisting of SEQ ID NOs: 6, 28, 30, 32, 34, 36, 38, 40, 42, 44, 46 and 105.

In any of the foregoing or related embodiments, the isolated agonistic monoclonal antibody or antigen-binding fragment thereof comprises heavy and light chain variable regions comprising amino acid sequences at least 90% identical to the amino acid sequences selected from the group consisting of:
(a) SEQ ID NO: 4 and 6, respectively;
(b) SEQ ID NO: 4 and 28, respectively;
(c) SEQ ID NO: 4 and 30, respectively;
(d) SEQ ID NO: 4 and 32, respectively;
(e) SEQ ID NO: 4 and 34, respectively;
(f) SEQ ID NO: 4 and 36, respectively;
(g) SEQ ID NO: 4 and 38, respectively;
(h) SEQ ID NO: 4 and 40, respectively;
(i) SEQ ID NO: 4 and 42, respectively;
(j) SEQ ID NO: 4 and 44, respectively;
(k) SEQ ID NO: 4 and 46, respectively;
(l) SEQ ID NO: 8 and 6, respectively;
(m) SEQ ID NO: 10 and 6, respectively;
(n) SEQ ID NO: 12 and 6, respectively;
(o) SEQ ID NO: 14 and 6, respectively;
(p) SEQ ID NO: 16 and 6, respectively;
(q) SEQ ID NO: 18 and 6, respectively;
(r) SEQ ID NO: 20 and 6, respectively;
(s) SEQ ID NO: 22 and 6, respectively;
(t) SEQ ID NO: 24 and 6, respectively;
(u) SEQ ID NO: 26 and 6, respectively;
(v) SEQ ID NO: 101 and 6, respectively;
(w) SEQ ID NO: 103 and 6, respectively; and
(x) SEQ ID NO: 4 and 105, respectively.

In any of the foregoing or related embodiments, the isolated agonistic monoclonal antibody or antigen-binding fragment thereof comprises heavy and light chain sequences comprising amino acid sequences selected from the group consisting of:
(a) SEQ ID NOs: 129 and 133, respectively; and
(b) SEQ ID NOs: 131 and 133, respectively.

In any of the foregoing or related embodiments, the isolated agonistic monoclonal antibody or antigen-binding fragment thereof comprises heavy and light chain sequences having amino acid sequences set forth in SEQ ID NOs: 129 and 133, respectively.

In any of the foregoing or related embodiments, the isolated agonistic monoclonal antibody or antigen-binding fragment thereof comprises heavy and light chain sequences having amino acid sequences set forth in SEQ ID NOs: 131 and 133, respectively.

In any of the foregoing or related embodiments, the isolated agonistic monoclonal antibody or antigen-binding fragment thereof exhibits at least one or more of the following properties selected from the group consisting of:
(a) induces or enhances dimerization of CD137 trimers;
(b) induces or enhances multimerization of CD137 trimers;
(c) induces or enhances T cell activation;
(d) induces or enhances a cytotoxic T cell response;
(e) induces or enhances T cell proliferation;
(f) induces or enhances immune cell cytokine production; and
(g) any combination of properties (a)-(f).

In any of the foregoing or related embodiments, the isolated agonistic monoclonal antibody or antigen-binding fragment thereof exhibits at least one or more of the following properties relative to a reference antibody that binds human CD137, selected from the group consisting of:
(a) does not induce or enhance intrahepatic T cell activation;
(b) does not induce or enhance intrahepatic T cell proliferation;

(c) does not induce or enhance intrasplenic T cell activation;

(d) does not induce or enhance intrasplenic T cell proliferation;

(e) does not induce or enhance macrophage activation;

(f) does not induce or enhance macrophage differentiation;

(g) does not induce or enhance alanine aminotransferase (ALT) activity; and (h) any combination of properties (a)-(g).

In some embodiments, the reference antibody is urelumab.

In any of the foregoing or related embodiments, the properties of the isolated agonistic monoclonal antibody or antigen-binding fragment thereof are not dependent on Fc receptor binding. In some embodiments, the properties of the isolated agonistic monoclonal antibody or antigen-binding fragment thereof are enhanced by Fc receptor binding.

In any of the foregoing or related embodiments, the isolated agonistic monoclonal antibody or antigen-binding fragment thereof cross-reacts with cynomolgus CD137, mouse CD137, or both.

In any of the foregoing or related embodiments, the isolated agonistic monoclonal antibody is selected from the group consisting of an IgG1, an IgG2, an IgG3, an IgG4, an IgM, an IgA1, an IgA2, an IgD, and an IgE antibody. In some embodiments, the isolated agonistic monoclonal antibody is an IgG1 antibody or IgG4 antibody.

In any of the foregoing or related embodiments, the isolated agonistic monoclonal antibody comprises an IgG1 heavy chain constant region or an IgG4 heavy chain constant region. In some embodiments, the isolated agonistic monoclonal antibody comprises an IgG1 heavy chain constant region. In some embodiments, the IgG1 heavy chain constant region is a wild-type human IgG1 heavy chain constant region. In some embodiments, the IgG1 heavy chain constant region comprises an amino acid substitution relative to a wild-type human IgG1 heavy chain constant region. In some embodiments, the isolated agonistic monoclonal antibody comprises an IgG4 heavy chain constant region. In some embodiments, the IgG4 heavy chain constant region is a wild-type human IgG4 heavy chain constant region. In some embodiments, the IgG4 heavy chain constant region comprises an amino acid substitution relative to a wild-type human IgG4 heavy chain constant region. In some embodiments, the amino acid substitution is an amino acid substitution at position Ser228 according to EU numbering. In some embodiments, the amino acid substitution at position Ser228 is S228P. In some embodiments, the IgG4 heavy chain constant region comprises an amino acid substitution relative to a wild-type human IgG4 heavy chain constant region, wherein the amino acid substitution is an amino acid substitution at position Ser228 according to EU numbering, and wherein amino acid substitution at position Ser228 is S228P.

In any of the foregoing or related embodiments, the isolated agonistic monoclonal antibody or antigen-binding fragment thereof induces or enhances T cell activation in the subject. In some embodiments, the T cell activation occurs in a tumor microenvironment.

In any of the foregoing or related embodiments, the isolated agonistic monoclonal antibody or antigen-binding fragment thereof induces or enhances a cytotoxic T cell response in the subject. In some embodiments, the cytotoxic T cell response occurs in a tumor microenvironment.

In any of the foregoing or related embodiments, the isolated agonistic monoclonal antibody or antigen-binding portion thereof induces or enhances cytokine production mediated by human CD137. In some embodiments, the cytokine produced is IL-2, TNFα, IL-13, IFNγ, or combinations thereof. In some embodiments, the cytokine produced is IL-2. In some embodiments, the cytokine produced is TNFα. In some embodiments, the cytokine produced is IL-13. In some embodiments, the cytokine produced is IFNγ. In some embodiments, the cytokine produced is IL-2 and TNFα. In some embodiments, the cytokine produced is IL-2 and IL-13. In some aspects, the cytokine produced is IL-2 and IFNγ. In some embodiments, the cytokine produced is TNFα and IL-13. In some embodiments, the cytokine produced is TNFα and IFNγ. In some embodiments, the cytokine produced is IL-13 and IFNγ. In some aspects, the cytokine produced is IL-2, TNFα and IL-13. In some embodiments, the cytokine produced is IL-2, TNFα and IFNγ. In some aspects, the cytokine produced is IFNγ TNFα and IL-13. In other embodiments, cytokine production occurs in a tumor microenvironment. In yet other embodiments, cytokine production does not significantly occur in the spleen and/or liver of the subject.

In any of the foregoing or related embodiments, the isolated agonistic monoclonal antibody or antigen-binding portion thereof induces or enhances T cell proliferation in the subject. In some embodiments, the T cell proliferation occurs in a tumor microenvironment.

In any of the foregoing or related embodiments, the isolated agonistic monoclonal antibody or antigen-binding portion thereof reduces or inhibits tumor growth in the subject.

In any of the foregoing or related embodiments, the isolated agonistic monoclonal antibody or antigen-binding fragment thereof increases infiltration of immune cells into a tumor microenvironment in the subject. In some embodiments, the immune cells express CD45.

In any of the foregoing or related embodiments, the isolated agonistic monoclonal antibody or antigen-binding portion thereof reduces the quantity of T regulatory (Treg) cells in a tumor microenvironment in the subject. In some embodiments, the Treg cells express CD4, FOXP-3 and CD25.

In any of the foregoing or related embodiments, the isolated agonistic monoclonal antibody or antigen-binding portion thereof reduces the quantity of macrophages in a tumor microenvironment in the subject. In some embodiments, the macrophages express CD45 and CD11b.

In any of the foregoing or related embodiments, the isolated agonistic monoclonal antibody or antigen-binding portion thereof reduces T cell exhaustion in a tumor microenvironment in the subject. In some embodiments, reduction of T cell exhaustion comprises a decrease in expression of TIGIT, PD-1, LAG-3, or combinations thereof. In some embodiments, reduction of T cell exhaustion comprises a decrease in expression of a combination of TIGIT and PD-1.

In any of the foregoing or related embodiments, the cancer is selected from the group consisting of melanoma, glioma, renal, breast, hematological, and head and neck cancer. In some embodiments, the hematological cancer is a B cell lymphoma. In some embodiments, the cancer is breast cancer.

In any of the foregoing or related embodiments, the isolated agonistic monoclonal antibody or antigen-binding portion thereof induces an anti-tumor memory immune response in the subject.

In any of the foregoing or related embodiments, the isolated agonistic monoclonal antibody or antigen-binding portion thereof binds Fc gamma receptor.

In any of the foregoing or related embodiments, depletion of CD4+ T cells, CD8+ T cells, Natural Killer cells, or combinations thereof, reduces the efficacy of the isolated agonistic monoclonal antibody or antigen-binding portion thereof.

In some aspects, the disclosure provides a use of any one of the aforementioned compositions, and an optional pharmaceutically acceptable carrier, in the manufacture of a first medicament for treating cancer, delaying cancer progression, or enhancing a cancer-specific immune response in a subject in need thereof, wherein the first medicament comprises the agonistic monoclonal antibody that specifically binds human CD137 and an optional pharmaceutically acceptable carrier, and wherein the first medicament is administered in combination with a second medicament comprising the PD-1 antagonist, and optionally a pharmaceutically acceptable carrier.

In some aspects, the disclosure provides a kit comprising a first medicament comprising any one of the aforementioned compositions, and an optional pharmaceutically acceptable carrier, and a package insert comprising instructions for administration of the first medicament in combination with a second medicament comprising a composition comprising the PD-1 antagonist, and an optional pharmaceutically acceptable carrier, for treating cancer, delaying cancer progression, or enhancing a cancer-specific immune response in a subject in need thereof.

In some aspects, the disclosure provides a kit comprising a container comprising any one of the aforementioned compositions, and an optional pharmaceutically acceptable carrier, and a package insert comprising instructions for administration of the composition in combination with a second composition comprising the PD-1 antagonist, and an optional pharmaceutically acceptable carrier, for treating cancer, delaying cancer progression, or enhancing a cancer-specific immune response in a subject in need thereof.

BRIEF DESCRIPTION OF THE DRAWINGS

FIG. 3A shows the amino acid sequence of human CD137 (residues 24-159 of SEQ ID NO: 3) wherein residues comprising an epitope bound by mAb1, mAb4 or mAb5 are indicated in bold.

FIG. 5B is a graph showing the mean tumor volumes provided in FIG. 5A.

FIG. 5C is a Kaplan-Meier graph showing overall survival of mice with tumors after treatment with anti-CD137 antibodies.

FIG. 5D is a graph showing tumor volume in mice re-challenged with tumorigenic CT26 cells.

FIGS. 10A-10C show the in vivo anti-tumor efficacy of anti-CD137 antibodies administered at 150 µg/mouse. Individual tumor volumes are shown in 10A, mean tumor volumes are shown in 10B and percent survival is shown in 10C.

FIGS. 11A-11C show the in vivo anti-tumor efficacy of anti-CD137 antibodies administered at 20 µg/mouse. Individual tumor volumes are shown in 11A, mean tumor volumes are shown in 11B and percent survival is shown in 11C.

FIG. 13A shows mAb1 as an IgG4 isotype or an IgG4 aglycosylated isotype. Mean tumor volumes are shown on the top and individual tumor volumes are shown on the bottom. FIG. 13B shows mAb1 as an IgG4 isotype or an IgG1 aglycosylated isotype. Mean tumor volumes are shown on the top and individual tumor volumes are shown on the bottom.

FIGS. 14A-14D show the in vivo anti-tumor efficacy of anti-CD137 antibodies in mice with large established tumors (i.e., 500 mm$^3$) prior to receiving treatment. Individual tumor volumes are shown in 14A and 14D, mean tumor volumes are shown in 14B and percent survival is shown in 14C.

FIG. 20A is a graph showing percentage of CD8+ T cells in the liver after administration of the anti-CD137 antibodies. FIG. 20B is a graph showing alanine aminotransferase (ALT) activity in the plasma of mice administered anti-CD137 antibodies. FIG. 20C is a graph showing the levels of TNFα in the plasma of mice administered anti-CD137 antibodies.

FIG. 22A shows overall immune cell infiltration based on CD45 expression. FIG. 22B shows reduction in Treg cells as measured by FOXP-3 and CD25 expression. FIG. 22C shows reduction of T-cell exhaustion as measured by PD-1 and TIGIT expression. FIG. 22D shows reduction of tumor-associated macrophages as measured by F4/80 and CD11b expression.

FIGS. 27A-27C provide graphs depicting the dose-response of IFNγ production in a mixed lymphocyte reaction following treatment with anti-CD137 antibodies. An anti-PD1 antibody (KEYTRUDA; Merck) was used as a control.

DETAILED DESCRIPTION

Figure 1:
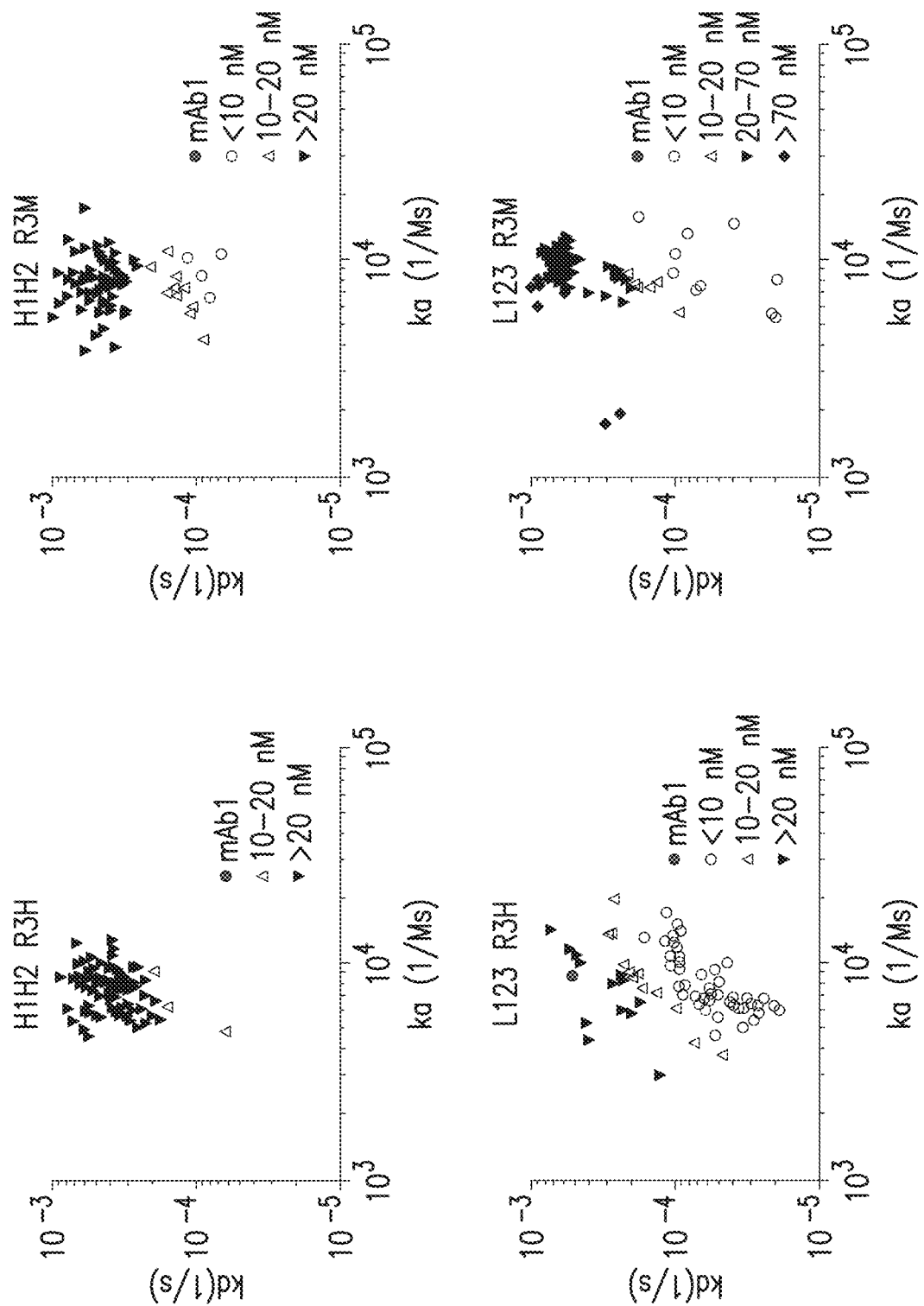
FIG. 1 provides graphs depicting the distribution of binding affinities of affinity matured clones of the parental anti-CD137 antibody mAb1.

Various diseases are characterized by the development of progressive immunosuppression in a patient. The presence of an impaired immune response in patients with malignancies has been particularly well-documented. Cancer patients exhibit a variety of altered immune functions, such as a decrease in delayed hypersensitivity, and decrease in lytic function and proliferation response of lymphocytes. Augmenting immune functions in cancer patients may have beneficial effects for tumor control.

Cancer therapy with agonist anti-CD137 antibodies has been shown to induce immune-mediated tumor rejections in mice, and analogous agents of this kind are currently being tested in cancer patients. Previous reports have indicated that administration of anti-CD137 antibodies can induce significant accumulations of polyclonal infiltrates of T lymphocytes in the liver (Dubrot et al., (2010) Cancer Immunology, Immunotherapy 59(8):1223-1233), suggestive of hepatic inflammation and the potential for drug-induced liver toxicity. A recent report on the clinical evaluation of an agonistic CD137 antibody (Urelumab, BMS-663513; Bristol-Myers Squibb) documented the observation of treatment-related adverse events in human subjects, including indications of severe hepatotoxicity (transaminitis) correlating with antibody dose (Segal et al., (2016) Clin Cancer Res 23(8):1929-1936).

The present disclosure provides, in some aspects, isolated monoclonal antibodies, or antigen-binding portions thereof, that specifically bind to an epitope of human CD137 and agonize human CD137. In some embodiments, the antibody or antigen-binding portion thereof competes with mAb1 for binding to the epitope of human CD137. In some embodiments, the anti-CD137 agonist antibodies of the disclosure induce cytokine production and expansion of CD8+ T cells in the tumor microenvironment, and protective anti-tumor immunity in vivo with a concomitant reduction in the potential for toxicity-related events, as compared to the anti-mouse CD137 3H3 antibody (Melero et al. (1997) Nature Medicine 3(6):682-685; Uno et al. (2006) Nature Medicine 12(6):693-696) and to at least two anti-human CD137 antibodies in clinical development (BMS-663513/Urelumab, Bristol-Meyers Squibb, and PF-05082566/Utomilumab, Pfizer).

Moreover, tumor survival and proliferation is sustained by tumor-mediated immune checkpoint modulation for several cancers. Disruption of this anti-cancer immune system function has been a recent development in cancer therapy. Accordingly, provided herein are methods and uses of anti-CD137 agonistic antibodies with antagonists of the PD-1/PD-L1 signaling pathway, such as antibody antagonists of the PD-1/PD-L1 signaling pathway.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "agonist" refers to any molecule that partially or fully promotes, induces, increases, and/or activates a biological activity of a native polypeptide disclosed herein (e.g., CD137). Suitable agonist molecules specifically include agonist antibodies or antibody fragments, fragments or amino acid sequence variants of native polypeptides, peptides, antisense oligonucleotides, small organic molecules, etc. In some embodiments, activation in the presence of the agonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Also disclosed herein, are methods of identifying agonists suitable for use in the methods of the disclosure. For example, these methods include, but are not limited to, binding assays such as enzyme-linked immuno-absorbent assay (ELISA), Forte Bio© systems, and radioimmunoassay (RIA). These assays determine the ability of an agonist to bind the polypeptide of interest (e.g., a receptor or ligand, e.g., CD137) and therefore indicate the ability of the agonist to promote, increase or activate the activity of the polypeptide. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response.

As used herein, the term "alanine scanning" refers to a technique used to determine the contribution of a specific wild-type residue to the stability or function(s) (e.g., binding affinity) of a given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

The term "ameliorating" refers to any therapeutically beneficial result in the treatment of a disease state, e.g., cancer, including prophylaxis, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. As used here, a "polar amino acid" refers to an amino acid comprising a side chain that prefers to reside in an aqueous environment. In some embodiments, a polar amino acid is selected from the group consisting of: arginine, asparagine, aspartic acid, glutamic acid, glutamine, histidine, lysine, serine, threonine, and tyrosine. Polar amino acids can be positive, negatively or neutrally charged. As used herein, a "non-polar amino acid" refers to an amino acid selected from the group consisting of: alanine, cysteine, glycine, isoleucine, leucine, methionine, phenylalanine, proline, tryptophan and valine.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g., insertion of about three to about five or even up to about ten, fifteen, or twenty amino acid residues. The inserted residue(s) can be naturally occurring or non-naturally occurring as disclosed above. An "amino acid deletion" refers to the removal of at least one amino acid residue from a predetermined amino acid sequence.

As used herein, the term "amount" or "level" refers to a detectable quantity, level or abundance of a substance (e.g., a protein). When referring to a polypeptide, such as those described herein, the terms "level of expression" or "expression level" in general are used interchangeably and generally refer to a detectable amount of a polypeptide in a biological sample (e.g., on the surface of a cell).

As used herein, the term "angiogenesis" or "neovascularization" refers to the process by which new blood vessels develop from pre-existing vessels (Varner et al., (1999) *Angiogen.* 3:53-60; Mousa et al. (2000) *Angiogen. Stim. Inhib.* 35:42-44; Kim et al., (2000) *Amer. J. Path.* 156:1345-1362; Kim et al., (2000) *J. Biol. Chem.* 275:33920-33928; Kumar et al. (2000) *Angiogenesis: From Molecular to Integrative Pharm.* 169-180). Endothelial cells from pre-existing blood vessels or from circulating endothelial stem cells (Takahashi et al., (1995) *Nat. Med.* 5:434-438: Isner et al., (1999) *J. Clin. Invest.* 103:1231-1236) become activated to migrate, proliferate, and differentiate into structures with lumens, forming new blood vessels, in response to growth factor or hormonal cues, or hypoxic or ischemic conditions. During ischemia, such as occurs in cancer, the need to increase oxygenation and delivery of nutrients apparently induces the secretion of angiogenic factors by the affected tissue; these factors stimulate new blood vessel formation. Several additional terms are related to angiogenesis.

As used herein, the term "antagonist" refers to any molecule that partially or fully blocks, inhibits, or neutralizes a biological activity of a native polypeptide disclosed herein (e.g., PD1 and/or PD-L1 and/or PD-L2). Suitable antagonist molecules specifically include antagonist antibodies or antibody fragments, fragments or amino acid sequence variants of native polypeptides, peptides, antisense oligonucleotides, small organic molecules, etc. In some embodiments, inhibition in the presence of the antagonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions.

Also disclosed herein, are methods of identifying antagonists suitable for use in the methods of the disclosure. For example, these methods include, but are not limited to, binding assays such as enzyme-linked immuno-absorbent assay (ELISA), Forte Bio© systems, and radioimmunoassay (RIA). These assays determine the ability of an antagonist to bind the polypeptide of interest (e.g., a receptor or ligand) and therefore indicate the ability of the antagonist to inhibit, neutralize or block the activity of the polypeptide. Efficacy of an antagonist can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the term "anti-CD137 agonist antibody" (used interchangeably with the term "anti-CD137 antibody") refers to an antibody that specifically binds to CD137 and partially or fully promotes, induces, increases, and/or activates CD137 biological activity, response, and/or downstream pathway(s) mediated by CD137 signaling or other CD137-mediated function. In some embodiments, an anti-CD137 agonist antibody binds to CD137 and allows binding of CD137L. In some embodiments, an anti-CD137 agonist antibody binds to CD137 and induces multimerization of CD137. In some embodiments, an anti-CD137 agonist antibody binds to CD137 and induces the dimerization of CD137 trimers. In some embodiments, an anti-CD137 agonist antibody binds to CD137 and induces the multimerization of CD137 trimers. Examples of anti-CD137 agonist antibodies are provided herein. Methods for detecting formation of a trimer:trimer complex are known to those of skill in the art. For example, electron microscopy has been shown to detect such complexes, see, e.g., Won, E. The Journal of Biological Chemistry, Vol. 285 (12): 9202-9210 (2010).

As used herein, the term "anti-CD137 mAb1" (used interchangeably with "mAb1") refers to an exemplary anti-CD137 agonist antibody that comprises the variable heavy chain ($V_H$) amino acid sequence:

(SEQ ID NO: 4)
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

DSPFLLDDYYYYYMDVWGKGTTVTVSS, and the variable light chain ($V_L$) amino acid sequence:

(SEQ ID NO: 6)
DIQMTQSPSSVSASVGDRVTITCRASQGISSWLAWYQQKPGKAPKLLIY

AASSLQSGVPSRFSGSGSGTDFTLTISSLQPEDFATYYCQQGHLFPITF

GGGTKVEIK.

As used herein, the term "anti-CD137 mAb8" (used interchangeably with "mAb8") refers to an exemplary anti-CD137 agonist antibody that comprises the variable heavy chain (($V_H$) amino acid sequence:

(SEQ ID NO: 101)
EVQLLESGGGLVQPGGSLRLSCAASGFTFRNYAMSWVRQAPGKGLEWVS

AISGSGDTTYYADSVKGRFTISRDNSKNTLYLQMNSLRAEDTAVYYCAK

DSPFLLDDYYYYYMDVWGKGTTVTVSS;

and the variable light chain ($V_L$) amino acid sequence:

(SEQ ID NO: 6)
DIQMTQSPSSVSASVGDRVTITCRASQGISSWLAWYQQKPGKAPKLLIY

AASSLQSGVPSRFSGSGSGTDFTLTISSLQPEDFATYYCQQGHLFPITF

GGGTKVEIK.

As used herein, the term "anti-CD137 mAb10" (used interchangeably with "mAb10") refers to an exemplary anti-CD137 agonist antibody that comprises the variable heavy chain (($V_H$) amino acid sequence:

(SEQ ID NO: 26)
EVQLLESGGGLVQPGGSLRLSCAASGFTFYGYAMSWVRQAPGKGLEWVA

AISGSGDSTYYADSVKGRFTISRDNSKNTLYLQMNSLRAEDTAVYYCAK

DSPFLLDDYYYYYMDVWGKGTTVTVSS;

and the variable light chain ($V_L$) amino acid sequence:

(SEQ ID NO: 6)
DIQMTQSPSSVSASVGDRVTITCRASQGISSWLAWYQQKPGKAPKLLIY

AASSLQSGVPSRFSGSGSGTDFTLTISSLQPEDFATYYCQQGHLFPITF

GGGTKVEIK.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the terms "antibody fragment," "antigen-binding fragment," "antigen-binding portion," or similar terms, refer to a fragment of an antibody that retains the ability to bind to a target antigen (e.g., CD137, PD-1 or PD-L1) and inhibit the activity of the target antigen. Such fragments include, e.g., a single chain antibody, a single chain Fv fragment (scFv), an Fd fragment, a Fab fragment, a Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al., (2001) *J. Immunol. Methods* 248(1):47-66; Hudson and Kortt, (1999) *J. Immunol. Methods* 231(1):177-189; Poljak, (1994) *Structure* 2(12):1121-1123; Rondon and Marasco, (1997) *Annu. Rev. Microbiol.* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al., (2001) *Trends Biochem. Sci.* 26:230-235; Nuttall et al., (2000) *Curr. Pharm. Biotech.* 1:253-263; Reichmann et al., (1999) *J. Immunol. Meth.* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

In some embodiment, an antigen-binding fragment includes the variable region of a heavy chain polypeptide and the variable region of a light chain polypeptide. In some embodiments, an antigen-binding fragment described herein comprises the CDRs of the light chain and heavy chain polypeptide of an antibody.

The term "antigen presenting cell" or "APC" is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "apoptosis" refers to the process of programmed cell death that occurs in multicellular organisms (e.g. humans). The highly-regulated biochemical and molecular events that result in apoptosis can lead to observable and characteristic morphological changes to a cell, including membrane blebbing, cell volume shrinkage, chromosomal DNA condensation and fragmentation, and mRNA decay. A common method to identify cells, including T cells, undergoing apoptosis is to expose cells to a fluorophore-conjugated protein (Annexin V). Annexin V is commonly used to detect apoptotic cells by its ability to bind to phosphatidylserine on the outer leaflet of the plasma membrane, which is an early indicator that the cell is undergoing the process of apoptosis.

As used herein, the term "binds to immobilized CD137," refers to the ability of a human antibody of the disclosure to bind to CD137, for example, expressed on the surface of a cell or which is attached to a solid support.

As used herein, the term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992) *J. Immunol.* 148:1547-1553.

Traditionally, the recombinant production of bispecific antibodies is based on the co-expression of two immunoglobulin heavy-chain/light-chain pairs, where the two heavy chain/light-chain pairs have different specificities (Milstein and Cuello, (1983) *Nature* 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. For further details of illustrative currently known methods for generating bispecific antibodies see, e.g., Suresh et al., (1986) *Methods Enzymol.* 121:210; PCT Publication No. WO 96/27011; Brennan et al., (1985) *Science* 229:81; Shalaby et al., *J. Exp. Med.* (1992) 175:217-225; Kostelny et al., (1992) *J. Immunol.* 148(5): 1547-1553; Hollinger et al., (1993) *Proc. Natl. Acad. Sci. USA* 90:6444-6448; Gruber et al., (1994) *J. Immunol.* 152: 5368; and Tutt et al., (1991) *J. Immunol.* 147:60. Bispecific antibodies also include cross-linked or heteroconjugate antibodies. Heteroconjugate antibodies can be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins can be linked to the Fab' portions of two different antibodies by gene fusion. The antibody homodimers can be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) J Immunol 152:5368. Alternatively, the antibodies can be "linear antibodies" as described in, e.g., Zapata et al. (1995) Protein Eng. 8(10):1057-1062. Briefly, these antibodies comprise a pair of tandem Fd segments (VH-CH1-VH-CH1) which form a pair of antigen-binding regions. Linear antibodies can be bispecific or monospecific.

Antibodies with more than two valencies (e.g., trispecific antibodies) are contemplated and described in, e.g., Tutt et al. (1991) J Immunol 147:60.

The disclosure also embraces variant forms of multi-specific antibodies such as the dual variable domain immunoglobulin (DVD-Ig) molecules described in Wu et al. (2007) Nat Biotechnol 25(11): 1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. Methods for making DVD-Ig molecules from two parent antibodies are further described in, e.g., PCT Publication Nos. WO 08/024188 and WO 07/024715. In some embodiments, the bispecific antibody is a Fabs-in-Tandem immunoglobulin, in which the light chain variable region with a second specificity is fused to the heavy chain variable region of a whole antibody. Such antibodies are described in, e.g., International Patent Application Publication No. WO 2015/103072.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, the term "cancer-specific immune response" refers to the immune response induced by the presence of tumors, cancer cells, or cancer antigens. In certain embodiments, the response includes the proliferation of cancer antigen specific lymphocytes. In certain embodiments, the response includes expression and upregulation of antibodies and T-cell receptors and the formation and release of lymphokines, chemokines, and cytokines. Both innate and acquired immune systems interact to initiate antigenic responses against the tumors, cancer cells, or cancer antigens. In certain embodiments, the cancer-specific immune response is a T cell response.

The term "carcinoma" is art recognized and refers to malignancies of epithelial or endocrine tissues, including respiratory system carcinomas, gastrointestinal system carcinomas, genitourinary system carcinomas, testicular carcinomas, breast carcinomas, prostatic carcinomas, endocrine system carcinomas, and melanomas. The anti-CD137 antibodies and PD-1 antagonists described herein can be used to treat patients who have, who are suspected of having, or who may be at high risk for developing any type of cancer, including renal carcinoma or melanoma. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein the term "compete", when used in the context of antigen-binding proteins (e.g., immunoglobulins, antibodies, or antigen-binding fragments thereof) that compete for binding to the same epitope, refers to a interaction between antigen-binding proteins as determined by an assay (e.g., a competitive binding assay; a cross-blocking assay), wherein a test antigen-binding protein (e.g., a test antibody) inhibits (e.g., reduces or blocks) specific binding of a reference antigen-binding protein (e.g., a reference antibody, such as mAb1) to a common antigen (e.g., CD137 or a fragment thereof). In some embodiments, the antibodies described herein cross compete with mAb1 (i.e., an antibody comprising the heavy and light chain variable sequences of SEQ ID NOs: 4 and 6, respectively), mab8 (i.e., an antibody comprising the heavy and light chain variable sequences of SEQ ID NOs: 101 and 6, respectively) or mAb10 (i.e., an antibody comprising the heavy and light chain variable sequences of SEQ ID NOs: 26 and 6, respectively).

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide can have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant has an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived there from. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from a sequence set forth in Table 3 or Table 4. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from a sequence set forth in Table 3 or Table 4. In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from a sequence set forth in Table 3 or Table 4. In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from a sequence set forth in Table 3 or Table 4.

In certain embodiments, the antibodies of the disclosure are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like. In certain embodiments, the nucleotide sequence of the invention comprises, consists of, or consists essentially of, a nucleotide sequence selected from a sequence set forth in Table 3 or Table 4. In certain embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence selected from a sequence set forth in Table 3 or Table 4. In certain embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence selected from a sequence set forth in Table 3 or Table 4. In certain embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence selected from a sequence set forth in Table 3 or Table 4.

It will also be understood by one of ordinary skill in the art that the antibodies suitable for use in the methods disclosed herein can be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues can be made. Mutations can be introduced by standard techniques, such as site-directed mutagenesis and PCR-mediated mutagenesis.

The antibodies suitable for use in the methods disclosed herein can, in some embodiments, comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations can be introduced randomly along all or part of a coding sequence, such as by saturation mutagenesis, and the resultant mutants can be incorporated into binding polypeptides of the invention and screened for their ability to bind to the desired target.

As used herein, the term antigen "cross-presentation" refers to presentation of exogenous protein antigens to T cells via MHC class I and class II molecules on APCs.

As used herein, the term "cross-reacts" refers to the ability of an antibody of the disclosure to bind to CD137, PD-1, or PD-L1 from a different species. For example, an antibody of the present disclosure which binds human CD137, PD-1, or PD-L1 can, in some embodiments, also bind another species of CD137, PD-1, or PD-L1. As used herein, cross-reactivity is measured by detecting a specific reactivity with purified antigen in binding assays (e.g., SPR, ELISA) or binding to, or otherwise functionally interacting with, cells physiologically expressing CD137, PD-1 or PD-L1. Methods for determining cross-reactivity include standard binding assays as described herein, for example, by BIACORE™ surface plasmon resonance (SPR) analysis using a BIACORE™ 2000 SPR instrument (Biacore AB, Uppsala, Sweden), or flow cytometric techniques.

As used herein, the term "cytotoxic T lymphocyte (CTL) response" refers to an immune response induced by cytotoxic T cells. CTL responses are mediated primarily by $CD8^+$ T cells.

As used herein, the term "dimerization" refers to the formation of a macromolecular complex by two, usually non-covalently bound, macromolecules, such as proteins or multimers of proteins. Homodimerization refers to the process of dimerization when the macromolecules (e.g., proteins) are identical in nature. Heterodimerization refers to the process of dimerization when the macromolecules (e.g., proteins) are non-identical in nature. Methods for determining dimerization are known to those of skill in the art. For example, such methods include, but are not limited to, yeast two-hybrid assay, fluorescence resonance energy transfer (FRET), bioluminescence resonance energy transfer (BRET), protein mass spectrometry, evanescent wave methods, size exclusion chromatography, analytical ultracentrifugation, scattering techniques, NMR spectroscopy, isothermal titration calorimetry, fluorescence anisotropy, fluorescence correlation spectroscopy (FCS), fluorescence recovery after photobleaching (FRAP), proximity imaging (PRIM) and bimolecular fluorescence complementation (BiFC) (see e.g., Gell D. A., Grant R. P., Mackay J. P. (2012) The Detection and Quantitation of Protein Oligomerization. In: Matthews J. M. (eds) Protein Dimerization and Oligomerization in Biology. Advances in Experimental Medicine and Biology, vol 747. Springer, New York, N.Y.; and Xie, Q. et al. Methods Mol Biol, 2011; 680: 3-28).

As used herein, the term "dimerization of CD137" refers to the dimerization of two CD137 trimers. In some embodiments, the anti-CD137 agonist antibodies described herein induce or enhance dimerization of CD137. In some embodiments, the anti-CD137 agonist antibodies described herein induce or enhance dimerization of CD137 relative to the amount of dimerization in the absence of an anti-CD137 agonist antibody. In some embodiments, the anti-CD137 agonist antibodies described herein induce or enhance dimerization of CD137 relative to the amount of dimerization in the presence of a reference anti-CD137 agonist antibody. In some embodiments, dimerization is increased by at least 5%, 10%, 15%, 20%, 25%, 30%, 35%, 40%, 45%, 50%, 55%, 60%, 65%, 70%, 75%, 80%, 85%, 90%, 95%, or 100%.

As used herein, the term "$EC_{50}$" refers to the concentration of an antibody or an antigen-binding portion thereof, which induces a response, either in an in vitro or an in vivo assay, which is 50% of the maximal response, i.e., halfway between the maximal response and the baseline.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a determinant or site on an antigen (e.g., CD137) to which an antigen-binding protein (e.g., an immunoglobulin, antibody, or antigen-binding fragment) specifically binds. The epitopes of protein antigens can be demarcated into "linear epitopes" and "conformational epitopes". As used herein, the term "linear epitope" refers to an epitope formed from a contiguous, linear sequence of linked amino acids. Linear epitopes of protein antigens are typically retained upon exposure to chemical denaturants (e.g., acids, bases, solvents, cross-linking reagents, chaotropic agents, disulfide bond reducing agents) or physical denaturants (e.g. thermal heat, radioactivity, or mechanical shear or stress). In some embodiments, an epitope is non-linear, also referred to as an interrupted epitope. As used herein, the term "conformational epitope" or "non-linear epitope" refers to an epitope formed from noncontiguous amino acids juxtaposed by tertiary folding of a polypeptide. Conformational epitopes are typically lost upon treatment with denaturants. An epitope typically includes at least 3, 4, 5, 6, 7, 8, 9, 10, 11, 12, 13, 14 or 15 amino acids in a unique spatial conformation. In some embodiments, an epitope includes fewer than 25, 24, 23, 22, 21, 20, 19, 18, 17, 16, 15, 14, 13, 12, 11, 10, 9, 8, 7, 6 or 5 amino acids in a unique spatial conformation. Generally, an antibody, or antigen-binding fragment thereof, specific for a particular target molecule will preferentially recognize and bind to a specific epitope on the target molecule within a complex mixture of proteins and/or macromolecules. In some embodiments, an epitope does not include all amino acids of the extracellular domain of human CD137.

Also encompassed by the present disclosure are antibodies that bind to an epitope on CD137 which comprises all or a portion of an epitope recognized by the particular antibodies described herein (e.g., the same or an overlapping region or a region between or spanning the region).

As used herein, the term "epitope mapping" refers to a process or method of identifying the binding site, or epitope, of an antibody, or antigen-binding fragment thereof, on its target protein antigen. Epitope mapping methods and techniques are provided herein.

As used herein, the term "CD137" refers to a specific member of the tumor necrosis factor receptor (TNFR) family of transmembrane proteins. Alternative names and acronyms for CD137 in the art include "tumor necrosis factor receptor superfamily member 9" (TNFRSF9), 4-1BB and "induced by lymphocyte activation" (ILA) (Alderson et al., (1994) Eur J Immunol 24(9):2219-2227; Schwarz et al., (1993) Gene 134(2):295-298). An exemplary amino acid sequence of full-length human CD137, including leader, transmembrane, and cytoplasmic domains is set forth in

```
Table 4 (SEQ ID NO: 3) and here:
MGNSCYNIVATLLLVLNFERTRSLQDPCSNCPAGTFCDNNRNQICSPCP

PNSFSSAGGQRTCDICRQCKGVFRTRKECSSTSNAECDCTPGFHCLGAG

CSMCEQDCKQGQELTKKGCKDCCFGTFNDQKRGICRPWTNCSLDGKSVL

VNGTKERDVVCGPSPADLSPGASSVTPPAPAREPGHSPQUISFFLALTS

TALLFLLFFLTLRFSVVKRGRKKLLYIFKQPFMRPVQTTQEEDGCSCRF

PEEEEGGCEL.
```

As used herein, the term "CD137L" or "CD137 ligand" refers to a member of the tumor necrosis factor (TNF) family of transmembrane proteins. Alternative names and acronyms for CD137L in the art include "tumor necrosis factor superfamily member 9" (TNFSF9) and 4-1BB ligand (4-1BBL) (Alderson et al., (1994) Eur J Immunol 24(9):2219-2227). An exemplary amino acid sequence of full-length CD137L is set forth in Table 4 (SEQ ID NO: 97).

As used herein, the terms "Fc-mediated effector functions" or "Fc effector functions" refer to the biological activities of an antibody other than the antibody's primary function and purpose. For example, the effector functions of a therapeutic agnostic antibody are the biological activities other than the activation of the target protein or pathway. Examples of antibody effect functions include C1q binding and complement dependent cytotoxicity; Fc receptor binding; antibody-dependent cell-mediated cytotoxicity (ADCC); phagocytosis; antibody-dependent cell phagocytosis (ADCP); down regulation of cell surface receptors (e.g., B cell receptor); lack of activation of platelets that express Fc receptor; and B cell activation. Many effector functions begin with Fc binding to an Fcγ receptor.

As used herein, the term "Fc receptor" refers to a polypeptide found on the surface of immune effector cells, which is bound by the Fc region of an antibody. In some embodiments, the Fc receptor is an Fcγ receptor. There are three subclasses of Fcγ receptors, FcγRI (CD64), FcγRII (CD32) and FγcRIII (CD16). All four IgG isotypes (IgG1, IgG2, IgG3 and IgG4) bind and activate Fe receptors FcγRI, FcγRIIA and FcγRIIIA. FcγRIIB is an inhibitory receptor, and therefore antibody binding to this receptor does not activate complement and cellular responses. FcγRI is a high affinity receptor that binds to IgG in monomeric form, whereas FcγRIIA and FcγRIIA are low affinity receptors that bind IgG only in multimeric form and have slightly lower affinity. The binding of an antibody to an Fc receptor and/or C1q is governed by specific residues or domains within the Fc regions. Binding also depends on residues located within the hinge region and within the CH2 portion of the antibody. In some embodiments, the agonistic and/or therapeutic activity of the antibodies described herein is dependent on binding of the Fc region to the Fc receptor (e.g., FcγR). In some embodiments, the agonistic and/or therapeutic activity of the antibodies described herein is enhanced by binding of the Fc region to the Fc receptor (e.g., FcγR).

As used herein, the term "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

As used herein, the term "hematological cancer" includes a lymphoma, leukemia, mycloma or a lymphoid malignancy, as well as a cancer of the spleen and lymph nodes. Exemplary lymphomas include both B cell lymphomas (a B-cell hematological cancer) and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-associated cancers are encompassed by the term hematological malignancy.

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) *Nature* 368(6474): 856-859); Lonberg, (1994) *Handbook of Experimental Pharmacology* 113: 49-101; Lonberg & Huszar, (1995) *Intern. Rev. Immunol.* 13:65-93, and Harding & Lonberg, (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e. humanized antibodies).

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The terms "inducing an immune response" and "enhancing an immune response" are used interchangeably and refer to the stimulation of an immune response (i.e., either passive or adaptive) to a particular antigen. The term "induce" as used with respect to inducing CDC or ADCC refer to the stimulation of particular direct cell killing mechanisms.

As used herein, the terms "inhibits", "blocks" or "reduces" (e.g., when referring to inhibition/blocking of the PD-1/PD-L1 signaling pathway) are used interchangeably and encompass both partial and complete inhibition/blocking as well as direct and allosteric inhibition/blocking. As used herein, "inhibition", "blocking" or "reducing" are also intended to include any measurable decrease in biological function and/or activity of a target (e.g., PD-1, PD-L1). For example, when an antibody or an antigen-binding fragment thereof (e.g., an anti-PD-1 or an anti-PD-L1 antibody) is in contact with the target as compared to the target not in contact with an antibody or antigen-binding fragment. In some embodiments, an antibody or antigen-binding fragment thereof, that targets PD-1 or PD-L1, inhibits or reduces PD-1 or PD-L1 function and/or activity in a given system by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or 100%.

As used herein, the term "inhibits growth" (e.g., referring to cells) is intended to include any measurable decrease in the growth of a cell, e.g., the inhibition of growth of a cell by at least about 10%, about 20%, about 30%, about 40%, about 50%, about 60%, 70%, about 80%, about 90%, about 99%, or 100%.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-CD137 antibody and/or PD-1 antagonist).

The term "in vivo" refers to processes that occur in a living organism.

As used herein, the terms "induces", "increases", "enhances", or "stimulates" (e.g., when referring to an increase in CD137 activity) are used interchangeably and encompass both increases in activity and de novo activity (e.g., inducing activity from a previously undetectable level). The enhancement of CD137 increases the normal level or type of activity that occurs from CD137 in a given system in the absence of an anti-CD137 antibody or fragment thereof as the enhancer. Enhancement, induction, or stimulation are also intended to include any measurable increase in CD137 activity (or effect on a given cell type) when in contact with an anti-CD137 antibody as compared to CD137 not in contact with an anti-CD137 antibody, e.g., enhances/increases CD137 activity in a given system (CD137-mediated increases in T cell activity) by at least about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or 100%, or at least about 1.5-fold, 2-fold, 3-fold, 4-fold, 5-fold, 10-fold, 20-fold, 50-fold, and the like.

As used herein, the term "isolated antibody" is intended to refer to an antibody which is substantially free of other antibodies having different antigenic specificities (e.g., an isolated antibody that specifically binds to human CD137, PD-1, or PD-L1 is substantially free of antibodies that specifically bind antigens other than CD137, PD-1, or PD-L1). An isolated antibody that specifically binds to an epitope may, however, have cross-reactivity to other CD137, PD-A or PD-L1 proteins from different species. However, the antibody continues to display specific binding to human CD137, PD-1, or PD-L1 in a specific binding assay as described herein. In addition, an isolated antibody is typically substantially free of other cellular material and/or chemicals. In some embodiments, a combination of "isolated" antibodies having different CD137, PD-1, or PD-L1 specificities is combined in a well-defined composition.

As used herein, the term "isolated nucleic acid molecule" refers to nucleic acids encoding antibodies or antibody portions (e.g., $V_H$, $V_L$, CDR3) that bind to CD137, PD-1, or PD-L1, is intended to refer to a nucleic acid molecule in which the nucleotide sequences encoding the antibody or antibody portion are free of other nucleotide sequences encoding antibodies or antibody portions that bind antigens other than CD137, PD-1, or PD-L1, which other sequences may naturally flank the nucleic acid in human genomic DNA. For example, a sequence selected from a sequence set forth in Table 3 or Table 4 corresponds to the nucleotide sequences comprising the heavy chain ($V_H$) and light chain ($V_L$) variable regions of anti-CD137, PD-1, or PD-L1 monoclonal antibodies described herein.

As used herein, "isotype" refers to the antibody class (e.g., IgM or IgG1) that is encoded by heavy chain constant region genes. In some embodiments, a human monoclonal antibody of the disclosure is of the IgG1 isotype. In some embodiments, a human monoclonal antibody of the disclosure is of the IgG1 isotype and comprises a mutation. In some embodiments, a human monoclonal antibody of the disclosure is of the IgG2 isotype. In some embodiments, a human monoclonal antibody of the disclosure is of the IgG3 isotype. In some embodiments, a human monoclonal antibody of the disclosure is of the IgG4 isotype. In some embodiments, a human monoclonal antibody of the disclosure is of the IgG4 isotype and comprises a mutation. In some embodiments, the mutation is a substitution at Ser228 according to EU numbering. In some embodiments, the substitution at Ser228 is S228P.

As used herein, the term "isotype switching" refers to the phenomenon by which the class, or isotype, of an antibody changes from one Ig class to one of the other Ig classes.

As used herein the term "KD" or "$K_D$" refers to the equilibrium dissociation constant of a binding reaction between an antibody and an antigen. The value of $K_D$ is a numeric representation of the ratio of the antibody off-rate constant (kd) to the antibody on-rate constant (ka). The value of $K_D$ is inversely related to the binding affinity of an antibody to an antigen. The smaller the $K_D$ value the greater the affinity of the antibody for its antigen. Affinity is the strength of binding of a single molecule to its ligand and is typically measured and reported by the equilibrium dissociation constant ($K_D$), which is used to evaluate and rank order strengths of bimolecular interactions.

As used herein, the term "kd" or "$k_d$" (alternatively "koff" or "$k_{off}$") is intended to refer to the off-rate constant for the dissociation of an antibody from an antibody/antigen complex. The value of kd is a numeric representation of the fraction of complexes that decay or dissociate per second, and is expressed in units sec.

As used herein, the term "ka" or "ka" (alternatively "kon" or "$k_{on}$") is intended to refer to the on-rate constant for the association of an antibody with an antigen. The value of ka is a numeric representation of the number of antibody/antigen complexes formed per second in a 1 molar (1M) solution of antibody and antigen, and is expressed in units $M^{-1}$ $sec^{-1}$.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, "MHC molecules" refers to two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the term "monoclonal antibody" refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "multimerization" refers to the formation of a macromolecular complex comprising more than two macromolecules such as proteins, typically bound by non-covalent interactions. Methods for determining multimerization are known to those of skill in the art and are described supra for dimerization. In some embodiments, the anti-CD137 agonist antibodies described herein induce or enhance multimerization of CD137. In some embodiments, the anti-CD137 agonist antibodies described herein induce or enhance multimerization of CD137 relative to the amount of multimerization in the absence of an anti-CD137 agonist antibody. In some embodiments, the anti-CD137 agonist antibodies described herein induce or enhance multimerization of CD137 relative to the amount of multimerization in the presence of a reference anti-CD137 agonist antibody. In some embodiments, multimerization is increased by at least 5%, 10%, 15%, 20%, 25%, 30%, 35%, 40%, 45%, 50%, 55%, 60%, 65%, 70%, 75%, 80%, 85%, 90%, 95%, or 100%.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, the term "paratope", also "antigen-binding site" refers to a portion of an antibody, or antigen-binding fragment thereof, which recognizes and binds to an epitope on an antigen, comprising the set of complementarity determining regions (CDRs) located within variable heavy and light chains.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

As used herein, the term "PD-1 antagonist" refers to any chemical compound or biological molecule that inhibits the PD-1 signaling pathway or that otherwise inhibits PD-1 function in a cell (e.g., an immune cell). In some embodiments, a PD-1 antagonist blocks binding of PD-L1 to PD-1 and/or PD-L2 to PD-1. In some embodiments, the PD-1 antagonist specifically binds PD-1. In some embodiments, the PD-1 antagonist specifically binds PD-L1. In some embodiments, the PD-1 antagonist is an isolated monoclonal antibody that specifically binds human PD-1, or an antigen-binding fragment thereof. Exemplary PD-1 antagonists comprising anti-PD-1 antibodies, or antigen-binding fragments thereof, are described herein. In some embodiments, the PD-1 antagonist is an isolated monoclonal antibody that specifically binds human PD-L1, or an antigen-binding fragment thereof. Exemplary PD-1 antagonists comprising anti-PD-L1 antibodies, or antigen-binding fragments thereof, are described herein.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide," and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "Programmed Cell Death Protein 1" or "PD-1" refers to the Programmed Cell Death Protein 1 polypeptide, an immune-inhibitory receptor belonging to the CD28 family and is encoded by the PDCD1 gene in humans. Alternative names or synonyms for PD-1 include: PDCD1, PD1, CD279, and SLEB2. PD-1 is expressed predominantly on previously activated T cells, B cells, and myeloid cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773 (SEQ ID NO: 134).

As used herein, the term "Programmed Death Ligand-1" or "PD-L1" is one of two cell surface glycoprotein ligands for PD-1 (the other being PD-L2) that downregulates T cell activation and cytokine secretion upon binding to PD-1. Alternative names and synonyms for PD-L1 include: PDCD1L1, PDL1, B7H1, B7-4, CD274, and B7-H. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7 (SEQ ID NO: 135).

As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "rearranged" refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

As used herein, the term "receptor clustering" refers to a cellular process that results in grouping or local accumulation of a set of receptors at a particular cellular location, often to induce or amplify a signaling response. Many protein receptors bind cognate ligands and cluster, i.e., form dimers, trimers, oligomers or multimers, upon binding their cognate ligands. For example, the PDGF receptor and TNF receptor superfamily members form dimers and trimers upon ligand binding, respectively. Cognate ligand-induced clustering (e.g., dimerization, multimerization) induces signal transduction through the receptor. Accordingly, the antibodies, or antigen-binding fragments thereof, of the present disclosure can activate a receptor by binding to more than one receptor and induce or stabilize dimerization, trimerization, and/or multimerization with or without cognate ligand binding.

Receptor clustering and multimerization is needed for TNFR signaling (Wajant (2015) Cell Death Differ 22(11): 1727-1741), and in particular for TNFRSF activation. 4-1BB (CD137), CD40, GITR, CD27, DR3, DR5, and Fas are some of the TNFSF receptors known to require clustering in order to trigger downstream signaling. Experimental evidence that the 4-1BB receptor must be cross-linked to signal comes from Rabu et al. These authors reported that a 1-trimer form of human 4-1BBL had no activating effects on human T cells whereas cross-linking the protein into 2- or more trimers led to a strongly activating protein (Rabu et al., (2005) J Biol Chem 280:41472-41481). Accordingly, in some embodiments, an anti-CD137 agonist antibody induces the multimerization of 2 or more trimers of CD137.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen-binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

As used herein, the term "reference antibody" (used interchangeably with "reference mAb") or "reference antigen-binding protein" refers to an antibody, or an antigen-binding fragment thereof, that binds to a specific epitope on human CD137 and is used to establish a relationship between itself and one or more distinct antibodies. In some embodiments, the relationship is the binding of the reference antibody and the one or more distinct antibodies to the same epitope on CD137. As used herein, the term connotes an anti-CD137 antibody that is useful in a test or assay, such as those described herein, (e.g., a competitive binding assay), as a competitor, wherein the assay is useful for the discovery, identification or development, of one or more distinct antibodies that bind to the same epitope. The variable heavy ($V_H$) and light chain ($V_L$) amino acid sequences of an exemplary reference antibody (mAb1) are provided in Table 4 ($V_H$1, SEQ ID NO. 4; $V_H$2, SEQ ID NO. 6). In some embodiments, the term connotes an anti-CD137 antibody that is useful in a test or assay, as a comparator, wherein the assay is useful for distinguishing characteristics of the antibodies (e.g., hepatotoxicity, anti-tumor efficacy). In some embodiments, the reference antibody is urclumab. In some embodiments, the reference antibody is utomilumab.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-6}$ M, such as approximately less than $10^{-7}$, $10^{-8}$ M, $10^{-9}$ M or $10^{-10}$ M or even lower when determined by surface plasmon resonance (SPR) technology in a BIACORE 2000 instrument using recombinant human CD137, PD-1, or PD-L1 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ,ε, etc.). As there is no specific site where recombination always occurs, the final gene sequence will typically not be predictable from the construct.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.geg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg-.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, el al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, the term "tumor microenvironment" (alternatively "cancer microenvironment"; abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

The term "T cell" refers to a type of white blood cell that can be distinguished from other white blood cells by the presence of a T cell receptor on the cell surface. There are several subsets of T cells, including, but not limited to, T helper cells (a.k.a. TH cells or CD4$^+$ T cells) and subtypes, including $T_H1$, $T_H2$, $T_H3$, $T_H17$, $T_H9$, and $T_{FH}$ cells, cytotoxic T cells (i.e., Tc cells, CD8$^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including CD4$^+$ FOXP3$^+$ $T_{reg}$ cells, CD4$^+$FOXP3$^-$ $T_{reg}$ cells, Tr1 cells, Th3 cells, and $T_{reg}$17 cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

As used herein, the terms "T cell activation" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. T cell activation requires at least two signals to become fully activated. The first occurs after engagement of the T cell antigen-specific receptor (TCR) by the antigen-major histocompatibility complex (MHC), and the second by subsequent engagement of co-stimulatory molecules (e.g., CD28). These signals are transmitted to the nucleus and result in clonal expansion of T cells, upregulation of activation markers on the cell surface, differentiation into effector cells, induction of cytotoxicity or cytokine secretion, induction of apoptosis, or a combination thereof.

As used herein, the term "T cell-mediated response" refers to any response mediated by T cells, including, but not limited to, effector T cells (e.g., $CD8^+$ cells) and helper T cells (e.g., $CD4^+$ cells). T cell mediated responses include, for example, T cell cytotoxicity and proliferation.

As used herein, the terms "therapeutically effective amount" or "therapeutically effective dose," or similar terms used herein are intended to mean an amount of an agent (e.g., an anti-CD137 antibody or an antigen-binding fragment thereof or PD-1 antagonist) that will elicit the desired biological or medical response (e.g., an improvement in one or more symptoms of a cancer).

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "unrearranged" or "germline configuration" refers to the configuration wherein the V segment is not recombined so as to be immediately adjacent to a D or J segment.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Anti-CD137 Antibodies and Antigen-Binding Fragments Thereof

The present disclosure provides antibodies that specifically bind to and agonize CD137. In some aspects, the disclosure provides anti-CD137 agonist antibodies that are useful for the treatment of cancer. In some embodiments, the anti-CD137 agonist antibodies induce cytokine production. In some embodiments, the anti-CD137 agonist antibodies increase the number of $CD8^+$ T cells in the tumor microenvironment. In some embodiments, the anti-CD137 agonist antibodies induce protective anti-tumor immunity. The disclosure also provides, in some embodiments, anti-CD137 agonist antibodies that, upon administration in vivo, do not substantially increase intrasplenic or intrahepatic $CD4^+$ and/or $CD8^+$ T cell populations.

Human CD137 is a 255 amino acid transmembrane polypeptide (SEQ ID NO: 3; Accession No. NM_001561; NP_001552) and a member of the phylogenetically-conserved tumor necrosis factor receptor (TNFR) superfamily. CD137 (alternatively 4-1BB, TNFR superfamily 9) and its ligand (CD137L) are involved in the regulation of a wide range of immune activities. CD137 ligand cross-links its receptor, CD137, which is expressed on activated T cells, and co-stimulates T cell activities. CD137 is an activation-induced co-stimulatory molecule. Recent studies have revealed that CD137-mediated anti-cancer effects are largely based on its ability to activate T cells, in particular, to induce a cytotoxic T lymphocyte (CTL) response, and induce cytokine production, in particular, high amounts of IFNγ (Ye et al., (2014) Clin Cancer Res 20(1):44-55). CD137 ligand is a transmembrane protein on the cell surface and transmit signals into the cells on which it is expressed, a phenomenon referred to as "reverse signaling" or "back signaling"). CD137 ligand expression is found on most types of leukocytes and on some nonimmune cells. In monocytic cells (monocytes, macrophages, and DCs), CD137 ligand signaling induces activation, migration, survival, and differentiation.

Accordingly, in some embodiments, an isolated anti-CD137 agonist antibody, or antigen-binding fragment thereof, described herein, binds to and agonizes CD137 and allows or promotes CD137L binding. In some embodiments, an isolated anti-CD137 agonist antibody, or antigen-binding fragment thereof, described herein, binds to and agonizes CD137. In some embodiments, the anti-CD137 antibodies provided by the disclosure bind to and agonize CD137 and co-stimulate activation of T cells.

In some embodiments, an isolated anti-CD137 agonist antibody, or antigen-binding fragment thereof, described herein, has one or more of the following properties or characteristics:
  a) specifically binds to human CD137;
  b) binds to human and cynomolgus CD137; and
  c) binds to human and mouse CD137.

In some embodiments, an anti-CD137 agonist antibody, or antigen-binding fragment thereof, described herein, binds to CD137 and co-stimulates T cell activities. In some embodiments, an anti-CD137 agonist antibody, or antigen-binding fragment thereof, described herein, binds to CD137 and induces or enhances T cell activation, a cytotoxic T lymphocyte (CTL) response, T cell proliferation, cytokine production, or a combination thereof. In some embodiments, an anti-CD137 agonist antibody, or antigen-binding fragment thereof, described herein, binds to CD137 and induces or enhances T cell activation, a cytotoxic T lymphocyte (CTL) response, T cell proliferation, cytokine production, or a combination thereof, in a tumor microenvironment. In some embodiments, an anti-CD137 antibody, or antigen-binding fragment thereof, described herein, does not significantly induce or enhance intrahepatic and/or intrasplenic T cell activation and/or T cell proliferation. In some embodiments, an anti-CD137 antibody, described herein, binds to CD137 and induces the production of IFNγ. In some embodiments, the antibodies provided by the disclosure bind to CD137 and induce the production of IL-2, TNF-α, IL-13, or a combination thereof.

In some embodiments, the anti-CD137 antibodies described herein specifically bind to and agonize CD137. In some embodiments, agonism of CD137 is measured by determining the concentration of cytokines produced by immune cells. Methods for analyzing cytokine production are known in the art and utilized in the Examples. In some embodiments, an increase in cytokine production by immune cells indicates CD137 agonism. In some embodiments, agonism of CD137 is measured by analyzing T cell proliferation. In some embodiments, an increase in T cell proliferation indicates CD137 agonism. In some embodiments, agonism of CD137 is measured by measuring the level of cell signaling either through quantitation of phosphorylation of relevant molecules or expression of a gene reporter after a relevant promoter. In some embodiments, an increase in cell signaling indicates CD137 agonism. In some embodiments, agonism of CD137 is measured by measuring the volume of a tumor. In some embodiments, a decrease in the volume of a tumor indicates CD137 agonism.

In some embodiments, the anti-CD137 antibodies described herein induce, increase or stabilize oligomerization, multimerization, or other higher order clustering of CD137. In some embodiments, the clustering of CD137 on the cell surface is observed via fluorescence microscopy.

Provided herein, in some aspects, are isolated monoclonal antibodies or antigen-binding fragments thereof, that bind to and agonize CD137. In some embodiments, the antibodies or antigen-binding fragments thereof, (i) bind human CD137 with an affinity ($K_D$) of about 40-100 nM (e.g., between about 40 nM and about 100 nM); (ii) bind an epitope on human CD137 described herein; and/or (iii) comprise a heavy chain CDR3 comprising the amino acid sequence DXXXXLXXXXYXYYX (SEQ ID NO: 126). In some embodiments, the antibodies or antigen-binding fragments thereof, (i) bind human CD137 with an affinity ($K_D$) of about 30-100 nM (e.g., between about 30 nM and about 100 nM); (ii) bind an epitope on human CD137 described herein; and/or (iii) comprise a heavy chain CDR3 comprising the amino acid sequence DXXXXLXXXXYXYYX (SEQ ID NO: 126).

Affinity for CD137

In some embodiments, an isolated anti-CD137 agonist antibody, or antigen-binding fragment thereof, described herein, binds human CD137 with an affinity ($K_D$) of about 40-100 nM (e.g., between about 40 nM and about 100 nM). In some embodiments, an isolated anti-CD137 agonist antibody, or antigen-binding fragment thereof, described herein, binds human CD137 with an affinity (KD) of about 30-100 nM (e.g., between about 30 nM and about 100 nM or between about 40 nM and about 100 nM). In some embodiments, the affinity of the anti-CD137 antibody to human CD137 is at least two (e.g., at least three, four, five, six, seven, eight, nine, or 10) fold higher than the affinity of mAb10 for mouse CD137. In some embodiments, the affinity of the anti-CD137 antibody is no greater than 500, 450, 400, 350, 300, 250, 200, 250, 200, 175, 150, 125, 110, or 100 nM. In some embodiments, the affinity of the anti-CD137 antibody to human CD137 is at least two (e.g., at least three, four, five, six, seven, eight, nine, or 10) fold higher than the affinity of mAb10 for mouse CD137, but no greater than 500, 450, 400, 350, 300, 250, 200, 250, 200, 175, 150, 125, 110, or 100 nM. The affinity of the antibody is the strength of binding to a single CD137 polypeptide. In some embodiments, affinity is indicated by the equilibrium dissociation constant ($K_D$). The value of $K_D$ is inversely related to the binding affinity of an antibody to an antigen. Accordingly, the smaller the $K_D$ value, the greater the affinity of the antibody for its antigen.

Methods for determining the affinity of an antibody for its antigen are known in the art. An exemplary method for determining binding affinity employs surface plasmon resonance. Surface plasmon resonance is an optical phenomenon that allows for the analysis of realtime biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51: 19-26; Jonsson, U., i (1991) et al. Biotechniques 11:620-627; Johnsson, B., et al. (1995) J. Mol. Recognit. 8: 125-131; and Johnsson, B., et al. (1991) Anal. Biochem. 198:268-277.

In some embodiments, the anti-CD137 antibodies described herein bind human CD137 with an affinity ($K_D$) of about 30-100 nM (e.g., between about 30 nM and about 100 nM). In some embodiments, the anti-CD137 antibodies described herein bind human CD137 with an affinity ($K_D$) of about 40-100 nM. In some embodiments, the anti-CD137 antibodies described herein bind human CD137 with an affinity ($K_D$) of about 30-40 nM, about 40-50 nM, about 50-60 nM, about 60-70 nM, about 70-80 nM, about 80-90 nM, about 90-100 nM, about 45-55 nM, about 55-65 nM, about 75-85 nM, about 85-95 nM, about 45-95 nM, about 50-90 nM, about 55-85 nM, about 60-80 nM, about 65-75 nM, about 55-75 nM, about 40-70 nM, about 50-80 nM, or about 60-90 nM. In some embodiments, the anti-CD137 antibodies described herein bind human CD137 with an affinity ($K_D$) of about 60-80 nM. In some embodiments, the anti-CD137 antibodies described herein bind human CD137 with an affinity ($K_D$) of about 60-75 nM.

In some embodiments, the anti-CD137 antibodies described herein bind human CD137 with an affinity (KD) of about 60-90 nM. In some embodiments, the anti-CD137 antibodies described herein bind human CD137 with an affinity ($K_D$) of about 50-80 nM. In some embodiments, the anti-CD137 antibodies described herein bind human CD137 with an affinity ($K_D$) of about 40-70 nM. In some embodiments, the anti-CD137 antibodies described herein bind human CD137 with an affinity ($K_D$) of about 55-75 nM. In some embodiments, the anti-CD137 antibodies described herein bind human CD137 with an affinity ($K_D$) of about 65-75 nM. In some embodiments, the anti-CD137 antibodies described herein bind human CD137 with an affinity ($K_D$) of about 60-80 nM. In some embodiments, the anti-CD137 antibodies described herein bind human CD137 with an affinity ($K_D$) of about 55-85 nM. In some embodiments, the anti-CD137 antibodies described herein bind human CD137 with an affinity ($K_D$) of about 50-90 nM. In some embodiments, the anti-CD137 antibodies described herein bind human CD137 with an affinity ($K_D$) of about 45-95 nM.

In some embodiments, the anti-CD137 antibodies described herein bind human CD137 with an affinity ($K_D$) of about 85-95 nM. In some embodiments, the anti-CD137 antibodies described herein bind human CD137 with an affinity ($K_D$) of about 75-85 nM. In some embodiments, the anti-CD137 antibodies described herein bind human CD137 with an affinity (KD) of about 75-85 nM. In some embodiments, the anti-CD137 antibodies described herein bind human CD137 with an affinity ($K_D$) of about 55-65 nM. In some embodiments, the anti-CD137 antibodies described herein bind human CD137 with an affinity ($K_D$) of about 45-55 nM. In some embodiments, the anti-CD137 antibodies described herein bind human CD137 with an affinity (KD) of about 80-90 nM. In some embodiments, the anti-CD137 antibodies described herein bind human CD137 with an affinity (KD) of about 70-80 nM. In some embodiments, the anti-CD137 antibodies described herein bind human CD137 with an affinity (KD) of about 60-70 nM. In some embodiments, the anti-CD137 antibodies described herein bind human CD137 with an affinity ($K_D$) of about 50-60 nM. In some embodiments, the anti-CD137 antibodies described herein bind human CD137 with an affinity ($K_D$) of about 40-50 nM. In some embodiments, the anti-CD137 antibodies described herein bind human CD137 with an affinity ($K_D$) of about 30-40 nM. In some embodiments, the anti-CD137 antibodies described herein bind human CD137 with an affinity (KD) of about 30 nM, about 31 nM, about 32 nM, about 33 nM, about 34 nM, about 35 nM, about 36 nM, about 37 nM, about 38 nM, about 39 nM, about 40 nM, about 41 nM, about 42 nM, about 43 nM, about 44 nM, about 45 nM, about 46 nM, about 47 nM, about 48 nM, about 49 nM, about 50 nM, about 51 nM, about 52 nM, about 53 nM, about 54 nM, about 55 nM, about 56 nM, about 57 nM, about 58 nM, about 59 nM, about 60 nM, about 61 nM, about 62 nM, about 63 nM, about 64 nM, about 65 nM, about 66 nM, about 67 nM, about 68 nM, about 69 nM, about 70 nM, about 71 nM, about 72 nM, about 73 nM, about 74 nM, about 75 nM, about 76 nM, about 77 nM, about 78 nM, about 79 nM, about 80 nM, about 81 nM, about 82 nM, about 83 nM, about 84 nM, about 85 nM, about 86 nM, about 87 nM, about 88 nM, about 89 nM, about 90 nM, about 91 nM, about 92 nM, about 93 nM, about 94 nM, about 95 nM, about 96 nM, about 97 nM, about 98 nM, about 99 nM, about 100 nM, about 101 nM, about 102 nM, about 103 nM, about 104 nM, about 105 nM, about 106 nM, about 107 nM, about 108 nM, about 109 nM or about 110 nM.

In some embodiments, the anti-CD137 antibodies described herein bind human CD137 with an affinity (KD) of at least 30 nM but less than about 110 nM, at least 31 nM but less than about 109 nM, at least 32 nM but less than about 108 nM, at least 33 nM but less than about 107 nM, at least 34 nM but less than about 106 nM, at least 35 nM but less than about 105 nM, at least 36 nM but less than about 104 nM, at least 37 nM but less than about 103 nM at least 38 nM but less than about 102 nM, at least 39 nM but less than about 101 nM, at least 40 nM but less than about 100 nM; at least 41 nM but less than about 99 nM; least 42 nM but less than about 98 nM; least 43 nM but less than about 97 nM; at least 44 nM but less than about 96 nM; at least 45 nM but less than about 95 nM; at least 46 nM but less than about 94 nM; at least 47 nM but less than about 93 nM; at least 48 nM but less than about 92 nM; at least 49 nM but less than about 91 nM; at least 50 nM but less than about 90 nM; at least 51 nM but less than about 89 nM; at least 52 nM but less than about 88 nM; at least 53 nM but less than about 87 nM; at least 54 nM but less than about 86 nM; at least 55 nM but less than about 85 nM; at least 56 nM but less than about 84 nM; at least 57 nM but less than about 83 nM; at least 58 nM but less than about 82 nM; at least 59 nM but less than about 81 nM; at least 60 nM but less than about 80 nM; at least 61 nM but less than about 79 nM; at least 62 nM but less than about 78 nM; at least 63 nM but less than about 77 nM; at least 64 nM but less than about 76 nM; or at least 65 nM but less than about 75 nM. In some embodiments, the anti-CD137 antibodies described herein bind human CD137 with an affinity ($K_D$) of at least 40 nM but less than about 100 nM.

In some embodiments, the anti-CD137 antibodies described herein cross-react with CD137 polypeptides from more than one species. In some embodiments, the anti-CD137 antibodies described herein bind cynomolgus CD137 and human CD137. In some embodiments, the anti-CD137 antibodies described herein bind mouse CD137 and human CD137. In some embodiments, the anti-CD137 antibodies described herein bind human CD137, mouse CD137 and cynomolgus CD137.

CD137 Epitope Binding

In some embodiments, the isolated monoclonal antibody, or antigen-binding portion thereof, that specifically binds to human CD137, binds to an epitope on human CD137 comprising one or more (e.g., one, two, three, four, five, six, seven, eight, nine, 10, 11, 12, 13, 14, 15, 16, 17, 18, 19, 20, 21, 22, 23, 24, or all 25) of amino acids 111-132 of SEQ ID NO: 3. In some embodiments, the isolated monoclonal antibody, or antigen-binding portion thereof, that specifically binds to human CD137, binds to an epitope within amino acids 111-132 of SEQ ID NO: 3. In some aspects, the disclosure provides an isolated monoclonal antibody, or antigen-binding portion thereof, that specifically binds to human CD137, binds to all or a portion of amino acids 111-132 of SEQ ID NO: 3. In some embodiments, an isolated anti-CD137 agonist antibody, or antigen-binding fragment thereof, described herein, binds to an epitope of human CD137 comprising residue K114 of SEQ ID NO: 3. In some embodiments, an isolated anti-CD137 agonist antibody, or antigen-binding fragment thereof, described herein, binds to an epitope of human CD137 comprising residues E11, T113 and K114 of SEQ ID NO: 3. In some embodiments, an isolated anti-CD137 agonist antibody, or antigen-binding fragment thereof, described herein, binds to an epitope of human CD137 comprising residues E111, T113, K114, N126 and 1132 of SEQ ID NO: 3. In some embodiments, an isolated anti-CD137 agonist antibody, or antigen-binding fragment thereof, described herein, binds to an epitope of human CD137 comprising E111, T113, K114, N126, 1132 and P135 of SEQ ID NO: 3. In some embodiments, an isolated anti-CD137 agonist antibody, or antigen-binding fragment thereof, described herein, binds to an epitope of human CD137 comprising one or more residues E111, T113, K114, N126, 1132 and P135 of SEQ ID NO: 3.

In some embodiments, an isolated anti-CD137 agonist antibody, or antigen-binding fragment thereof, described herein, binds to an epitope of human CD137 comprising a sequence of one or more amino acid residues corresponding to amino acid positions 100 to 135, 101 to 135, 102 to 135, 103 to 135, 104 to 135, 105 to 135, 106 to 135, 107 to 135, 108 to 135, 109 to 135, 110 to 135, or 111 to 135 of SEQ ID NO: 3. In some embodiments, an isolated anti-CD137 agonist antibody, or antigen-binding fragment thereof, described herein, binds to an epitope of human CD137 comprising a sequence of one or more amino acid residues corresponding to amino acid positions 111 to 135 of SEQ ID NO: 3. In some embodiments, the epitope comprises 2, 3, 4, 5, 6, 7, 8, 9, 10, 11, 12, 13, 14, 15, 16, 17, 18, 19, 20, 21, 22, 23, 24, or 25 amino acid residues corresponding to amino acid positions 111 to 135 of SEQ ID NO: 3.

In some embodiments, an isolated anti-CD137 agonist antibody, or antigen-binding fragment thereof, described herein, binds to an epitope of human CD137 within amino acid positions 100 to 135, 101 to 135, 102 to 135, 103 to 135, 104 to 135, 105 to 135, 106 to 135, 107 to 135, 108 to 135, 109 to 135, 110 to 135, or 111 to 135 of SEQ ID NO: 3. In some embodiments, an isolated anti-CD137 agonist antibody, or antigen-binding fragment thereof, described herein, binds to an epitope of human CD137 within amino acid positions 111 to 135 of SEQ ID NO: 3. In some embodiments, the epitope comprises 2, 3, 4, 5, 6, 7, 8, 9, 10, 11, 12, 13, 14, 15, 16, 17, 18, 19, 20, 21, 22, 23, 24, or 25 amino acid residues corresponding to amino acid positions 111 to 135 of SEQ ID NO: 3.

In some embodiments, an isolated anti-CD137 agonist antibody, or antigen-binding fragment thereof, described herein, binds to an epitope of human CD137 comprising ELTK (corresponding to amino acid residues 111-114 of SEQ ID NO: 3). In some embodiments, amino acid residue L112 can be another amino acid residue.

In some embodiments, the epitope is a non-linear epitope. In some embodiments, mutation of amino acid residue K114 abrogates bindings of an isolated anti-CD137 agonist antibody, or antigen-binding fragment thereof, described herein, to human CD137.

In some embodiments, isolated anti-CD137 agonist antibody, or antigen-binding fragment thereof, described herein, binds to an epitope of human CD137 comprising a sequence of one or more amino acid residues corresponding to amino acid positions 111 to 135 of SEQ ID NO: 3, wherein the epitope comprises at least amino acid K114, and wherein the antibody or antigen-binding portion thereof binds mouse CD137 and does not bind rat CD137. In some embodiments, the epitope is a non-linear epitope. In some embodiments, the antibody or antigen-binding portion thereof binds mouse CD137 and cynomolgus CD137 and does not bind rat CD137. In some embodiments, binding of an isolated anti-CD137 agonist antibody, or antigen-binding fragment thereof, described herein, to human, mouse, rat and cynomolgus CD137 is determined by surface plasmon resonance (SPR).

In some embodiments, the antibody or antigen-binding portion thereof binds to mouse, cynomolgus or human CD137 with an affinity that is at least 10, 20, 30, 40, 50, 100, 200, 500 or 1000 times greater than the antibody's affinity for rat CD137. In some embodiments, the antibody or antigen-binding portion thereof binds to mouse, cynomolgus or human CD137 with an affinity that is at least 10, 20, 30, 40, 50, 100, 200, 500 or 1000 times greater than the antibody's affinity for a CD137 polypeptide that does not comprise a lysine at position 114 relative to human CD137 of SEQ ID NO: 3.

In some embodiments, an isolated anti-CD137 agonist antibody, or antigen-binding fragment thereof, described herein, binds to an epitope of human CD137 and competes with mAb1 for binding to the epitope of human CD137. In some embodiments, an isolated anti-CD137 agonist antibody, or antigen-binding fragment thereof, described herein, binds to and agonizes CD137. In some embodiments, the anti-CD137 antibodies provided by the disclosure bind to and agonize CD137 and co-stimulate activation of T cells.

The present disclosure provides antibodies that compete for binding to an epitope on CD137 which comprises all or a portion of an epitope recognized by one or more particular reference antibodies described herein (e.g., mAb1). In some embodiments, the anti-CD137 antibodies bind to an epitope of human CD137 and compete with a reference antibody (e.g., mAb1) for binding to the epitope of human CD137 and wherein the antibody, or antigen-binding fragment thereof, binds human CD137 with an equilibrium dissociation constant $K_D$ of $1 \times 10^{-6}$ or less. In some embodiments, the anti-CD137 antibodies bind to an epitope on CD137, wherein one or more mutations to the epitope inhibit, reduce, or block binding to both the antibodies and a reference antibody (e.g., mAb1). In some embodiments, the reference antibody is the mAb1 antibody, described herein. In some embodiments, the reference antibody is any one antibody provided in Table 3 or Table 4.

Accordingly, the anti-CD137 antibodies provided by the disclosure can be assessed through x-ray crystallographic analysis of a crystal structure comprising an antibody bound to CD137, or a fragment or portion thereof. In some embodiments, the epitopes that are bound by the antibodies provided by the disclosure are identified by determining the residues on the human CD137 antigen that reside or are located within 4 angstroms (Å) of an antibody paratope residue, e.g., mAb1.

In some embodiments, the epitope bound by the anti-CD137 antibodies described herein is at least 3 amino acid residues. In some embodiments, the epitope bound by the anti-CD137 antibodies described herein is at least 4 amino acid residues. In some embodiments, the epitope bound by the anti-CD137 antibodies described herein is at least 5 amino acid residues. In some embodiments, the epitope bound by the anti-CD137 antibodies described herein is at least 6 amino acid residues. In some embodiments, the epitope bound by the anti-CD137 antibodies described herein is at least 7 amino acid residues. In some embodiments, the epitope bound by the anti-CD137 antibodies described herein is at least 8 amino acid residues. In some embodiments, the epitope bound by the anti-CD137 antibodies described herein is at least 9 amino acid residues. In some embodiments, the epitope bound by the anti-CD137 antibodies described herein is at least 10 amino acid residues. In some embodiments, the epitope bound by the anti-CD137 antibodies described herein is at least 12 amino acid residues. In some embodiments, the epitope bound by the anti-CD137 antibodies described herein is at least 3 amino acid residues. In some embodiments, the epitope bound by the anti-CD137 antibodies described herein is at least 13 amino acid residues. In some embodiments, the epitope bound by the anti-CD137 antibodies described herein is at least 14 amino acid residues. In some embodiments, the epitope bound by the anti-CD137 antibodies described herein is at least 15 amino acid residues.

In some embodiments, the epitope bound by the anti-CD137 antibodies described herein is fewer than 25 amino acid residues. In some embodiments, the epitope bound by the anti-CD137 antibodies described herein is fewer than 24 amino acid residues. In some embodiments, the epitope bound by the anti-CD137 antibodies described herein is fewer than 23 amino acid residues. In some embodiments, the epitope bound by the anti-CD137 antibodies described herein is fewer than 22 amino acid residues. In some embodiments, the epitope bound by the anti-CD137 antibodies described herein is fewer than 21 amino acid residues. In some embodiments, the epitope bound by the anti-CD137 antibodies described herein is fewer than 20 amino acid residues. In some embodiments, the epitope bound by the anti-CD137 antibodies described herein is fewer than 19 amino acid residues. In some embodiments, the epitope bound by the anti-CD137 antibodies described herein is fewer than 18 amino acid residues. In some embodiments, the epitope bound by the anti-CD137 antibodies described herein is fewer than 17 amino acid residues. In some embodiments, the epitope bound by the anti-CD137 antibodies described herein is fewer than 16 amino acid residues. In some embodiments, the epitope bound by the anti-CD137 antibodies described herein is fewer than 15 amino acid residues. In some embodiments, the epitope bound by the anti-CD137 antibodies described herein is fewer than 14 amino acid residues. In some embodiments, the epitope bound by the anti-CD137 antibodies described herein is fewer than 13 amino acid residues. In some embodiments, the epitope bound by the anti-CD137 antibodies described herein is fewer than 12 amino acid residues. In some embodiments, the epitope bound by the anti-CD137 antibodies described herein is fewer than 11 amino acid residues. In some embodiments, the epitope bound by the anti-CD137 antibodies described herein is fewer than 10 amino acid residues. In some embodiments, the epitope bound by the anti-CD137 antibodies described herein is fewer than 9 amino acid residues. In some embodiments, the epitope bound by the anti-CD137 antibodies described herein is fewer than 8 amino acid residues. In some embodiments, the epitope bound by the anti-CD137 antibodies described herein is fewer than 7 amino acid residues. In some embodiments, the epitope bound by the anti-CD137 antibodies described herein is fewer than 6 amino acid residues. In some embodiments, the epitope bound by the anti-CD137 antibodies described herein is fewer than 5 amino acid residues.

In some embodiments, the anti-CD137 antibodies described herein bind to an epitope of fewer than 25, 24, 23, 22, 21, 20, 19, 18, 17, 16, 15, 14, 13, 12, 11, 10, 9, 8, 7, 6 or 5 amino acids and comprises amino acid residue K114 of SEQ ID NO: 3.

Variable Regions

In some embodiments, provided herein are isolated monoclonal antibodies or antigen-binding fragments thereof, comprising heavy and light chain variable sequences as set forth in Tables 3 and 4.

In some embodiments, the anti-CD137 antibodies described herein comprise heavy and light chain CDRs selected from the group consisting of:

(a) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively;

(b) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 70, 79 and 90, respectively;

(c) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 71, 80 and 91, respectively;

(d) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 72, 81 and 92, respectively;

(e) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 73, 82 and 91, respectively;

(f) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 74, 83 and 93, respectively;

(g) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 75, 84 and 91, respectively;

(h) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 74, 85 and 94, respectively;

(i) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 76, 86 and 95, respectively;

(j) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 77, 87 and 93, respectively;

(k) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 88 and 90, respectively;

(l) heavy chain CDR1, CDR2 and CDR3 sequences set forth in SEQ ID NOs: 49, 57 and 68, respectively, and light chain CDR1, CDR2 and CDR3 sequences set forth in SEQ ID NOs: 69, 78 and 89, respectively;

(m) heavy chain CDR1, CDR2 and CDR3 sequences set forth in SEQ ID NOs: 49, 58 and 68, respectively, and light chain CDR1, CDR2 and CDR3 sequences set forth in SEQ ID NOs: 69, 78 and 89, respectively;

(n) heavy chain CDR1, CDR2 and CDR3 sequences set forth in SEQ ID NOs: 49, 59 and 68, respectively, and light chain CDR1, CDR2 and CDR3 sequences set forth in SEQ ID NOs: 69, 78 and 89, respectively;

(o) heavy chain CDR1, CDR2 and CDR3 sequences set forth in SEQ ID NOs: 49, 60 and 68, respectively, and light chain CDR1, CDR2 and CDR3 sequences set forth in SEQ ID NOs: 69, 78 and 89, respectively;

(p) heavy chain CDR1, CDR2 and CDR3 sequences set forth in SEQ ID NOs: 50, 61 and 68, respectively, and light chain CDR1, CDR2 and CDR3 sequences set forth in SEQ ID NOs: 69, 78 and 89, respectively;

(q) heavy chain CDR1, CDR2 and CDR3 sequences set forth in SEQ ID NOs: 50, 58 and 68, respectively, and light chain CDR1, CDR2 and CDR3 sequences set forth in SEQ ID NOs: 69, 78 and 89, respectively;

(r) heavy chain CDR1, CDR2 and CDR3 sequences set forth in SEQ ID NOs: 51, 62 and 68, respectively, and light chain CDR1, CDR2 and CDR3 sequences set forth in SEQ ID NOs: 69, 78 and 89, respectively;

(s) heavy chain CDR1, CDR2 and CDR3 sequences set forth in SEQ ID NOs: 52, 63 and 68, respectively, and light chain CDR1, CDR2 and CDR3 sequences set forth in SEQ ID NOs: 69, 78 and 89, respectively;

(t) heavy chain CDR1, CDR2 and CDR3 sequences set forth in SEQ ID NOs: 50, 64 and 68, respectively, and light chain CDR1, CDR2 and CDR3 sequences set forth in SEQ ID NOs: 69, 78 and 89, respectively;

(u) heavy chain CDR1, CDR2 and CDR3 sequences set forth in SEQ ID NOs: 50, 65 and 68, respectively, and light chain CDR1, CDR2 and CDR3 sequences set forth in SEQ ID NOs: 69, 78 and 89, respectively;

(v) heavy chain CDR1, CDR2 and CDR3 sequences set forth in SEQ ID NOs: 51, 108 and 68, respectively, and light chain CDR1, CDR2 and CDR3 sequences set forth in SEQ ID NOs: 69, 78 and 89, respectively;

(w) heavy chain CDR1, CDR2 and CDR3 sequences set forth in SEQ ID NOs: 107, 56 and 68, respectively, and light chain CDR1, CDR2 and CDR3 sequences set forth in SEQ ID NOs: 69, 78 and 89, respectively; and (x) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 109, 110 and 92, respectively.

In some embodiments, the anti-CD137 antibodies described herein comprise heavy and light chain variable regions, wherein the heavy chain variable region comprises an amino acid sequence selected from the group consisting of SEQ ID NOs: 4, 8, 10, 12, 14, 16, 18, 20, 22, 24, 26, 101 and 103; and wherein the light chain variable region comprises an amino acid sequence selected from the group consisting of SEQ ID NOs: 6, 28, 30, 32, 34, 36, 38, 40, 42, 44, 46 and 105.

In some embodiments, the anti-CD137 antibodies described herein comprise heavy and light chain CDRs, wherein heavy chain CDR3 comprises the amino acid sequence set forth in SEQ ID NO: 68.

In some embodiments, the anti-CD137 antibodies described herein comprise heavy and light chain variable regions comprising amino acid sequences selected from the group consisting of:
  (a) SEQ ID NO: 4 and 6, respectively;
  (b) SEQ ID NO: 4 and 28, respectively;
  (c) SEQ ID NO: 4 and 30, respectively;
  (d) SEQ ID NO: 4 and 32, respectively;
  (e) SEQ ID NO: 4 and 34, respectively;
  (f) SEQ ID NO: 4 and 36, respectively;
  (g) SEQ ID NO: 4 and 38, respectively;
  (h) SEQ ID NO: 4 and 40, respectively;
  (i) SEQ ID NO: 4 and 42, respectively;
  (j) SEQ ID NO: 4 and 44, respectively;
  (k) SEQ ID NO: 4 and 46, respectively;
  (l) SEQ ID NO: 8 and 6, respectively;
  (m) SEQ ID NO: 10 and 6, respectively;
  (n) SEQ ID NO: 12 and 6, respectively;
  (o) SEQ ID NO: 14 and 6, respectively;
  (p) SEQ ID NO: 16 and 6, respectively;
  (q) SEQ ID NO: 18 and 6, respectively;
  (r) SEQ ID NO: 20 and 6, respectively;
  (s) SEQ ID NO: 22 and 6, respectively;
  (t) SEQ ID NO: 24 and 6, respectively;
  (u) SEQ ID NO: 26 and 6, respectively;
  (v) SEQ ID NO: 101 and 6, respectively;
  (w) SEQ ID NO: 103 and 6, respectively; and
  (x) SEQ ID NO: 4 and 105, respectively.

In some embodiments, the anti-CD137 antibodies described herein comprise heavy and light chain variable regions, wherein the heavy chain variable region comprises an amino acid sequence which is at least 90% identical to the amino acid sequence selected from the group consisting of SEQ ID NOs: 4, 8, 10, 12, 14, 16, 18, 20, 22, 24, 26, 101 and 103; and wherein the light chain variable region comprises an amino acid sequence which is at least 90% identical to the amino acid sequence selected from the group consisting of SEQ ID NOs: 6, 28, 30, 32, 34, 36, 38, 40, 42, 44, 46 and 105.

In some embodiments, the anti-CD137 antibodies described herein comprise heavy and light chain variable regions comprising amino acid sequences at least 90% identical to the amino acid sequences selected from the group consisting of:
  (a) SEQ ID NO: 4 and 6, respectively;
  (b) SEQ ID NO: 4 and 28, respectively;
  (c) SEQ ID NO: 4 and 30, respectively;
  (d) SEQ ID NO: 4 and 32, respectively;
  (e) SEQ ID NO: 4 and 34, respectively;
  (f) SEQ ID NO: 4 and 36, respectively;
  (g) SEQ ID NO: 4 and 38, respectively;
  (h) SEQ ID NO: 4 and 40, respectively;
  (i) SEQ ID NO: 4 and 42, respectively;
  (j) SEQ ID NO: 4 and 44, respectively;
  (k) SEQ ID NO: 4 and 46, respectively;
  (l) SEQ ID NO: 8 and 6, respectively;
  (m) SEQ ID NO: 10 and 6, respectively;
  (n) SEQ ID NO: 12 and 6, respectively;
  (o) SEQ ID NO: 14 and 6, respectively;
  (p) SEQ ID NO: 16 and 6, respectively;
  (q) SEQ ID NO: 18 and 6, respectively;
  (r) SEQ ID NO: 20 and 6, respectively;
  (s) SEQ ID NO: 22 and 6, respectively;
  (t) SEQ ID NO: 24 and 6, respectively;
  (u) SEQ ID NO: 26 and 6, respectively;
  (v) SEQ ID NO: 101 and 6, respectively;
  (w) SEQ ID NO: 103 and 6, respectively; and
  (x) SEQ ID NO: 4 and 105, respectively.

In some embodiments, provided herein are antibodies that specifically bind human CD137 comprising heavy chain and light chain variable regions encoded by nucleotide sequences selected from the group consisting of:
  (a) SEQ ID NO: 5 and 7, respectively;
  (b) SEQ ID NO: 5 and 29, respectively;
  (c) SEQ ID NO: 5 and 31, respectively;
  (d) SEQ ID NO: 5 and 33, respectively;
  (e) SEQ ID NO: 5 and 35, respectively;
  (f) SEQ ID NO: 5 and 37, respectively;
  (g) SEQ ID NO: 5 and 39, respectively;
  (h) SEQ ID NO: 5 and 41, respectively;
  (i) SEQ ID NO: 5 and 43, respectively;
  (j) SEQ ID NO: 5 and 45, respectively;
  (k) SEQ ID NO: 5 and 47, respectively;
  (l) SEQ ID NO: 9 and 7, respectively;
  (m) SEQ ID NO: 11 and 7, respectively;
  (n) SEQ ID NO: 13 and 7, respectively;
  (o) SEQ ID NO: 15 and 7, respectively;
  (p) SEQ ID NO: 17 and 7, respectively;
  (q) SEQ ID NO: 19 and 7, respectively;
  (r) SEQ ID NO: 21 and 7, respectively;
  (s) SEQ ID NO: 23 and 7, respectively;
  (t) SEQ ID NO: 25 and 7, respectively;
  (u) SEQ ID NO: 27 and 7, respectively;
  (v) SEQ ID NO: 102 and 7, respectively;
  (w) SEQ ID NO: 104 and 7, respectively; and
  (x) SEQ ID NO: 5 and 106, respectively.

In some embodiments, provided herein are antibodies that specifically bind human CD137 comprising heavy chain and light chain variable regions encoded by nucleotide sequences having at least 90% identity to the nucleotide sequences selected from the group consisting of:
  (a) SEQ ID NO: 5 and 7, respectively;
  (b) SEQ ID NO: 5 and 29, respectively;
  (c) SEQ ID NO: 5 and 31, respectively;
  (d) SEQ ID NO: 5 and 33, respectively;
  (e) SEQ ID NO: 5 and 35, respectively;
  (f) SEQ ID NO: 5 and 37, respectively;
  (g) SEQ ID NO: 5 and 39, respectively;
  (h) SEQ ID NO: 5 and 41, respectively;
  (i) SEQ ID NO: 5 and 43, respectively;
  (j) SEQ ID NO: 5 and 45, respectively;
  (k) SEQ ID NO: 5 and 47, respectively;
  (l) SEQ ID NO: 9 and 7, respectively;

(m) SEQ ID NO: 11 and 7, respectively;
(n) SEQ ID NO: 13 and 7, respectively;
(o) SEQ ID NO: 15 and 7, respectively;
(p) SEQ ID NO: 17 and 7, respectively;
(q) SEQ ID NO: 19 and 7, respectively;
(r) SEQ ID NO: 21 and 7, respectively;
(s) SEQ ID NO: 23 and 7, respectively;
(t) SEQ ID NO: 25 and 7, respectively;
(u) SEQ ID NO: 27 and 7, respectively;
(v) SEQ ID NO: 102 and 7, respectively;
(w) SEQ ID NO: 104 and 7, respectively; and
(x) SEQ ID NO: 5 and 106, respectively.

In some embodiments, the anti-CD137 antibodies described herein comprise heavy and light chain variable regions, wherein the heavy chain variable region is encoded by a nucleotide sequence selected from the group consisting of SEQ ID NOs: 5, 9, 11, 13, 15, 17, 19, 21, 23, 25, 27, 102 and 104; and wherein the light chain variable region is encoded by a nucleotide sequence selected from the group consisting of SEQ ID NOs: 7, 29, 31, 33, 35, 37, 39, 41, 43, 45, 47 and 106.

In some embodiments, the anti-CD137 antibodies described herein comprise heavy and light chain variable regions, wherein the heavy chain variable region is encoded by a nucleotide sequence having at least 90% identity to a nucleotide sequence selected from the group consisting of SEQ ID NOs: 5, 9, 11, 13, 15, 17, 19, 21, 23, 25, 27, 102 and 104; and wherein the light chain variable region is encoded by a nucleotide sequence having at least 90% identity to a nucleotide sequence selected from the group consisting of SEQ ID NOs: 7, 29, 31, 33, 35, 37, 39, 41, 43, 45, 47 and 106.

In some embodiments, provided herein are anti-CD137 antibodies that specifically bind to human CD137 and comprise a heavy chain CDR3 having the amino acid sequence DXXXXLXXXXYXYYX (SEQ ID NO: 126), wherein X is any amino acid. In some embodiments, X is any amino acid except for alanine. In some embodiments, mutation of residues D95, L100, Y100E, Y100G, and/or Y100H of SEQ ID NO: 126, results in loss of binding to human CD137. In some embodiments, mutation of residues D95, L100, Y100E, Y100G, Y100H, or combinations thereof, of SEQ ID NO: 126, to alanine results in loss of binding to human CD137. In some embodiments, mutation of residues D95, L100, Y100E, Y100G, Y100H, or combinations thereof, of SEQ ID NO: 126, to any residue except alanine results in an increase in binding to human CD137.

In some embodiments, provided herein are anti-CD137 antibodies that specifically bind to human CD137 and comprise a heavy chain CDR3 having the amino acid sequence DXPFXLDXXYYYYYX (SEQ ID NO: 127), wherein X is any amino acid. In some embodiments, X is any amino acid except for alanine. In some embodiments, mutation of residues D95, L100, Y100E, Y100G, and/or Y100H of SEQ ID NO: 126, results in loss of binding to human CD137. In some embodiments, mutation of residues D95, L100, Y100E, Y100G, Y100H, or combinations thereof, of SEQ ID NO: 126, to alanine results in loss of binding to human CD137. In some embodiments, mutation of residues D95, L100, Y100E, Y100G, Y100H, or combinations thereof, of SEQ ID NO: 126, to any residue except alanine results in an increase in binding to human CD137. In some embodiments, mutation of residues P97, F98, D100A, Y100D, and/or Y100F, and/or Y100H of SEQ ID NO: 127, results in loss of binding to human CD137. In some embodiments, mutation of residues P97, F98, D100A, Y100D, and/or Y100F, and/or Y00H of SEQ ID NO: 127 to alanine results in loss of binding to human CD137. In some embodiments, mutation of residues P97, F98, D100A, Y100D, and/or Y100F, and/or Y100H of SEQ ID NO: 127, to any residue except for alanine, results in an increase in binding to human CD137.

In some embodiments, provided herein are anti-CD137 antibodies that specifically bind to human CD137 and comprise a heavy chain CDR3 having the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid. In some embodiments, $X_2$ is proline, wherein $X_3$ is phenylalanine or tryptophan, wherein $X_5$ is aspartic acid or glutamic acid, wherein $X_8$ is tyrosine, and wherein $X_9$ is tyrosine.

The role of an amino acid residue within the heavy chain CDR3 of an antibody or antigen-binding portion thereof, in binding to a specified target (e.g., CD137) can be determined by methods known to one of skill in the art. In some embodiments, an initial analysis using alanine scanning is completed to determine the critical residues for antigen-binding. As described herein, alanine scanning is a technique used to determine the contribution of a specific wild-type residue to the stability or function(s) (e.g., binding affinity) of given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. In some embodiments, the residues identified as not critical are further evaluated to modulate the binding of the antibody to the antigen (e.g., increase or decrease binding). A non-limiting example of such analysis is deep mutational scanning. This method allows for the evaluation of large numbers of mutations. In some embodiments, each amino acid residue within the heavy chain CDR3 is mutated to every amino acid residue (except for alanine), and binding is assessed. Other methods for analyzing the effect of amino acid residue mutations are known in the art. In some embodiments, these methods are utilized to assess the role of residues in all of the heavy chain and light chain CDRs in binding to human CD137.

Exemplary CD137 Binding Antibodies

In some embodiments, the anti-CD137 antibodies described herein bind human CD137 with an affinity ($K_D$) of about 30-100 nM (e.g., between about 30 nM and about 100 nM). In some embodiments, the anti-CD137 antibodies described herein bind human CD137 with an affinity ($K_D$) of about 40-100 nM (e.g., between about 40 nM and about 100 nM). In some embodiments, the anti-CD137 antibodies described herein bind an epitope on human CD137 described supra (e.g., comprising K114). In some embodiments, the anti-CD137 antibodies described herein comprise a heavy chain CDR3 comprising the amino acid sequence DXXXXLXXXXYXYYX (SEQ ID NO: 126). In some embodiments, the anti-CD137 antibodies described herein bind human CD137 with an affinity ($K_D$) of 30-100 nM (e.g., between about 30 nM and about 100 nM) and bind an epitope on human CD137 described supra (e.g., comprising K114). In some embodiments, the anti-CD137 antibodies described herein bind human CD137 with an affinity ($K_D$) of 30-100 nM (e.g., between about 30 nM and about 100 nM) and comprise a heavy chain CDR3 comprising the amino acid sequence DXXXXLXXXXYXYYX (SEQ ID NO: 126). In some embodiments, the anti-CD137 antibodies described herein bind an epitope on human CD137 described supra (e.g., comprising K114) and comprise a heavy chain CDR3 comprising the amino acid sequence DXXXXLXXXXYXYYX (SEQ ID NO: 126). In some embodiments, the anti-CD137 antibodies described herein bind human CD137 with an affinity ($K_D$) of 30-100 nM (e.g., between about 30 nM and about 100 nM), bind an epitope on human CD137 described supra (e.g., comprising K114), and comprise a heavy chain CDR3 comprising the amino acid sequence DXXXXLXXXXYXYYX (SEQ ID NO: 126).

In some embodiments, the anti-CD137 antibodies (i) bind human CD137 with an affinity ($K_D$) of about 30-100 nM (e.g., between about 30 nM and about 100 nM); and (ii) comprise a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

In some embodiments, the anti-CD137 antibodies (i) bind human CD137 with an affinity ($K_D$) of about 30-100 nM (e.g., between about 30 nM and about 100 nM); and (ii) bind to an epitope on human CD137 comprising one or more residues E111, T113, K114, N126, I132 and P135 of SEQ ID NO: 3.

In some embodiments, the anti-CD137 antibodies (i) bind human CD137 with an affinity ($K_D$) of about 30-100 nM (e.g., between about 30 nM and about 100 nM);

(ii) bind to an epitope on human CD137 comprising one or more residues E111, T113, K114, N126, I132 and P135 of SEQ ID NO: 3;

(iii) comprise a heavy chain CDR3 comprising the amino acid sequence DXXXXLXXXXYXYYX (SEQ ID NO: 126), wherein X is any amino acid; or (iv) combinations thereof.

In some embodiments, the anti-CD137 antibodies (i) bind human CD137 with an affinity ($K_D$) of about 30-100 nM (e.g., between about 30 nM and about 100 nM);

(ii) bind to an epitope on human CD137 comprising one or more residues E111, T113, K114, N126, I132 and P135 of SEQ ID NO: 3;

(iii) comprise a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or (iv) combinations thereof.

In some embodiments, the anti-CD137 antibodies (i) bind human CD137 with an affinity ($K_D$) of about 30-100 nM (e.g., between about 30 nM and about 100 nM);

(ii) specifically bind to an epitope on human CD137 comprising one or more residues E111, T113, K114, N126, I132 and P135 of SEQ ID NO: 3; and (iii) comprise a heavy chain CDR3 comprising the amino acid sequence DXXXXLXXXXYXYYX (SEQ ID NO: 126), wherein X is any amino acid.

In some embodiments, the anti-CD137 antibodies (i) bind human CD137 with an affinity ($K_D$) of about 30-100 nM (e.g., between about 30 nM and about 100 nM);

(ii) bind to an epitope on human CD137 comprising one or more residues E111, T113, K114, N126, I132 and P135 of SEQ ID NO: 3; and (iii) comprise a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_8$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

In some embodiments, the anti-CD137 antibodies (i) bind human CD137 with an affinity ($K_D$) of about 30-100 nM (e.g., between about 30 nM and about 100 nM); and (ii) bind to an epitope comprising a sequence of one or more amino acid residues corresponding to amino acid positions 111 to 135 of SEQ ID NO: 3.

In some embodiments, the anti-CD137 antibodies (i) bind human CD137 with an affinity ($K_D$) of about 30-100 nM (e.g., between about 30 nM and about 100 nM);

(ii) bind to an epitope comprising a sequence of one or more amino acid residues corresponding to amino acid positions 111 to 135 of SEQ ID NO: 3;

(iii) comprise a heavy chain CDR3 comprising the amino acid sequence DXXXXLXXXXYXYYX (SEQ ID NO: 126), wherein X is any amino acid; or (iv) combinations thereof.

In some embodiments, the anti-CD137 antibodies (i) bind human CD137 with an affinity ($K_D$) of about 30-100 nM (e.g., between about 30 nM and about 100 nM);

(ii) bind to an epitope comprising a sequence of one or more amino acid residues corresponding to amino acid positions 111 to 135 of SEQ ID NO: 3;

(iii) comprise a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or (iv) combinations thereof.

In some embodiments, the anti-CD137 antibodies (i) bind human CD137 with an affinity ($K_D$) of about 30-100 nM (e.g., between about 30 nM and about 100 nM);

(ii) bind to an epitope comprising a sequence of one or more amino acid residues corresponding to amino acid positions 111 to 135 of SEQ ID NO: 3; and (iii) comprise a heavy chain CDR3 comprising the amino acid sequence DXXXXLXXXXYXYYX (SEQ ID NO: 126), wherein X is any amino acid.

In some embodiments, the anti-CD137 antibodies (i) bind human CD137 with an affinity ($K_D$) of about 30-100 nM (e.g., between about 30 nM and about 100 nM);

(ii) bind to an epitope comprising a sequence of one or more amino acid residues corresponding to amino acid positions 111 to 135 of SEQ ID NO: 3; and (iii) comprise a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

In some embodiments, the anti-CD137 antibodies
(i) bind human CD137 with an affinity of about 30-100 nM (e.g., between about 30 nM and about 100 nM); and
(ii) bind to an epitope comprising ELTK (corresponding to amino acid residues 111-114 of SEQ ID NO: 3).

In some embodiments, the anti-CD137 antibodies
(i) bind human CD137 with an affinity ($K_D$) of about 30-100 nM (e.g., between about 30 nM and about 100 nM);
(ii) bind to an epitope comprising ELTK (corresponding to amino acid residues 111-114 of SEQ ID NO: 3);
(iii) comprise a heavy chain CDR3 comprising the amino acid sequence DXXXXLXXXXYXYYX (SEQ ID NO: 126), wherein X is any amino acid; or
(iv) combinations thereof.

In some embodiments, the anti-CD137 antibodies
(i) bind human CD137 with an affinity ($K_D$) of about 30-100 nM (e.g., between about 30 nM and about 100 nM);
(ii) bind to an epitope comprising ELTK (corresponding to amino acid residues 111-114 of SEQ ID NO: 3);
(iii) comprise a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or
(iv) combinations thereof.

In some embodiments, the anti-CD137 antibodies
(i) bind human CD137 with an affinity ($K_D$) of about 30-100 nM (e.g., between about 30 nM and about 100 nM);
(ii) bind to an epitope comprising ELTK (corresponding to amino acid residues 111-114 of SEQ ID NO: 3); and
(iii) comprise a heavy chain CDR3 comprising the amino acid sequence DXXXXLXXXXYXYYX (SEQ ID NO: 126), wherein X is any amino acid.

In some embodiments, the anti-CD137 antibodies
(i) bind human CD137 with an affinity ($K_D$) of about 30-100 nM (e.g., between about 30 nM and about 100 nM);
(ii) bind to an epitope comprising ELTK (corresponding to amino acid residues 111-114 of SEQ ID NO: 3); and
(iii) comprise a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

In some embodiments, the anti-CD137 antibodies described supra comprise heavy and light chain CDRs selected from the group consisting of:
(a) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively; and
(b) heavy chain CDR1, CDR2 and CDR3 sequences set forth in SEQ ID NOs: 51, 108 and 68, respectively, and light chain CDR1, CDR2 and CDR3 sequences set forth in SEQ ID NOs: 69, 78 and 89, respectively.

In some embodiments, the anti-CD137 antibodies comprise heavy and light chain variable regions, wherein the heavy chain variable region comprises an amino acid sequence selected from the group consisting of SEQ ID NOs: 4 and 101; and wherein the light chain variable region comprises an amino acid sequence of SEQ ID NO: 6.

In some embodiments, the anti-CD137 antibodies comprise heavy and light chain variable regions comprising amino acid sequences selected from the group consisting of:
(a) SEQ ID NOs: 4 and 6, respectively; and
(b) SEQ ID NOs: 101 and 6, respectively.

In some embodiments, the anti-CD137 antibodies comprise heavy and light chain variable regions comprising amino acid sequences selected from the group consisting of:
(a) SEQ ID NOs: 4 and 6, respectively;
(b) SEQ ID NOs: 101 and 6, respectively; and
(c) SEQ ID NOs: 26 and 6, respectively.

In some embodiments, the anti-CD137 antibodies comprise heavy and light chain variable regions encoded by nucleotide sequences selected from the group consisting of:
(a) SEQ ID NOs: 5 and 7, respectively; and
(b) SEQ ID NOs: 102 and 7, respectively.

In some embodiments, the anti-CD137 antibodies comprise heavy and light chain variable regions encoded by nucleotide sequences selected from the group consisting of:
(a) SEQ ID NOs: 5 and 7, respectively;
(b) SEQ ID NOs: 102 and 7, respectively; and
(c) SEQ ID NOs: 27 and 7, respectively.

In some embodiments, the anti-CD137 antibodies comprise heavy and light chain variable regions, wherein the heavy chain variable region comprises an amino acid sequence which is at least 90% identical to the amino acid sequence selected from the group consisting of SEQ ID NOs: 4 and 101; and wherein the light chain variable region comprises an amino acid sequence which is at least 90% identical to the amino acid sequence of SEQ ID NO: 6.

In some embodiments, the anti-CD137 antibodies comprise heavy and light chain variable regions, wherein the heavy chain variable region comprises an amino acid sequence which is at least 90% identical to the amino acid sequence selected from the group consisting of SEQ ID NOs: 4, 26 and 101; and wherein the light chain variable region comprises an amino acid sequence which is at least 90% identical to the amino acid sequence of SEQ ID NO: 6.

In some embodiments, the anti-CD137 antibodies comprise heavy and light chain variable regions, wherein the heavy chain variable region is encoded by a nucleotide sequence which is least 90% identical to the nucleotide sequence selected from the group consisting of SEQ ID NOs: 5 and 102; and wherein the light chain variable region is encoded by a nucleotide sequence which is at least 90% identical to the nucleotide sequence of SEQ ID NO: 7.

In some embodiments, the anti-CD137 antibodies comprise heavy and light chain variable regions, wherein the heavy chain variable region is encoded by a nucleotide sequence which is least 90% identical to the nucleotide sequence selected from the group consisting of SEQ ID NOs: 5, 27 and 102; and wherein the light chain variable region is encoded by a nucleotide sequence which is at least 90% identical to the nucleotide sequence of SEQ ID NO: 7.

In some embodiments, the anti-CD137 antibodies comprise heavy and light chain variable regions comprising amino acid sequences at least 90% identical to the amino acid sequences selected from the group consisting of:
(a) SEQ ID NOs: 4 and 6, respectively; and
(a) SEQ ID NOs: 101 and 6, respectively.

In some embodiments, the anti-CD137 antibodies comprise heavy and light chain variable regions comprising amino acid sequences at least 90% identical to the amino acid sequences selected from the group consisting of:

(a) SEQ ID NOs: 4 and 6, respectively;
(b) SEQ ID NOs: 101 and 6, respectively; and
(c) SEQ ID NOs: 26 and 6, respectively.

In some embodiments, the anti-CD137 antibodies comprise heavy and light chain variable regions encoded by nucleotide sequences at least 90% identical to the nucleotide sequences selected from the group consisting of:
(a) SEQ ID NOs: 5 and 7, respectively; and
(b) SEQ ID NOs: 102 and 7, respectively.

In some embodiments, the anti-CD137 antibodies comprise heavy and light chain variable regions encoded by nucleotide sequences at least 90% identical to the nucleotide sequences selected from the group consisting of:
(a) SEQ ID NOs: 5 and 7, respectively;
(b) SEQ ID NOs: 102 and 7, respectively; and
(c) SEQ ID NOs: 27 and 7, respectively.

In some embodiments, the anti-CD137 antibodies described herein have at least the functional properties of mAb1 (i.e., an antibody comprising the heavy and light chain variable sequences of SEQ ID NOs: 4 and 6, respectively), mab8 (i.e., an antibody comprising the heavy and light chain variable sequences of SEQ ID NOs: 101 and 6, respectively) or mAb10 (i.e., an antibody comprising the heavy and light chain variable sequences of SEQ ID NOs: 26 and 6, respectively). In some embodiments, the functional properties of an antibody described herein include but are not limited to: induction or enhancement of dimerization of CD137; induction or enhancement of multimerization of CD137; induction or enhancement of CD137-mediated T cell activation; induction or enhancement of CD137-mediated cytotoxic T cell response; induction or enhancement of CD137-mediated T cell proliferation; induction or enhancement of CD137-mediated cytokine production; lack of induction or enhancement of intrahepatic and/or intrasplenic T cell activation and/or T cell proliferation; and reduction or inhibition of tumor growth.

In some embodiments, the anti-CD137 antibodies described herein bind human CD137 with an equilibrium dissociation constant $K_D$ of $1\times10^{-6}$ or less. In some embodiments, the anti-CD137 antibodies described herein bind human CD137 with an equilibrium dissociation constant $K_D$ at least equivalent to that of mAb1 (i.e., an antibody comprising the heavy and light chain variable sequences of SEQ ID NOs: 4 and 6, respectively), mab8 (i.e., an antibody comprising the heavy and light chain variable sequences of SEQ ID NOs: 101 and 6, respectively) or mAb10 (i.e., an antibody comprising the heavy and light chain variable sequences of SEQ ID NOs: 26 and 6, respectively).

In some embodiments, the anti-CD137 antibodies described herein comprise a human IgG1 heavy chain constant region or a human IgG4 heavy chain constant region. In some embodiments, the anti-CD137 antibodies described herein comprise a human wild-type IgG1 heavy chain constant region or a human wild-type IgG4 heavy chain constant region. In some embodiments, the anti-CD137 antibodies described herein comprise a human wild-type IgG1 heavy chain constant region as set forth in SEQ ID NO: 1. In some embodiments, the anti-CD137 antibodies described herein comprise a human wild-type IgG4 heavy chain constant region as set forth in SEQ ID NO: 136. In some embodiments, the anti-CD137 antibodies described herein comprise a mutant IgG1 heavy chain constant region (i.e., an IgG1 heavy chain constant region comprising an amino acid mutation relative to the human wild-type IgG1) or a mutant IgG4 heavy chain constant region (i.e., an IgG4 heavy chain constant region comprising an amino acid mutation relative to the human wild-type IgG4). In some embodiments, the anti-CD137 antibodies described herein comprise a mutant IgG4 heavy chain constant region, wherein the mutant IgG4 heavy chain constant region comprises an amino acid substitution at residue Ser228 according to EU numbering. In some embodiments, the amino acid substitution at residue Ser228 is S228P. In some embodiments, the anti-CD137 antibodies described herein comprise an IgG4 heavy chain constant region, wherein the c-terminal lysine residue is removed. In some embodiments, the anti-CD137 antibodies described herein comprise an IgG4 heavy chain constant region wherein the c-terminal lysine residue is removed and comprises the S228P amino acid substitution. In some embodiments, the anti-CD137 antibodies described herein comprise an IgG4 heavy chain constant region as set forth in SEQ ID NO: 2.

In some embodiments, the anti-CD137 antibodies described herein comprise heavy and light chains comprising the amino acid sequences set forth in SEQ ID NOs: 129 and 133, respectively. In some embodiments, the anti-CD137 antibodies described herein comprise heavy and light chains comprising the amino acid sequences set forth in SEQ ID NOs: 130 and 133, respectively. In some embodiments, the anti-CD137 antibodies described herein comprise heavy and light chains comprising the amino acid sequences set forth in SEQ ID NOs: 131 and 133, respectively. In some embodiments, the anti-CD137 antibodies described herein comprise heavy and light chains comprising the amino acid sequences set forth in SEQ ID NOs: 132 and 133, respectively.

In some embodiments, the anti-CD137 antibodies described herein comprise heavy and light chains comprising amino acid sequences having at least 80%, at least 85%, at least 90%, at least 95%, at least, 96%, at least 97%, at least 98%, or at least 99% identity to SEQ ID NOs: 129 and 133, respectively. In some embodiments, the anti-CD137 antibodies described herein comprise heavy and light chains comprising amino acid sequences having at least 80%, at least 85%, at least 90%, at least 95%, at least, 96%, at least 97%, at least 98%, or at least 99% identity to SEQ ID NOs: 130 and 133, respectively. In some embodiments, the anti-CD137 antibodies described herein comprise heavy and light chains comprising amino acid sequences having at least 80%, at least 85%, at least 90%, at least 95%, at least, 96%, at least 97%, at least 98%, or at least 99% identity to SEQ ID NOs: 131 and 133, respectively. In some embodiments, the anti-CD137 antibodies described herein comprise heavy and light chains comprising amino acid sequences having at least 80%, at least 85%, at least 90%, at least 95%, at least, 96%, at least 97%, at least 98%, or at least 99% identity to SEQ ID NOs: 132 and 133, respectively.

Characterization and Functions of CD137 Binding Antibodies

I. Affinity

In some embodiments, an anti-CD137 antibody described herein binds human CD137 with an affinity ($K_D$) of about 40-100 nM (e.g., between about 40 nM and about 100 nM) as determined by an antigen-binding assay. In some embodiments, an anti-CD137 antibody described herein binds human CD137 with an affinity ($K_D$) of about 30-100 nM (e.g., between about 30 nM and about 100 nM) as determined by an antigen-binding assay. In some embodiments, an anti-CD137 antibody described herein binds human CD137 with an affinity ($K_D$) of about 45-95 nM, about 50-90 nM, about 55-85 nM, about 60-80 nM, about 65-75 nM, about 55-75 nM, about 40-70 nM, about 50-80 nM, or about 60-90 nM as determined by an antigen-binding assay.

In some embodiments, the antigen-binding assay determines a binding affinity of the anti-CD137 antibody for a CD137 polypeptide. In some embodiments, the antigen-binding assay is surface plasmon resonance. Accordingly, in some embodiments an anti-CD137 antibody described herein binds human CD137 with an affinity ($K_D$) of about 40-100 nM (e.g., between about 40 nM and about 100 nM) as determined using surface plasmon resonance. In some embodiments, an anti-CD137 antibody described herein binds human CD137 with an affinity ($K_D$) of about 30-100 nM (e.g., between about 30 nM and about 100 nM) as determined using surface plasmon resonance. In some embodiments, an anti-CD137 antibody described herein binds human CD137 with an affinity ($K_D$) of about 45-95 nM, about 50-90 nM, about 55-85 nM, about 60-80 nM, about 65-75 nM, about 55-75 nM, about 40-70 nM, about 50-80 nM, or about 60-90 nM as determined using surface plasmon resonance.

The phrase "surface plasmon resonance" includes an optical phenomenon that allows for the analysis of real-time biospecific interactions by detection of alterations in protein concentrations within a biosensor matrix, for example using the BIACORE system (Pharmacia Biosensor AB, Uppsala, Sweden and Piscataway, N.J.). For further descriptions, see Jönsson, U., In 1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277. In some embodiments, the antigen-binding assay is biolayer interferometry (BLI). Accordingly, in some embodiments an anti-CD137 antibody described herein binds human CD137 with an affinity (KD) of about 40-100 nM (e.g., between about 40 nM and about 100 nM) as determined using biolayer interferometry. In some embodiments, an anti-CD137 antibody described herein binds human CD137 with an affinity (KD) of about 30-100 nM (e.g., between about 30 nM and about 100 nM) as determined using biolayer interferometry. In some embodiments, an anti-CD137 antibody described herein binds human CD137 with an affinity (KD) of about 45-95 nM, 50-90 nM, 55-85 nM, 60-80 nM, 65-75 nM, 55-75 nM, 40-70 nM, 50-80 nM, or 60-90 nM as determined using biolayer interferometry.

The phrase "biolayer interferometry" or "BLI" includes an optical phenomenon that allows for the measurement of sub-nanometer changes in the thickness of its optical layer detection surface. In some embodiments, biomolecules bind at a sensor surface and change the optical layer thickness. The magnitude of the optical layer thickness change is proportional to the mass or molecular weight of the binding molecule. In some embodiments, CD137 is immobilized to the sensor surface to measure binding by an antibody, wherein binding creates a change in the molecular weight to produce a corresponding change in the optical layer thickness. In some embodiments, BLI is performed with an OCTET system (ForteBio).

II. Immune Cell Effects

In some embodiments, an anti-CD137 antibody described herein induces or enhances cytokine production by an immune cell as determined by a cytokine assay. In some embodiments, the cytokine assay determines an amount of at least one cytokine secreted from an immune cell contacted with the anti-CD137 antibody, wherein an increase in the amount of the at least one cytokine indicates induction or enhancement of cytokine production by the anti-CD137 antibody. In some embodiments, an increase in cytokine production is at least 1 fold, 2 fold, 3 fold, 4 fold or 5 fold more compared to a control antibody (e.g., an antibody that does not bind to CD137 and does not induce cytokine production).

In some embodiments, an anti-CD137 antibody described herein induces or enhances cytokine production by an immune cell as determined by a cytokine assay, wherein the cytokine assay comprises the following steps:

(i) contacting the immune cell with the anti-CD137 antibody; and (ii) determining an amount of at least one cytokine produced by the immune cell, wherein an increase in the amount of the at least one cytokine indicates the anti-CD137 antibody induces or enhances cytokine production by the immune cell.

In some embodiments, an anti-CD137 antibody described herein induces or enhances cytokine production by an immune cell as determined by a cytokine assay, wherein the cytokine assay comprises the following steps:

(i) contacting the immune cell with an anti-CD137 antibody; and (ii) determining an amount of at least one cytokine produced by the immune cell, and (iii) comparing the amount of the at least one cytokine produced by the immune cell to an amount secreted from a reference immune cell, wherein the reference immune cell is contacted with a control antibody, and wherein an increase in the amount of the at least one cytokine produced from the immune cell relative to the reference immune cell indicates induction or enhancement of human CD137-mediated cytokine production.

In some embodiments, an anti-CD137 antibody described herein induces or enhances cytokine production by an immune cell as determined by a cytokine assay, wherein the cytokine assay comprises the following steps:

(i) contacting an immune cell with an anti-CD137 antibody;

(ii) determining an amount of at least one cytokine produced by the immune cell, and (iii) comparing the amount of the at least one cytokine produced by the immune cell to an amount or level secreted from a reference immune cell, wherein the reference immune cell is not contacted with the anti-CD137 antibody, and wherein an increase in the amount of the at least one cytokine produced from the immune cell relative to the reference immune cell indicates induction or enhancement of human CD137-mediated cytokine production by the immune cell.

In some embodiments, the at least one cytokine is selected from a group consisting of IL-2, IFNγ, TNFα, IL-13, and combinations thereof. In some embodiments, the cytokine is IL-2. In some embodiments, the cytokine is IFNγ. In some embodiments, the cytokine is TNFα. In some embodiments, the cytokine is IL-13. In some embodiments, an anti-CD137 antibody induces or enhances IL-2 production. In some embodiments, an anti-CD137 antibody induces or enhances TNFα production. In some embodiments, an anti-CD137 antibody induces or enhances IL-13 production. In some embodiments, the cytokine produced is IL-2. In some embodiments, the cytokine produced is TNFα. In some embodiments, the cytokine produced is IL-13. In some embodiments, the cytokine produced is IFNγ. In some embodiments, the cytokine produced is IL-2 and TNFα. In some embodiments, the cytokine produced is IL-2 and IL-13. In some embodiments, the cytokine produced is IL-2 and IFNγ. In some embodiments, the cytokine produced is TNFα and IL-13. In some embodiments, the cytokine produced is TNFα and IFNγ. In some embodiments, the cytokine produced is IL-13 and IFNγ. In some embodiments, the cytokine produced is IL-2, TNFα and IL-13. In some embodiments, the cytokine produced is IL-2, TNFα and IFNγ. In some embodiments, the cytokine produced is IFNγ, TNFα and IL-13.

In some embodiments, the immune cell is a T cell. In some embodiments, the reference immune cell is a T cell. In some embodiments the T cell is a $CD8^+$ T cell.

In some embodiments, the cytokine assay is a cytokine bead array assay. A cytokine bead array assay is a bead-based immunoassay that allows for multianalyte flow cytometric determination of multiple cytokines in a sample. The use of microspheres of different size or color is the basis of a cytokine bead array assay, wherein each microsphere (or "bead") is coated with an antibody that specifically binds to an antigen (e.g., a cytokine). Antibody-coated beads are then introduced to a sample in combination with detector antibodies. The bead:antigen:detector antibody complexes are then analyzed by flow cytometry. Commercially available cytokine bead array assays include, but are not limited to, BD™ Cytometric Bead Array Systems (BD Biosciences) and LUMINEX® Assays (R&D Systems). In some embodiments, induction or enhancement of human CD137-mediated cytokine production is determined by a cytokine bead array assay. In some embodiments, induction or enhancement of human CD137-mediated cytokine production is determined by a LUMINEX® Assay.

In some embodiments, the cytokine assay is a Meso Scale Discovery (MSD) assay (Meso Scale Diagnostics; Rockville, Md.). An MSD assay is a commercially available assay based on detection of electrochemiluminescent-labeled antibodies that specifically bind to an antigen (e.g., a cytokine) of interest. An MSD assay comprises high binding carbon electrodes in the bottom of microplate wells that allow for attachment of biological reagents (e.g., capture antibodies specific for a cytokine). MSD assays use electrochemiluminescent labels that are conjugated to detection antibodies. A sample is added to the microplate wells and electricity is applied to the plate electrodes by an MSD instrument leading to light emission by the electrochemiluminescent labels. Light intensity is measured to quantify analytes (e.g., cytokines) in the sample. In some embodiments, induction or enhancement of human CD137-mediated cytokine production is determined by a Meso Scale Discovery (MSD) assay.

In some embodiments, an anti-CD137 antibody described herein induces or enhances T cell activation as determined by a T cell activation assay. In some embodiments, the T cell activation assay determines an amount of at least one cytokine secreted from T cells contacted with an anti-CD137 antibody described herein, wherein an increase in the amount of the at least one cytokine indicates induction or enhancement of T cell activation. In some embodiments, an increase in cytokine production is at least 1 fold, 2 fold, 3 fold, 4 fold or 5 fold more compared to a control antibody (e.g., an antibody that does not bind to CD137 and does not induce cytokine production).

In some embodiments, an anti-CD137 antibody described herein induces or enhances T cell activation as determined by a T cell activation assay, wherein the T cell activation assay comprises the following steps:
 (i) isolating T cells from a subject;
 (ii) contacting the T cells with an anti-CD137 antibody; and
 (iii) determining an amount of at least one cytokine secreted by the T cells after (ii),
wherein an increase in the level of the at least one cytokine indicates the anti-CD137 antibody induces or enhances T cell activation.

In some embodiments, an anti-CD137 antibody described herein induces or enhances T cell activation as determined by a T cell activation assay, wherein the T cell activation assay comprises the following steps:
 (i) isolating T cells from a subject;
 (ii) contacting the T cells with an anti-CD137 antibody;
 (iii) determining an amount of at least one cytokine secreted by the T cells; and
 (iv) comparing the amount of the at least one cytokines produced by the T cells to an amount or level secreted from reference T cells,
wherein the reference T cells are not contacted with the anti-CD137 antibody, and wherein an increase in the amount of the at least one cytokine produced from the T cells relative to the reference T cells indicates the anti-CD137 antibody induces or enhances T cell activation.

In some embodiments, an anti-CD137 antibody described herein induces or enhances T cell activation as determined by a T cell activation assay, wherein the T cell activation assay comprises the following steps:
 (i) isolating T cells from a subject;
 (ii) contacting the T cells with an anti-CD137 antibody;
 (iii) determining an amount of at least one cytokine secreted by the T cells; and
 (iv) comparing the amount of the at least one cytokine produced by the T cells to an amount secreted from reference T cells,
wherein the reference T cells are contacted with a control antibody, and wherein an increase in the amount of the at least one cytokine produced from the T cells relative to the reference T cells indicates the anti-CD137 antibody induces or enhances T cell activation.

In some embodiments, the T cell activation assay comprises determining the level of at least one cytokine secreted by the T cells after contact with an anti-CD137 antibody described herein, wherein the at least one cytokine is selected from the group consisting of IL-2, IFNγ, TNFα and IL-13. In some embodiments, the cytokine is IL-2. In some embodiments, the cytokine is IFNγ. In some embodiments, the cytokine is TNFα. In some embodiments, the cytokine is IL-13. In some embodiments, the T cell activation assay comprises a cytokine assay, such as those described herein, to determine the amount of the at least one cytokine. In some embodiments, the cytokine produced is IL-2. In some embodiments, the cytokine produced is TNFα. In some embodiments, the cytokine produced is IL-13. In some embodiments, the cytokine produced is IFNγ. In some embodiments, the cytokine produced is IL-2 and TNFα. In some embodiments, the cytokine produced is IL-2 and IL-13. In some embodiments, the cytokine produced is IL-2 and IFNγ. In some embodiments, the cytokine produced is TNFα and IL-13. In some embodiments, the cytokine produced is TNFα and IFNγ. In some embodiments, the cytokine produced is IL-13 and IFNγ. In some embodiments, the cytokine produced is IL-2, TNFα and IL-13. In some embodiments, the cytokine produced is IL-2, TNFα and IFNγ. In some embodiments, the cytokine produced is IFNγ, TNFα and IL-13.

In some embodiments, an anti-CD137 antibody described herein induces or enhances T cell activation as determined by a T cell activation assay, wherein the T cell activation assay comprises detecting surface expression of at least one activation marker on T cells, and wherein an increase in the expression level of the at least one activation marker indicates induction or enhancement of T cell activation. In some embodiments, "increase in surface expression" refers to at least a 5%, 10%, 15%, 20%, 25%, 30%, 35%, 40%, 45%, 50%, 55%, 60%, 65%, 70%, 75%, 80%, 85%, 90%, 95% or 100% increase in surface expression relative to surface expression in the presence of a control antibody or in the absence of an antibody.

In some embodiments, an anti-CD137 antibody described herein induces or enhances T cell activation as determined by a T cell activation assay in vitro, wherein the T cell activation assay comprises the following steps:
(i) isolating T cells from a subject;
(ii) contacting the T cells with an anti-CD137 antibody; and
(iii) detecting surface expression of at least one activation marker on the T cells, wherein an increase in surface expression of at least one activation marker indicates the anti-CD137 antibody induces or enhances T cell activation.

In some embodiments, an anti-CD137 antibody described herein induces or enhances T cell activation as determined by a T cell activation assay, wherein the T cell activation assay comprises the following steps:
(i) isolating T cells from a subject;
(ii) contacting the T cells with an anti-CD137 antibody;
(iii) determining surface expression of at least one activation marker on the T cells; and
(iv) comparing surface expression of at least one activation marker on the T cells to surface expression of the at least one activation marker on reference T cells,
wherein the reference T cells are not contacted with the anti-CD137 antibody, and wherein an increase in surface expression of at least one activation marker on the T cells relative to the reference T cells indicates the anti-CD137 antibody induces or enhances T cell activation.

In some embodiments, an anti-CD137 antibody described herein induces or enhances T cell activation as determined by a T cell activation assay, wherein the T cell activation assay comprises the following steps:
(i) isolating T cells from a subject;
(ii) contacting the T cells with an anti-CD137 antibody;
(iii) determining surface expression of at least one activation marker on the T cells,
(iv) comparing the surface expression of the at least one activation marker on the T cells to surface expression of the at least one activation marker on reference T cells,
wherein the reference T cells are contacted with a control antibody, and wherein an increase in surface expression of the at least one activation marker on the T cells relative to surface expression of the at least one activation marker on the reference T cells indicates the anti-CD137 antibody induces or enhances T cell activation.

In some embodiments, an anti-CD137 antibody described herein induces or enhances T cell activation as determined by a T cell activation assay in vivo, wherein the T cell activation assay comprises the following steps:
(i) administering the anti-CD137 antibody to a subject;
(ii) isolating T cells from the subject; and
(iii) detecting surface expression of at least one activation marker on the T cells,
wherein an increase in surface expression of at least one activation marker indicates the anti-CD137 antibody induces or enhances CD137-mediated T cell activation.

In some embodiments, an anti-CD137 antibody described herein induces or enhances T cell activation as determined by a T cell activation assay, wherein the T cell activation assay comprises the following steps:
(i) administering the anti-CD137 antibody to a subject;
(ii) isolating T cells from the subject;
(iii) determining surface expression of at least one activation marker on the T cells after; and
(iv) comparing surface expression of the at least one activation marker on the T cells to surface expression of the at least one activation marker on reference T cells,
wherein the reference T cells are isolated from a subject not administered the anti-CD137 antibody, and wherein an increase in surface expression of the at least one activation marker on the T cells relative to the reference T cells indicates the anti-CD137 antibody induces or enhances T cell activation.

In some embodiments, an anti-CD137 antibody described herein induces or enhances T cell activation as determined by a T cell activation assay, wherein the T cell activation assay comprises the following steps:
(i) administering the anti-CD137 antibody to a subject;
(ii) isolating T cells from the subject;
(iii) determining surface expression of at least one activation marker on the T cells; and
(iv) comparing surface expression of the at least one activation marker on the T cells to surface expression of the at least one activation marker on reference T cells,
wherein the reference T cells are isolated from a subject contacted with a control antibody, and wherein an increase in surface expression of the at least one activation marker on the T cells relative to surface expression of the at least one activation marker on the reference T cells indicates the anti-CD137 antibody induces or enhances T cell activation.

In some embodiments, an anti-CD137 antibody described herein does not induce or enhance intrahepatic T cell activation as determined by a T cell activation assay in vivo, wherein the T cell activation assay comprises the following steps:
(i) administering the anti-CD137 to a subject;
(ii) isolating T cells from the liver of the subject;
(iii) detecting surface expression of at least one activation marker on the T cells; and
(iv) comparing the surface expression of the at least one activation marker on the T cells to surface expression of the at least one activation marker on reference T cells,
wherein the reference T cells are isolated from a subject not administered the anti-CD137 antibody, optionally, wherein the reference T cells are isolated from a subject administered a control antibody, and wherein an absence of an increase in surface expression of the at least one activation marker on the T cells relative to surface expression of the at least one activation marker on the reference T cells indicates the anti-CD137 antibody induces or enhances T cell activation.

In some embodiments, an anti-CD137 antibody described herein does not induce or enhance intrasplenic T cell activation as determined by a T cell activation assay in vivo, wherein the T cell activation assay comprises the following steps:
(i) administering the anti-CD137 to a subject;
(ii) isolating T cells from the spleen of the subject;
(iii) detecting surface expression of at least one activation marker on the T cells; and
(iv) comparing surface expression of the at least one activation marker on the T cells to surface expression of the at least one activation marker on reference T cells,
wherein the reference T cells are isolated from a subject not administered the anti-CD137 antibody, optionally, wherein the reference T cells are isolated from a subject administered a control antibody, and wherein an absence in an increase in surface expression of the at least one activation marker on the T cells relative to surface expression of the at least one activation marker on the reference T cells indicates the anti-CD137 antibody induces or enhances T cell activation.

In some embodiments "does not induce or enhance" is intended to refer to the absence of an activity (e.g., T cell activation) or a lack of increase of an activity relative to an increase by a reference antibody.

In some embodiments, a surface expression of a T cell activation marker is equivalent to the surface expression in the absence of an antibody. In some embodiments a surface expression of a T cell activation marker is less than the surface expression in the presence of a reference antibody that induces or enhance surface expression at least 1 fold, 5 fold, 10 fold, 50 fold, or 100 fold higher compared to surface expression in the absence of an antibody.

In some embodiments, the at least one activation marker is selected from the group consisting of CD25, CD69 and CD40L. In some embodiments, the one or more activation markers is CD25.

In some embodiments, T cells are isolated from a subject having a tumor. In some embodiments, the T cells are isolated from the tumor. In some embodiments, the control antibody is an isotype control antibody.

In some embodiments, an anti-CD137 antibody described herein induces or enhances infiltration of one or more immune cells into a tumor microenvironment as determined by an immune cell infiltration assay. In some embodiments, an anti-CD137 antibody described herein decreases infiltration of one or more immune cells into a tumor microenvironment as determined by an immune cell infiltration assay.

In some embodiments, the immune cell infiltration assay determines a quantity of immune cells expressing one or more immune cell markers in a tumor. In some embodiments, the one or more immune cell markers is labeled with an antibody. In some embodiments, the one or more immune cell markers is selected from the group consisting of CD45, CD25, FOXP3, CD4, CD8, F4/80, CD11b, TIGIT and PD-1. In some embodiments, the quantity of immune cells expressing the one or more immune cell markers in a tumor is determined by flow cytometry. Methods of quantifying immune cells expressing one or more immune cell markers by flow cytometry are known in the art.

In some embodiments, the anti-CD137 antibody induces or enhances infiltration of one or more immune cells into a tumor microenvironment relative to a reference antibody, as determined by an immune cell infiltration assay. In some embodiments, the reference antibody is an antibody comprising the same isotype as the anti-CD137 antibody and does not specifically bind to CD137. In some embodiments, the reference antibody is an antibody comprising the same isotype as the anti-CD137 antibody and specifically binds to CD137. In some embodiments, the reference antibody is an antibody comprising the different isotype as the anti-CD137 antibody and does not specifically bind to CD137. In some embodiments, the reference antibody is an antibody comprising a different isotype as the anti-CD137 antibody and specifically binds to CD137.

In some embodiments, an anti-CD137 antibody described herein increases infiltration of immune cells expressing CD45 into a tumor microenvironment in a subject as determined by an immune cell infiltration assay, wherein the assay comprises the following steps:
(i) administering the anti-CD137 antibody to a subject having a tumor;
(ii) obtaining a sample of the tumor;
(iii) contacting the sample with an fluorescently-labeled detection antibody that specifically binds to CD45, wherein the detection antibody fluorescently-labels the immune cells expressing CD45; and
(iv) determining a quantity of the fluorescently-labeled immune cells expressing CD45 by flow cytometry,
wherein an increase in the quantity of fluorescently-immune cells expressing CD45 in the tumor indicates the anti-CD137 antibody induces or enhances infiltration of immune cells into the tumor microenvironment. In some embodiments, an increase in the quantity of immune cells expressing CD45 is at least 25%, 30%, 35%, 40%, 45%, 50%, 55%, 60%, 65%, 70%, 75%, or 80% of total cells in the tumor microenvironment.

In some embodiments, an anti-CD137 antibody described herein reduces or inhibits infiltration of one or more immune cells into a tumor microenvironment as determined by an immune cell infiltration assay. In some embodiments, the anti-CD137 antibody decreases infiltration of one or more immune cells into a tumor microenvironment relative to a reference antibody, as determined by an immune cell infiltration assay. In some embodiments, the reference antibody is an antibody comprising the same isotype as the anti-CD137 antibody and does not specifically bind to CD137. In some embodiments, the reference antibody is an antibody comprising the same isotype as the anti-CD137 antibody and specifically binds to CD137. In some embodiments, the reference antibody is an antibody comprising the different isotype as the anti-CD137 antibody and does not specifically bind to CD137. In some embodiments, the reference antibody is an antibody comprising a different isotype as the anti-CD137 antibody and specifically binds to CD137. In some embodiments, a decrease in immune cells is less than 40%, less than 35%, less than 30%, less than 25%, less than 20%, less than 15%, less than 10%, or less than 5% of total cells in a tumor microenvironment.

In some embodiments, an anti-CD137 antibody described herein decreases infiltration of tumor associated macrophages into a tumor microenvironment in a subject as determined by an immune cell infiltration assay, wherein the assay comprises the following steps:
(i) obtaining a sample of the tumor;
(ii) contacting the sample with one or more antibodies that label the tumor associated macrophage, wherein the one or more antibodies specifically bind to an immune cell marker selected from the group consisting of F4/80, CD11b, CD45, and a combination thereof; and
(iii) determining a quantity of the labeled tumor associated macrophages by flow cytometry. In some embodiments, tumor-associated macrophages are less than 40%, less than 35%, less than 30%, less than 25%, less than 20%, less than 15%, less than 10%, or less than 5% of immune cells in the tumor microenvironment. In some embodiments, tumor-associated macrophages express F4/80, CD11b, and CD45.

In some embodiments, an anti-CD137 antibody described herein decreases infiltration of T regulatory cells (Tregs) into a tumor microenvironment in a subject as determined by an immune cell infiltration assay, wherein the assay comprises the following steps:
(i) obtaining a sample of the tumor;
(ii) contacting the sample with one or more antibodies that label the tumor associated macrophage, wherein the one or more antibodies specifically bind to an immune cell marker selected from the group consisting of CD25, FOXP-3, CD4, and a combination thereof; and
(iii) determining a quantity of the labeled Treg cells by flow cytometry. In some embodiments, Treg cells are less than 35%, less than 30%, less than 25%, less than 20%, less than 15%, less than 10%, or less than 5% % of $CD4^+$ T cells in the tumor microenvironment. In some embodiments, Treg cells express CD4, FOXP-3, and CD25.

In some embodiments, an anti-CD137 antibody described herein protects T cells from T cell exhaustion and/or reverses T cell exhaustion as determined by a T cell exhaustion assay. Exhausted T cells can be distinguished from other T cell dysfunctions such as anergy and senescence based on their underlying molecular mechanisms (Crespo et al., (2013) Curr Opin Immunol 25(2):241-221). Whereas anergy occurs during priming due to the absence of costimulatory signals, and senescence is growth arrest after extensive proliferation, exhausted T cells arise from T cells which initially gained and provided T cell effector function, but that exhibit a gradual deterioration of T cell effector function due to continuous T cell receptor (TCR) stimulation from persistent antigen and inflammatory mediators, both of which commonly occur in tumors (Wherry & Kurachi (2015) Nat Rev Immunol 15(8):486-99). Hallmarks of T cell exhaustion include, but are not limited to, continuous deterioration of in vivo and/or ex vivo T cell function, an increased expression of multiple inhibitory receptors (IRs) (e.g., PD-1, CTLA-4, LAG-3, TIM-3, CD244, CD160, TIGIT), progressive loss or decrease of effector cytokine secretion (e.g., IL-2, interferon gamma (IFNγ), tumor necrosis factor alpha (TNFα)), loss or decrease of CC chemokine (p-chemokine) production, poor responsiveness to IL-7 and IL-15, loss or decrease of proliferative capacity, loss or decrease of in vivo and/or ex vivo cytolytic activity, altered cell metabolism, and a different transcriptional profile relative to non-exhausted T cells. Severely exhausted T cells can succumb to deletion (Yi et al., (2010) Immunology 129(4):474-481).

In some embodiments, an anti-CD137 antibody described herein protects T cells from T cell exhaustion and/or reverses T cell exhaustion as determined by a T cell exhaustion assay, wherein the T cell exhaustion assay determines an amount or level of one or more effector cytokines secreted from T cells treated with an anti-CD137 antibody described herein, wherein the amount or level of the one or more effector cytokines indicates protection from or reversion of T cell exhaustion. In some embodiments, the T cell exhaustion assay comprises the following steps:

(i) isolating of T cells from a subject (e.g., a human subject);

(ii) contacting the T cells with an antigen that induces T cell exhaustion;

(iii) contacting the T cells with the anti-CD137 antibody;

(iv) determining an amount of one or more effector cytokines secreted from the T cells; and;

(v) comparing the amount or level of the one or more effector cytokines secreted from the T cells to an amount or level secreted from reference T cells, wherein the reference T cells are not contacted with the antigen that induces T cell exhaustion, and wherein the difference in the amount or level of the one or more effector cytokines secreted from the T cells and reference T cells indicates protection from or reversion of T cell exhaustion.

In some embodiments, the one or more effector cytokines is selected from IL-2, IFNγ, and TNFα. In some embodiments, the amount or level of the one or more effector cytokines is determined by ELISA. ELISAs suitable for the determination of the amount or level of the one or more effector cytokines are known in the art. In some embodiments, the amount or level of the one or more effector cytokines is determined by Meso Scale Discovery. In some embodiments, the amount or level of the one or more effector cytokines is determined by any one of the cytokine production assays described herein.

The gradual dysfunction of exhausted T cells is accompanied by the expression of IRs, which transmit inhibitory signals to the nucleus upon interaction with ligands on target cells. Accordingly, in some embodiments, an anti-CD137 antibody described herein protects T cells from T cell exhaustion and/or reverses T cell exhaustion as determined by a T cell exhaustion assay, wherein the T cell exhaustion assay determines an expression level of one or more inhibitory receptors on T cells treated with an anti-CD137 antibody described herein, wherein the expression level of the one or more inhibitory receptors indicates protection from or reversion of T cell exhaustion. In some embodiments, the T cell exhaustion assay comprises the following steps:

(i) isolating of T cells from a subject (e.g., a human subject);

(ii) contacting the T cells with an antigen that induces T cell exhaustion;

(iii) contacting the T cells with the anti-CD137 antibody;

(iv) determining an expression level of one or more inhibitory receptors on T cells; and (v) comparing the expression level of one or more inhibitory receptors on T cells to an amount or level secreted from reference T cells, wherein the reference T cells are not contacted with the antigen that induces T cell exhaustion, and wherein the difference in the expression level of one or more inhibitory receptors on T cells and reference T cells indicates protection from or reversion of T cell exhaustion.

In some embodiments, the one or more inhibitory receptors is selected from TIGIT and PD-1 In some embodiments, the expression level of the one or more inhibitory receptors is determined by flow cytometry. Methods to determine expression levels of inhibitory receptors on immune cells (e.g. T cells) by flow cytometry are known in the art.

In some embodiments, the amount of exhausted T cells is less than 20%, 15%, 10% or 5% of total CD8+ or CD4+ T cells in a tumor microenvironment.

Where the assays described herein refer to 'isolating T cells from a subject'; it is to be understood that the assay can suitably be performed on T cells previously isolated from a subject.

Where the assays described herein refer to (i) administering the anti-CD137 antibody to a subject and (ii) isolating T cells from the subject; it is to be understood that the assay can suitably be performed on T cells previously isolated from a subject to whom the anti-CD137 antibody has been administered.

Where the assays described herein refer to 'obtaining a sample of the tumor'; it is to be understood that the assay can suitably be performed on a sample of a tumor previously isolated from a subject.

Where the assays described herein refer to (i) administering the anti-CD137 antibody to a subject having a tumor and (ii) obtaining a sample of the tumor; it is to be understood that the assay can suitably be performed a sample of a tumor previously isolated from a subject to whom the anti-CD137 antibody has been administered.

III. Non-Ligand Binding

In some embodiments, an anti-CD137 antibody described herein binds to a non-ligand binding region of CD137, as determined by a ligand binding assay. A ligand binding assay (LBA) is an assay, or an analytic procedure, that provides a measure of the interactions that occur between two reactant molecules (e.g., a receptor and ligand polypeptides). Suitably, the LBA provides a measure of the degree of affinity between the two reactant molecules (e.g., a receptor and ligand polypeptides). For example, in some embodiments a ligand binding assay is used to determine the presence, rate, extent of binding, or combinations thereof, of a ligand molecule (e.g., CD137L) to a receptor (e.g., CD137). In some embodiments, to determine the presence, rate and/or extent of ligand binding to a receptor, a ligand binding assay comprises detecting the formation of a ligand:receptor complex. In some embodiments, to determine the presence, rate and/or extent of ligand binding to a receptor, a ligand binding assay comprises determining the dissociation of a ligand:receptor complex.

In some embodiments, the formation and/or dissociation of a ligand:receptor complex is determined by detection of a fluorescently-labeled ligand in complex with a receptor. In some embodiments, the formation and/or dissociation of a ligand:receptor complex is determined by detection and/or quantification of an amount of fluorescently-labeled receptor in complex with a ligand. In some embodiments, the formation and/or dissociation of a ligand:receptor complex is determined by detection and/or quantification of an amount of a fluorescently-labeled antibody that specifically binds to the ligand:receptor complex. Methods of detecting and quantifying fluorescence are known in the art and include, but are not limited to, fluorescence polarization (FP) and fluorescence anisotropy (FA).

In some embodiments, the formation and/or dissociation of a ligand:receptor complex is determined by detection and/or quantification of an amount of a radioactively-labeled ligand in complex with a receptor. In some embodiments, the formation and/or dissociation of a ligand:receptor complex is determined by detection and/or quantification of an amount of radioactively-labeled receptor in complex with a ligand. In some embodiments, the formation and/or dissociation of a ligand:receptor complex is determined by detection and/or quantification of an amount of a radioactively-labeled antibody that specifically binds to the ligand:receptor complex. Methods of detecting and quantifying radioactivity are known in the art and include, but are not limited to, quantitative autoradiography and scintillation counting.

In some embodiments, the formation and/or dissociation of a ligand:receptor complex is determined by detection and/or quantification of an amount of a bioluminescently-labeled ligand in complex with a receptor. In some embodiments, the formation and/or dissociation of a ligand:receptor complex is determined by detection and/or quantification of an amount of bioluminescently-labeled receptor in complex with a ligand. In some embodiments, the formation and/or dissociation of a ligand:receptor complex is determined by detection and/or quantification of an amount of a bioluminescently-labeled antibody that specifically binds to the ligand:receptor complex. Methods of detecting and quantifying bioluminescence are known in the art and include, but are not limited to, luminometry.

In some embodiment, formation and/or dissociation of the ligand:receptor complex is determined by surface plasmon resonance (SPR) as described supra.

In some embodiments, a ligand binding assay determines if an antibody that specifically binds to a receptor (e.g., an anti-CD137 antibody) affects the formation of a ligand: receptor complex by determining the presence, rate and/or extent of ligand binding to the receptor in the presence of the antibody. In some embodiments, an antibody (e.g., an anti-CD137 antibody) that specifically binds to a receptor (e.g., CD137) and decreases, disrupts or blocks the formation of a ligand:receptor complex (e.g., a CD137:CD137L complex) is known as a "ligand blocking antibody". In some embodiments, a "ligand blocking antibody" can decrease the formation of a ligand:receptor complex (e.g., a CD137: CD137L complex) by at least 10%, at least 20%, at least 30%, at least 40%, or at least 50% compared to the formation of the ligand:receptor complex (e.g., the CD137: CD137L complex) which occurs in the absence of the ligand blocking antibody. In some embodiments, an antibody (e.g., an anti-CD137 antibody) that specifically binds to a receptor (e.g., CD137) and does not decrease, disrupt or block the formation of a ligand:receptor complex (e.g., a CD137: CD137L complex) is referred to as a "non-ligand blocking antibody". In some embodiments, a "non-ligand blocking antibody" can decrease the formation of a ligand:receptor complex (e.g., a CD137:CD137L complex) by less than 10%, less than 5%, less than 2% or less than 1% compared to the formation of the ligand:receptor complex (e.g., the CD137:CD137L complex) which occurs in the absence of the non-ligand blocking antibody. Accordingly, in some embodiments a ligand binding assay characterizes an antibody that binds to a receptor as a "ligand blocking antibody" or a "non-ligand blocking antibody".

In some embodiments, a ligand binding assay characterizes an antibody that specifically binds to a receptor and promotes the formation of a ligand:receptor complex. In some embodiments, a ligand binding assay characterizes an antibody that specifically binds to a receptor and stabilizes the formation of a ligand:receptor complex. In some embodiments, the induction and/or stabilization of the formation of a ligand:receptor complex by an antibody contributes to the antibody's agonistic effect. In some embodiments, an anti-CD137 antibody described herein agonizes CD137, as determined by a ligand binding assay.

In some embodiments, an isolated anti-CD137 antibody, or antigen-binding fragment thereof, described herein, binds to CD137 and induces CD137L binding as determined by a ligand binding assay (LBA).

In some embodiments, an isolated anti-CD137 antibody, or antigen-binding fragment thereof, described herein, binds to CD137 and induces CD137L binding as determined by a ligand binding assay, wherein the ligand binding assay comprises the following steps:

(i) combining an anti-CD137 antibody with CD137 and CD137L at various concentrations, wherein CD137 and CD137L form a CD137:CD137L complex, and (ii) detecting the CD137:CD137L complex in the presence of the anti-CD137 antibody over time, wherein an increase in CD137:CD137L complex in the presence of the anti-CD137 antibody indicates the anti-CD137 antibody induces CD137L binding to CD137. The increase in CD137: CD137L complex in the presence of the anti-CD137 antibody may be at least 1.5-fold, at least 2-fold, at least 5-fold, at least 10-fold, or at least 20-fold greater that the amount CD137:CD137L complex in the absence of the anti-CD137 antibody.

In some embodiments, an isolated anti-CD137 antibody, or antigen-binding fragment thereof, described herein, binds to a non-ligand binding region of CD137 as determined by a ligand binding assay, wherein the ligand binding assay comprises the following steps:

(i) combining an anti-CD137 antibody with CD137 and CD137L at various concentrations, wherein CD137 and CD137L form a CD137:CD137L complex, and (ii) detecting the CD137:CD137L complex in the presence of the anti-CD137 antibody over time, wherein no change in the CD137:CD137L complex in the presence of the anti-CD137 antibody indicates the anti-CD137 antibody binds to a non-ligand binding region of CD137. In some embodiments, less than a 2% change in CD137:CD137L complex indicates the anti-CD137 antibody binds to a non-ligand binding region of CD137. In some embodiments, less than a 5% change in CD137:CD137L complex indicates the anti-CD137 antibody binds to a non-ligand binding region of CD137. In some embodiments, less than a 10% change in CD137:CD137L complex indicates the anti-CD137 antibody binds to a non-ligand binding region of CD137.

In some embodiments, an anti-CD137 antibody described herein binds to a non-ligand binding region of CD137, as determined by biolayer interferometry. In some embodiments, an anti-CD137 antibody described herein binds to a non-ligand binding region of CD137, as determined by surface plasmon resonance imaging (SPRi). In some embodiments, CD137 and CD137L is sequentially applied to a sensor pre-loaded with an anti-CD137 antibody (i.e., the antibody is captured on a sensor). In some embodiments, the binding of an anti-CD137 antibody to a non-ligand binding region is indicated by an increase in response upon exposure to CD137L.

IV. Functions of CD137 Binding Antibodies

In some embodiments, the anti-CD137 agonist antibodies described herein bind to human CD137 with an affinity ($K_D$) of about 30-100 nM (e.g., between about 30 nM and about 100 nM) and inhibit or reduce T cell exhaustion. In some embodiments, the anti-CD137 agonist antibodies described herein bind to human CD137 with an affinity ($K_D$) of about 30-100 nM (e.g., between about 30 nM and about 100 nM) and induce or enhance T cell activation. In some embodiments, the anti-CD137 agonist antibodies described herein bind to human CD137 with an affinity ($K_D$) of about 30-100 nM (e.g., between about 30 nM and about 100 nM) and induce or enhance cytokine production by immune cells. In some embodiments, the anti-CD137 agonist antibodies described herein bind to human CD137 with an affinity ($K_D$) of about 30-100 nM (e.g., between about 30 nM and about 100 nM) and induce or enhance T cell proliferation. In some embodiments, the anti-CD137 agonist antibodies described herein bind to human CD137 with an affinity ($K_D$) of about 30-100 nM (e.g., between about 30 nM and about 100 nM) and exhibit anti-tumor efficacy. In some embodiments, the anti-CD137 agonist antibodies described herein bind to human CD137 with an affinity ($K_D$) of about 30-100 nM (e.g., between about 30 nM and about 100 nM) and inhibit or reduce macrophage differentiation and/or activation. In some embodiments, the anti-CD137 agonist antibodies described herein bind to human CD137 with an affinity ($K_D$) of about 30-100 nM (e.g., between about 30 nM and about 100 nM) and induce or enhance NFκβ signaling. In some embodiments, the anti-CD137 agonist antibodies described herein bind to human CD137 with an affinity ($K_D$) of about 30-100 nM (e.g., between about 30 nM and about 100 nM) and induce or enhance immune cell infiltration into a tumor microenvironment. In some embodiments, the anti-CD137 agonist antibodies described herein bind to human CD137 with an affinity ($K_D$) of about 30-100 nM (e.g., between about 30 nM and about 100 nM) and do not induce hepatotoxicity. In some embodiments, the anti-CD137 agonist antibodies described herein bind to human CD137 with an affinity ($K_D$) of about 30-100 nM (e.g., between about 30 nM and about 100 nM) and bind to a non-ligand binding domain on extracellular CD137. In some embodiments, the anti-CD137 agonist antibodies described herein bind to human CD137 with an affinity ($K_D$) of about 30-100 nM (e.g., between about 30 nM and about 100 nM) and do not inhibit CD137 and CD137L interaction. In some embodiments, the anti-CD137 agonist antibodies described herein bind to human CD137 with an affinity ($K_D$) of about 30-100 nM (e.g., between about 30 nM and about 100 nM) and bind to an epitope comprising K114 of SEQ ID NO: 3.

In some embodiments, the anti-CD137 agonist antibodies described herein inhibit or reduce T cell exhaustion and induce or enhance T cell activation. In some embodiments, the anti-CD137 agonist antibodies described herein inhibit or reduce T cell exhaustion and induce or enhance cytokine production by immune cells. In some embodiments, the anti-CD137 agonist antibodies described herein inhibit or reduce T cell exhaustion and induce or enhance T cell proliferation. In some embodiments, the anti-CD137 agonist antibodies described herein inhibit or reduce T cell exhaustion and exhibit anti-tumor efficacy. In some embodiments, the anti-CD137 agonist antibodies described herein inhibit or reduce T cell exhaustion and inhibit or reduce macrophage differentiation and/or activation. In some embodiments, the anti-CD137 agonist antibodies described herein inhibit or reduce T cell exhaustion and induce or enhance NFκβ signaling. In some embodiments, the anti-CD137 agonist antibodies described herein inhibit or reduce T cell exhaustion and induce or enhance immune cell infiltration into a tumor microenvironment. In some embodiments, the anti-CD137 agonist antibodies described herein inhibit or reduce T cell exhaustion and do not induce hepatotoxicity. In some embodiments, the anti-CD137 agonist antibodies described herein inhibit or reduce T cell exhaustion and bind to a non-ligand binding domain on extracellular CD137. In some embodiments, the anti-CD137 agonist antibodies described herein inhibit or reduce T cell exhaustion and do not inhibit CD137 and CD137L interaction. In some embodiments, the anti-CD137 agonist antibodies described herein inhibit or reduce T cell exhaustion and bind to an epitope comprising K114 of SEQ ID NO: 3.

In some embodiments, the anti-CD137 agonist antibodies described herein induce or enhance T cell activation and induce or enhance cytokine production by immune cells. In some embodiments, the anti-CD137 agonist antibodies described herein induce or enhance T cell activation and induce or enhance T cell proliferation. In some embodiments, the anti-CD137 agonist antibodies described herein induce or enhance T cell activation and exhibit anti-tumor efficacy. In some embodiments, the anti-CD137 agonist antibodies described herein induce or enhance T cell activation and inhibit or reduce macrophage differentiation and/or activation. In some embodiments, the anti-CD137 agonist antibodies described herein induce or enhance T cell activation and induce or enhance NFκβ signaling. In some embodiments, the anti-CD137 agonist antibodies described herein induce or enhance T cell activation and induce or enhance immune cell infiltration into a tumor microenvironment. In some embodiments, the anti-CD137 agonist antibodies described herein induce or enhance T cell activation and do not induce hepatotoxicity. In some embodiments, the anti-CD137 agonist antibodies described herein induce or enhance T cell activation and bind to a non-ligand binding domain on extracellular CD137. In some embodiments, the anti-CD137 agonist antibodies described herein induce or enhance T cell activation and do not inhibit CD137 and CD137L interaction. In some embodiments, the anti-CD137 agonist antibodies described herein induce or enhance T cell activation and bind to an epitope comprising K114 of SEQ ID NO: 3.

In some embodiments, the anti-CD137 agonist antibodies described herein induce or enhance cytokine production by immune cells and induce or enhance T cell proliferation. In some embodiments, the anti-CD137 agonist antibodies described herein induce or enhance cytokine production by immune cells and exhibit anti-tumor efficacy. In some embodiments, the anti-CD137 agonist antibodies described herein induce or enhance cytokine production by immune cells and inhibit or reduce macrophage differentiation and/or activation. In some embodiments, the anti-CD137 agonist antibodies described herein induce or enhance cytokine production by immune cells and induce or enhance NFκβ signaling. In some embodiments, the anti-CD137 agonist antibodies described herein induce or enhance cytokine production by immune cells and induce or enhance immune cell infiltration into a tumor microenvironment. In some embodiments, the anti-CD137 agonist antibodies described herein induce or enhance cytokine production by immune cells and do not induce hepatotoxicity. In some embodiments, the anti-CD137 agonist antibodies described herein induce or enhance cytokine production by immune cells and bind to a non-ligand binding domain on extracellular CD137. In some embodiments, the anti-CD137 agonist antibodies described herein induce or enhance cytokine production by immune cells and do not inhibit CD137 and CD137L interaction. In some embodiments, the anti-CD137 agonist antibodies described herein induce or enhance cytokine production by immune cells and bind to an epitope comprising K114 of SEQ ID NO: 3.

In some embodiments, the anti-CD137 agonist antibodies described herein induce or enhance T cell proliferation and exhibit anti-tumor efficacy. In some embodiments, the anti-CD137 agonist antibodies described herein induce or enhance T cell proliferation and inhibit or reduce macrophage differentiation and/or activation. In some embodiments, the anti-CD137 agonist antibodies described herein induce or enhance T cell proliferation and induce or enhance NFκβ signaling. In some embodiments, the anti-CD137 agonist antibodies described herein induce or enhance T cell proliferation and induce or enhance immune cell infiltration into a tumor microenvironment. In some embodiments, the anti-CD137 agonist antibodies described herein induce or enhance T cell proliferation and do not induce hepatotoxicity. In some embodiments, the anti-CD137 agonist antibodies described herein induce or enhance T cell proliferation and bind to a non-ligand binding domain on extracellular CD137. In some embodiments, the anti-CD137 agonist antibodies described herein induce or enhance T cell proliferation and do not inhibit CD137 and CD137L interaction. In some embodiments, the anti-CD137 agonist antibodies described herein induce or enhance T cell proliferation and bind to an epitope comprising K114 of SEQ ID NO: 3.

In some embodiments, the anti-CD137 agonist antibodies described herein exhibit anti-tumor efficacy and inhibit or reduce macrophage differentiation and/or activation. In some embodiments, the anti-CD137 agonist antibodies described herein exhibit anti-tumor efficacy and induce or enhance NFκβ signaling. In some embodiments, the anti-CD137 agonist antibodies described herein exhibit anti-tumor efficacy and induce or enhance immune cell infiltration into a tumor microenvironment. In some embodiments, the anti-CD137 agonist antibodies described herein exhibit anti-tumor efficacy and do not induce hepatotoxicity. In some embodiments, the anti-CD137 agonist antibodies described herein exhibit anti-tumor efficacy and bind to a non-ligand binding domain on extracellular CD137. In some embodiments, the anti-CD137 agonist antibodies described herein exhibit anti-tumor efficacy and do not inhibit CD137 and CD137L interaction. In some embodiments, the anti-CD137 agonist antibodies described herein exhibit anti-tumor efficacy and bind to an epitope comprising K114 of SEQ ID NO: 3.

In some embodiments, the anti-CD137 agonist antibodies described herein inhibit or reduce macrophage differentiation and/or activation and induce or enhance NFκβ signaling. In some embodiments, the anti-CD137 agonist antibodies described herein inhibit or reduce macrophage differentiation and/or activation and induce or enhance immune cell infiltration into a tumor microenvironment. In some embodiments, the anti-CD137 agonist antibodies described herein inhibit or reduce macrophage differentiation and/or activation and do not induce hepatotoxicity. In some embodiments, the anti-CD137 agonist antibodies described herein inhibit or reduce macrophage differentiation and/or activation and bind to a non-ligand binding domain on extracellular CD137. In some embodiments, the anti-CD137 agonist antibodies described herein inhibit or reduce macrophage differentiation and/or activation and do not inhibit CD137 and CD137L interaction. In some embodiments, the anti-CD137 agonist antibodies described herein inhibit or reduce macrophage differentiation and/or activation and bind to an epitope comprising K114 of SEQ ID NO: 3.

In some embodiments, the anti-CD137 agonist antibodies described herein induce or enhance NFκβ signaling and induce or enhance immune cell infiltration into a tumor microenvironment. In some embodiments, the anti-CD137 agonist antibodies described herein induce or enhance NFκβ signaling and do not induce hepatotoxicity. In some embodiments, the anti-CD137 agonist antibodies described herein induce or enhance NFκβ signaling and bind to a non-ligand binding domain on extracellular CD137. In some embodiments, the anti-CD137 agonist antibodies described herein induce or enhance NFκβ signaling and do not inhibit CD137 and CD137L interaction. In some embodiments, the anti-CD137 agonist antibodies described herein induce or enhance NFκβ signaling and bind to an epitope comprising K114 of SEQ ID NO: 3.

In some embodiments, the anti-CD137 agonist antibodies described herein induce or enhance immune cell infiltration into a tumor microenvironment and do not induce hepatotoxicity. In some embodiments, the anti-CD137 agonist antibodies described herein induce or enhance immune cell infiltration into a tumor microenvironment and bind to a non-ligand binding domain on extracellular CD137. In some embodiments, the anti-CD137 agonist antibodies described herein induce or enhance immune cell infiltration into a tumor microenvironment and do not inhibit CD137 and CD137L interaction. In some embodiments, the anti-CD137 agonist antibodies described herein induce or enhance immune cell infiltration into a tumor microenvironment and bind to an epitope comprising K114 of SEQ ID NO: 3. In some embodiments, the anti-CD137 agonist antibodies described herein do not induce hepatotoxicity and bind to a non-ligand binding domain on extracellular CD137. In some embodiments, the anti-CD137 agonist antibodies described herein do not induce hepatotoxicity and do not inhibit CD137 and CD137L interaction. In some embodiments, the anti-CD137 agonist antibodies described herein do not induce hepatotoxicity and bind to an epitope comprising K114 of SEQ ID NO: 3.

In some embodiments, the anti-CD137 agonist antibodies described herein bind to a non-ligand binding domain on extracellular CD137 and do not inhibit CD137 and CD137L interaction. In some embodiments, the anti-CD137 agonist antibodies described herein bind to a non-ligand binding domain on extracellular CD137 and bind to an epitope comprising K114 of SEQ ID NO: 3. In some embodiments, the anti-CD137 agonist antibodies described herein do not inhibit CD137 and CD137L interaction and bind to an epitope comprising K114 of SEQ ID NO: 3.

Epitope Mapping

The disclosure provides anti-CD137 antibodies, or antigen-binding fragments thereof, that specifically bind to an epitope of human CD137 and compete with a reference mAb (e.g., mAb1) for binding to the epitope of human CD137. Methods to characterize, map, or otherwise elucidate the epitope of an anti-CD137 antibody can be grouped into structural, functional, or computational methods. A particularly suitable structural method to determine the precise molecular architecture of the interaction between an antibody and the corresponding antigen to which it binds is x-ray crystallography (alternatively "x-ray co-crystallography). A crystal structure of a bonded antibody-antigen pair enables very accurate determination of key interactions between individual amino acids from both side chains and main chain atoms in both the epitope of the antigen and the paratope of the antibody. Amino acids that are within 4 angstroms (Å) of each other are generally considered to be contacting residues. The methodology typically involves purification of antibody and antigen, formation and purification of the complex, followed by successive rounds of crystallization screens and optimization to obtain diffraction-quality crystals. Structural solution is obtained following x-ray crystallography frequently at a synchrotron source. Other structural methods for epitope mapping include, but are not limited to, hydrogen-deuterium exchange coupled to mass spectrometry, crosslinking-coupled mass spectrometry, and nuclear magnetic resonance (NMR) (see, e.g., Epitope Mapping Protocols in Methods in Molecular Biology, Vol. 66, G. E. Morris, Ed. (1996); Abbott et al., (2014) Immunology 142(4):526-535).

Functional methods for epitope mapping are well known in the art and typically involve an assessment or quantification of antibody binding to whole proteins, protein fragments or peptides. Functional methods for epitope mapping can be used, for example, to identify linear or conformational epitopes and/or can be used to infer when two or more distinct antibodies bind to the same or similar epitopes. Functional methods for epitope mapping include, for example, immunoblotting and immunoprecipitation assays, wherein overlapping or contiguous peptides from CD137 are tested for reactivity with an anti-CD137 antibody, e.g., mAb1. Other functional methods for epitope mapping include array-based oligopeptide scanning (alternatively known as "overlapping peptide scanning" or "pepscan analysis"), site-directed mutagenesis (e.g., alanine-scanning mutagenesis), and high-throughput mutagenesis mapping (e.g., shotgun mutagenesis mapping).

Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such assays involve the use of purified antigen bound to a solid surface or cells and either 1) an unlabeled test antigen-binding protein and a labeled reference antigen-binding protein, or 2) a labeled test antigen-binding protein and an unlabeled reference antigen-binding protein. Competitive inhibition is measured by determining the amount of label bound to the solid surface or cells in the presence of the test antigen-binding protein. Usually the test antigen-binding protein is present in excess. Antigen-binding proteins identified by competition assay (competing antigen-binding proteins) include antigen-binding proteins binding to the same epitope as the reference antigen-binding proteins (e.g., mAb1) and antigen-binding proteins binding to an adjacent epitope sufficiently proximal to the epitope bound by the reference antigen-binding protein (e.g., mAb1) for steric hindrance to occur. Additional details regarding methods for determining competitive binding are provided in the examples herein. Usually, when a competing antigen-binding protein is present in excess (e.g., about 1-, about 5-, about 10-, about 20-about 50-, or about 100-fold excess), it will inhibit (e.g., reduce or block) specific binding of a reference antigen-binding protein to a common antigen by at least about 40-45%, about 45-50%, about 50-55%, about 55-60%, about 60-65%, about 65-70%, about 70-75% or about 75% or more. In some instances, binding is inhibited by at least about 80-85%, about 85-90%, about 90-95%, about 95-97%, or about 97% or more.

The site-directed mutagenesis method involves targeted site-directed mutagenesis where critical amino acids are identified by systematically introducing substitutions along the protein sequence and then determining the effects of each substitution on antibody binding. This may be done by "alanine scanning mutagenesis" (Cunningham and Wells (1989) Science 244:1081-085), or some other form of point mutagenesis of amino acid residues in CD137. Without being bound by theory, two or more antibodies (e.g., a test antibody and a reference antibody, e.g., mAb1) have the same epitope if essentially all amino acid mutations in the antigen that reduce or eliminate binding of the first antibody reduce or eliminate binding of the second or more antibodies.

Shotgun mutagenesis mapping utilizes a comprehensive plasmid-mutation library for the target gene, with each clone in the library bearing a unique amino acid mutation and the entire library covering every amino acid in the target protein. The clones that constitute the mutation library are individually arranged in microplates, expressed within living mammalian cells, and tested for immunoreactivity with antibodies of interest. Amino acids critical for antibody epitopes are identified by a loss of reactivity and are then mapped onto a protein structure to visualize epitopes. Expression of the target protein antigen within mammalian cells often provides the native structure of the target protein antigen, which allows both linear and conformational epitope structures to be mapped on complex proteins. (Paes et al., J. Am. Chem. Soc. 131 (20): 6952-6954 (2009); Banik and Doranz, Genetic Engineering and Biotechnology News 3(2): 25-28 (2010)).

The epitope bound by an anti-CD137 antibody can also be determined using peptide scanning methods. In peptide scanning, libraries of short peptide sequences from overlapping segments of the target protein, CD137 are tested for their ability to bind antibodies of interest. The peptides are synthesized and screened for binding, e.g. using ELISA or BIACORE, or on a chip, by any of the multiple methods for solid-phase screening (Reineke et al, Curr. Opin. Biotechnol. 12: 59-64, 2001) as in the "pepscan" methodology (WO 84/03564; WO 93/09872).

A recently developed technology termed CLIPS (chemical linkage of peptides onto scaffolds) may be used to map conformational epitopes. The loose ends of the peptides are affixed onto synthetic scaffolds, so that the scaffolded peptide may be able to adopt the same spatial structure as the corresponding sequence in the intact protein. CLIPS technology is used to fix linear peptides into cyclic structures ('single-loop' format), and to bring together different parts of a protein binding site ('double-loop', 'triple-loop', etc. format), so as to create conformational epitopes that may be assayed for antibody binding. (U.S. Pat. No. 7,972,993).

The epitopes bound by antibodies provided by the disclosure can also be mapped using computational methods. In these methods, for example, libraries of peptide fragments are displayed on the surface of the phage or cell. Epitopes are then mapped by screening antibodies against these fragments using selective binding assays. A number of computational tools have been developed which allow the prediction of conformational epitopes based upon linear affinity-selected peptides obtained using phage display (Mayrose et al., (2007) Bioinformatics 23:3244-3246). Methods are also available for the detection of conformational epitopes by phage display. Microbial display systems can also be used to express properly folded antigenic fragments on the cell surface for identification of conformational epitopes (Cochran et al., J. Immunol. Meth. 287: 147-158, 2004; Rockberg et al., Nature Methods 5: 1039-1045, 2008).

Methods involving proteolysis and mass spectroscopy can also be used to determine antibody epitopes (Baerga-Ortiz et al., Protein Sci. 2002 June; 1 1 (6): 1300-1308). In limited proteolysis, the antigen is cleaved by different proteases, in the presence and in the absence of the antibody, and the fragments are identified by mass spectrometry. The epitope is the region of the antigen that becomes protected from proteolysis upon binding of the antibody (Suckau et al., Proc. Natl. Acad. Sci. USA 87: 9848-9852, 1990). Additional proteolysis based methods include, for example, selective chemical modification (Fiedler et al., Bioconjugate Chemistry 1998, 9(2): 236-234, 1998), epitope excision (Van de Water et al., Clin. Immunol. Immunopathol. 1997, 85(3): 229-235, 1997), and the recently developed method of hydrogen-deuterium (H/D) exchange (Flanagan, N., Genetic Engineering and Biotechnology News 3(2): 25-28, 2010).

In some embodiments, the anti-CD137 antibodies described herein bind to an epitope located within amino acid residues 111-135 of SEQ ID NO: 3 as determined by mutagenesis and mammalian display. In some embodiments, the anti-CD137 antibodies described herein bind to an epitope comprising K114 of SEQ ID NO: 3 as determined by mutagenesis and mammalian display. In some embodiments, the anti-CD137 antibodies described herein bind to an epitope comprising E111, T113 and K114 of SEQ ID NO: 3 as determined by mutagenesis and mammalian display. In some embodiments, the anti-CD137 antibodies described herein bind to an epitope comprising E111, T113, K114 and P135 of SEQ ID NO: 3 as determined by mutagenesis and mammalian display. In some embodiments, the anti-CD137 antibodies described herein bind to an epitope comprising E111, T113, K114, N126, I132 and P135 of SEQ ID NO: 3 as determined by mutagenesis and mammalian display.

PD-1 and PD-L1 Checkpoint Signaling and Therapeutic Antagonism

Various cancers are often highly refractory to conventional chemotherapeutic agents and regimens, necessitating the development of other therapeutic approaches. The loss of immunologic control is characterized as one of the emerging hallmarks of cancer (Hanahan and Weinberg, (2011) Cell 144(5):646-674). Targeting the components and mechanisms employed by tumors to pathologically modulate the immune system has recently emerged as a novel therapeutic approach.

The Programmed Cell Death Protein 1 (PD-1), also known as CD279 (Cluster of Differentiation 279), is a 55 kDa type I transmembrane inhibitory receptor and a member of the extended CD28/CTLA-4 family of T cell regulators (Agata et al., (1996) Int Immunol 8:765-772; Okazaki et al., (2002) Curr Opin Immunol 14: 391779-82; Bennett et al., (2003) J Immunol 170:711-8). The PD-1 protein in humans is encoded by the PDCD1 gene. Other members of the CD28 family include CD28, CTLA-4, ICOS, and BTLA. PD-1 is expressed on activated B cells, T cells, and monocytes/myeloid cells. Two ligands for PD-1 have been identified, PD-L1 (B7-H1) and PD-L2 (B7-DC), that have been shown to downregulate T cell activation upon binding to PD-1 (Freeman et al., (2000) J Exp Med 192:1027-1034; Carter et al. (2002) Eur. J. Immunol. 32:634-43). Both PD-L1 and PD-L2 are B7 homologs that bind to PD-1, but do not bind to other CD28 family members.

PD-1 is known as an immunoinhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745). The interaction between PD-1 and PD-L1 can act as an immune checkpoint, which can lead to a decrease in T-cell receptor mediated proliferation (Dong et al. (2003) J. Mol. Med. 81:281-7; Blank et al. (2005) Cancer Immunol. Immunother. 54:307-314; Konishi et al. (2004)). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

For several cancers, tumor survival and proliferation are sustained by tumor-mediated immune checkpoint modulation. This modulation can result in the disruption of anti-cancer immune system functions. For example, recent studies have indicated that the expression of immune checkpoint receptors ligands, such as PD-L1 or PD-L2, by tumor cells can downregulate immune system activity in the tumor microenvironment and promote cancer immune evasion. particularly by suppressing T cells. PD-L1 is abundantly expressed by a variety of human cancers (Dong et al., (2002) Nat Med 8:787-789). The receptor for PD-L1, PD-1, is expressed on lymphocytes (e.g., activated T cells) and is normally involved in down-regulating the immune system and promoting self-tolerance, particularly by suppressing T cells. However, when PD-1 receptors expressed on T cells bind to cognate PD-L1 ligands on tumor cells, the resulting T cell suppression contributes to an impaired immune response against the tumor (e.g., a decrease in tumor infiltrating lymphocytes or the establishment of immune evasion by cancer cells).

In large sample sets of, e.g., ovarian, renal, colorectal, pancreatic, liver cancers and melanoma, it was shown that PD-L1 expression correlated with poor prognosis and reduced overall survival irrespective of subsequent treatment (see e.g., Dong et al., (2002) Nat Med 8(8):793-800; Yang et al., (2008) Invest Ophthalmol Vis Sci 49(6):2518-2525; Ghebeh et al., (2006) Neoplasia 8:190-198; Hamanishi et al., (2007) Proc Nat Acad Sci USA 104:3360-3365; Thompson et al., (2006) Clin Genitourin Cancer 5:206-211; Nomi et al., (2005) Clin Cancer Res 11:2947-2953; Inman et al., (2007) Cancer 109:1499-1505; Shimauchi et al., (2007) Int J Cancer 121:2585-2590; Gao et al., (2009) Clin Cancer Res 15:971-979; Nakanishi et al., (2007) Cancer Immunol Immunother 56:1173-1182; Hino et al., (2010) Cancer 116(7):1757-1766). Similarly, PD-1 expression on tumor lymphocytes was found to mark dysfunctional T cells in breast cancer (Kitano et al., (2017) ESMO Open 2(2): e000150) and melanoma (Kleffel et al., (2015) Cell 162(6): 1242-1256).

Accordingly, immune checkpoint antagonists, such as those that affect the function of the PD-1/PD-L1/PD-L2 signaling axis and/or disrupt the interaction between PD-1 and PD-L1 and/or PD-L2, for example, have been developed and represent a novel class of anti-tumor inhibitors that function via modulation of immune cell-tumor cell interaction. Numerous immune checkpoint antagonists have emerged from discovery and development efforts into clinical candidates undergoing evaluation or further into frontline treatments for multiple cancers, such as, for example, metastatic melanoma, non-small cell lung cancer (NSCLC), renal cell carcinoma (RCCs), and bladder or urothelial cancer. Immune checkpoint inhibitors are also being assessed in numerous other cancer types, including breast cancer, head and neck cancer, and some advanced solid and hematological malignancies.

Accordingly, provided herein are PD-1 antagonists that specifically bind to human PD-1 or PD-L1 and inhibit PD-1/PD-L1 biological activity and/or downstream pathway(s) and/or cellular processed mediated by human PD-1/PD-L1 signaling or other human PD-1/PD-L1-mediated functions. Provided herein are PD-1 antagonists that directly or allosterically block, antagonize, suppress, inhibit or reduce PD-1/PD-L1 biological activity, including downstream pathways and/or cellular processes mediated by PD-1/PD-L1 signaling, such as receptor binding and/or elicitation of a cellular response to PD-1/PD-L1. Also provided herein are PD-1 antagonists that reduce the quantity or amount of human PD-1 or PD-L1 produced by a cell or subject.

In some embodiments, the disclosure provides a PD-1 antagonist that binds human PD-1 and prevents, inhibits or reduces PD-L1 binding to PD-1. In some embodiments, the PD-1 antagonist binds to the mRNA encoding PD-1 or PD-L1 and prevents translation. In some embodiments, the PD-1 antagonist binds to the mRNA encoding PD-1 or PD-L1 and causes degradation and/or turnover.

In some embodiments, the PD-1 antagonist inhibits PD-1 signaling or function. In some embodiments, the PD-1 antagonist blocks binding of PD-1 to PD-L1, PD-L2, or to both PD-L1 and PD-L2. In some embodiments, the PD-1 antagonist blocks binding of PD-1 to PD-L1. In some embodiments, the PD-1 antagonist blocks binding of PD-1 to PD-L2. In some embodiments, the PD-1 antagonist blocks the binding of PD-1 to PD-L1 and PD-L2. In some embodiments, the PD-1 antagonist specifically binds PD-1. In some embodiments, the PD-1 antagonist specifically binds PD-L1. In some embodiments, the PD-1 antagonist specifically binds PD-L2.

In some embodiments, the PD-1 antagonist inhibits the binding of PD-1 to its cognate ligand. In some embodiments, the PD-1 antagonist inhibits the binding of PD-1 to PD-L1, PD-1 to PD-L2, or PD-1 to both PD-L1 and PD-L2. In some embodiments, the PD-1 antagonist does not inhibit the binding of PD-1 to its cognate ligand.

In some embodiments, the PD-1 antagonist is an isolated monoclonal antibody (mAb), or antigen-binding fragment thereof, which specifically binds to PD-1 or PD-L1. In some embodiments, the PD-1 antagonist is an antibody or antigen-binding fragment thereof that specifically binds to human PD-1. In some embodiments, the PD-1 antagonist is an antibody or antigen-binding fragment thereof that specifically binds to human PD-L1. In some embodiments, the PD-1 antagonist is an antibody or antigen-binding fragment that binds to human PD-L1 and inhibits the binding of PD-L1 to PD-1. In some embodiments, the PD-1 antagonist is an antibody or antigen-binding fragment that binds to human PD-1 and inhibits the binding of PD-L1 to PD-1.

Several immune checkpoint antagonists that inhibit or disrupt the interaction between PD-1 and either one or both of its ligands PD-L1 and PD-L2 are in clinical development or are currently available to clinicians for treating cancer.

Examples of anti-human PD-1 monoclonal antibodies, or antigen-binding fragments thereof, that can comprise the PD-1 antagonist in any of the compositions, methods, and uses provided by the disclosure include, but are not limited to: KEYTRUDA® (pembrolizumab, MK-3475, h409A11; see U.S. Pat. Nos. 8,952,136, 8,354,509, 8,900,587, and EP2170959, all of which are included herein by reference in their entirety; Merck), OPDIVO® (nivolumab, BMS-936558, MDX-1106, ONO-4538; see U.S. Pat. Nos. 7,595,048, 8,728,474, 9,073,994, 9,067,999, EP1537878, U.S. Pat. Nos. 8,008,449, 8,779,105, and EP2161336, all of which are included herein by reference in their entirety; Bristol Myers Squibb), MEDI0680 (AMP-514), BGB-A317 and BGB-108 (BeiGene), 244C8 and 388D4 (see WO2016106159, which is incorporated herein by reference in its entirety; Enumeral Biomedical), PDR001 (Novartis), and REGN2810 (Regeneron). Accordingly, in some embodiments, the PD-1 antagonist is pembrolizumab. In some embodiments, the PD-1 antagonist is nivolumab.

Examples of anti-human PD-L1 monoclonal antibodies, or antigen-binding fragments thereof, that can comprise the PD-1 antagonist in any of the compositions, methods, and uses provided by the disclosure include, but are not limited to: BAVENCIO® (avelumab, MSB0010718C, see WO2013/79174, which is incorporated herein by reference in its entirety; Merck/Pfizer), IMFINZI® (durvalumab, MEDI4736), TECENTRIQ® (atezolizumab, MPDL3280A, RG7446; see WO2010/077634, which is incorporated herein by reference in its entirety; Roche), MDX-1105 (BMS-936559, 12A4; see U.S. Pat. No. 7,943,743 and WO2013/173223, both of which are incorporated herein by reference in their entirety; Medarex/BMS), and FAZ053 (Novartis). Accordingly, in some embodiments, the PD-1 antagonist is avelumab. In some embodiments, the PD-1 antagonist is durvalumab. In some embodiments, the PD-1 antagonist is atezolizumab.

In some embodiments, the PD-1 antagonist is an immunoadhesin that specifically binds to human PD-1 or human PD-L1, e.g., a fusion protein containing the extracellular or PD-1 binding portion of PD-L1 or PD-L2 fused to a constant region, such as an Fc region of an immunoglobulin molecule. Examples of immunoadhesion molecules that specifically bind to PD-1 are described in WO2010/027827 and WO2011/066342, both of which are incorporated herein by reference in their entirety. In some embodiments, the PD-1 antagonist is AMP-224 (also known as B7-DCIg), which is a PD-L2-FC fusion protein that specifically binds to human PD-1.

It will be understood by one of ordinary skill that any PD-1 antagonist which binds to PD-1 or PD-L1 and disrupts the PD-1/PD-L1 signaling pathway, is suitable for compositions, methods, and uses disclosed herein. In some embodiments, the PD-1/PD-L1 antagonist is a small molecule, a nucleic acid, a peptide, a peptide mimetic, a protein, a carbohydrate, a carbohydrate derivative, or a glycopolymer. Exemplary small molecule PD-1 inhibitors are described in Zhan et al., (2016) *Drug Discov Today* 21(6): 1027-1036. Methods for assaying whether PD-1 or PD-L1 biological activity has been directly or allosterically blocked, antagonized, suppressed, inhibited, or reduced are known in the art and can be readily designed by those of skill in the art. Such assays include, for example, testing the effects of any downstream signaling pathway(s) of PD-1 in vitro or in vivo. As described herein, PD-1 is an immune checkpoint inhibitory receptor that contains an "Immunoreceptor Tyrosine-based Inhibition Motif" or "ITIM", comprising a conserved sequence of amino acids (S/I/V/L)xYxx (I/V/L) where x is any amino acid. After PD-1 interacts with its ligand, the ITIM motif becomes phosphorylated by enzymes of, e.g., the Src kinase family, allowing them to recruit other enzymes, e.g., the phosphotyrosine phosphatases SHP-1 and SHP-2, or the inositol-phosphatase called SHIP. These phosphatases have been shown to decrease the activation of molecules involved in cell signaling. See, e.g., Barrow & Trowsdale (2006) *Eur J Immunol.* 36 (7): 1646-53. A list of human candidate ITIM-containing proteins has been generated by proteome-wide scans. See, e.g., Staub, E. et al. (2004), *Cell Signal*. 16 (4): 435-456. Thus, the phosphorylation state of the ITIM motif within PD-1 can be assessed using known methods in the art. Also, the presence of downstream factors, such as phosphotyrosine phosphatases can also be examined. Moreover, various cell-based assays and kits that detect the presence of downstream factors (e.g., nuclear factor of activated T-cells—NFAT—as a measure of PD-1 inhibition) as a proxy for PD-1 activity state are known in the art. In other examples, simple binding assays can be used to determine whether the construct of the present disclosure can block binding PD-1 and its ligand, as discussed above.

Methods for Producing Antibodies and Antigen-Binding Fragments Thereof

The disclosure also features, in some aspects, methods for producing any of the antibodies or antigen-binding fragments thereof described herein. In some embodiments, methods for preparing an antibody described herein can include immunizing a subject (e.g., a non-human mammal) with an appropriate immunogen. Suitable immunogens for generating any of the antibodies described herein are set forth herein. For example, to generate an antibody that binds to CD137 or to generate an antibody that binds to PD-1 or PD-L1, a skilled artisan can immunize a suitable subject (e.g., a non-human mammal such as a rat, a mouse, a gerbil, a hamster, a dog, a cat, a pig, a goat, a horse, or a non-human primate) with a full-length CD137 polypeptide such as a full-length human CD137 polypeptide comprising the amino acid sequence depicted in SEQ ID NO. 3, or with human PD-1 (e.g., having SEQ ID NO: 129 or with human PD-L1 (e.g., having SEQ ID NO: 130).

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle bacillus, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) *Autoimmunity* 31(1):15-24. See also, e.g., Lodmell et al. (2000) *Vaccine* 18:1059-1066; Johnson et al. (1999) *J Med Chem* 42:4640-4649; Baldridge et al. (1999) *Methods* 19:103-107; and Gupta et al. (1995) *Vaccine* 13(14): 1263-1276.

In some embodiments, the methods include preparing a hybridoma cell line that secretes a monoclonal antibody that binds to the immunogen. For example, a suitable mammal such as a laboratory mouse is immunized with a CD137 polypeptide, PD-1 polypeptide, or PD-L1 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybridoma cells are then screened for secretion of the desired antibodies, e.g., an antibody that binds to CD137, PD-1, or PD-L1.

In some embodiments, a skilled artisan can identify an antibody of interest from a nonimmune biased library as described in, e.g., U.S. Pat. No. 6,300,064 (to Knappik et al.; Morphosys AG) and Schoonbroodt et al. (2005) *Nucleic Acids Res* 33(9):e81.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen-binding domains are expressed as a recombinantly-fused protein to any of the phage coat proteins pIII, pVIII, or pIX. See, e.g., Shi et al. (2010) *JMB* 397:385-396.

Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with CD137 polypeptide, PD-1 polypeptide, or PD-L1 polypeptide as described above. mRNA can be isolated from the cells and converted to cDNA using standard molecular biology techniques. See, e.g., Green and Sambrook (2012) "Molecular Cloning: A Laboratory Manual, 4th Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388 (Pt 3):889-894; and Engberg et al. (1995) *Methods Mol Biol* 51:355-376.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some embodiments, require use of a helper phage. In some embodiments, no helper phage is required (see, e.g., Chasteen et al., (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., human CD137, human PD-1, or human PD-L1) using any immunological or biochemical based method known in the art. For example, specific binding of an antibody to CD137, PD-1, or PD-L1, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

It is understood that the above methods can also be used to determine if, e.g., an anti-CD137 antibody, an anti-PD-1 antibody, or an anti-PD-L1 antibody does not bind to full-length, human CD137 and/or CD137 proteins, human PD-1 and/or PD-1 proteins, or human PD-L1 and/or PD-L1 proteins.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody. Alternatively, fragments of chemically synthesized nucleic acids, together capable of encoding an antibody, can be joined together using DNA assembly techniques known in the art (e.g. Gibson Assembly).

In some embodiments, the anti-CD137, anti-PD-1, or anti-PD-L1 antibodies described herein comprise an altered heavy chain constant region that has reduced (or no) effector function relative to its corresponding unaltered constant region. Effector functions involving the constant region of the anti-CD137, anti-PD-1, or anti-PD-L1 antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR can possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity can exhibit either increased or reduced ADCC and/or CDC activity compared to the unaltered constant region. For example, in some embodiments, the anti-CD137 antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-CD137 antibody described herein comprising an altered constant region displaying reduced ADCC and/or CDC can exhibit reduced or no ADCC and/or CDC activity.

In some embodiments, an anti-CD137, anti-PD-1 or anti-PD-L1 antibody described herein exhibits reduced or no effector function. In some embodiments, an anti-CD137, anti-PD-1, or anti-PD-L1 antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In some embodiments, an anti-CD137, anti-PD-1, or anti-PD-L1 antibody can contain an altered constant region exhibiting enhanced or reduced complement dependent cytotoxicity (CDC). Modulated CDC activity can be achieved by introducing one or more amino acid substitutions, insertions, or deletions in an Fc region of the antibody. See, e.g., U.S. Pat. No. 6,194,551. Alternatively, or additionally, cysteine residue(s) can be introduced in the Fc region, thereby allowing interchain disulfide bond formation in this region. The homodimeric antibody thus generated can have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

Recombinant Antibody Expression and Purification

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or antigen-binding fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2:155-159; and Pollock et al. (1999) *J Immunol Methods* 231 1-):147-157.

The antibodies and antigen-binding fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression varies with the choice of the expression vector and the host cell, and can easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or antigen-binding fragment thereof) described herein can be expressed in mammalian cells or in other expression systems including, but not limited to, yeast, baculovirus, and in vitro expression systems (see, e.g., Kaszubska et al. (2000) *Protein Expression and Purification* 18:213-220).

Following expression, the antibodies and antigen-binding fragments thereof can be isolated. An antibody or antigen-binding fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3$^{rd}$ edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or antigen-binding fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

Modification of the Antibodies or Antigen-Binding Fragments Thereof

The antibodies or antigen-binding fragments thereof can be modified following their expression and purification. The modifications can be covalent or non-covalent modifications.

Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO. 98)), polyhistidine (6-His; HHHHHH (SEQ ID NO. 99)), hemagglutinin (HA; YPYDVPDYA (SEQ ID NO. 100)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}$P, $^{33}$P, $^{14}$C, $^{125}$I, $^{131}$I, $^{35}$S, and $^{3}$H. Suitable fluorescent labels include, without limitation, fluorescein, fluorescein isothiocyanate (FITC), green fluorescent protein (GFP), DYLIGHT™ 488, phycoerythrin (PE), propidium iodide (PI), PerCP, PE-ALEXA FLUOR® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies or antigen-binding fragments can be modified, e.g., with a moiety that improves the stabilization and/or retention of the antibodies in circulation, e.g., in blood, serum, or other tissues. For example, the antibody or antigen-binding fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or [HESylated (Fresenius Kabi, Germany; see, e.g., Pavisid et al. (2010) *Int J Pharm* 387(1-2):110-119). The stabilization moiety can improve the stability, or retention of, the antibody (or antigen-binding fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Pharmaceutical Compositions and Formulations

In some embodiments, an anti-CD137 antibody, or antigen-binding fragment thereof, and a PD-1 antagonist, are administered together (simultaneously or sequentially). In some embodiments, an anti-CD137 antibody, or antigen-binding fragment thereof, and a PD-1 antagonist are administered separately.

In certain embodiments, the invention provides for a pharmaceutical composition comprising an anti-CD137 antibody or antigen-binding fragment thereof with a pharmaceutically acceptable diluent, carrier, solubilizer, emulsifier, preservative and/or adjuvant, and a pharmaceutical composition comprising a PD-1 antagonist with a pharmaceutically acceptable diluent, carrier, solubilizer, emulsifier, preservative and/or adjuvant. In certain embodiments, each of the agents, e.g., anti-CD137 antibody, antigen-binding fragment thereof, PD-1 antagonist, can be formulated as separate compositions.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition is determined by one skilled in the art depending upon, for example, the intended route of administration, delivery format and desired dosage. See, for example, Remington's Pharmaceutical Sciences, supra. In certain embodiments, such compositions influence the physical state, stability, rate of in vivo release and/or rate of in vivo clearance of the anti-CD137 antibody and/or PD-1 antagonist.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an anti-CD137 antibody can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an anti-CD137 antibody or antigen-binding fragment thereof and/or PD-1 antagonist can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising an anti-CD137 antibody or antigen-binding fragment thereof and/or PD-1 antagonist, in a pharmaceutically acceptable vehicle. In certain embodiments, a vehicle for parenteral injection is sterile distilled water in which an anti-CD137 antibody or antigen-binding fragment thereof and/or PD-1 antagonist is formulated as a sterile, isotonic solution, and properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an anti-CD137 antibody or antigen-binding fragment thereof and/or PD-1 antagonist can be formulated as a dry powder for inhalation. In certain embodiments, an inhalation solution comprising an anti-CD137 antibody or antigen-binding fragment thereof and/or PD-1 antagonist can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, an anti-CD137 antibody or antigen-binding fragment and/or PD-1 antagonist that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an anti-CD137 antibody or antigen-binding fragment thereof and/or PD-1 antagonist. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an anti-CD137 antibody or antigen-binding fragment thereof and/or PD-1 antagonist in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an anti-CD137 antibody or antigen-binding fragment thereof and/or PD-1 antagonist in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, *Proc. Natl. Acad. Sci. USA*, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an anti-CD137 antibody or antigen-binding fragment thereof and/or PD-1 antagonist to be employed therapeutically will depend, for example, upon the therapeutic context and objectives. One skilled in the art will appreciate that the appropriate dosage levels for treatment, according to certain embodiments, varies depending, in part, upon the molecule delivered, the indication for which an anti-CD137 antibody or antigen-binding fragment thereof and/or PD-1 antagonist is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing takes into account the pharmacokinetic parameters of an anti-CD137 antibody or antigen-binding fragment thereof and/or PD-1 antagonist in the formulation used. In certain embodiments, a clinician administers the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy can be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an anti-CD137 antibody or antigen-binding fragment and/or PD-1 antagonist in an ex vivo manner. In such instances, cells, tissues and/or organs that have been removed from the patient are exposed to a pharmaceutical composition comprising an anti-CD137 antibody or antigen-binding fragment and/or PD-1 antagonist after which the cells, tissues and/or organs are subsequently implanted back into the patient.

In certain embodiments, an anti-CD137 antibody or antigen-binding fragment and/or PD-1 antagonist can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Applications

The compositions described herein can be used in diagnostic and therapeutic applications. For example, detectably-labeled antigen-binding molecules can be used in assays to detect the presence or amount of the target antigens in a sample (e.g., a biological sample). The compositions can be used in in vitro assays for studying inhibition of target antigen function (e.g. CD137-mediated cellular signaling or response). In some embodiments, e.g., in which the compositions bind to and activate a target antigen (e.g. a protein or polypeptide), the compositions can be used as positive controls in assays designed to identify additional novel compounds that also induce activity of the target protein or polypeptide and/or are otherwise are useful for treating a disorder associated with the target protein or polypeptide. For example, a CD137-activating composition can be used as a positive control in an assay to identify additional compounds (e.g., small molecules, aptamers, or antibodies) that induce, increase, or stimulate CD137 function. The compositions can also be used in therapeutic methods as elaborated on below.

Kits

In some embodiments, the disclosure provides a kit comprising an anti-CD137 antibody as described herein, and instruction for use in combination with a PD-1 antagonist described herein. In some embodiments, the kit comprises, in a suitable container, an anti-CD137 antibody, one or more controls, and various buffers, reagents, enzymes and other standard ingredients well known in the art.

In some embodiments, the disclosure provides a kit comprising an anti-CD137 antibody or antigen-binding fragment thereof and a PD-1 antagonist described herein. In some embodiments, a kit includes an anti-CD137 antibody or antigen-binding fragment thereof and a PD-1 antagonist as disclosed herein, and instructions for use. The kits may comprise, in a suitable container, an anti-CD137 antibody or antigen-binding fragment thereof, a PD-1 antagonist, one or more controls, and various buffers, reagents, enzymes and other standard ingredients well known in the art. Certain embodiments include a kit with an anti-CD137 antibody or antigen-binding fragment thereof and a PD-1 antagonist in the same vial. In certain embodiments, a kit includes an anti-CD137 antibody or antigen-binding fragment thereof and a PD-1 antagonist in separate vials.

The container can include at least one vial, well, test tube, flask, bottle, syringe, or other container means, into which an anti-CD137 antibody or antigen-binding fragment thereof and PD-1 antagonist may be placed, and in some instances, suitably aliquoted. Where an additional component is provided, the kit can contain additional containers into which this component may be placed. The kits can also include a means for containing an anti-CD137 antibody or antigen-binding fragment thereof, a PD-1 antagonist and any other reagent containers in close confinement for commercial sale. Such containers may include injection or blow-molded plastic containers into which the desired vials are retained. Containers and/or kits can include labeling with instructions for use and/or warnings.

In some embodiments, a kit comprises a containing comprising an anti-CD137 antibody, and a pharmaceutically acceptable carrier, or a pharmaceutical composition comprising the anti-CD137 antibody, and instructions for treating or delaying progression of cancer or reducing or inhibiting tumor growth with a PD-1 antagonist, in a subject in need thereof. In some embodiments, a kit comprises a containing comprising an anti-CD137 antibody or antigen-binding fragment thereof, a PD-A antagonist, and a pharmaceutically acceptable carrier, or a pharmaceutical composition comprising the anti-CD137 antibody or antigen-binding fragment thereof, a PD-1 antagonist, and instructions for treating or delaying progression of cancer or reducing or inhibiting tumor growth in a subject in need thereof. In some embodiments, a kit comprises a containing comprising an anti-CD137 antibody or antigen-binding fragment thereof, a PD-1 antagonist, and a pharmaceutically acceptable carrier, or a pharmaceutical composition comprising the anti-CD137 antibody or antigen-binding fragment thereof, a PD-1 antagonist, and instructions for administering the anti-CD137 antibody or antigen-binding fragment thereof and the PD-1 antagonist to a subject in need thereof, alone or in combination with another agent, for treating or delaying progression of cancer or reducing or inhibiting tumor growth in the subject.

Methods of Use

The compositions of the present invention have numerous in vitro and in vivo utilities involving the detection and/or quantification of CD137 and/or the agonism of CD137 function.

The above-described compositions are useful in, inter alia, methods for treating or preventing a variety of cancers in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), or intrathecal injection (IT). The injection can be in a bolus or a continuous infusion.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems. In some embodiments, an anti-CD137 antibody or antigen-binding fragment thereof and PD-1 antagonist is therapeutically delivered to a subject by way of local administration.

As exemplified in the working Examples, treatment regimens in which an agonist anti-CD137 antibody or antigen-binding fragment thereof is administered first in time and PD-1 antagonist is administered second in time, result in a synergistic enhancement of anti-tumor efficacy and cytokine production by immune cells. As used herein, the term "synergistic effect" refers to a combination of therapies (e.g., a combination of a CD137 agonist and a PD-1 antagonist), which is more effective than the additive effects of each of the therapies alone. A synergistic effect of a combination of therapies (e.g., a combination of a CD137 agonist and a PD-1 antagonist) permits the use of lower dosages of one or more of the therapeutic agents and/or less frequent administration of said therapeutic agents to a patient with a solid tumor. The ability to utilize lower dosages of therapeutic agents and/or to administer said therapies less frequently reduces the toxicity associated with the administration of said therapies to a subject without reducing the efficacy of said therapies in the treatment of a disease (e.g., cancer). In addition, a synergistic effect can result in improved efficacy of therapeutic agents in the management, treatment, or amelioration of a disease (e.g., cancer). The synergistic effect of a combination of therapeutic agents can avoid or reduce adverse or unwanted side effects associated with the use of either single therapy.

Accordingly, in some embodiments, an anti-CD137 antibody or antigen-binding fragment thereof is administered to a subject prior to administration of a PD-1 antagonist. In some embodiments, an anti-CD137 antibody or antigen-binding fragment thereof is administered to a subject at least 1 day, 2 days, 3 days, 4 days, 5 days, 6 days, 7 days, 8 days, 9 days, 10 days, 11 days, 12 days, 13 days or 14 days prior to administration of a PD-1 antagonist. In some embodiments, an anti-CD137 antibody or antigen-binding fragment thereof is administered with a PD-1 antagonist. In some embodiments, frequency of administration varies between the ant-CD137 antibody or antigen-binding fragment thereof and the PD-1 antagonist. For example, in some embodiments an anti-CD137 antibody or antigen-binding fragment thereof is administered four times, whereas a PD-1 antagonist is administered three times. In some embodiments, a PD-1 antagonist is administered after initiating treatment with an anti-CD137 or antigen-binding fragment thereof, thus resulting in the possibility of treatment overlap. In some embodiments, an anti-CD137 antibody or antigen-binding fragment thereof is therapeutically delivered to a subject by way of local administration.

A suitable dose of an antibody or antigen-binding fragment thereof described herein, which dose is capable of treating or preventing cancer in a subject, can depend on a variety of factors including, e.g., the age, sex, and weight of a subject to be treated, and the particular inhibitor compound used. For example, a different dose of a whole anti-CD137 antibody can be required to treat a subject with cancer as compared to the dose of a CD137-binding Fab' antibody fragment required to treat the same subject. Other factors affecting the dose administered to the subject include, e.g., the type or severity of the cancer. For example, a subject having metastatic melanoma may require administration of a different dosage of an anti-CD137 antibody than a subject with glioblastoma. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject also depends upon the judgment of the treating medical practitioner (e.g., doctor or nurse). Suitable dosages are described herein. In some embodiments, the anti-CD137 antibodies or antigen-binding fragments thereof described herein are effective at both high and low doses.

A pharmaceutical composition can include a therapeutically effective amount of an anti-CD137 antibody or antigen-binding fragment thereof, and a PD-1 antagonist described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody or fragment thereof described herein can also vary according to factors such as the disease state, age, sex, and weight of the individual, and the ability of the antibody (and one or more additional active agents) to elicit a desired response in the individual, e.g., reduction in tumor growth. For example, a therapeutically effective amount of an anti-CD137 antibody or antigen-binding fragment thereof and/or PD-1 antagonist can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the antibodies or antagonists described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

In some embodiments, the composition contains any of the antibodies or antagonists described herein and one or more (e.g., two, three, four, five, six, seven, eight, nine, 10, or 11 or more) additional therapeutic agents, such that the composition as a whole is therapeutically effective. For example, a composition can contain an anti-CD137 antibody or antigen-binding fragment thereof and/or PD-1 antagonist described herein and an alkylating agent, wherein the antibody and/or antagonist and agent are each at a concentration that when combined are therapeutically effective for treating or preventing a cancer (e.g., melanoma) in a subject.

Toxicity and therapeutic efficacy of such compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An antibody or antigen-binding fragment thereof that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. For an anti-CD137 antibody or antigen-binding fragment thereof and PD-1 antagonist described herein, the therapeutically effective dose can be estimated initially from cell culture assays. A dose can be formulated in animal models to achieve a circulating plasma concentration range that includes the $EC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for cancer. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

As described above, the compositions described herein (e.g., anti-CD137 and PD-1 antagonist compositions) can be used to treat a variety of cancers such as but not limited to: Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system. In some embodiments, the cancer is breast cancer.

In some embodiments, anti-CD137 antibodies or antigen-binding fragments thereof can be used in combination with a PD-1 antagonist to treat cancer. In some embodiments, an anti-CD137 antibody or antigen-binding fragment thereof and a PD-1 antagonist described herein can be administered to a subject as a combination therapy with another treatment, e.g., another treatment for a cancer. For example, the combination therapy can include administering to the subject (e.g., a human patient) one or more additional agents that provide a therapeutic benefit to a subject who has, or is at risk of developing, cancer. Chemotherapeutic agents suitable for co-administration with compositions of the present invention include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g. mechlorethamine, thioTEPA, chlorambucil, melphalan, carmustine (BSNU), lomustine (CCNU), cyclophosphamide, busulfan, dibromomannitol, streptozotocin, mitomycin C, cis-dichlordiamine platinum (II)(DDP), procarbazine, altretamine, cisplatin, carboplatin, oxaliplatin, nedaplatin, satraplatin, or triplatin tetranitrate), anthracycline (e.g. daunorubicin (formerly daunomycin) and doxorubicin), antibiotics (e.g. dactinomcin (formerly actinomycin), bleomycin, mithramycin, and anthramycin (AMC)), and anti-mitotic agents (e.g. vincristine and vinblastine) and temozolomide. In some embodiments, an anti-CD137 antibody or antigen-binding fragment thereof, PD-1 antagonist and the one or more additional active agents are administered at the same time. In other embodiments, the anti-CD137 antibody or antigen-binding fragment thereof and PD-1 antagonist is administered first in time and the one or more additional active agents are administered second in time. In some embodiments, the one or more additional active agents are administered first in time and the anti-CD137 antibody or antigen-binding fragment thereof and PD-1 antagonist is administered second in time.

A combination of an anti-CD137 antibody or an antigen-binding fragment thereof and a PD-1 antagonist described herein can replace or augment a previously or currently administered therapy. For example, upon treating with an anti-CD137 antibody or antigen-binding fragment thereof and a PD-1 antagonist, administration of the one or more additional active agents can cease or diminish, e.g., be administered at lower levels or dosages. In some embodiments, administration of the previous therapy can be maintained. In some embodiments, a previous therapy will be maintained until the level of the anti-CD137 antibody or antigen-binding fragment thereof and PD-1 antagonist reaches a level sufficient to provide a therapeutic effect. The two therapies can be administered in combination.

Monitoring a subject (e.g., a human patient) for an improvement in a cancer, as defined herein, means evaluating the subject for a change in a disease parameter, e.g., a reduction in tumor growth. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer described herein.

In some embodiments, the anti-CD137 antibody or an antigen-binding fragment thereof and PD-1 antagonist described herein, inhibits or reduces tumor growth. In some embodiments, the tumor expresses PD-L1. In some embodiments, the tumor overexpresses PD-L1. In some embodiments, the tumor expresses more PD-L1 following administration of an anti-CD137 antibody or antigen-binding fragment thereof. Methods for analyzing protein expression (e.g., PD-L1 expression) on a tumor are known in the art.

In some embodiments, an anti-CD137 antibody or an antigen-binding fragment thereof and PD-1 antagonist described herein is administered to modulate a T-cell response in a patient, for example, by increasing T-cell activation and/or proliferation. Crosslinking of CD137 strongly enhances T cell proliferation, IFNγ production and secretion, and the cytolytic activity of T cells. Accordingly, in some embodiments, an anti-CD137 agonist antibody, or an antigen-binding fragment thereof, and PD-1 antagonist is administered to a patent in need thereof to induce or increase T-cell activation, enhance T cell proliferation, induce the production and/or secretion of IFNγ, and/or induce a cytolytic T cell response.

In some embodiments, an anti-CD137 antibody or an antigen-binding fragment thereof and PD-1 antagonist described herein is useful to modulate or shift the T-cell population in a patient from a $T_H2/T_{reg}$ T cell population to a $TH1/T_H17$ T cell population to thereby improve or enhance an anti-tumor response in the patient. Studies have shown that while CD137 is expressed in both T-cell subsets, Th1 and Th2 T cells, CD137 is expressed at higher levels on $CD8^+$ T cells than on $CD4^+$ T cells. Accordingly, CD137 mainly co-stimulates $CD8^+$ T cells. Accordingly, an anti-CD137 antibody, or an antigen-binding fragment thereof, and PD-1 antagonist is administered to a patient to enhance an anti-tumor response, for example, by modulating or shifting the T-cell response and/or T cell population in the patient from a $T_H2/T_{reg}$ T cell response and or T cell population to a $T_H1/T_H17$ T cell response and/or T cell population in the patient.

In some cancers (e.g. melanoma and ovarian cancer), natural tumor-infiltrating lymphocytes (TILs) can be enriched through optimized cell culture methods and provide a source of tumor-reactive lymphocytes useful for adoptive immunotherapy. Adoptive TIL therapy can result in durable tumor regression for some types of cancer, which warrants the development and optimization of TIL-based approaches for cancer. Currently, the identification and expansion of natural tumor-reactive TILs remains challenging due to low level and/or rarity of antigen-specific $CD8^+$ T cells. CD137 expression by T cells is activation dependent, which provides an opportunity to capture CD137-expressing activated T cells from circulation or from tumor samples. Accordingly, an anti-CD137 antibody, or an antigen-binding fragment thereof, and PD-1 antagonist can be employed for the selective enrichment of activated, antigen-specific T cells.

In some embodiments, the efficacy of the anti-CD137 antibodies and PD-1 antagonists described herein is dependent on a competent immune system. Specifically, in some embodiments, depletion of CD4+ T cells, CD8+ T cells and/or Natural Killer cells reduces the efficacy of the anti-CD137 antibodies. In some embodiments, depletion of CD4+ T cells, CD8+ T cells and/or Natural Killer cells reduces the inhibition or reduction of tumor growth by the anti-CD137 antibodies described herein. In some embodiments, depletion of CD4+ T cells, CD8+ T cells and/or Natural Killer cells reduces the inhibition or reduction of tumor growth by the anti-CD137 antibodies described herein. In some embodiments, depletion of CD4+ T cells, CD8+ T cells and/or Natural Killer cells reduces the inhibition or reduction of tumor growth by the anti-CD137 antibodies described herein. In some embodiments, the efficacy of the anti-CD137 antibodies and PD-1 antagonists described herein is dependent on an infiltration of immune cells into a tumor microenvironment. In some embodiments, the infiltration of immune cells into a tumor microenvironment is coupled with a lack of infiltration into the spleen and/or liver.

In some embodiments, the anti-CD137 antibodies or antigen-binding fragments thereof and PD-1 antagonists described herein induce a protective anti-tumor memory immune response. Memory T cells are a subset of antigen-specific T cells that persist long-term after having encountered and responded to their cognate antigen. Such cells quickly expand to large numbers of effector cells upon re-exposure to their cognate antigen. Accordingly, in some embodiments the anti-CD137 antibodies or antigen-binding fragment thereof and PD-1 antagonists described herein stimulate the production of memory T cells to a cancer antigen. In some embodiments, a subject that has received an anti-CD137 antibody or antigen-binding fragment thereof and a PD-1 antagonist described herein to treat or cure a cancer, develops memory T cells specific to the cancer. In some embodiments, a subject that has received an anti-CD137 antibody or antigen-binding fragment thereof and a PD-1 antagonist described herein to treat or cure a cancer, develops an anti-tumor memory immune response upon re-exposure to the cancer. In some embodiments, the anti-tumor memory immune response comprises stimulating memory T cells to become effector cells. In some embodiments, a subject that has received an anti-CD137 antibody or antigen-binding fragment thereof and a PD-1 antagonist described herein to treat or cure a cancer, develops an anti-tumor memory immune response to a cancer antigen.

In some embodiments, the anti-CD137 antibodies or antigen-binding fragments thereof and PD-1 antagonists described herein induce immune re-programming with a tumor microenvironment. Specifically, in some embodiments, the anti-CD137 antibodies or antigen-binding fragments thereof and PD-1 antagonists induce immune infiltration; reduce, inhibit or prevent Treg proliferation; reduce, inhibit or prevent tumor-associated macrophage proliferation; and/or protect or reverse T cell exhaustion.

In some embodiments, the anti-CD137 antibodies or antigen-binding fragments thereof and PD-1 antagonists induce infiltration of immune cells into a tumor microenvironment relative to the amount of immune cell infiltration in the absence of the anti-CD137 antibody and PD-1 antagonist. In some embodiments, the anti-CD137 antibodies or antigen-binding fragments thereof and PD-1 antagonists increase immune cell infiltration by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, or at least 150%. In some embodiments, immune cell infiltration is determined by measuring the level of CD45 expression on cells isolated from a tumor microenvironment. Methods for measuring protein expression are known to those of skill in the art and described herein.

In some embodiments, the anti-CD137 antibodies or antigen-binding fragments thereof and PD-1 antagonists prevent or inhibit an increase in Treg cells in a tumor microenvironment. In some embodiments, prevention or inhibition is relative to the amount of Treg cells in a tumor microenvironment in the absence of an anti-CD137 antibody or antigen-binding fragment thereof and a PD-1 antagonist. In some embodiments, prevention or inhibition of an increase in Treg cells is relative to a reference antibody. In some embodiments, Treg cells are detected by expression of CD25 and FOX-3P on $CD4^+$ T cells isolated from a tumor microenvironment. Methods for measuring protein expression are known to those of skill in the art and described herein.

In some embodiments, the anti-CD137 antibodies or antigen-binding fragments thereof and PD-1 antagonists prevent or inhibit an increase in tumor-associated macrophages in a tumor microenvironment. In some embodiments, prevention or inhibition is relative to the amount of tumor-associated macrophages in a tumor microenvironment in the absence of an anti-CD137 antibody or antigen-binding fragment thereof and a PD-1 antagonist. In some embodiments, prevention or inhibition of an increase in tumor-associated macrophages is relative to a reference antibody. In some embodiments, tumor-associated macrophages are detected by expression of CD11b and F4/80 on CD45+ immune cells isolated from a tumor microenvironment. Methods for measuring protein expression are known to those of skill in the art and described herein.

In some embodiments, the anti-CD137 antibodies or antigen-binding fragments thereof and PD-1 antagonists protect T cells from T cell exhaustion in a tumor microenvironment. In some embodiments, the anti-CD137 antibodies reverse T cell exhaustion in a tumor microenvironment. In some embodiments, T cell exhaustion in a tumor microenvironment is reduced in the presence of an anti-CD137 antibody or antigen-binding fragment thereof and a PD-1 antagonist described herein, relative to a tumor microenvironment in the absence of the anti-CD137 antibody or antigen-binding fragment thereof and the PD-1 antagonist. In some embodiments, T cell exhaustion is determined by analyzing CD8+ T cells or CD4+ T cells for expression of co-inhibitory receptors (e.g., PD-1, TIGIT or LAG-3). In some embodiments, T cell exhaustion is detected by expression of PD-1 and TIGIT on CD4+ or CD8+ T cells isolated from a tumor microenvironment.

In some embodiments, an anti-CD137 antibody, or an antigen-binding fragment thereof, described herein, can be employed in methods of detection and/or quantification of human CD137 in a biological sample. Accordingly, an anti-CD137 antibodies, or an antigen-binding fragment thereof, as described herein, is used to diagnose, prognose, and/or determine progression of disease (e.g., cancer) in a patient.

OTHER EMBODIMENTS

The disclosure relates to the following embodiments. Throughout this section, the term embodiment is abbreviated as 'E' followed by an ordinal. For example, E1 is equivalent to Embodiment 1.

E1. A method for treating cancer in a subject, the method comprising: administering to the subject an effective amount of:
  (i) an agonistic isolated monoclonal antibody that specifically binds to human CD137,
  or antigen-binding fragment thereof; and
  (ii) a PD-1 antagonist,
  wherein administration of (ii) begins after first administering (i) to the subject,
  thereby treating the subject.

E2. The method of embodiment 1, wherein administration of (i) and (ii) overlap.

E3. The method of embodiment 2, wherein (i) is administered at least 4 days, at least 5 days, at least 6 days, at least 7 days, at least 8 days, at least 9 days, or at least 10 days before (ii) is administered.

E4. A method for treating cancer in a subject in need thereof who has received or is receiving treatment with an agonistic isolated monoclonal antibody that specifically binds to human CD137, or antigen-binding fragment thereof, the method comprising administering to the subject an effective amount of a PD-1 antagonist, thereby treating the subject.

E5. A method for enhancing a cancer-specific immune response in a subject in need thereof who has received or is receiving treatment with an agonistic isolated monoclonal antibody that specifically binds to human CD137, or antigen-binding fragment thereof, the method comprising: administering to the subject an effective amount of a PD-1 antagonist thereby enhancing a cancer-specific immune response in the subject as compared to the cancer-specific immune response in the subject following administration of the agonistic isolated monoclonal antibody, or antigen-binding fragment thereof, alone.

E6. The method of embodiments 4 or 5, wherein the PD-1 antagonist is administered at least 4 days, at least 5 days, at least 6 days, at least 7 days, at least 8 days, at least 9 days, or at least 10 days after treatment with the agonistic isolated monoclonal antibody.

E7. A method for enhancing a cancer-specific immune response in a subject in need thereof, the method comprising: administering to the subject an effective amount of: (i) an agonistic isolated monoclonal antibody that specifically binds to human CD137, or antigen-binding fragment thereof; and (ii) a PD-1 antagonist, thereby enhancing a cancer-specific immune response in the subject as compared to the cancer-specific immune response in the subject following administration of either the PD-A antagonist or the agonistic isolated monoclonal antibody, or antigen-binding fragment thereof, alone.

E8. The method of any one of the preceding embodiments, wherein the subject comprises a tumor expressing or overexpressing PD-L1.

E9. The method of embodiment 8, wherein the tumor expresses more PD-L1 following administration of the agonistic isolated monoclonal antibody.

E10. The method of any one of embodiments 1 to 9, wherein the PD-1 antagonist is an isolated monoclonal antibody that specifically binds to human PD-L1, or antigen-binding fragment thereof.

E11. The method of any one of embodiments 1 to 9, wherein the PD-1 antagonist is an isolated monoclonal antibody that specifically binds to human PD-1, or antigen-binding fragment thereof.

E12. The method of any one of embodiments 5-11, wherein the cancer-specific immune response is a T cell response.

E13. The method of embodiment 12, wherein the T cell response comprises the production of IFNγ by one or both of CD4$^+$ T cells and CD8$^+$ T cells.

E14. The method of embodiment 12, wherein the T cell response comprises the production of IL-2 by one or both of CD4$^+$ T cells and CD8$^+$ T cells.

E15. The method of embodiment 12, wherein the T cell response comprises proliferation of one or both of CD4$^+$ T cells and CD8$^+$ T cells.

E16. The method of any of embodiments 1-4,6, and 8-15, wherein treatment comprises delaying cancer progression in the subject.

E17. The method of any of embodiments 1-4, 6, and 8-15, wherein treatment comprises enhancing a tumor-specific immune response in the subject.

E18. The method of any one of the preceding embodiments, wherein the cancer is breast cancer.

E19. The method of any one of embodiments 1-18, wherein the agonistic isolated monoclonal antibody, or antigen-binding fragment thereof, binds human CD137 with an affinity ($K_D$) of about 40-100 nM.

E20. The method of any one of embodiments 1-18, wherein the agonistic isolated monoclonal antibody, or antigen-binding fragment thereof, (i) binds human CD137 with an affinity ($K_D$) of about 40-100 nM; and (ii) comprises a heavy chain CDR3 comprising the amino acid sequence DXXXXLXXXXYXYYX (SEQ ID NO: 126), wherein X is any amino acid.

E21. The method of any one of embodiments 1-18, wherein the agonistic isolated monoclonal antibody, or antigen-binding fragment thereof, (i) binds human CD137 with an affinity ($K_D$) of about 40-100 nM; and (ii) comprises a heavy chain CDR3 comprising the amino acid sequence DX$_1$X$_2$X$_3$X$_4$LX$_5$X$_6$X$_7$X$_8$YX$_9$YYX$_{10}$ (SEQ ID NO: 128), wherein X$_1$ is any amino acid, wherein X$_2$ is a non-polar amino acid, wherein X$_3$ is a non-polar amino acid, wherein X$_4$ is any amino acid, wherein X$_5$ is a polar amino acid, wherein X$_6$ is any amino acid, wherein X$_7$ is any amino acid, wherein X$_8$ is a polar amino acid, wherein X$_9$ is a polar amino acid, and wherein X$_{10}$ is any amino acid.

E22. The method of any one of embodiments 1-18, wherein the agonistic isolated monoclonal antibody, or antigen-binding fragment thereof, (i) binds human CD137 with an affinity ($K_D$) of about 40-100 nM; and (ii) specifically binds to an epitope on human CD137 comprising one or more residues E111, T113, K114, P135 and W136 of SEQ ID NO: 3.

E23. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; (iii) comprises a heavy chain CDR3 comprising the amino acid sequence DXXXXLXXXXYXYYX (SEQ ID NO: 126), wherein X is any amino acid; or (iv) combinations thereof.

E24. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; (iii) comprises a heavy chain CDR3 comprising the amino acid sequence DX$_1$X$_2$X$_3$X$_4$LX$_5$X$_6$X$_7$X$_8$YX$_9$YYX$_{10}$ (SEQ ID NO: 128), wherein X$_1$ is any amino acid, wherein X$_2$ is a non-polar amino acid, wherein X$_3$ is a non-polar amino acid, wherein X$_4$ is any amino acid, wherein X$_5$ is a polar amino acid, wherein X$_6$ is any amino acid, wherein X$_7$ is any amino acid, wherein X$_8$ is a polar amino acid, wherein X$_9$ is a polar amino acid, and wherein X$_{10}$ is any amino acid; or (iv) combinations thereof.

E25. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; and (iii) comprises a heavy chain CDR3 comprising the amino acid sequence DXXXXLXXXXYXYYX (SEQ ID NO: 126), wherein X is any amino acid.

E26. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; and (iii) comprises a heavy chain CDR3 comprising the amino acid sequence DX$_1$X$_2$X$_3$X$_4$LX$_5$X$_6$X$_7$X$_8$YX$_9$YYX$_{10}$ (SEQ ID NO: 128), wherein X$_1$ is any amino acid, wherein X$_2$ is a non-polar amino acid, wherein X$_3$ is a non-polar amino acid, wherein X$_4$ is any amino acid, wherein X$_5$ is a polar amino acid, wherein X$_6$ is any amino acid, wherein X$_7$ is any amino acid, wherein X$_8$ is a polar amino acid, wherein X$_9$ is a polar amino acid, and wherein X$_{10}$ is any amino acid.

E27. The method of any one of embodiments 19-26, wherein the epitope comprises residues E111, T113, K114, P135 and W136 of SEQ ID NO: 3.

E28. The method of any one of embodiments 1-18, wherein the agonistic isolated monoclonal antibody, or antigen-binding fragment thereof, (i) binds human CD137 with an affinity ($K_D$) of about 40-100 nM; and (ii) specifically binds to an epitope comprising a sequence of one or more amino acid residues corresponding to amino acid positions 111 to 136 of SEQ ID NO: 3.

E29. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; (iii) comprises a heavy chain CDR3 comprising the amino acid sequence DXXXXLXXXXYXYYX (SEQ ID NO: 126), wherein X is any amino acid; or (iv) combinations thereof.

E30. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or (iv) combinations thereof.

E31. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; and (iii) comprises a heavy chain CDR3 comprising the amino acid sequence DXXXXLXXXXYXYYX (SEQ ID NO: 126), wherein X is any amino acid.

E32. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; and (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

E33. The method of any one of embodiments 28-32, wherein the epitope comprises 2, 3, 4, 5, 6, 7, 8, 9, 10, 11, 12, 13, 14, 15, 16, 17, 18, 19, 20, 21, 22, 23, 24, 25 or 26 amino acid residues corresponding to amino acid positions 111 to 136 of SEQ ID NO: 3.

E34. The method of any one of embodiments 28-33, wherein the epitope comprises 6 amino acid residues corresponding to amino acid positions 111 to 136 of SEQ ID NO: 3.

E35. The method of any one of embodiments 1-18, wherein the agonistic isolated monoclonal antibody, or antigen-binding fragment thereof, (i) binds human CD137 with an affinity of about 40-100 nM; and (ii) binds to an epitope comprising one or both of ELTK (corresponding to amino acid residues 111-114 of SEQ ID NO: 3) and PW (corresponding to amino acid residues 135-136 of SEQ ID NO: 3.

E36. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; (iii) comprises a heavy chain CDR3 comprising the amino acid sequence DXXXXLXXXXYXYYX (SEQ ID NO: 126), wherein X is any amino acid; or (iv) combinations thereof.

E37. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or (iv) combinations thereof.

E38. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; and (iii) comprises a heavy chain CDR3 comprising the amino acid sequence DXXXXLXXXXYXYYX (SEQ ID NO: 126), wherein X is any amino acid.

E39. The method of any one of embodiments 1-18, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; and (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

E40. The method of any one of embodiments 35-39, wherein the epitope comprises the residues ELTK of SEQ ID NO: 3 (corresponding to amino acid residues 111-114 of SEQ ID NO: 3).

E41. The method of any one of embodiments 35-39, wherein the epitope comprises the residues PW of SEQ ID NO: 3 (corresponding to amino acid residues 135-136 of SEQ ID NO: 3).

E42. The method of any one of embodiments 35-39, wherein the epitope comprises the residues ELTK of SEQ ID NO: 3 (corresponding to amino acid residues 111-114 of SEQ ID NO: 3) and residues PW of SEQ ID NO: 3 (corresponding to amino acid residues 135-136 of SEQ ID NO: 3).

E43. The method of any one of embodiments 22-42, wherein the epitope is a non-linear epitope.

E44. The method of any one of embodiments 22-43, wherein mutation of residue K114 of SEQ ID NO: 3 abrogates binding of the agonistic antibody, or antigen-binding fragment thereof.

E45. The method of any one of the preceding embodiments, wherein the agonistic antibody, or antigen-binding fragment thereof, comprises a heavy chain CDR3 comprising the amino acid sequence DXPFXLDXXYYYYYX (SEQ ID NO: 126), wherein X is any amino acid.

E46. The method of embodiments 45, wherein mutation of residues D95, L100, Y100E, Y100G, Y100H, or combinations thereof, of the heavy chain CDR3, results in loss of binding to human CD137.

E47. The method of embodiment 45 or 46, wherein mutation of residues P97, F98, D100A, Y100D, Y100F, or combinations thereof to alanine results in reduction of binding to human CD137.

E48. The method of embodiment 45 or 46, wherein mutation of residues P97, F98, D100A, Y100D, Y100F, or combinations thereof to any residue except alanine, results in an increase in binding to human CD137.

E49. The method of any one of embodiments 20, 23, 25, 27, 29, 31, 33, 34, 36, 38 and 40-48, wherein X is any amino acid except for alanine.

E50. The method of any one of embodiments 21, 24, 26, 27, 30, 32, 33, 34, 37, 39-44 and 46-48, wherein $X_2$ is proline, wherein $X_3$ is phenylalanine or tryptophan, wherein $X_5$ is aspartic acid or glutamic acid wherein $X_8$ is tyrosine, and wherein $X_9$ is tyrosine E51. The method of any one of the preceding embodiments, wherein the agonistic antibody or antigen-binding fragment binds human CD137 with an affinity ($K_D$) of about 45-95 nM, 50-90 nM, 55-85 nM, 60-80 nM, 65-75 nM, 55-75 nM, 40-70 nM, 50-80 nM, or 60-90 nM.

E52. The method of any one of the preceding embodiments, wherein the agonistic antibody or antigen-binding fragment comprises heavy and light chain CDRs, wherein heavy chain CDR3 comprises the amino acid sequence set forth in SEQ ID NO: 68.

E53. The method of any one of embodiments 1-51, wherein the agonistic antibody or antigen-binding fragment comprises heavy and light chain CDRs selected from the group consisting of:
(a) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively; and
(b) heavy chain CDR1, CDR2 and CDR3 sequences set forth in SEQ ID NOs: 51, 108 and 68, respectively, and light chain CDR1, CDR2 and CDR3 sequences set forth in SEQ ID NOs: 69, 78 and 89, respectively.

E54. The method of any one of embodiments 1-51, wherein the agonistic antibody or antigen-binding fragment comprises heavy and light chain variable regions, wherein the heavy chain variable region comprises an amino acid sequence selected from the group consisting of SEQ ID NOs: 4 and 101; and wherein the light chain variable region comprises an amino acid sequence of SEQ ID NO: 6.

E55. The method of any one of embodiments 1-51, wherein the agonistic antibody or antigen-binding fragment comprises heavy and light chain variable regions comprising amino acid sequences selected from the group consisting of:
(a) SEQ ID NO: 4 and 6, respectively; and
(b) SEQ ID NO: 101 and 6, respectively.

E56. The method of any one of embodiments 1-51, wherein the agonistic antibody or antigen-binding fragment comprises heavy and light chain variable regions, wherein the heavy chain variable region comprises an amino acid sequence which is at least 90% identical to the amino acid sequence selected from the group consisting of SEQ ID NOs: 4 and 101; and wherein the light chain variable region comprises an amino acid sequence which is at least 90% identical to the amino acid sequence of SEQ ID NO: 6.

E57. The method of any one of embodiments 1-51, wherein the agonistic antibody or antigen-binding fragment comprises heavy and light chain variable regions comprising amino acid sequences at least 90% identical to the amino acid sequences selected from the group consisting of:
(a) SEQ ID NO: 4 and 6, respectively; and
(b) SEQ ID NO: 101 and 6, respectively.

E58. A method for treating cancer in a subject, the method comprising: administering to the subject an effective amount of: an agonistic isolated monoclonal antibody that specifically binds to human CD137, or antigen-binding fragment thereof, wherein the antibody binds human CD137 with an affinity ($K_D$) of 40-100 nM, wherein the subject received or is receiving administration of a PD-1 antagonist, thereby treating the subject.

E59. A method for treating cancer in a subject, the method comprising: administering to the subject an effective amount of: an agonistic isolated monoclonal antibody that specifically binds to human CD137, or antigen-binding fragment thereof, wherein the antibody comprises a heavy chain CDR3 comprising the amino acid sequence DXXXXLXXXXYXYYX (SEQ ID NO: 126), wherein X is any amino acid, wherein the subject received or is receiving administration of a PD-1 antagonist, thereby treating the subject.

E60. A method for treating cancer in a subject, the method comprising: administering to the subject an effective amount of: an agonistic isolated monoclonal antibody that specifically binds to human CD137, or antigen-binding fragment thereof, wherein the antibody comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_8$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid, wherein the subject received or is receiving administration of a PD-1 antagonist, thereby treating the subject.

E61. A method for treating cancer in a subject, the method comprising: administering to the subject an effective amount of: an agonistic isolated monoclonal antibody that specifically binds to human CD137, or antigen-binding fragment thereof, wherein the antibody specifically binds to an epitope on human CD137 comprising one or more residues E111, T113, K114, P135 and W136 of SEQ ID NO: 3, wherein the subject received or is receiving administration of a PD-1 antagonist, thereby treating the subject.

E62. A method for treating cancer in a subject, the method comprising: administering to the subject an effective amount of: an agonistic isolated monoclonal antibody that specifically binds to human CD137, or antigen-binding fragment thereof, wherein the antibody specifically binds to an epitope comprising a sequence of one or more amino acid residues corresponding to amino acid positions 111 to 136 of SEQ ID NO: 3, wherein the subject received or is receiving administration of a PD-1 antagonist, thereby treating the subject.

E63. A method for treating cancer in a subject, the method comprising: administering to the subject an effective amount of: an agonistic isolated monoclonal antibody that specifically binds to human CD137, or antigen-binding fragment thereof, wherein the antibody specifically binds to an epitope comprising one or both of ELTK (corresponding to amino acid residues 111-114 of SEQ ID NO: 3) and PW (corresponding to amino acid residues 135-136 of SEQ ID NO: 3, wherein the subject received or is receiving administration of a PD-1 antagonist, thereby treating the subject.

E64. The method of any one of embodiments 58-63, wherein the cancer is breast cancer.

E65. The method of any one of embodiments 58-64, wherein (i) is administered prior to administration of (ii).

E66. The method of embodiment 65, wherein (i) is administered at least 4 days, at least 5 days, at least 6 days, at least 7 days, at least 8 days, at least 9 days, or at least 10 days before (ii) is administered.

E67. The method of any one of embodiments 58-66, wherein the subject comprises a tumor expressing or overexpressing PD-L1.

E68. The method of embodiment 67, wherein the tumor expresses more PD-L1 following administration of the agonistic isolated monoclonal antibody.

E69. The method of any one of embodiments 58-68, wherein the agonistic antibody or antigen-binding fragment comprises heavy and light chain CDRs, wherein heavy chain CDR3 comprises the amino acid sequence set forth in SEQ ID NO: 68.

E70. The method of any one of embodiments 58-68, wherein the agonistic antibody or antigen-binding fragment comprises heavy and light chain CDRs selected from the group consisting of:
  (a) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively; and
  (b) heavy chain CDR1, CDR2 and CDR3 sequences set forth in SEQ ID NOs: 51, 108 and 68, respectively, and light chain CDR1, CDR2 and CDR3 sequences set forth in SEQ ID NOs: 69, 78 and 89, respectively.

E71. The method of any one of embodiments 58-68, wherein the agonistic antibody or antigen-binding fragment comprises heavy and light chain variable regions, wherein the heavy chain variable region comprises an amino acid sequence selected from the group consisting of SEQ ID NOs: 4 and 101; and wherein the light chain variable region comprises an amino acid sequence of SEQ ID NO: 6.

E72. The method of any one of embodiments 58-68, wherein the agonistic antibody or antigen-binding fragment comprises heavy and light chain variable regions comprising amino acid sequences selected from the group consisting of:
  (a) SEQ ID NO: 4 and 6, respectively; and
  (b) SEQ ID NO: 101 and 6, respectively.

E73. The method of any one of embodiments 58-68, wherein the agonistic antibody or antigen-binding fragment comprises heavy and light chain variable regions, wherein the heavy chain variable region comprises an amino acid sequence which is at least 90% identical to the amino acid sequence selected from the group consisting of SEQ ID NOs: 4 and 101; and wherein the light chain variable region comprises an amino acid sequence which is at least 90% identical to the amino acid sequence of SEQ ID NO: 6.

E74. The method of any one of embodiments 58-68, wherein the agonistic antibody or antigen-binding fragment comprises heavy and light chain variable regions comprising amino acid sequences at least 90% identical to the amino acid sequences selected from the group consisting of:
  (a) SEQ ID NO: 4 and 6, respectively; and
  (b) SEQ ID NO: 101 and 6, respectively.

E75. The method of any one of the preceding embodiments, wherein the agonistic antibody or antigen-binding fragment exhibits at least one or more of the following properties:
  (a) induces or enhances dimerization of CD137 trimers;
  (b) induces or enhances multimerization of CD137 trimers;
  (c) induces or enhances human CD137-mediated T cell activation;
  (d) induces or enhances a human CD137-mediated cytotoxic T cell response;
  (e) induces or enhances human CD137-mediated T cell proliferation;
  (f) induces or enhances human CD137-mediated cytokine production;
  (g) does not significantly induce or enhance intrahepatic and/or intrasplenic T cell activation and/or T cell proliferation
  (h) binds to human CD137 with an equilibrium dissociation constant $K_D$ of $1 \times 10^{-6}$ or less; or
  (i) any combination of properties (a)-(h).

E76. The method of embodiment 75, wherein the agonistic antibody or antigen-binding fragment induces or enhances human CD137-mediated T cell activation in the tumor microenvironment, but does not significantly induce or enhance human CD137-mediated T cell activation in the spleen and/or liver.

E77. The method of embodiment 76, wherein the agonistic antibody or antigen-binding fragment induces or enhances human CD137-mediated cytotoxic T cell response in the tumor microenvironment, but does not significantly induce or enhance human CD137-mediated cytotoxic T cell response in the spleen and/or liver.

E78. The method of embodiment 76, wherein the agonistic antibody or antigen-binding fragment induces human CD137-mediated T cell proliferation in the tumor microenvironment, but does not significantly induce human CD137-mediated T cell proliferation in the spleen and/or liver.

E79. The method of embodiment 76, wherein the agonistic antibody or antigen binding fragment induces or enhances human CD137-mediated cytokine production in the tumor microenvironment, but does not significantly induce or enhance human CD137-mediated cytokine production in the spleen and/or liver.

E80. The method of any one of embodiments 75-79 wherein the properties of the agonistic antibody or antigen-binding fragment are not Fc gamma receptor binding dependent.

E81. The method of any one of embodiments 75-79, wherein the properties of the agonistic antibody or antigen-binding fragment are enhanced by Fc gamma receptor binding.

E82. The method of any one of the preceding embodiments, wherein the agonistic antibody or antigen-binding fragment cross-reacts with cynomolgus CD137 and/or mouse CD137.

E83. The method of any one of the preceding embodiments, wherein the agonistic antibody is selected from the group consisting of an IgG1, an IgG2, and IgG3, an IgG4, and IgM, and IgA1, and IgA2, and IgD, and an IgE antibody.

E84. The method of embodiment 83, wherein the agonistic antibody is an IgG1 antibody or IgG4 antibody.

E85. Use of an agonistic isolated monoclonal antibody that specifically binds to human CD137, or antigen-binding fragment thereof, and a PD-1 antagonist, for the treatment of cancer in a subject in need thereof, wherein the PD-1 antagonist is administered after administration of the agonistic isolated monoclonal antibody, or antigen-binding fragment thereof.

E86. The use of embodiment 85, wherein administration of the agonistic isolated monoclonal antibody, or antigen-binding fragment thereof, and the PD-1 antagonist overlap.
E87. The use of embodiment 86, wherein the agonistic isolated monoclonal antibody, or antigen-binding fragment thereof, is administered at least 4 days, at least 5 days, at least 6 days, at least 7 days, at least 8 days, at least 9 days, or at least 10 days before the PD-1 antagonist is administered.
E88. Use of a PD-1 antagonist, for the treatment of cancer in a subject in need thereof, wherein the subject has received or is receiving treatment with an agonistic isolated monoclonal antibody that specifically binds to human CD137, or antigen-binding fragment thereof.
E89. Use of a PD-1 antagonist, for enhancing a cancer-specific immune response in a subject in need thereof, wherein the subject has received or is receiving treatment with an agonistic isolated monoclonal antibody that specifically binds to human CD137, or antigen-binding fragment thereof, wherein the cancer-specific immune response is enhanced relative to the cancer-specific immune response induced by the agonistic isolated monoclonal antibody, or antigen-binding fragment thereof, alone.
E90. The use of embodiment 88 or 89, wherein the PD-1 antagonist is administered at least 4 days, at least 5 days, at least 6 days, at least 7 days, at least 8 days, at least 9 days, or at least 10 days after treatment with the agonistic isolated monoclonal antibody.
E91. The use of any one of embodiments 85-90, wherein the subject comprises a tumor expressing or overexpressing PD-L1.
E92. The use of embodiment 91, wherein the tumor expresses more PD-L1 following administration of the agonistic isolated monoclonal antibody.
E93. The use of any one of embodiments 89-92, wherein the PD-1 antagonist is an isolated monoclonal antibody that specifically binds to human PD-L1, or antigen-binding fragment thereof.
E94. The use of any one of embodiments 89-92, wherein the PD-1 antagonist is an isolated monoclonal antibody that specifically binds to human PD-1, or antigen-binding fragment thereof.
E95. The use of any one of embodiments 89-94, wherein the cancer-specific immune response is a T cell response.
E96. The use of embodiment 95, wherein the T cell response comprises the production of IFNγ by one or both of $CD4^+$ T cells and $CD8^+$ T cells.
E97. The use of embodiment 95, wherein the T cell response comprises the production of IL-2 by one or both of $CD4^+$ T cells and $CD8^+$ T cells.
E98. The use of embodiment 95, wherein the T cell response comprises proliferation of one or both of $CD4^+$ T cells and $CD8^+$ T cells.
E99. The use of any one of embodiments 85-88 and 90-94, wherein treatment comprises delaying cancer progression in the subject.
E100. The use of any one of embodiments 85-88 and 90-94, wherein treatment comprises enhancing a tumor-specific immune response in the subject.
E101. The use of any one of embodiments 89-100, wherein the cancer is breast cancer.
E102. The use of any one of embodiments 89-101, wherein the agonistic isolated monoclonal antibody, or antigen-binding fragment thereof, binds human CD137 with an affinity ($K_D$) of about 40-100 nM.
E103. The use of any one of embodiments 89-100, wherein the agonistic isolated monoclonal antibody, or antigen-binding fragment thereof, (i) binds human CD137 with an affinity ($K_D$) of about 40-100 nM; and (ii) comprises a heavy chain CDR3 comprising the amino acid sequence DXXXXLXXXXYXYYX (SEQ ID NO: 126), wherein X is any amino acid.
E104. The use of any one of embodiments 89-100, wherein the agonistic isolated monoclonal antibody, or antigen-binding fragment thereof, (i) binds human CD137 with an affinity ($K_D$) of about 40-100 nM; and (ii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.
E105. The use of any one of embodiments 89-100, wherein the agonistic isolated monoclonal antibody, or antigen-binding fragment thereof, (i) binds human CD137 with an affinity ($K_D$) of about 40-100 nM; and (ii) specifically binds to an epitope on human CD137 comprising one or more residues E111, T113, K114, P135 and W136 of SEQ ID NO: 3.
E106. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; (iii) comprises a heavy chain CDR3 comprising the amino acid sequence DXXXXLXXXXYXYYX (SEQ ID NO: 126), wherein X is any amino acid; or (iv) combinations thereof.
E107. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or (iv) combinations thereof.
E108. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; and (iii) comprises a heavy chain CDR3 comprising the amino acid sequence DXXXXLXXXXYXYYX (SEQ ID NO: 126), wherein X is any amino acid.
E109. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope on human CD137 comprising one or more residues E111, T113, K114, P135 and W136 of SEQ ID NO: 3; and (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

E110. The use of any one of embodiments 105-109, wherein the epitope comprises residues E111, T113, K114, P135 and W136 of SEQ ID NO: 3.

E111. The use of any one of embodiments 89-100, wherein the agonistic isolated monoclonal antibody, or antigen-binding fragment thereof, (i) binds human CD137 with an affinity ($K_D$) of about 40-100 nM; and (ii) specifically binds to an epitope comprising a sequence of one or more amino acid residues corresponding to amino acid positions 111 to 136 of SEQ ID NO: 3.

E112. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; (iii) comprises a heavy chain CDR3 comprising the amino acid sequence DXXXXLXXXXYXYYX (SEQ ID NO: 126), wherein X is any amino acid; or (iv) combinations thereof.

E113. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or (iv) combinations thereof.

E114. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; and (iii) comprises a heavy chain CDR3 comprising the amino acid sequence DXXXXLXXXXYXYYX (SEQ ID NO: 126), wherein X is any amino acid.

E115. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising a sequence of one or more amino acid residues corresponding to amino acid positions 111 to 136 of SEQ ID NO: 3; and (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

E116. The use of any one of embodiments 111-115, wherein the epitope comprises 2, 3, 4, 5, 6, 7, 8, 9, 10, 11, 12, 13, 14, 15, 16, 17, 18, 19, 20, 21, 22, 23, 24, 25 or 26 amino acid residues corresponding to amino acid positions 111 to 136 of SEQ ID NO: 3.

E117. The use of any one of embodiments 111-116, wherein the epitope comprises 6 amino acid resides.

E118. The use of any one of embodiments 89-100, wherein the agonistic isolated monoclonal antibody, or antigen-binding fragment thereof, (i) binds human CD137 with an affinity of about 40-100 nM; and (ii) binds to an epitope comprising one or both of ELTK (corresponding to amino acid residues 111-114 of SEQ ID NO: 3) and PW (corresponding to amino acid residues 135-136 of SEQ ID NO: 3.

E119. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; (iii) comprises a heavy chain CDR3 comprising the amino acid sequence DXXXXLXXXXYXYYX (SEQ ID NO: 126), wherein X is any amino acid; or (iv) combinations thereof.

E120. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid; or (iv) combinations thereof.

E121. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; and (iii) comprises a heavy chain CDR3 comprising the amino acid sequence DXXXXLXXXXYXYYX (SEQ ID NO: 126), wherein X is any amino acid.

E122. The use of any one of embodiments 89-100, wherein the agonistic isolated monoclonal antibody, or antigen-binding fragment thereof, (i) binds human CD137 with an affinity ($K_D$) of about 40-100 nM; (ii) specifically binds to an epitope comprising one or both of ELTK (corresponding to amino acid residues 111-114 of SEQ ID NO: 3) and PW (corresponding to amino acid residues 135-136 of SEQ ID NO: 3; and (iii) comprises a heavy chain CDR3 comprising the amino acid sequence $DX_1X_2X_3X_4LX_5X_6X_7X_8YX_9YYX_{10}$ (SEQ ID NO: 128), wherein $X_1$ is any amino acid, wherein $X_2$ is a non-polar amino acid, wherein $X_3$ is a non-polar amino acid, wherein $X_4$ is any amino acid, wherein $X_5$ is a polar amino acid, wherein $X_6$ is any amino acid, wherein $X_7$ is any amino acid, wherein $X_8$ is a polar amino acid, wherein $X_9$ is a polar amino acid, and wherein $X_{10}$ is any amino acid.

E123. The use of any one of embodiments 118-122, wherein the epitope comprises the residues ELTK of SEQ ID NO: 3 (corresponding to amino acid residues 111-114 of SEQ ID NO: 3).

E124. The use of any one of embodiments 118-122, wherein the epitope comprises the residues PW of SEQ ID NO: 3 (corresponding to amino acid residues 135-136 of SEQ ID NO: 3).

E125. The use of any one of embodiments 118-122, wherein the epitope comprises the residues ELTK of SEQ ID NO: 3 (corresponding to amino acid residues 111-114 of SEQ ID NO: 3) and residues PW of SEQ ID NO: 3 (corresponding to amino acid residues 135-136 of SEQ ID NO: 3).

E126. The use of any one of embodiments 105-125, wherein the epitope is a non-linear epitope.

E127. The use of any one of embodiments 105-126, wherein mutation of residue K114 of SEQ ID NO: 3 abrogates binding of the agonistic antibody, or antigen-binding fragment thereof.

E128. The use of any one of embodiments 85-127, wherein the agonistic antibody, or antigen-binding fragment thereof, comprises a heavy chain CDR3 comprising the amino acid sequence DXPFXLDXXYYYYYX (SEQ ID NO: 126), wherein X is any amino acid.

E129. The use of embodiment 128, wherein mutation of residues D95, L100, Y100E, Y100G, Y100H, or combinations thereof, of the heavy chain CDR3, results in loss of binding to human CD137.

E130. The use of embodiment 128 or 129, wherein mutation of residues P97, F98, D100A, Y100D, Y100F, or combinations thereof to alanine results in reduction of binding to human CD137.

E131. The use of embodiment 128 or 129, wherein mutation of residues P97, F98, D100A, Y100D, Y100F, or combinations thereof to any residue except alanine, results in an increase in binding to human CD137.

E132. The use of any one of embodiments 103, 106, 108, 110, 112, 114, 116, 117, 119, 121 and 123-129, wherein X is any amino acid except for alanine.

E133. The use of any one of embodiments 104, 107, 109, 110, 113, 115, 116, 117, 120 and 122-129, wherein $X_2$ is proline, wherein $X_3$ is phenylalanine or tryptophan, wherein $X_5$ is aspartic acid or glutamic acid wherein $X_8$ is tyrosine, and wherein $X_9$ is tyrosine E134. The use of any one of embodiments 85-133, wherein the agonistic antibody or antigen-binding fragment binds human CD137 with an affinity ($K_D$) of about 45-95 nM, 50-90 nM, 55-85 nM, 60-80 nM, 65-75 nM, 55-75 nM, 40-70 nM, 50-80 nM, or 60-90 nM.

E135. The use of any one of embodiments 85-134, wherein the agonistic antibody or antigen-binding fragment comprises heavy and light chain CDRs, wherein heavy chain CDR3 comprises the amino acid sequence set forth in SEQ ID NO: 68.

E136. The use of any one of embodiments 85-134, wherein the agonistic antibody or antigen-binding fragment comprises heavy and light chain CDRs selected from the group consisting of:
(a) heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively; and
(b) heavy chain CDR1, CDR2 and CDR3 sequences set forth in SEQ ID NOs: 51, 108 and 68, respectively, and light chain CDR1, CDR2 and CDR3 sequences set forth in SEQ ID NOs: 69, 78 and 89, respectively.

E137. The use of any one of embodiments 85-134, wherein the agonistic antibody or antigen-binding fragment comprises heavy and light chain variable regions, wherein the heavy chain variable region comprises an amino acid sequence selected from the group consisting of SEQ ID NOs: 4 and 101; and wherein the light chain variable region comprises an amino acid sequence of SEQ ID NO: 6.

E138. The use of any one of embodiments 85-134, wherein the agonistic antibody or antigen-binding fragment comprises heavy and light chain variable regions comprising amino acid sequences selected from the group consisting of:
(a) SEQ ID NO: 4 and 6, respectively; and
(b) SEQ ID NO: 101 and 6, respectively.

E139. The use of any one of embodiments 85-134, wherein the agonistic antibody or antigen-binding fragment comprises heavy and light chain variable regions, wherein the heavy chain variable region comprises an amino acid sequence which is at least 90% identical to the amino acid sequence selected from the group consisting of SEQ ID NOs: 4 and 101; and wherein the light chain variable region comprises an amino acid sequence which is at least 90% identical to the amino acid sequence of SEQ ID NO: 6.

E140. The use of any one of embodiments 85-134, wherein the agonistic antibody or antigen-binding fragment comprises heavy and light chain variable regions comprising amino acid sequences at least 90% identical to the amino acid sequences selected from the group consisting of:
(a) SEQ ID NO: 4 and 6, respectively; and
(b) SEQ ID NO: 101 and 6, respectively.

E141. The use of any one of embodiments 85-140, wherein the agonistic antibody or antigen-binding fragment exhibits at least one or more of the following properties:
(a) induces or enhances dimerization of CD137 trimers;
(b) induces or enhances multimerization of CD137 trimers;
(c) induces or enhances human CD137-mediated T cell activation;
(d) induces or enhances a human CD137-mediated cytotoxic T cell response;
(e) induces or enhances human CD137-mediated T cell proliferation;
(f) induces or enhances human CD137-mediated cytokine production;
(g) does not significantly induce or enhance intrahepatic and/or intrasplenic T cell activation and/or T cell proliferation
(h) binds to human CD137 with an equilibrium dissociation constant $K_D$ of $1\times10^{-6}$ or less; or
(i) any combination of properties (a)-(h).

E142. The use of embodiment 141, wherein the agonistic antibody or antigen-binding fragment induces or enhances human CD137-mediated T cell activation in the tumor microenvironment, but does not significantly induce or enhance human CD137-mediated T cell activation in the spleen and/or liver.

E143. The use of embodiment 142, wherein the agonistic antibody or antigen-binding fragment induces or enhances human CD137-mediated cytotoxic T cell response in the tumor microenvironment, but does not significantly induce or enhance human CD137-mediated cytotoxic T cell response in the spleen and/or liver.

E144. The use of embodiment 142, wherein the agonistic antibody or antigen-binding fragment induces human CD137-mediated T cell proliferation in the tumor microenvironment, but does not significantly induce human CD137-mediated T cell proliferation in the spleen and/or liver.

E145. The use of embodiment 142, wherein the agonistic antibody or antigen binding fragment induces or enhances human CD137-mediated cytokine production in the tumor microenvironment, but does not significantly induce or enhance human CD137-mediated cytokine production in the spleen and/or liver.

E146. The use of any one of embodiments 141-145, wherein the properties of the agonistic antibody or antigen-binding fragment are not Fc gamma receptor binding dependent.

E147. The use of any one of embodiments 141-145, wherein the properties of the agonistic antibody or antigen-binding fragment are enhanced by Fc gamma receptor binding.

E148. The use of any one of embodiments 85-147, wherein the agonistic antibody or antigen-binding fragment cross-reacts with cynomolgus CD137 and/or mouse CD137.

E149. The use of any one of embodiments 85-148, wherein the agonistic antibody is selected from the group consisting of an IgG1, an IgG2, and IgG3, an IgG4, and IgM, and IgA1, and IgA2, and IgD, and an IgE antibody.

E150. The use of embodiment 149, wherein the agonistic antibody is an IgG1 antibody or IgG4 antibody.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1: Synthetic Human Monoclonal Antibodies Produced in Yeast Exhibit Binding to Recombinant Human CD137

Purified CD137 protein antigen was biotinylated using the EZ-Link Sulfo-NHS-Biotinylation Kit (Thermo Scientific). CD137 antigens were concentrated to ~1 mg/mL and buffer exchanged into PBS before addition of 1:7.5 molar ratio biotinylation reagent (EZ-Link Sulfo-NHS-Biotinylation Kit, Thermo Scientific, Cat #21425.). The mixture was held at 4° C. overnight prior to another buffer exchange to remove free biotin in the solution. Biotinylation was confirmed through Streptavidin sensor binding of the labeled proteins on a ForteBio. Successful biotinylation of the CD137 protein antigen was confirmed via detectable binding to a streptavidin-linked biosensor installed on ForteBio OCTET™ Red384 Interferometer (Pall ForteBio, Menlo Park, Calif.) according to the manufacturer's guidelines (data not shown).

Eight naïve human synthetic yeast-based antibody libraries each of $\sim 10^9$ diversity were designed, generated, and propagated as described previously (see, e.g., WO2009036379; WO2010105256: WO2012009568; Xu et al., Protein Eng Des Sel. 2013 October; 26(10):663-70). Eight parallel selections were performed, using the eight naïve libraries against biotinylated human CD137-Fc fusion.

For the first two rounds of selection, a magnetic bead sorting technique utilizing the Miltenyi MACS system was performed, essentially as described (Siegel et al., J Immunol Methods. 2004 March; 286(1-2):141-53). Briefly, yeast cells ($\sim 10^{10}$ cells/library) were incubated with 10 mL of 10 nM biotinylated human CD137-Fc fusion antigen for 15 minutes at room temperature in FACS wash buffer PBS with 0.1% BSA. After washing once with 50 mL ice-cold wash buffer, the cell pellet was resuspended in 40 mL wash buffer, and 500 µl Streptavidin MicroBeads (Miltenyi Biotec, Bergisch Gladbach, Germany. Cat #130-048-101) were added to the yeast and incubated for 15 minutes at 4° C. Next, the yeast were pelleted, resuspended in 5 mL wash buffer, and loaded onto a MACS LS column (Miltenyi Biotec, Bergisch Gladbach, Germany. Cat. #130-042-401). After the 5 mL was loaded, the column was washed three times with 3 mL FACS wash buffer. The column was then removed from the magnetic field, and the yeast were eluted with 5 mL of growth media and then grown overnight.

Subsequent to the two rounds of MACS, three rounds of sorting were performed using flow cytometry (FACS), which are described in the following three paragraphs.

Selection Strategy Employing 8 Parallel Selections with Fc Antigen

The eight libraries from the MACS selections were taken through three rounds of FACS selections. Approximately $1 \times 10^8$ yeast per library were pelleted, washed three times with wash buffer, and incubated with 10 nM of biotinylated human CD137-Fc fusion and 10 nM of biotinylated murine CD137-Fc fusion antigen separately for 10 minutes at room temperature. Yeast were then washed twice and stained with goat anti-human F(ab')$_2$ kappa-FITC diluted 1:100 (Southern Biotech, Birmingham, Ala., Cat #2062-02) and either streptavidin-Alexa Fluor 633 (Life Technologies, Grand Island, N.Y., Cat #S21375) diluted 1:500, or Extravidin-phycoerthyrin (Sigma-Aldrich, St Louis, Cat #E4011) diluted 1:50, secondary reagents for 15 minutes at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only CD137 binding. The murine- and human-selected populations from the first round of FACS were brought forward into the next round.

The second and third round of FACS for the above selected populations involved positive sorts for binders to human and/or murine CD137 reagents; or negative sorts to decrease polyspecific reagent binders (Xu et al., PEDS. 2013 October; 26(10):663-70). Depending on the amount of polyspecific binding or target binding of a specific selection output, a positive sort followed a negative sort or vice versa, to enrich for a full binding population with limited amount of polyspecific binding. Competition selections were also performed with control mAbs from the literature. For competition selections, mAb4 (urclumab; Bristol-Myers Squibb; CAS Number: 934823-49-1) and mAb5 (utomilumab; Pfizer; CAS Number: 1417318-27-4) were pre-complexed to biotinylated human CD137-Fc fusion. Antibodies that bind and do not bind in the presence of the control mAbs were selected for on FACS. The outputs of these rounds were plated and isolates were picked for sequencing and characterization.

Affinity Maturation of Clones Identified in Naïve Selections

Heavy chains from the first FACS sorting round against biotinylated human CD137 Fc fusion outputs were used to prepare light chain diversification libraries used for four additional selection rounds. The first of these selection rounds utilized Miltenyi MACs heads conjugated with 10 nM biotinylated human CD137-Fc fusion as antigen.

Subsequent to the MACs bead selections, three rounds of FACS sorting were performed. The first of these rounds used biotinylated human CD137-Fc fusion at 10 nM. The second FACS round for the above involved positive sorts for binders to mouse CD137 reagents, competition sorts with previously mentioned control mAbs or negative sorts to decrease polyspecific reagent binders as described above. The third and final round of FACS selection was done using either biotinylated murine CD137 Fc fusion at 10 nM or biotinylated human monomeric CD137 at 50 nM. Individual colonies from each FACS selection round described above were picked for sequencing characterization.

IgG and Fab Production and Purification

Yeast clones were grown to saturation and then induced for 48 hours at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over CAPTURE-SELECT IgG-CH1 affinity matrix (LifeTechnologies, Cat #1943200250).

Example 2: Epitope Binning and Determination of Human Anti-CD137 Antibody Affinity to Recombinant CD137

Epitope binning of the antibodies isolated in Example 1 was performed on a Forte Bio OCTET Red384 system (Pall Forte Bio Corporation, Menlo Park, Calif.) using a standard sandwich format binning assay. CD137 control antibody IgGs were loaded onto AHQ sensors and unoccupied Fc-binding sites on the sensor were blocked with a non-relevant human IgG1 antibody. The sensors were then exposed to 100 nM target antigen followed by exposure to the isolated antibodies identified as described in Example 1. Data were processed using ForteBio's Data Analysis Software 7.0. Additional binding by the second antibody after antigen association indicates an unoccupied epitope (non-competitor), while no binding indicates epitope blocking (competitor) (data not shown).

Affinity of the CD137 antibodies was determined by measuring their kinetic constants ($k_a$, $k_d$, $K_D$) on ForteBio OCTET. ForteBio affinity measurements were performed generally as previously described (Estep et al., MAbs. 2013 5(2):270-8). Briefly, ForteBio affinity measurements were performed by loading antibodies (IgGs) on-line onto AHQ sensors. Sensors were equilibrated off-line in assay buffer for 30 minutes and then monitored on-line for 60 seconds for baseline establishment. For avid binding measurement, sensors with loaded IgGs were exposed to 100 nM antigen (human, cyno, or murine CD137) for 3 minutes, afterwards they were transferred to assay buffer for 3 minutes for off-rate measurement. Monovalent binding measurements were obtained by loading human CD137-Fc fusion on AHQ sensors followed by exposure to 200 nM antibody Fab in solution. Kinetics data were fit using a 1:1 binding model in the data analysis software provided by ForteBio (data not shown).

Determination of whether antibodies were ligand blocking was also assessed. Specifically, ligand blocking experiments were performed both on OCTET HTX (ForteBio) and on label-free MX96 SPRi (Caterra). mAb1 was captured on OCTETt sensor or MX96 chip sensor. CD137 and CD137L were sequentially applied to the sensors pre-loaded with mAb1. An increase in response upon exposure to CD137L indicated non-competition between mAb1 and CD137L for binding to CD137. On the other hand, a lack of change in the signal indicated competition, which was the case for control antibody mAb5. mAb1 did not inhibit binding of CD137L to CD137, and therefore was considered a non-ligand blocking antibody.

Example 3: Distribution of Binding Affinities of Affinity-Matured Anti-CD137 Antibodies Affinity matured anti-CD137 antibodies were generated using 2 mutant libraries. The first library contained mutations in the heavy chain and the second library contained mutations in the light chain, wherein donor diversity in light chain CDR1, CDR2 and CDR3 was created. The mutant libraries went through 3 rounds of phage panning aimed at increasing affinity and maintaining cross-reactivity with mouse CD137. In each round, an off-rate competition step was employed after initial binding to biotinylated antigens (i.e., 1 hour incubation with excess unlabeled antigen or parental IgG at 37° C.).

The resulting anti-CD137 antibodies from different selection rounds were plotted on $k_d/k_a$ double log plots. Apparent association and dissociation kinetic rate constants ($k_a$ and kd values) were determined on an SPRi reader (MX96, Carterra) in a running buffer of PBS-T 0.01%. Anti-human CD137 antibodies were covalently printed on a Carboxymethyldextran hydrogel 50 L chip (Xantec bioanalytics) on a CFM (Carterra). Freshly mixed activating reagents (150 ml 0.4 M EDC and 150 ml 0.1 M sulfo-NHS in H2O) were used to activate the surface of the SPR substrate for 7 minutes. Antibodies at 10 mg/ml in acetic acid buffer pH 4.5 were used for printing for 15 minutes. The printed chip was then quenched on SPRi reader (MX96, Carterra) with 1 M ethanolamine for 15 minutes. For kinetics analysis, purified recombinant his tagged human CD137 (0, 2.05, 5.12, 12.8, 32, 80, 200, 500 nM) was injected sequentially. For each concentration, there was 5 minutes of association followed by 10 minutes of dissociation. Data were processed and analyzed in SPR Inspection Tool and Scrubber softwares. The kinetic data were referenced with the interstitial reference spots and double-referenced to a buffer cycle, and then fit globally to a 1:1 binding model to determine their apparent association and dissociation kinetic rate constants ($k_a$ and $k_d$ values). The ratio kd/$k_a$ was used to derive the $K_D$ value of each antigen/mAb interaction, i.e., $K_D=k_d/k_a$.

Antibodies with $K_D$ ($k_d/k_a$) between 10-20 nM are shown as upright triangles, while the ones with $K_D$ lower than 10 nM are shown as upside down triangles (FIG. 1). Affinity maturation of only the heavy chains (top panels) or only the light chains (bottom panels) both resulted in the isolation of anti-CD137 antibodies with higher binding affinities than the parental antibody (mAb1) (FIG. 1). The heavy chain and light chain variable regions of mAb1 are set forth in SEQ ID NOs: 4 and 6, respectively.

Example 4: Identification of Critical Binding Residues Comprising Heavy Chain CDR3 (CDRH3) of Anti-CD137 Antibodies To determine which amino acid residues within CDRH3 are critical for the binding of mAb1 to mouse and human CD137 polypeptides, alanine scanning was performed. A set of polynucleotides encoding derivatives of the mAb1 open reading frame was generated, wherein each derivative contained a single alanine residue substitution at a wild-type amino acid residue position comprising CDRH3. Positions D95 through M100I of SEQ ID NO: 4 were each mutated to alanine by replacing the wild-type codon with the alanine codon GCC. The amino acid sequences of each CDRH3 of each mAb1 alanine-substituted derivative are set forth in SEQ ID NOs: 111-125. The polynucleotides encoding each of the 15 mAb1 alanine-substituted derivatives were individually cloned into an expression vector (aglyco-IgG1, DID-2600) via Gibson Assembly. Each mAb1 alanine-substituted derivative was expressed and purified using standard techniques known in the art. Binding affinities of each mAb1 alanine-substituted derivative for human and mouse CD137 were determined via Wasatch SPR kinetics measurements for human CD137 (huCD137) or equilibrium cell-binding assays for mouse CD137 (mCD137).

Table 1 provides the calculated dissociation constants ($K_D$) for each mutant. When "Weak" is noted in the table there was measurable binding above background but not enough confidence in the curve fitting to assign an accurate $K_D$ value. In Table 1, "NB" signifies that no binding was observed during the determination of binding affinities and indicates which alanine substitutions in CDRH3 resulted in an antibody that did not bind to CD137.

TABLE 1

Binding affinity (KD) of alanine scanning clones for human and mouse CD137

| Substitution | huCD137 | mCD137 | Substitution | huCD137 | mCD137 |
|---|---|---|---|---|---|
| D95A | NB | NB | Y(100C)A | 1 nM | 25 nM |
| S96A | 1.8 nM | 40 nM | Y(100D)A | Weak | 170 nM |
| P97A | Weak | Weak | Y(100E)A | NB | NB |
| F98A | Weak | Weak | Y(100F)A | Weak | Weak |
| L99A | 2.7 nM | 33 nM | Y(100G)A | NB | NB |
| L100A | NB | NB | Y(100H)A | NB | NB |
| D(100A)A | Weak | Weak | M(100I)A | 1.8 nM | 21 nM |
| D(100B)A | 1.3 nM | 54 nM | WT $K_D$ | 1nM | 11 nM |

The retention, weakening, or loss of binding affinity resulting from mutations to alanine informed the determination of which residues were required for CD137 binding and which residues tolerated mutations. FIG. 2 summarizes the binding data for alanine scanning of CDRH3 with wild-type amino acid identity indicated at each position. CDRH3 positions are color-coded based on the effects of mutating the position to alanine, as shown. This analysis resulted in the following consensus sequence: DXPFXLDXXYYYYYX (SEQ ID NO: 127) When bolded residues in the consensus sequence were mutated to alanine, there was a complete loss of binding and these residues were therefore necessary for mAb1 binding to CD137. When italicized residues in the consensus sequence were mutated to alanine, the antibody was still able to bind CD137 but with a weaker affinity indicating these residues played a partial role in binding but were not absolutely required. When residue positions denoted with an X in the consensus sequence were mutated to alanine there was little to no change in binding affinity. Thus, these residues tolerated mutations and were not critical to the binding interaction.

Example 5: Epitope Mapping by Scanning Saturation Mutagenesis and Homolog Comparison Functional mapping of the CD137 epitope by scanning saturation mutagenesis library and homology comparison were performed to identify residues important for antibody binding to CD137. Combinatorial libraries of CD137 mutants with single point mutations at all residue positions to every possible amino acid substitution except cysteine were generated and tested for their ability to bind to mAb1, mAb4, and mAb5. A library consisting of genes encoding each point mutant of CD137 were synthesized from a commercial supplier and cloned into a mammalian display expression vector. Mammalian display was used to present a library of variant human CD137 extracellular domains, with each variant having at least one point mutation relative to wild type human CD137.

The library of cells displaying CD137 variants was stained with non-overlapping antibodies (i) mAb4 and mAb1 or (ii) mAb4 and mAb5. Populations of cells with reduced binding to one antibody but not the other were enriched by FACS. Each population was sequenced by Illumina sequencing to identify mutations in positions that specifically disrupted binding to each antibody but did not affect correct folding of CD137 or binding to the non-overlapping antibody.

For mAb1, K114 was identified as the most important residue important for binding to CD137, with 34% of all mutations observed occurring in that position, and all amino acid substitutions observed. E111, T113, and P135 are also important for binding, with 10% of mutations observed in each of those positions. Additionally, N126 and I132 was observed in the population that had partial decrease in binding for mAb1. FIG. 3A shows the residues comprising the epitope for mAb1, mAb4 and mAb5. mAb4 and mAb5 had binding epitopes that were distinct from mAb1. For mAb4, N42 was the most important residue with 50% of all mutations observed in that position, followed by R41 and D38. For mAb5, I132 was the most important with 32% of all mutations occurring in that position, followed by N126, G96, K114, and L95.

Point mutants isolated from the library screen were expressed as soluble proteins and tested for binding to mAb1. All 4 mutations tested at K114 (R, E, N, T) abolished binding to mAb1. Mutations at T113 and P135 also disrupted binding. 1/2 point mutants at E111, 1/3 mutants at N126, and 1/4 mutants at I132 showed no binding. Likewise, 3/3 mutants at N42 did not bind to mAb4, and 3/4 mutants at I132 did not bind to mAb5.

Figure 3B:
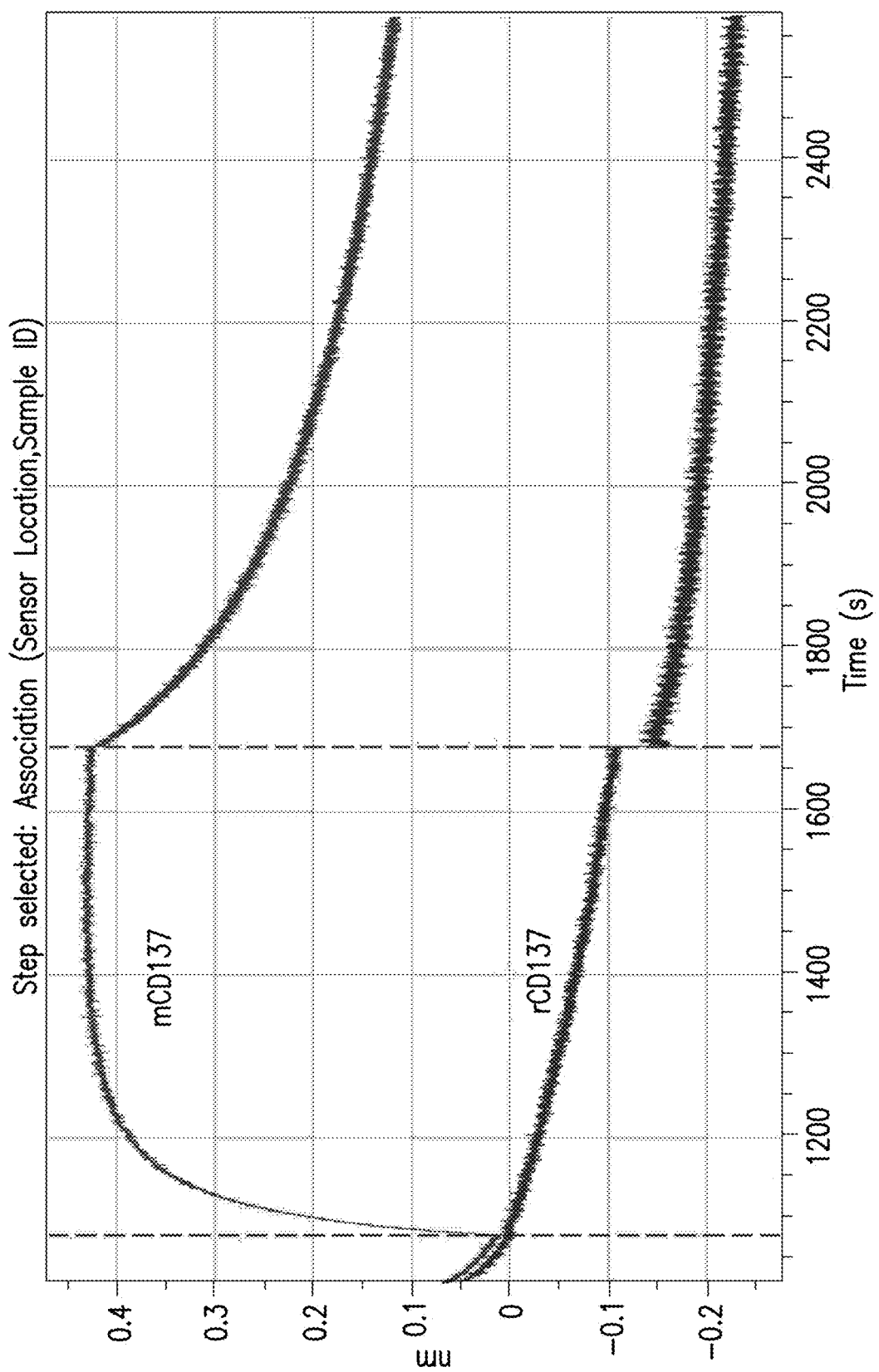
FIG. 3B is a graph depicting kinetic binding data of mAb1 to the extracellular domain of mouse and rat CD137 as determined by surface plasmon resonance.

Additionally, CD137 homologs were tested for their binding to mAb1. mAb1 was able to bind to mouse CD137, but not to rat CD137, as shown in FIG. 3B. To determine if there was a difference in the residues comprising the epitope for mAb1 between mouse CD137 and rat CD137, the amino acid sequences of CD137 homologs from human, cynomolgus monkey, rat, and mouse were aligned for comparison. All of the amino acid residues comprising the mAb1 epitope are present in human, cynomolgus monkey, and mouse, but not in rat. Lysine 114 (K114) of the human CD137 sequence, as well as the corresponding lysine in the cynomolgus monkey and mouse CD137 sequences, is glutamic acid (E) in the rat CD137 sequence, further indicating that K114 of the human CD137 sequence is at least one of the critical binding residues for mAb1.

Figure 3C:
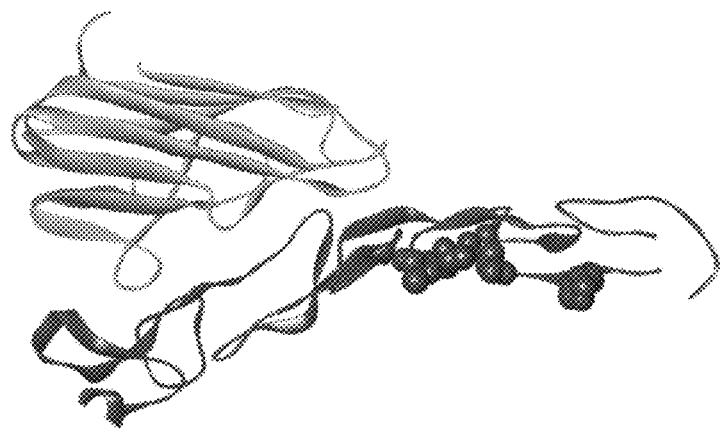
FIG. 3C provides x-ray crystallography images of human CD137 bound to CD137L (shown in grey) and residues E111, T113, K114 and P135 shown as spheres.
Figure 3C:
Figure 3C:
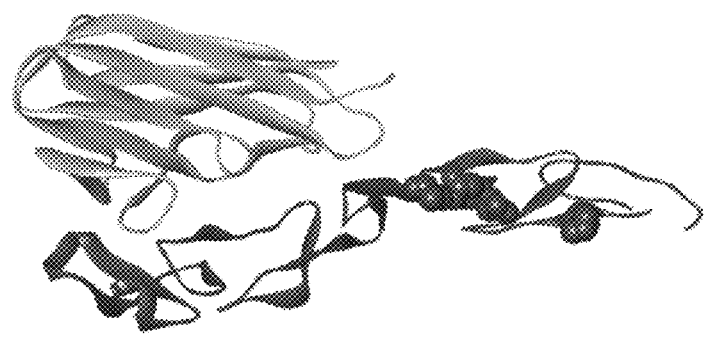
Figure 3D:
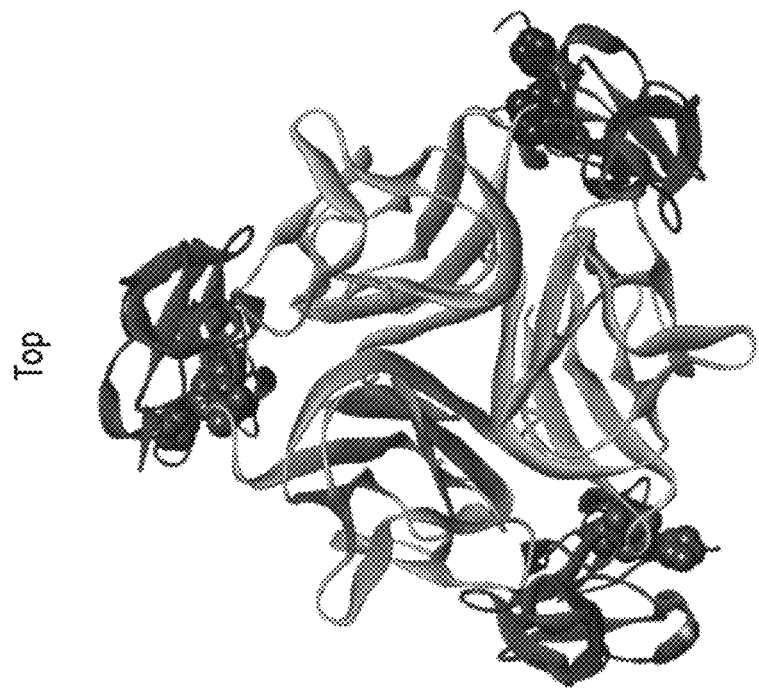
FIG. 3D provides x-ray crystallography images of human CD137 bound to CD137L (shown in grey) in trimeric formation, and residues E111, T113, K114 and P135 shown as spheres.
Figure 3D:
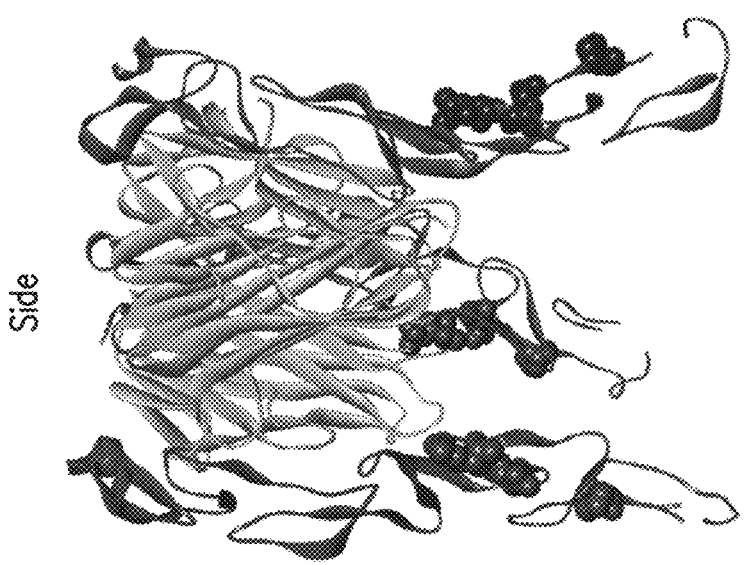

FIGS. 3C and 3D show the crystal structure of human CD137 bound to CD137L (Bitra A et al., *J Biol Chem* 2018, 293(26):9958-9969), wherein residues E111, T113, K114 and P135 are shown as spheres. As can be seen, these residues are located away from the CD137 ligand (CD137L) binding domain, shown in grey.

Example 6: Effect of Anti-CD137 Antibodies on Immune Regulators and CD8+ T Cells in Mice Three anti-CD137 antibodies generated in Example 1, mAb1, mAb2 and mAb3, were further analyzed for their efficacy. These antibodies were mouse cross-reactive and comprised the constant regions of the human IgG4 isotype containing the S228P mutation to prevent Fab shuffling. The 3H3 monoclonal antibody, known to stimulate mouse CD137 signaling in vivo and elicit anti-tumor immunity (Melero et al. (1997) Nature Medicine 3(6):682-685; Uno et al. (2006) Nature Medicine 12(6):693-696), was used as a comparator (BioXcell cat #BE0239; lot number 5926/1115). Notably, antibody 3H3 has similar properties to that of urelumab (Bristol-Myers Squibb; CAS Number: 934823-49-1), a fully human IgG4-S228P agonistic antibody that targets the extracellular domain of CD137, but does not block ligand binding. In addition, anti-Rat IgG4 was used as an isotype control (BioXcell cat #BE0089; lot number 5533/5679-316J1). Dilutions were made in PBS to achieve desired dose per mice, as indicated, in 100 µL injection volume.

The antibodies (100 µg) were administered intraperitoneally on days 0, 3, 6 to non-tumor bearing female Balb/c mice and spleens were harvested on day 9. Levels of PD-1 and TIGIT expression on CD8+CD44+ T cells were measured by flow cytometry. Specifically, single cell suspensions from the spleens were obtained by mechanical disruption and passing through a 40 µm cell strainer. Red blood cells were lysed using ACK buffer. The cell suspensions were stained with the following antibodies: CD45 (clone 30-F11, eBioscience), CD8 (clone 53-6.7, BD Biosciences), CD4 (clone RM-45, BD Biosciences), CD44 (clone IM7, eBioscience), PD-1 (RMP1-30, eBioscience) and TIGIT (GIGD7, eBioscience). Data acquisition was carried out on the MACSQuant Analyzer flow cytometer (Milenyi) and data were analyzed using the FlowJo software, version 10.

Figure 4A:
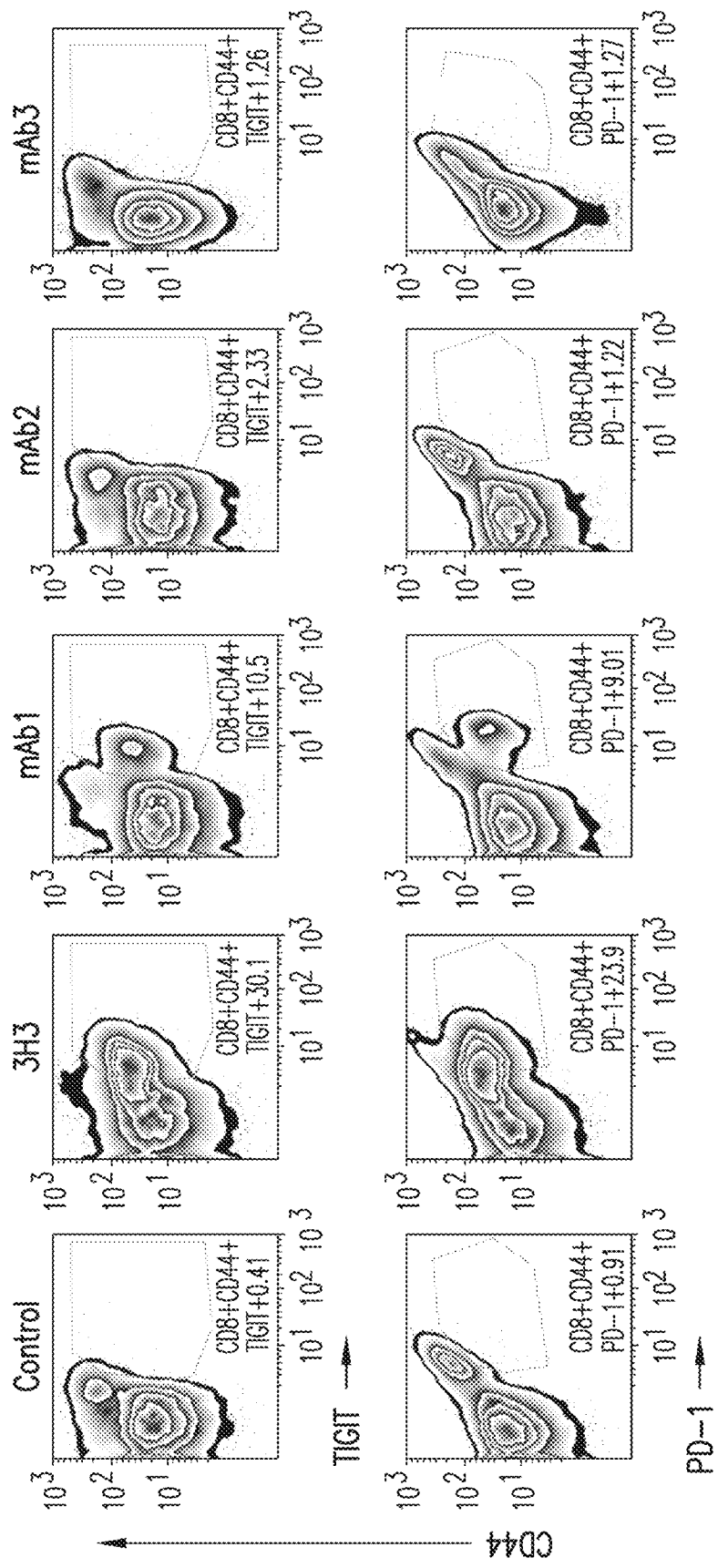
FIG. 4A provides a scatterplot of flow cytometric data depicting an increase in TIGIT (top) or PD-1 (bottom) expression on CD44+ T cells in response to anti-CD137 antibodies.
Figures 4B, 4C:
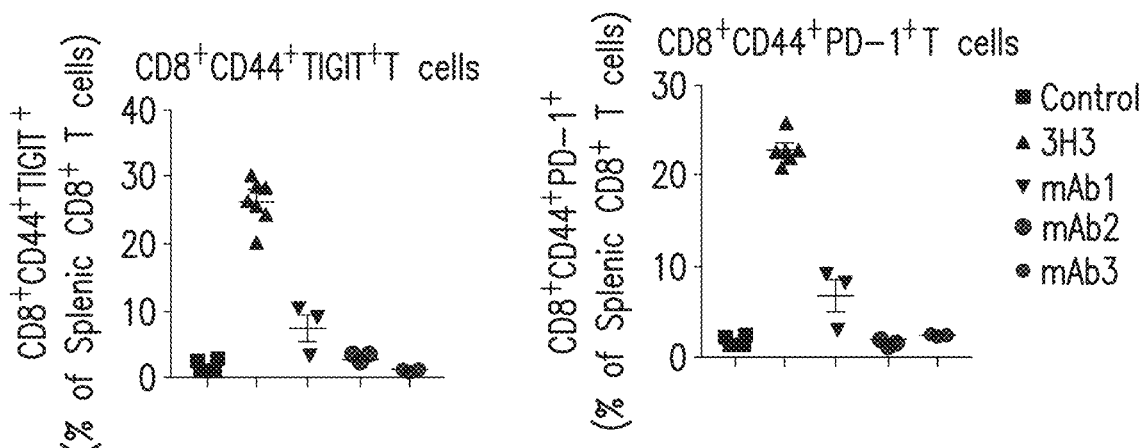
FIG. 4B provides graphs depicting the quantification of CD8+ CD44+ T cells expressing TIGIT (top) or PD-1 (bottom) in the spleen of mice after treatment with anti-CD137 antibodies.
FIG. 4C provides graphs depicting the quantification of CD8+ T cells in the spleen of mice after treatment with anti-CD137 antibodies, as percentage of CD45+ cells (left) or cell number per spleen (right).

Antibody 3H3 caused a significant increase in expression of both PD-1 and TIGIT, whereas only antibody mAb1 increased expression compared to mAb2 and mAb3 (FIGS. 4A and 4B). In addition, expansion of CD8+ T cells was assessed by analyzing the percentage of splenic CD45+ cells or number of CD8+ T cells per spleen. Similarly, antibody 3H3 caused the highest expansion of CD8+ T cells, with mAb1 resulting in the highest levels of CD8+ T cell expansion relative to mAb2 and mAb3 (FIG. 4C). Accordingly, mAb1 was selected for further testing.

Example 7: Efficacy of Anti-CD137 Antibodies in Tumor-Bearing Mice

Given the ability of mAb1 to enhance CD8+ T cell expansion, as shown in Example 6, mAb1 was further analyzed for anti-tumor activity using a subcutaneous model of syngeneic colon cancer. Specifically, CT26 tumor cells (passage 3) were maintained under aseptic conditions in DMEM Medium (Gibco cat #11965-092), containing 10% 56° C.—heat inactivated FBS (Gibco 10438-034), 1 mM sodium pyruvate (Gibco cat. #11360-070), 1× NEAA (Gibco cat #11140-050) and 1×MEM Vitamin solution (Gibco cat #11120-052). Cells were maintained at 37° C. and 5% $CO_2$. Upon reaching 50-70% confluence, cells were passaged at a ratio of 1:10, for a total of two passages, prior to in vivo implantation. Cells were harvested and counted using a Hemacytometer (Hausser Scientific Bright-Line #1492).

Balb/c female mice were purchased from Charles River Laboratories and were nine weeks old at the start of study. CT26 tumor cells ($1\times10^5$ cells per mouse in 0.1 mL PBS) were injected subcutaneously into the right flank of each mouse, and tumor volume was calculated twice weekly (Length*(Width^2)/2) using dial calipers. On day 7 post-tumor inoculation, animals were sorted into groups of eight, and treatments were initiated. Body weights were recorded three times per week for the duration of the study.

mAb1 was administered at three different dosages (100, 50 or 25 µg/mouse), 3H3 at two different dosages (50 or 10 µg/mouse) and the isotype control antibody at a dosage of 50 µg/mouse. All mice were dosed intraperitoneally at days 0, 3, 6 and 9.

Figure 5A:
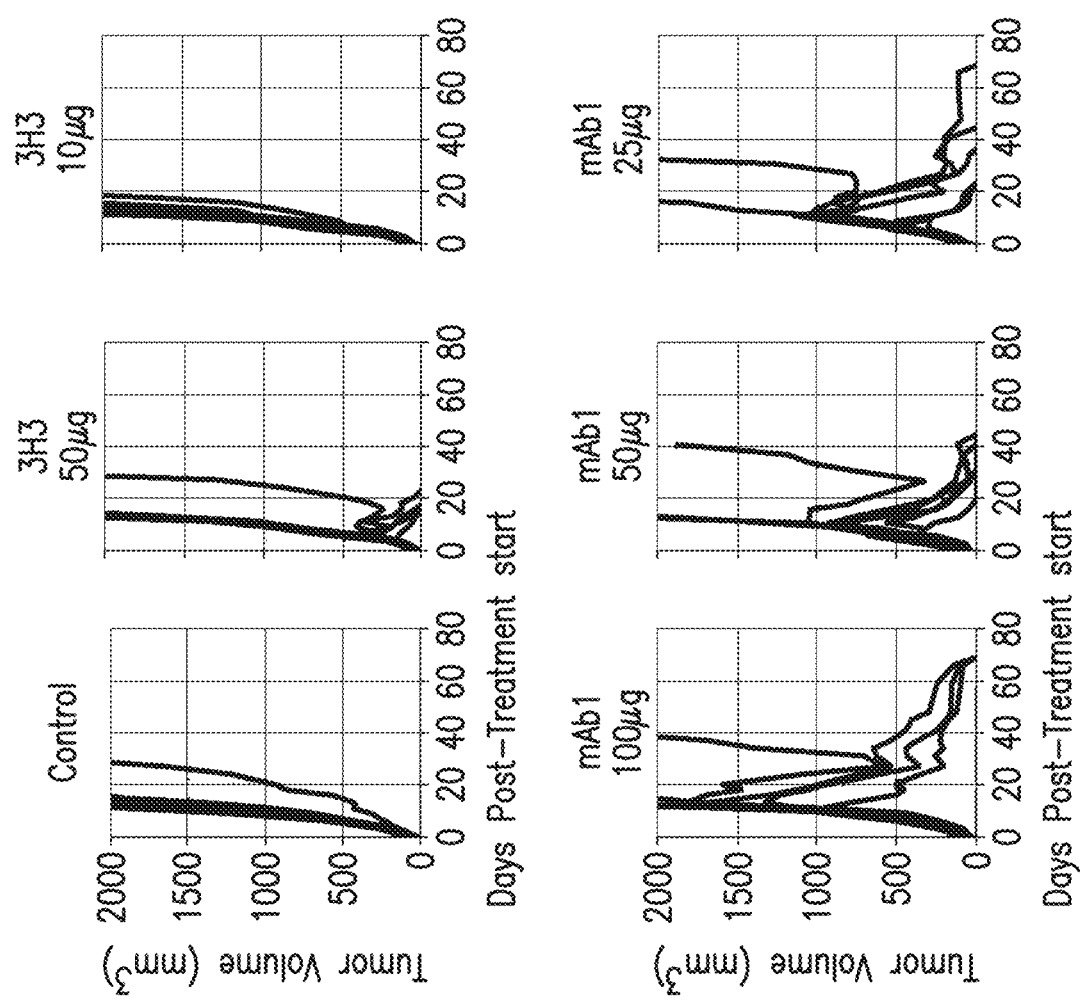
FIG. 5A provides graphs showing individual CT26 tumor volumes in mice after treatment with anti-CD137 antibodies at indicated dosages.

Expansion of CD8+ T cells in the tumors was confirmed in vivo for both mAb1 and 3H3 antibodies (data not shown). Individual tumor volumes are shown in FIG. 5A and mean tumor volumes are shown in FIG. 5B. mAb1 treatment resulted in inhibition of tumor growth compared to the control group at all three dosages. Moreover, treatment with mAb1 resulted in the complete regressions in 6 out of 8 mice at the 25 µg dose level, 5 out of 8 mice at the 50 µg dose level and 3 out of 8 mice at the 100 µg dose level.

Overall survival in each treatment group is shown in FIG. 5C. Strong anti-tumor activity of mAb1 against CT26 tumors was reflected as extended overall survival. Long term survival (>60 days) were observed in 80% of the mice at the 25 µg dose level, 62% of the mice at the 50 µg dose level and 38% of the mice at the 100 µg dose level.

Mice with no palpable tumor at day 70 were considered cured and re-challenged with subcutaneous injection of CT26 cells in the opposite flank. Specifically, mice with eradicated tumors were injected again with $1\times10^5$ CT26 cells in the left flank and tumor volume was calculated twice weekly (Length*(Width^2)/2) using dial calipers. Five non-immunized (naïve) mice were injected in the same manner as a control, respectively. Results of the re-challenge experiment are shown in FIG. 5D. Twenty-two days after the subcutaneous injection of CT26 cells, none of the re-challenged mice formed tumors. In contrast, all of the naïve mice that were injected with the same cells formed tumors. Therefore, all mice that were considered cured rejected CT26 tumors, suggesting that mAb1 can induce long-term protective memory.

Example 8: Efficacy of Affinity-Matured Anti-CD137 Antibodies in Tumor-Bearing Mice The affinity-matured monoclonal antibodies generated in Example 4 were analyzed for anti-tumor activity using the same subcutaneous model of syngeneic colon cancer (CT26) essentially as described in Example 7. Specifically, 6 affinity-matured clones (mAb7-mAb12) were generated with IgG4 constant regions and tested accordingly. The sequences of the heavy chain and light chain variable regions are provided in the chart below, along with their $K_D$ values to mouse CD137 (determined by ForteBio OCTET, described in Example 2) and human CD137 (determined by Carterra, described in Example 4).

| Antibody | $V_H$ Chain | $V_L$ Chain | Binding to Mouse CD137 $K_D$ (nM) | Binding to Human CD137 $K_D$ (nM) |
|---|---|---|---|---|
| mAb7 | SEQ ID NO: 8 | SEQ ID NO: 6 | 1.2 | 6.8 |
| mAb8 | SEQ ID NO: 101 | SEQ ID NO: 6 | 72 | 3.2 |
| mAb9 | SEQ ID NO: 103 | SEQ ID NO: 6 | 6.9 | 41.4 |
| mAb10 | SEQ ID NO: 26 | SEQ ID NO: 6 | 8.4 | 20 |
| mAb11 | SEQ ID NO: 4 | SEQ ID NO: 28 | 4.8 | 4.1 |
| mAb12 | SEQ ID NO: 4 | SEQ ID NO: 105 | 25.8 | 12.1 |

Parental mAb1, the 3H3 antibody, and an IgG4 isotype antibody were used as controls. All mice were dosed with 50 µg of mAb/mouse intraperitoneally at days 0, 3, 7 and 10. Spleens and livers were harvested on day 13 after therapy initiation.

Figure 6A:
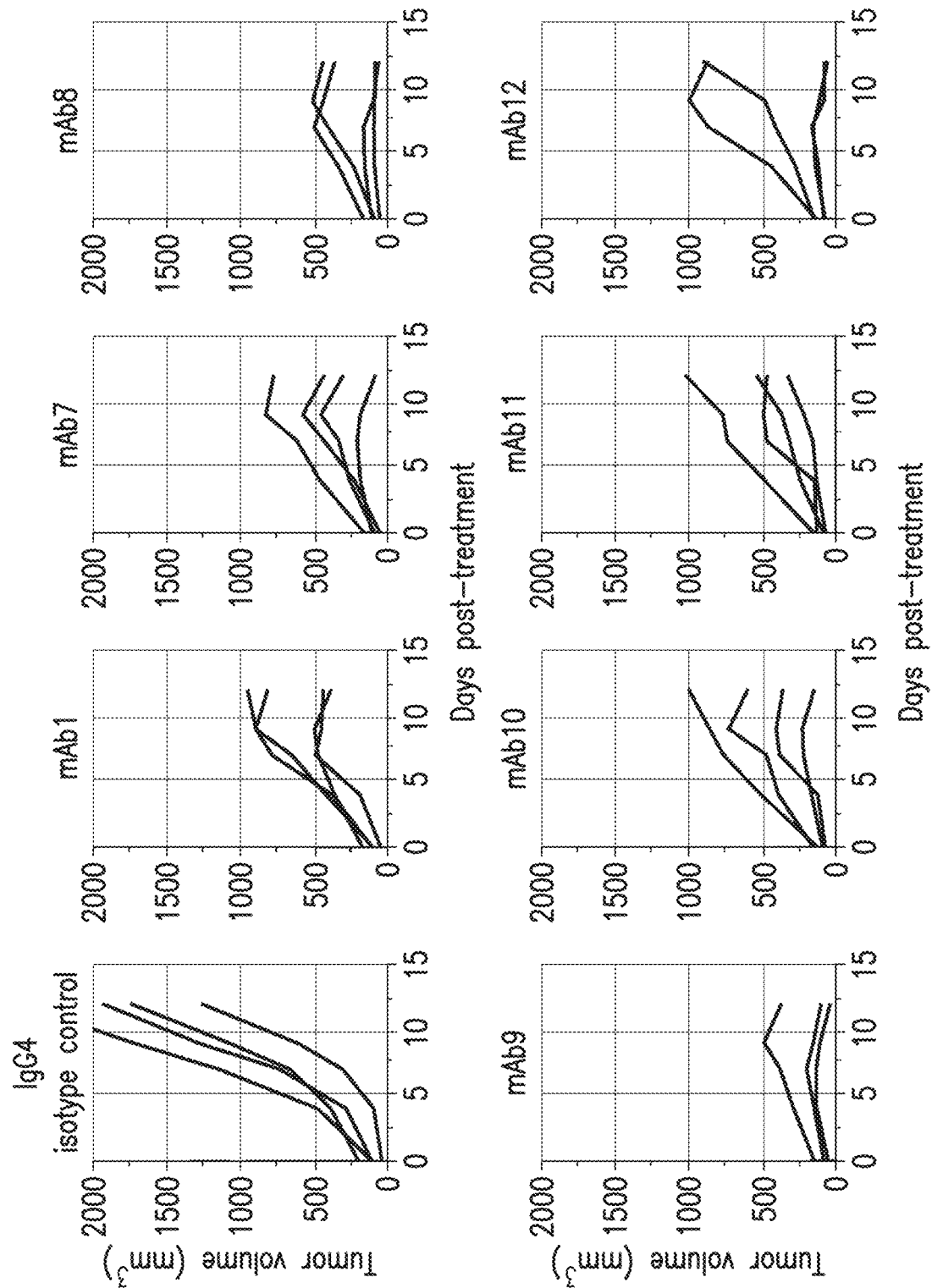
FIG. 6A provides graphs showing individual CT26 tumor volumes in mice after treatment with parental and affinity-matured anti-CD137 antibodies.
Figure 6B:
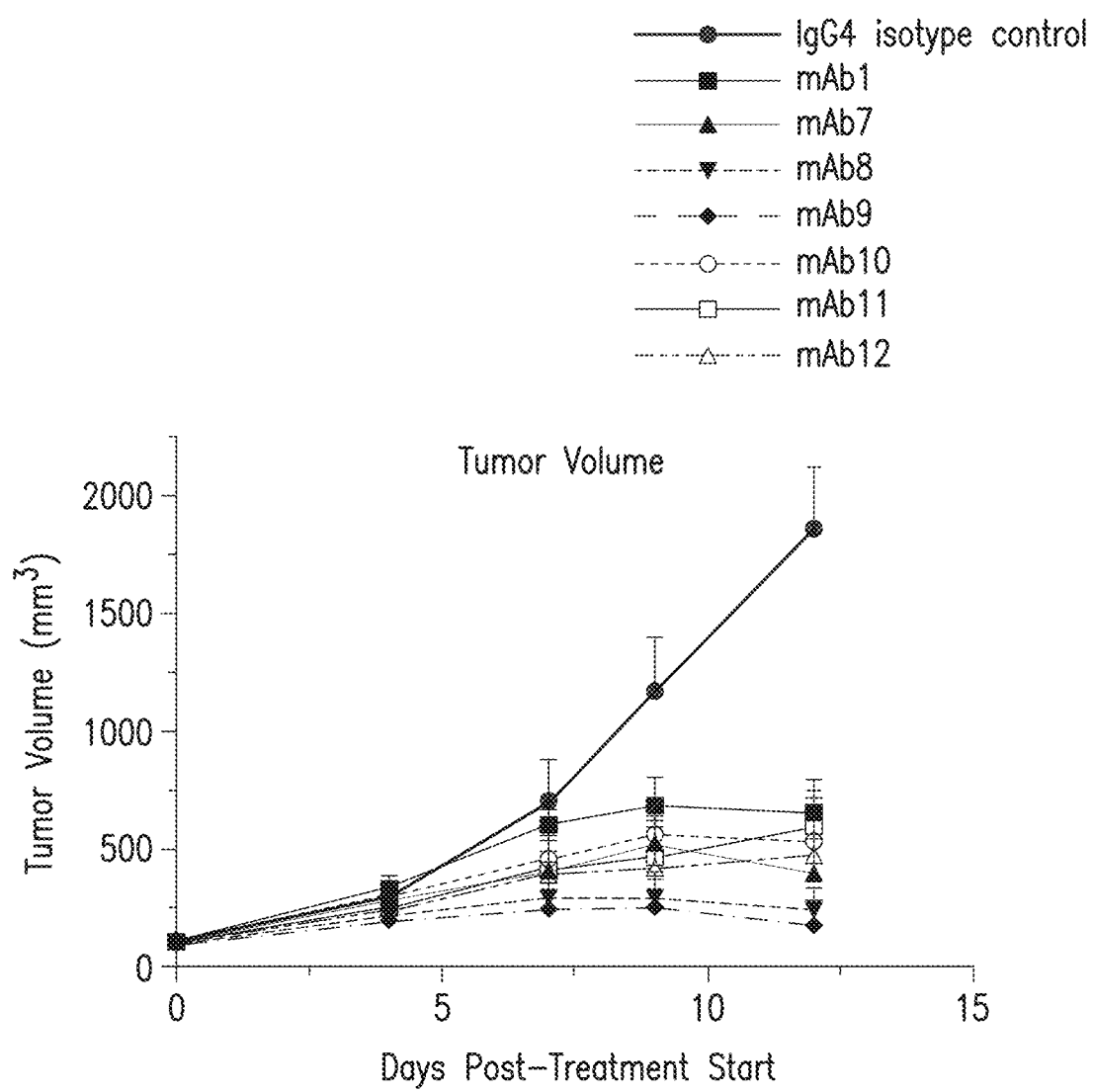
FIG. 6B is a graph providing the mean tumor volumes provided in FIG. 6A.

Individual tumor volumes are shown in FIG. 6A and mean tumor volumes are shown in FIG. 6B. Consistent with the results from Example 7, treatment with parental mAb1 resulted in a reduction in tumor volume. Further, administration of all affinity-matured clones derived from mAb1 (mAb7-mAb12), to tumor-bearing mice, resulted in an inhibition of tumor growth compared to mice treated with the isotype control antibody.

Example 9: Effect of Anti-CD137 Antibodies on T Cells in Tumor-Bearing Mice

To determine the effect of anti-CD137 antibodies (i.e., 3H3 and mAb1) on the level of T cells in tumor-bearing mice, Balb/c mice with CT26 tumors, as described in Example 7, were intraperitoneally injected with antibodies on days 0 and 3, and tissues were harvested on day 7. mAb1 was administered at three different dosages (100, 50 or 25 μg/mouse), 3H3 at two different dosages (50 or 10 μg/mouse) and the isotype control antibody at a dosage of 50 μg/mouse.

Single cell suspensions from the spleen were obtained as described in Example 6 and tumor cell suspensions were obtained by enzymatic and mechanical digestion using tumor dissociation kit (Miltenyi cat #130-096-730). Cell suspensions were treated with complete medium to inactivate the enzymes and then passed through a 40 μm cell strainer. Red blood cells were lysed using ACK buffer. Cells were stained with antibodies against CD45, CD8 and CD4, and analyzed as described in Example 6.

Figure 7:
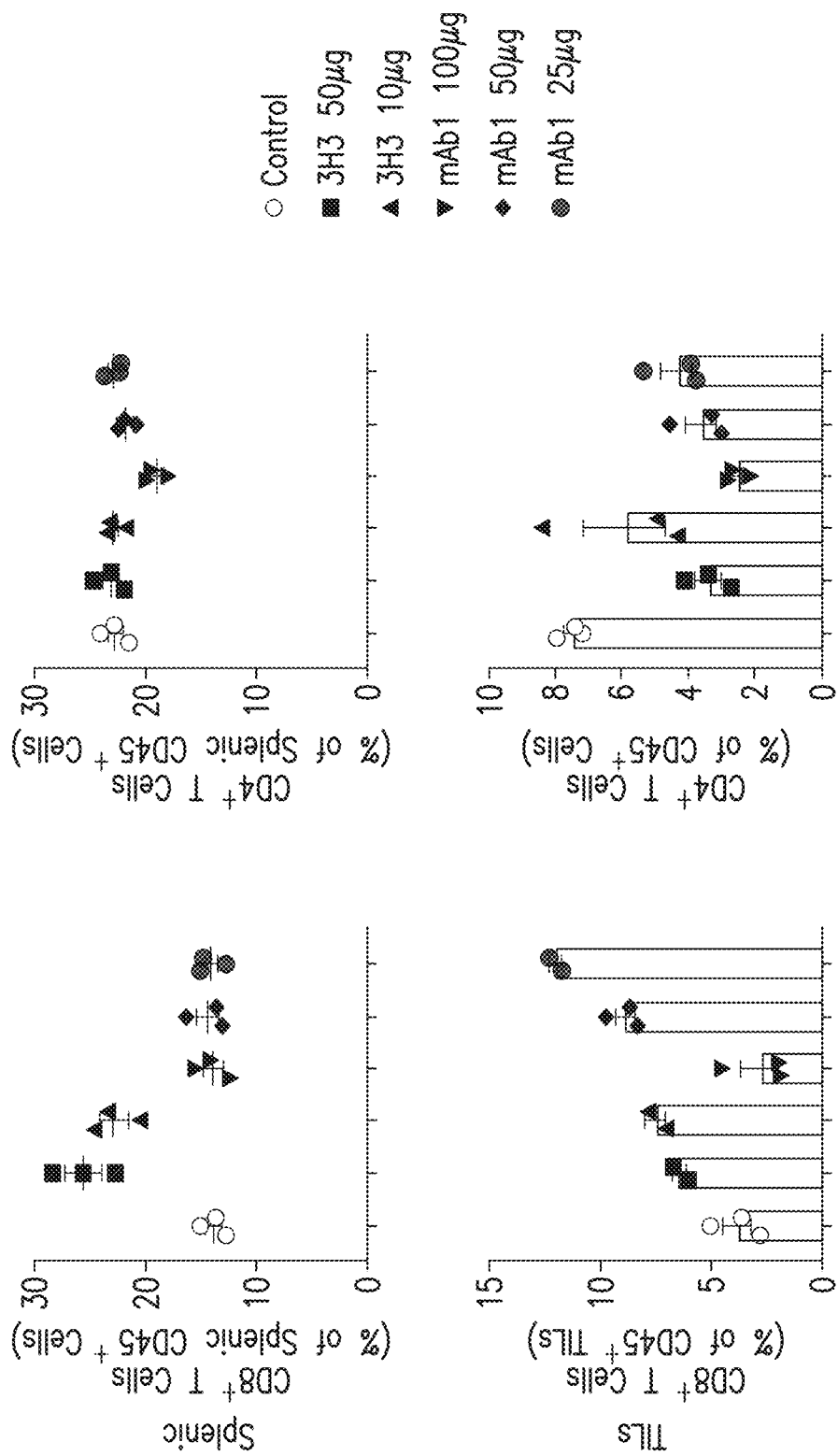
FIG. 7 provides graphs depicting the percentage of CD8+ or CD4+ T cells, from splenic T cells (top) and tumor infiltrating leukocytes (bottom) after treatment with anti-CD137 antibodies at indicated dosages.

FIG. 7 shows the number of CD4+ and CD8+ T cells, as a percentage of CD45+ cells, found in the spleen and tumor. These results indicated that mAb1 selectively expands tumor-infiltrating CD8+ T cells as compared to splenic CD8+ T cells.

Example 10: Effect of CD4+, CD8+, or NK Lymphocytes Depletion on Anti-Tumor Efficacy of Anti-CD137 Antibodies In Vivo To assess the mechanism of action of anti-CD137 antibodies, Balb/c mice with CT26 tumors, as described in Example 7, were intraperitoneally injected with mAb1 alone or in combination with anti-CD4 (GK1.5), anti-CD8 (YTS169.4), or anti-asialo-GM1 (targets NK cells) antibodies to deplete these specific lymphocyte subsets from the animals. Mice treated only with the mAb1 antibody were administered 150 μg of antibody on days 6, 9, 12, 19, and 26. The mice treated with 150 μg mAb1 in combination with 500 μg anti-CD4, anti-CD8, or 50 uL of anti-asialo-GM1 antibodies administered on days −1, 0, 5, 10, 15, and 20. Effective depletion was confirmed by FACS analysis (data not shown).

Figure 8:
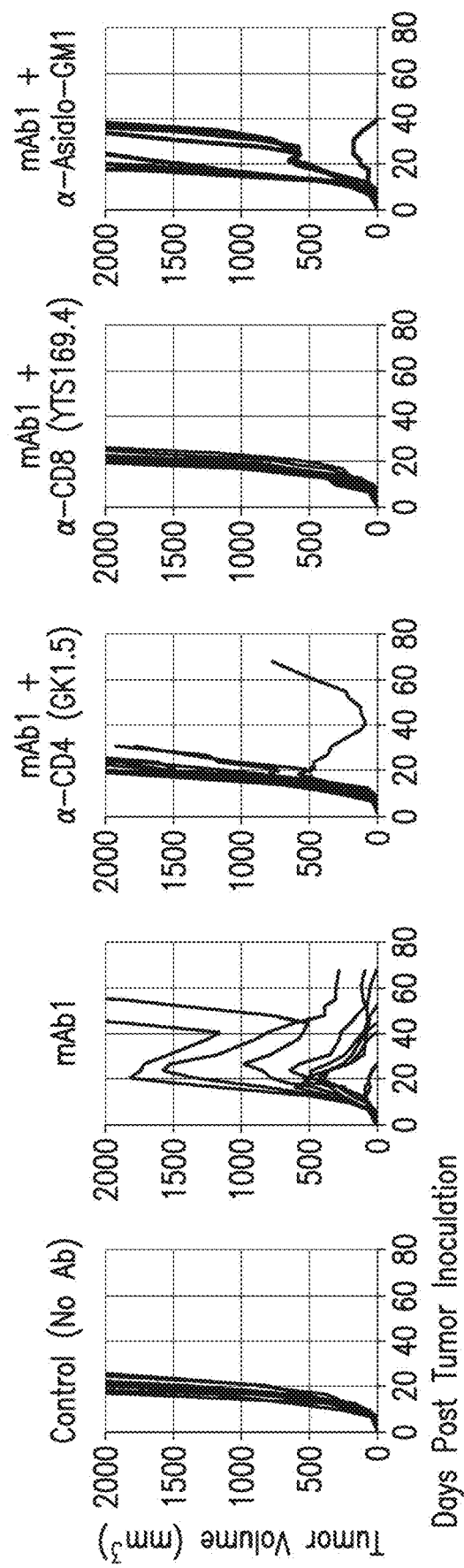
FIG. 8 provides graphs showing individual tumor volumes when mice were treated with mAb1, with or without lymphocyte depleting antibodies. CD4+ T cells were depleted with GK1.5 (middle graph), CD8+ T cells were depleted with YTS 169.4 (second graph from the right), and NK cells were depleted with an anti-asialo-GM1 antibody (last graph on the right).

Individual tumor volumes are shown in FIG. 8. Consistent with the results from Example 7, treatment with parental mAb1 resulted in a reduction in tumor volume. Further, administration of mAb1 in combination with lymphocyte-depleting anti-CD4, anti-CD8, or anti-asialo-GM1 antibodies reduced the anti-tumor activity of the mAb1 antibody. These results indicated cooperation between innate and adaptive immunity for anti-tumor efficacy of the anti-CD137 antibodies described herein.

Example 11: Anti-Tumor Efficacy of Anti-CD137 Antibodies in Various Tumor Models To determine whether an anti-CD137 antibody had anti-tumor efficacy in different tumor models, mAb8 was administered to mice having either CT26 tumors (colon carcinoma; as described above), EMT-6 tumors (breast carcinoma), A20 tumors (B cell lymphoma) or MC38 tumors (colon carcinoma).

For all tumor models, female mice were purchased from Charles River Laboratories and were 7-9 weeks old at the start of study. For each tumor type appropriate syngeneic mouse strain was used (Balb/c for CT26, EMT-6 and A20; C57BL/6 for MC38). EMT6 tumor cells ($5 \times 10^4$) cells per mouse in 0.05 mL PBS) were injected into the right mammary fat pad of each mouse. CT26 tumor cells ($1 \times 10^5$ cells per mouse), A20 tumor cells ($5 \times 10^6$ cells per mouse) and MC38 tumor cells ($5 \times 10^5$ cells per mouse) were injected subcutaneously into the right flank of each mouse, and tumor volume was calculated twice weekly (Length*(Width^2)/2) using dial calipers. Upon reaching 50-100 mm$^3$ sized tumors, the mice were randomized to receive mAb8 or isotype control (day 0). Mice with orthoptic EMT6 tumors received 12.5 μg on days 0, 3, 6 and 9. Mice with A20 (200 μg/mouse) and MC38 (12.5 μg/mouse) tumors received 5 doses once a week. All mice were dosed intraperitoneally.

Figure 9:
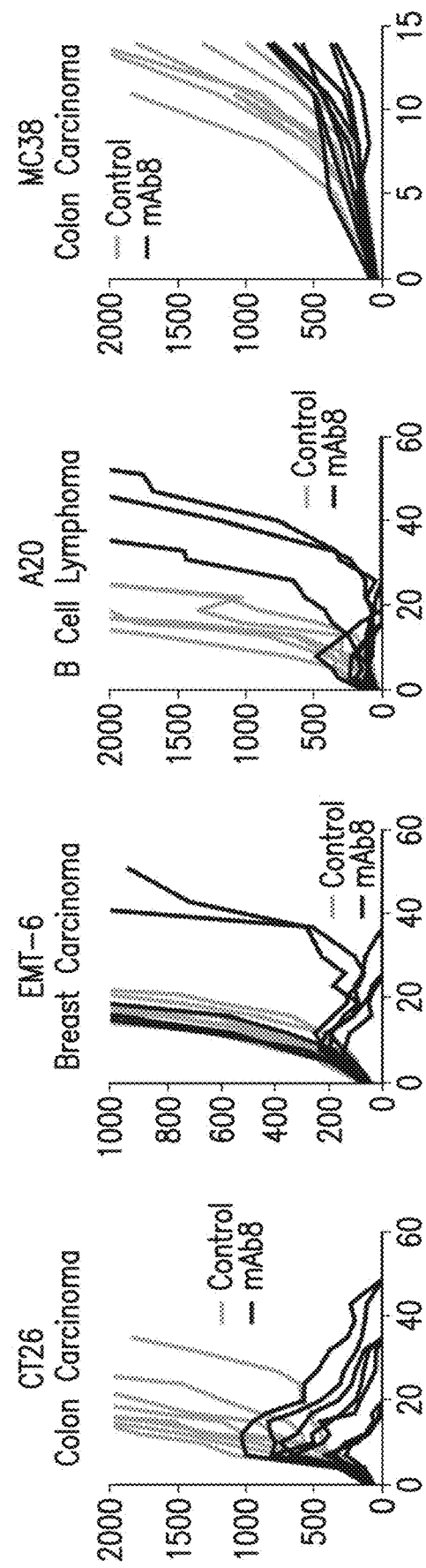
FIG. 9 provides graphs showing individual tumor volumes in mice having either CT26 tumors (colon carcinoma), EMT-6 tumors (breast carcinoma), A20 tumors (B cell lymphoma), or MC38 tumors (colon carcinoma) and treated with mAb8 or isotype control antibody.

As shown in FIG. 9, mAb8 was effective in all four tumor models tested, indicating a wide range of efficacy for varying cancer types. Treatment with mAb8 resulted in tumor regressions in mice carrying 8/8 CT26, 3/8 EMT6, 5/8 A20 tumors and delayed growth in majority of the remaining mice carrying EMT6, A20 and MC38.

Example 12: Effect of Dosage of Anti-CD137 Antibodies

To further characterize the anti-tumor efficacy of the anti-CD137 antibodies, a dosage study was performed using the same subcutaneous model of syngencic colon cancer (CT26) essentially as described in Example 7. Specifically, parental mAb1 and affinity matured antibodies mAb8 and mAb10 were administered intraperitoneally at doses of either 150 μg (high dose) or 20 μg (low dose) per mouse on days 0, 3, 6 and 9, with 8 mice per treatment group. One group of mice (n=8) was administered an IgG4 isotype control at a dose of 150 μg.

Individual tumor volumes, mean tumor volume and percent survival of mice treated at the 150 μg are shown in FIG. 10A, FIG. 10B, and FIG. 10C, respectively. Individual tumor volumes, mean tumor volume and percent survival of mice treated at the 20 μg are shown in FIG. 11A, FIG. 11B, and FIG. 11C, respectively. These results indicated that treatment with the parental mAb1 and the affinity-matured mAb8 and mAb10 antibodies resulted in a reduction in tumor volume and an increase in mouse survival at both high and low doses.

Figure 12:
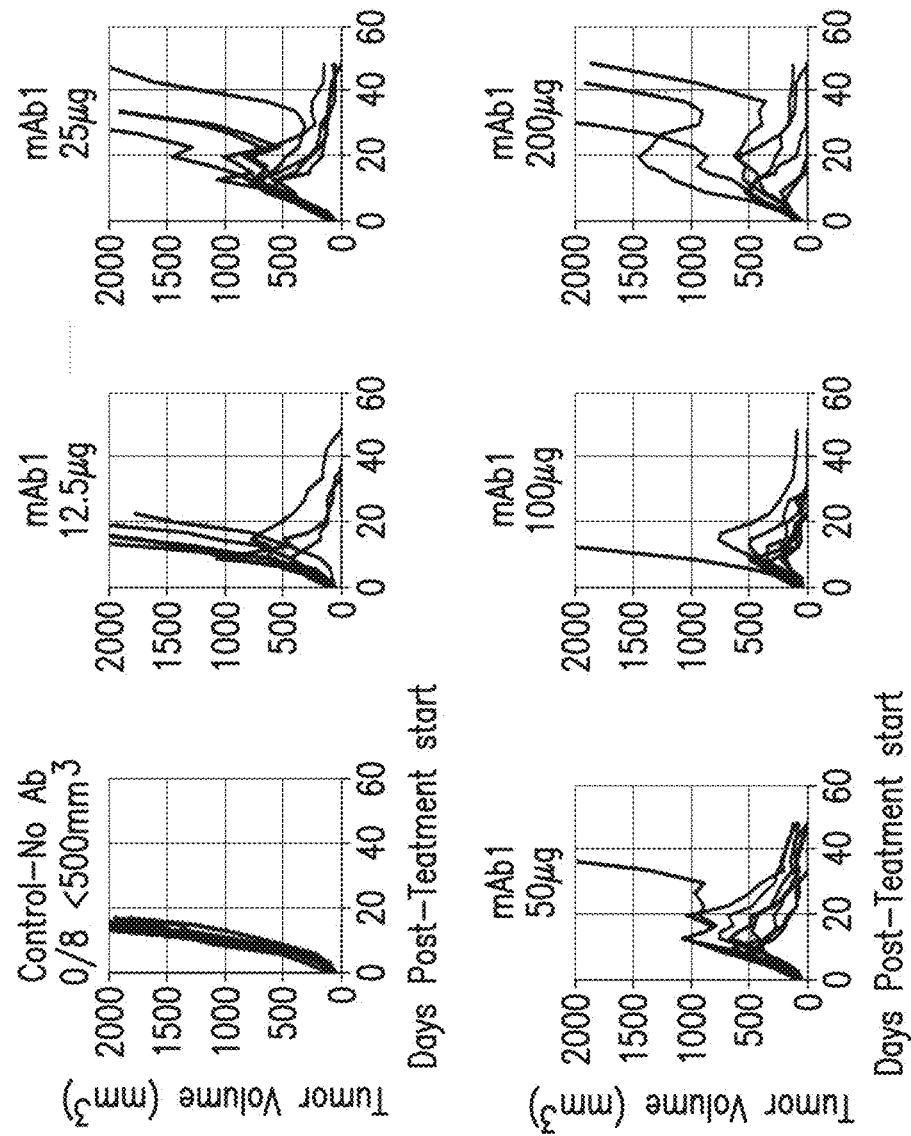
FIG. 12 provides graphs showing individual tumor volumes in mice having CT26 tumors and treated with varying doses of mAb1 (i.e., 12.5, 25, 50, 100 or 200 µg) or isotype control.

In a separate dosage study utilizing the CT26 tumor model, additional doses of parental mAb1 were tested. Specifically, mAb1 was administered intraperitoneally at the following doses: 12.5 μg, 25 μg, 50 μg, 100 μg and 200 μg. FIG. 12 shows the results of the dosage study, indicating efficacy over a wide dose range. Treatment with mAb1 resulted in tumor regressions in at least 3/8 mice in each dose level with optimum dose range (50-100 μg/mouse) leading to 7/8 mice with eradicated tumors.

Example 13: Effect of Fc-Receptor Binding on Anti-Tumor Efficacy of Anti-CD137 Antibodies To determine the contribution of Fc-receptor binding on the anti-tumor activity of anti-CD137 antibodies, aglycosylated IgG1 and IgG4 versions of mAb1 were generated.

Figure 13A:
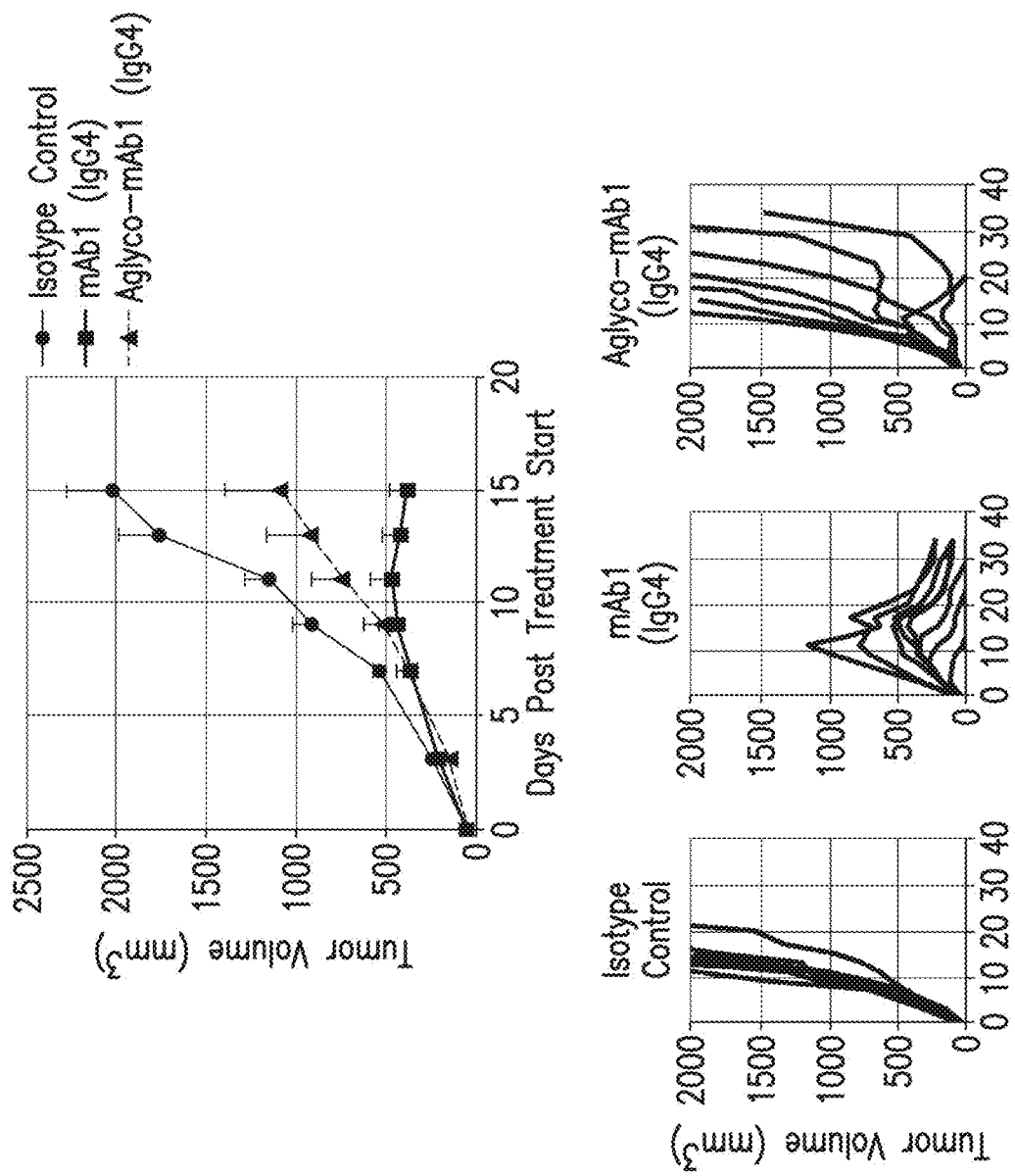
FIGS. 13A-13B show the contribution of Fc binding in the anti-tumor efficacy of mAb1.
Figure 13B:
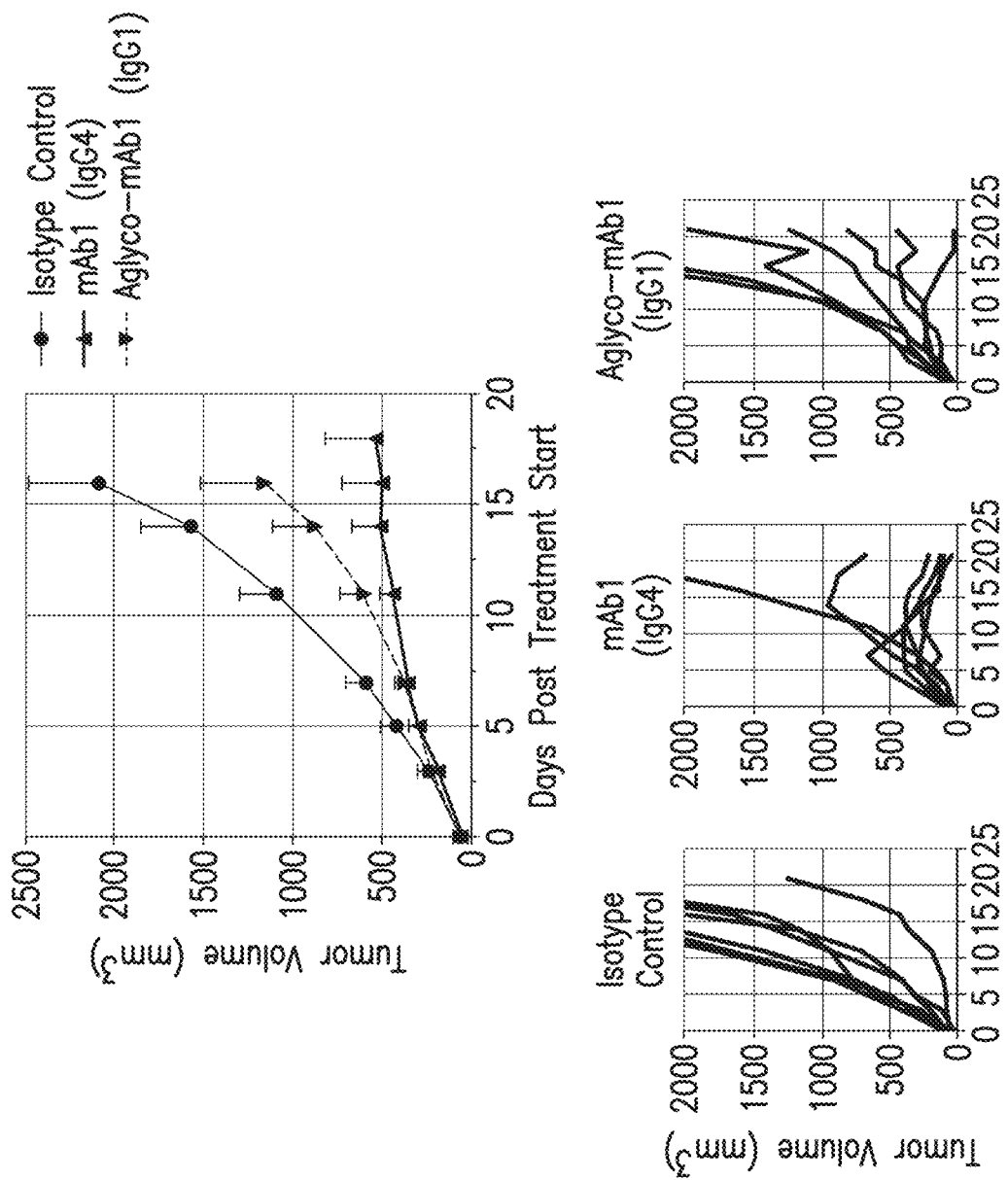

CT26 tumors were established in mice as described in Example 7. Mice received 150 ug of either (a) isotype control; (b) mAb1 as IgG4; (c) aglycosylated mAb1 as IgG4; or (d) aglycosylated mAb1 as IgG1. As shown in FIGS. 13A and 13B, aglycosylated IgG4 and IgG1 isotypes of the parental mAb1 antibody had reduced effect on tumor volume in comparison to mAb1. However, efficacy was not completely abolished. Accordingly, these results indicated that while the anti-tumor efficacy of mAb1 is not entirely Fc-dependent, it is enhanced by Fc receptor binding.

Example 14: Cross-Species Affinity of Anti-CD137 Antibodies

The anti-CD137 antibodies were further tested for their binding to CD137 from multiple species. Specifically, mAb1, mAb8 and mAb10 were analyzed for binding to human, mouse, cynomolgus and canine CD137. Kinetic experiments were performed on OCTET HTX (ForteBio) in kinetics buffer (1×PBS, pH 7.4, 0.1 mg/ml BSA, and 0.002% Tween 20). Fc-, mouse IgG2a-, or His-tagged CD137 (human, mouse, cyno or canine) were loaded for 5 minutes on pre-hydrated biosensors, AHC, AMC or NTA respectively. The sensors were then dipped into Fabs (0, 5.12, 12.8, 32, 80, 200 and 500 nM) for 5 minutes of association, following by 15 minutes of dissociation. Results were analyzed with ForteBio Data Analysis 9.0 and fit globally to a 1:1 binding model to determine the apparent $K_D$. $K_D$ for human and mouse CD137 binding were confirmed by using antigens from different sources (ACRO Biosystems, Sino Biological and internal). The results are shown in Table 2 below.

TABLE 2

| Cross-Species Affinity | | | |
| --- | --- | --- | --- |
| Species of CD137 | mAb1 | mAb8 | mAb10 |
| Human | 50-70 nM | 3-5 nM | 0.9 nM |
| Mouse | 300-500 nM | 50-90 nM | 10-30 nM |
| Cynomolgus | 30-100 nM | 3-7 nM | 1.8 nM |
| Canine | Poor fit | Poor fit | Poor fit |

Example 15: Effect of Size of Tumor on Anti-Tumor Efficacy of Anti-CD137 Antibodies To further characterize the anti-tumor efficacy of the anti-CD137 antibodies, the anti-tumor efficacy against large tumors was assessed. CT26 tumors were allowed to grow to approximately 500 mm$^3$ prior to treatment. Parental mAb1, and affinity matured mAb8 and mAb10 antibodies, were administered at 150 µg/mouse (n=6 mice/treatment group) on days 0, 3, 6 and 9 post tumor-establishment. The IgG4 isotype control antibody was used as a comparator.

Figure 14D:
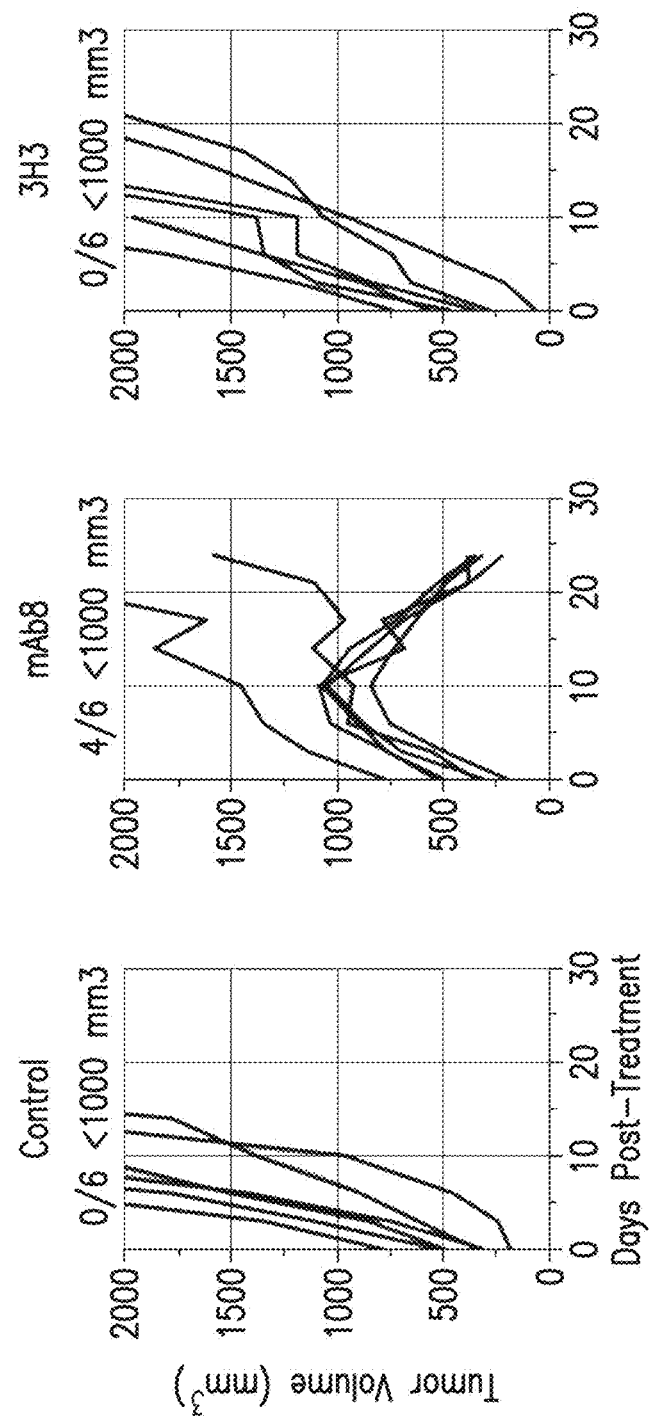

As shown in FIGS. 14A-14C, the parental mAb1 as well as the affinity-matured mAb8 and mAb10 reduced tumor volume (FIGS. 14A-14B) and increased mouse survival (FIG. 14C) relative to the isotype control. mAb8 resulted in significantly greater anti-tumor efficacy compared to mAb1 and mAb10. A separate study was conducted comparing the efficacy of mAb8 and 3H3 against large tumors using the same study design, except 25 µg of the antibodies were administered on days 0, 7 and 14. FIG. 14D provides the results, showing 3H3 had no efficacy against large tumors, whereas mAb8 induced tumor regression.

As described in Example 14, mAb8 has an affinity for mouse CD137 that is comparable with the affinity of mAb1 for human CD137. While the disclosure is not bound by any particular theory or mechanism of action, it is believed that agonist anti-CD137 antibodies with intermediate affinity may be even more useful for treating cancer.

Figure 15:
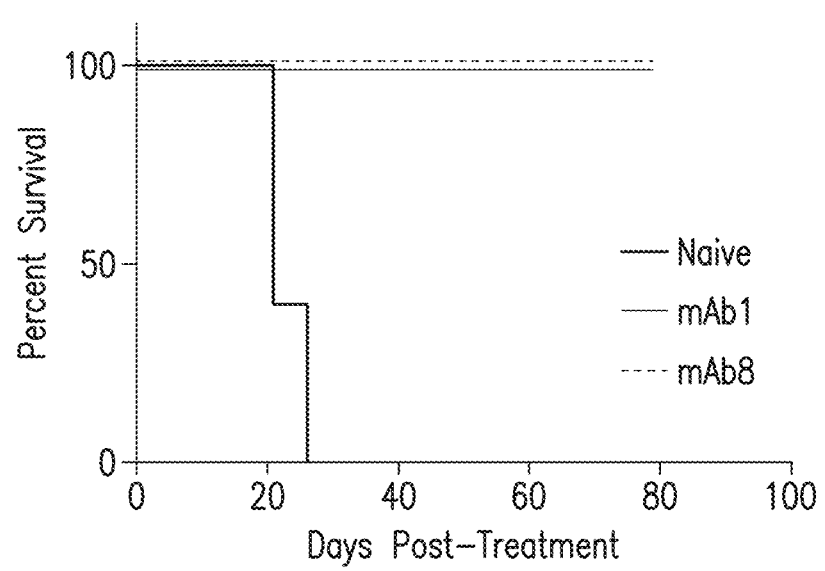
FIG. 15 provides a Kaplan-Meier survival graph showing protective anti-tumor immunity in mice previously treated with mAb1, mAb8 or isotype control from FIGS. 14A-14C and considered cured, re-challenged with CT26 cells in an opposing flank.

Mice with no palpable tumor at day 70 were considered cured and re-challenged with subcutaneous injection of CT26 cells in the opposite flank. Specifically, mice with eradicated tumors were injected again with 1×10$^5$ CT26 cells in the left flank and tumor volume was calculated twice weekly (Length*(Width^2)/2) using dial calipers. Five non-immunized (naïve) mice were injected in the same manner as a control, respectively. Results of the re-challenge experiment are shown in FIG. 15. Eighty days after the subcutaneous injection of CT26 cells, none of the re-challenged mice formed tumors. In contrast, all of the naïve mice that were injected with the same cells formed tumors. Therefore, all mice that were considered cured rejected CT26 tumors, suggesting that mAb1 can induce long-term protective memory immunity.

Example 16: Toxicity of Anti-CD137 Antibodies in Tumor-Bearing Mice

To determine the effect of anti-CD137 antibodies (i.e., 3H3 and mAb1) on the level of intrahepatic T cells in tumor-bearing mice, mice from Example 7 were analyzed. Liver lymphocytes were collected and analyzed via flow cytometry. Specifically, single cell suspensions from the liver were obtained using the liver dissociation kit (Miltenyi cat #130-105-807) and the gentle MACS Dissociator (Miltenyi). Cell suspensions were treated with complete medium to inactivate the enzymes and then passed through a 40 µm cell strainer. Red blood cells were lysed using ACK buffer. Cells were stained with antibodies against CD45, CD8 and CD4, and analyzed as described in Example 3.

Figure 16A:
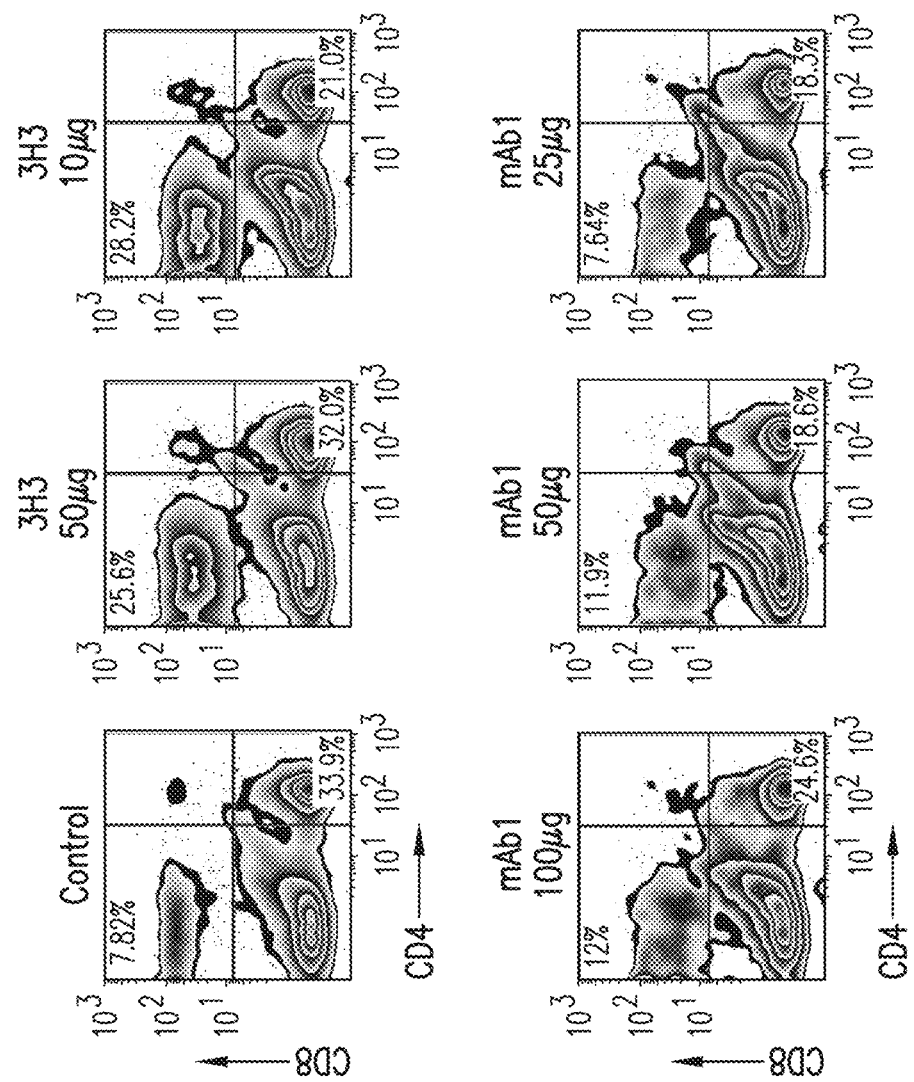
FIG. 16A provides scatterplots of flow cytometric data showing the expansion of CD45+ intrahepatic T cells following treatment with anti-CD137 antibodies at indicated dosages.
Figure 16B:
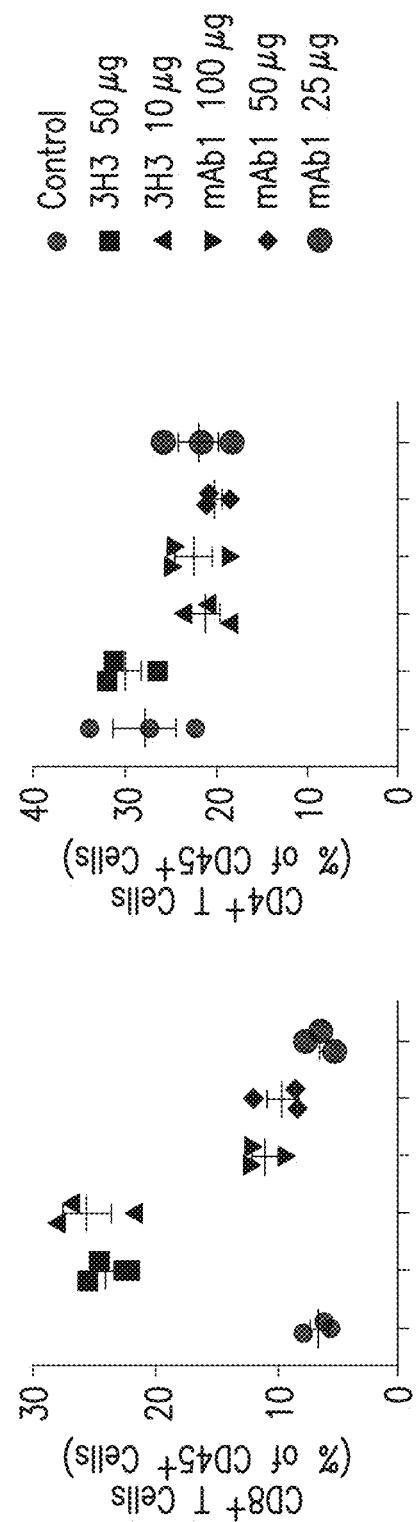
FIG. 16B provides graphs depicting the quantification of intrahepatic CD8+ T cells (left) and CD4+ T cells (right) following treatment with anti-CD137 antibodies at indicated dosages.

FIGS. 16A and 16B show the number of CD4+ and CD8+ T cells, as a percentage of CD45+ cells, found in the livers of treated mice. The results indicated mAb1 did not induce infiltration of intrahepatic T cells, demonstrating lower toxicity relative to antibody 3H3.

Example 17: Toxicity of Affinity-Matured Anti-CD137 Antibodies in Tumor-Bearing Mice To assess toxicity-related effects mediated by anti-CD137 antibodies (i.e., 3H3, mAb1, and mAb7-mAb12), the cellular composition of spleens and livers of tumor-bearing mice from Example 8 were analyzed following antibody administration.

Figure 17A:
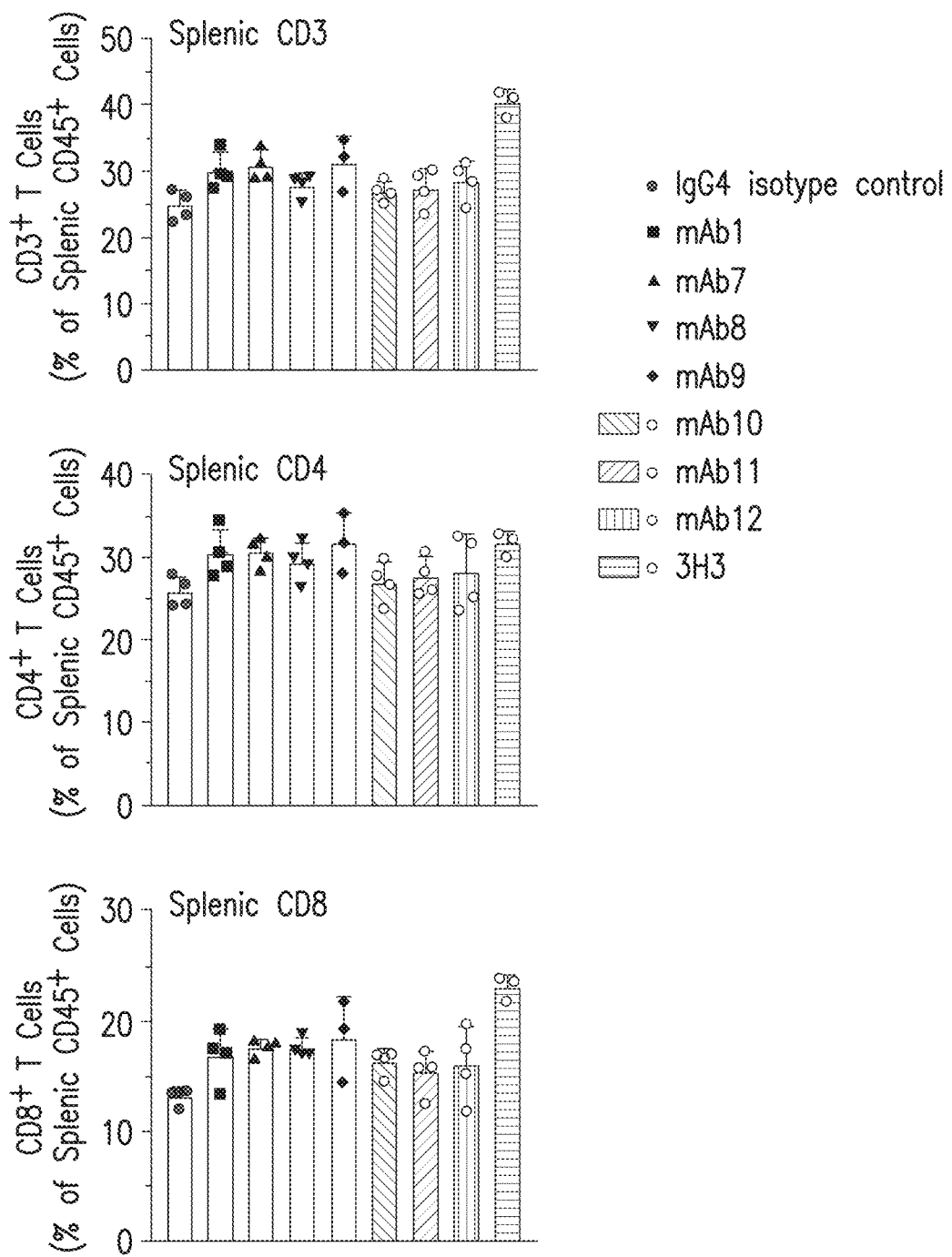
FIG. 17A provides graphs depicting the percentage of CD3+, CD4+, or CD8+ T cells, from splenic T cells after treatment of mice with affinity-matured anti-CD137 antibodies.
Figure 17B:
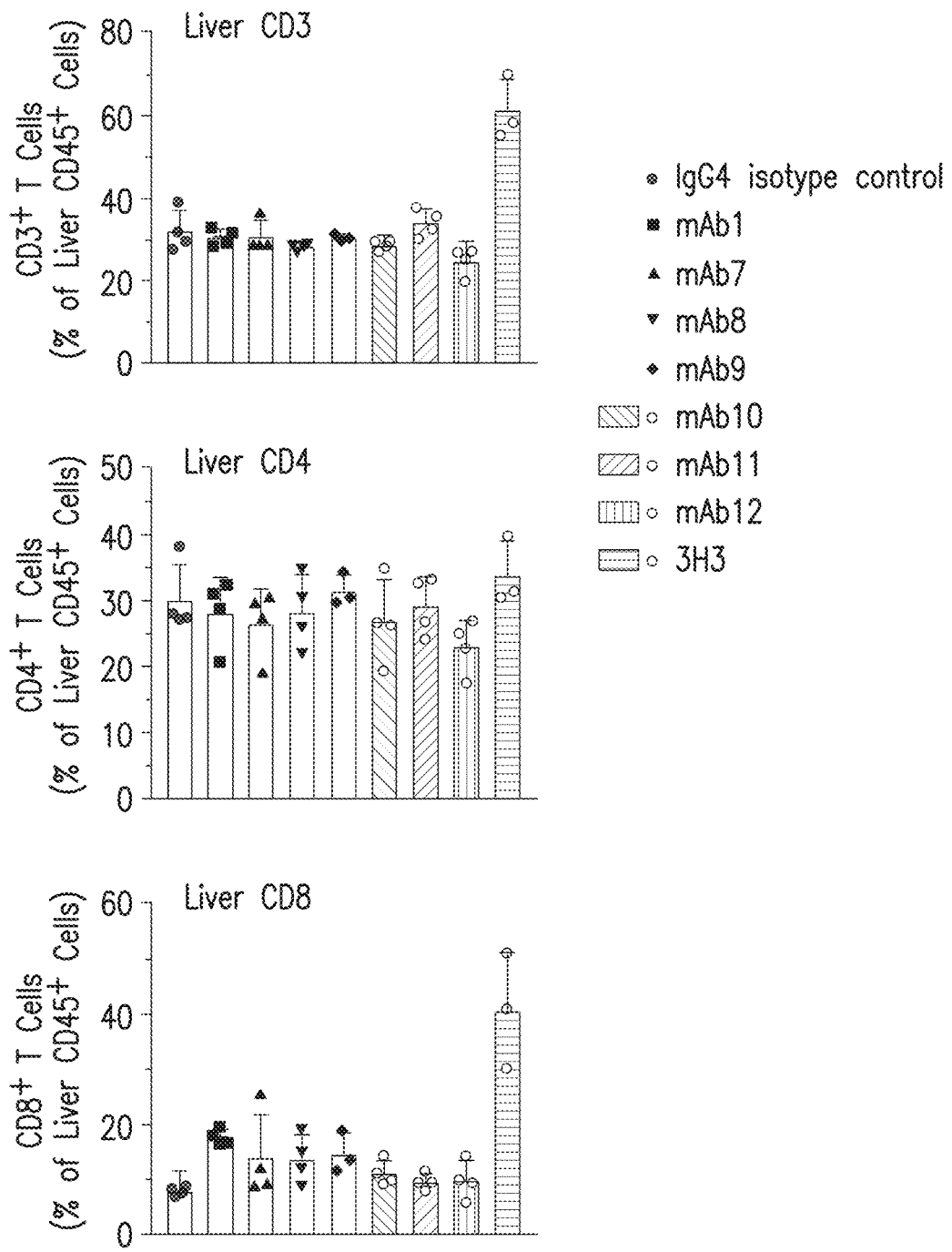
FIG. 17B provides graphs depicting the percentage of CD3+, CD4+, or CD8+ T cells from liver T cells after treatment of mice with affinity-matured anti-CD137 antibodies.
Figure 18A:
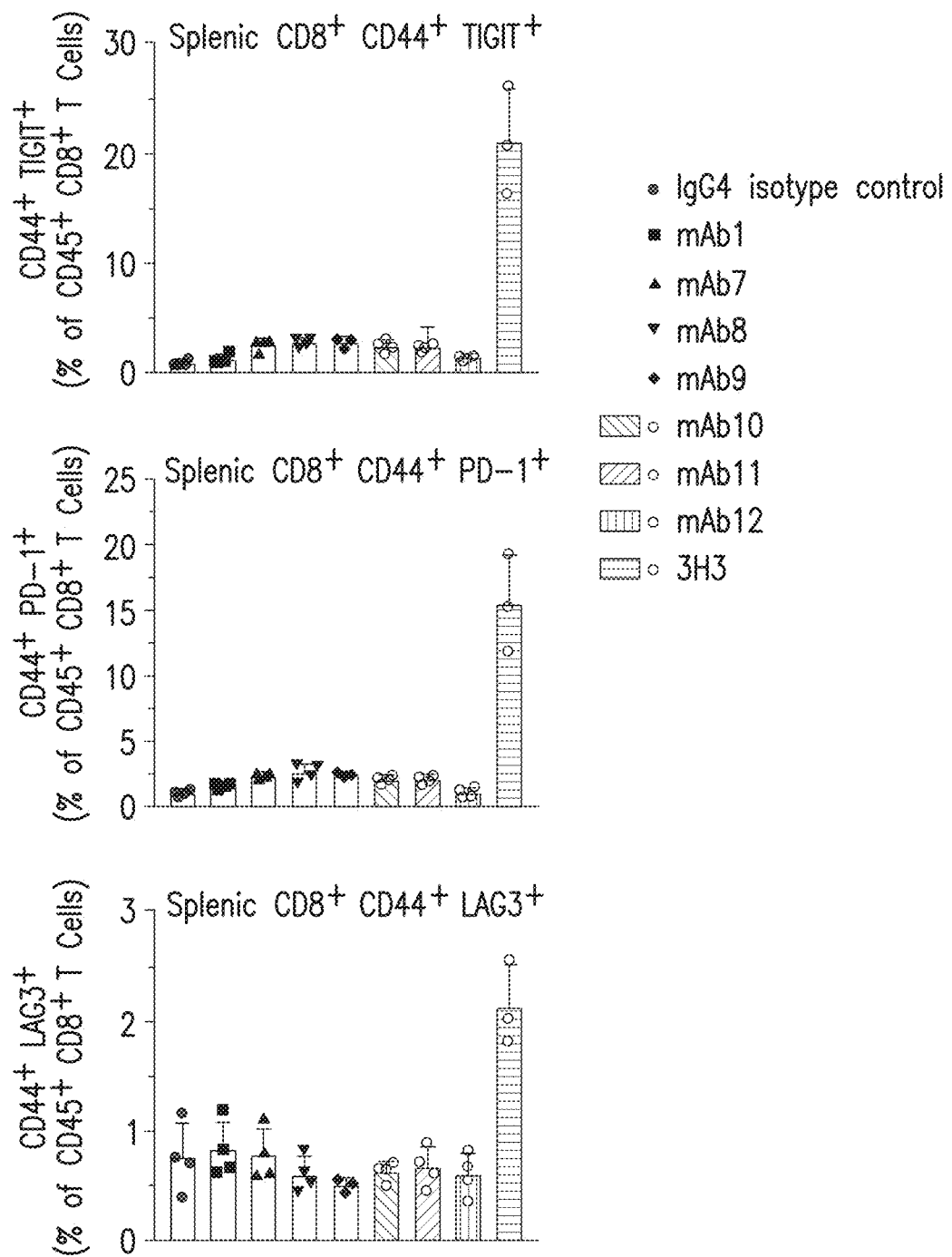
FIG. 18A provides graphs depicting the percentage of splenic CD8+CD44+ T cells expressing TIGIT, PD-1, or LAG3 after treatment of mice with affinity-matured anti-CD137 antibodies.
Figure 18B:
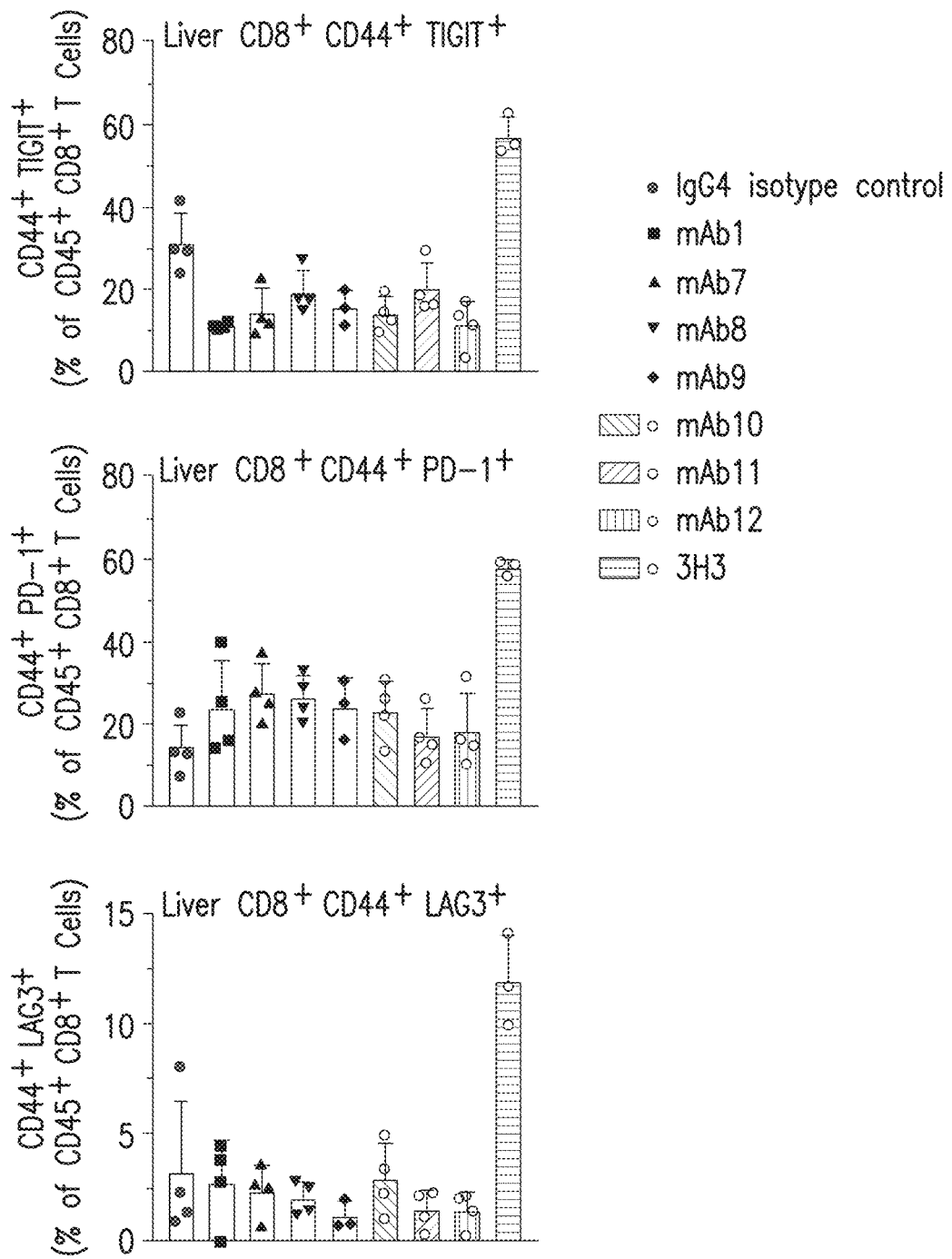
FIG. 18B provides graphs depicting the percentage of liver CD8+CD44+ T cells expressing TIGIT, PD-1, or LAG3 after treatment of mice with affinity-matured anti-CD137 antibodies.
Figure 19A:
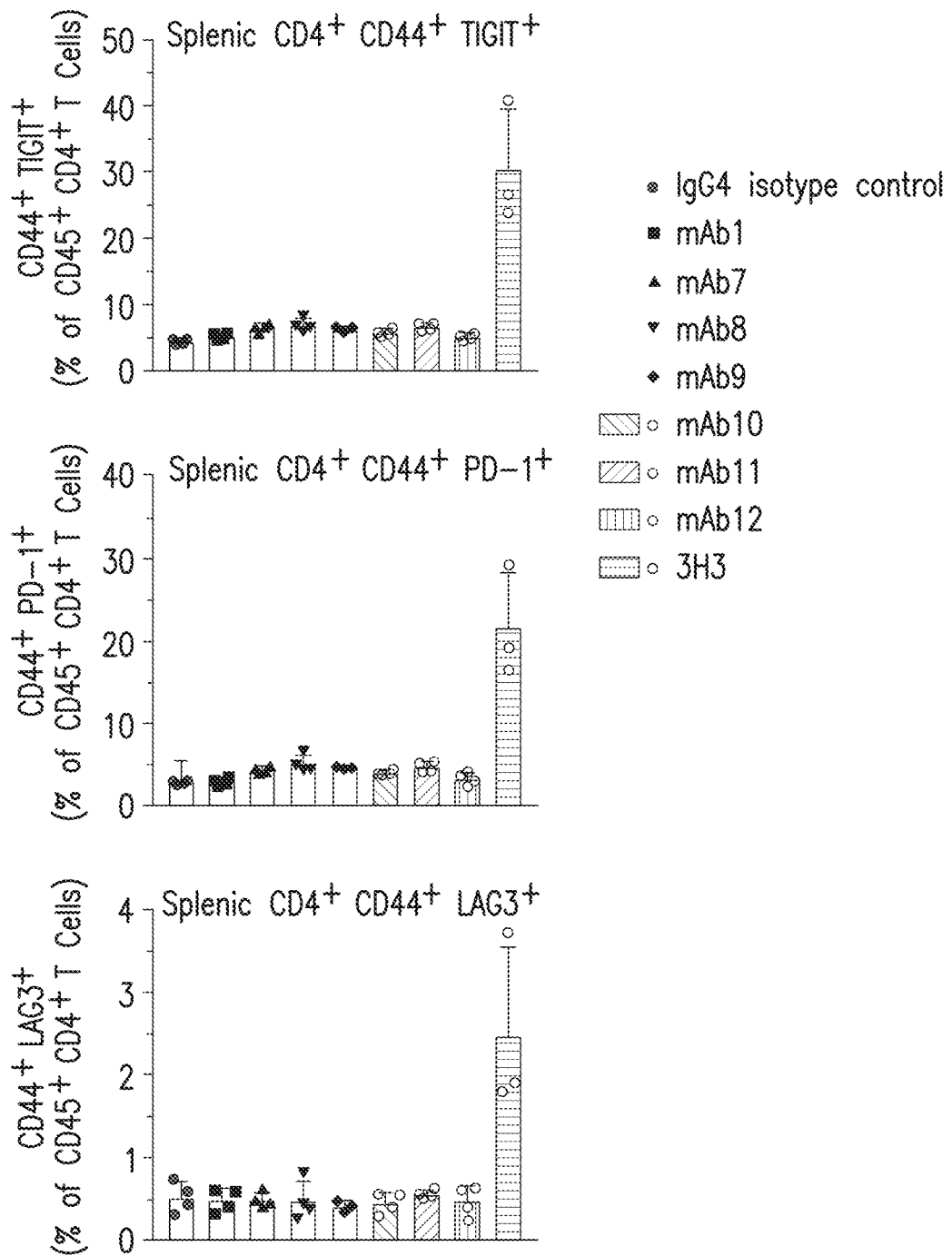
FIG. 19A provides graphs depicting the percentage of splenic CD4+CD44+ T cells expressing TIGIT, PD-1, or LAG3 after treatment of mice with affinity-matured anti-CD137 antibodies.
Figure 19B:
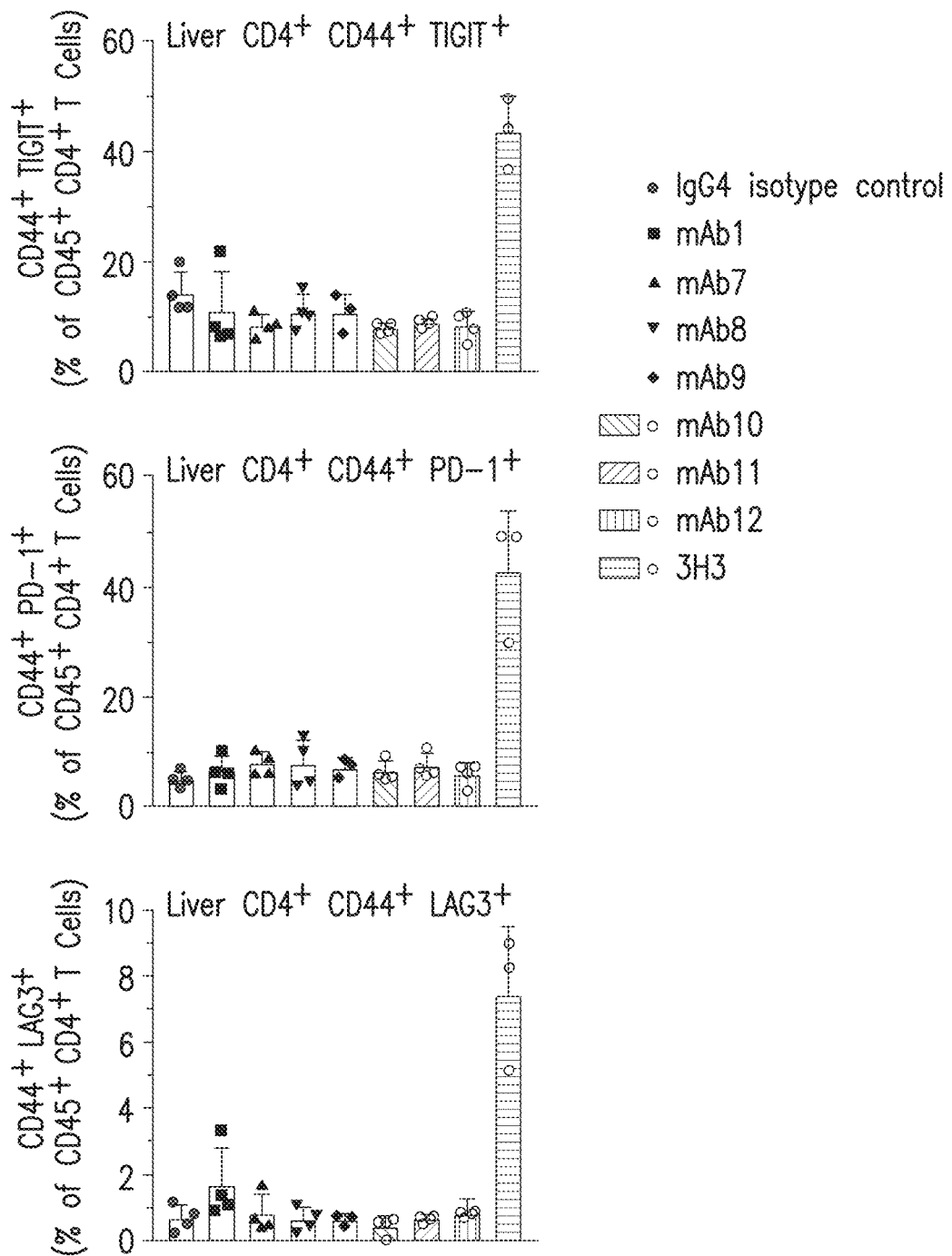
FIG. 19B provides graphs depicting the percentage of liver CD4+CD44+ T cells expressing TIGIT, PD-1, or LAG3 after treatment of mice with affinity-matured anti-CD137 antibodies.

Intrahepatic (liver) and intrasplenic (spleen) T cells in tumor-bearing mice from Example 8 were collected and analyzed via flow cytometry. CD45+ cells from livers and spleens were assessed for CD3+, CD4+, or CD8+ expression following administration of anti-CD137 antibodies or the isotype control antibody, as indicated. Results are shown in FIG. 17A (splenic) and 17B (liver). The results indicated that the administration of parental mAb1 as well as the affinity-matured antibodies (mAb7-mAb12) had little to no effect on the percentage of intrahepatic or intrasplenic T cells relative to administration of the isotype control antibody. In contrast, administration of the 3H3 antibody resulted in elevated T cells in both the spleens and livers relative to the isotype control antibody, particularly CD3+ T cells and CD8+ T cells.

Further, CD45+CD8+ T cells and CD45+CD4+ T cells from the livers and spleens of treated mice were assessed for expression of TIGIT, PD-1, or LAG-3 co-inhibitory receptors, as indicators of T cell activation or exhaustion, following administration of anti-CD137 antibodies or the isotype control antibody. Levels of TIGIT, PD-1, and LAG-3 expression on CD8+ T cells and CD4+ T cells were measured by flow cytometry as described in previous Examples. FIGS. 18A-18B and 19A-19B show that administration of the 3H3 antibody caused a significant increase in expression of these co-inhibitory receptor in both CD8+ T cells and CD4+ T cells, whereas administration of the parental mAb1 or affinity-matured mAb7-mAb12 antibodies resulted in expression of TIGIT, PD-1, or LAG-3 to a similar extent as seen after administration of the isotype control antibody. These results indicated the affinity matured antibodies did not induce systemic CD8+ T cell or CD4+ T cell activation.

Taken together, these results indicate that the parental mAb1 and affinity-matured mAb7-mAb12 antibodies exhibit lower potential for in vivo toxicity relative to the 3H3 comparator antibody. Absence of systemic T cell activation and expansion, particularly in the liver, after treatment with mAb1 and affinity-matured mAb7-mAb12 antibodies might translate into lower possibility of hepatotoxicity (transaminitis) in patients.

Example 18: Toxicity of Multiple Doses of Anti-CD137 Antibodies in Tumor-Bearing Mice To confirm the lack of toxicity induced by mAb1, a repeated-dose toxicity study was conducted. Specifically, mice were administered anti-CD137 antibodies mAb1, mAb8, or 3H3 weekly, for 4 weeks. mAb1 and mAb8 were administered at either 10, 20, 40 or 80 mg/kg, whereas 3H3 was administered at either 10 or 80 mg/kg. On day 35, alanine aminotransaminase (ALT) levels in the plasma was determined using a fluorometric activity assay (Sigma, cat #MAK052), CD8+ T cells in the liver was determined using flow cytometry (as described above), and concentration of TNFα in the plasma was determined using an electrochemiluminscence assay (Meso Scale Discovery, custom kit) according to manufacturer's instructions.

Figure 20B:
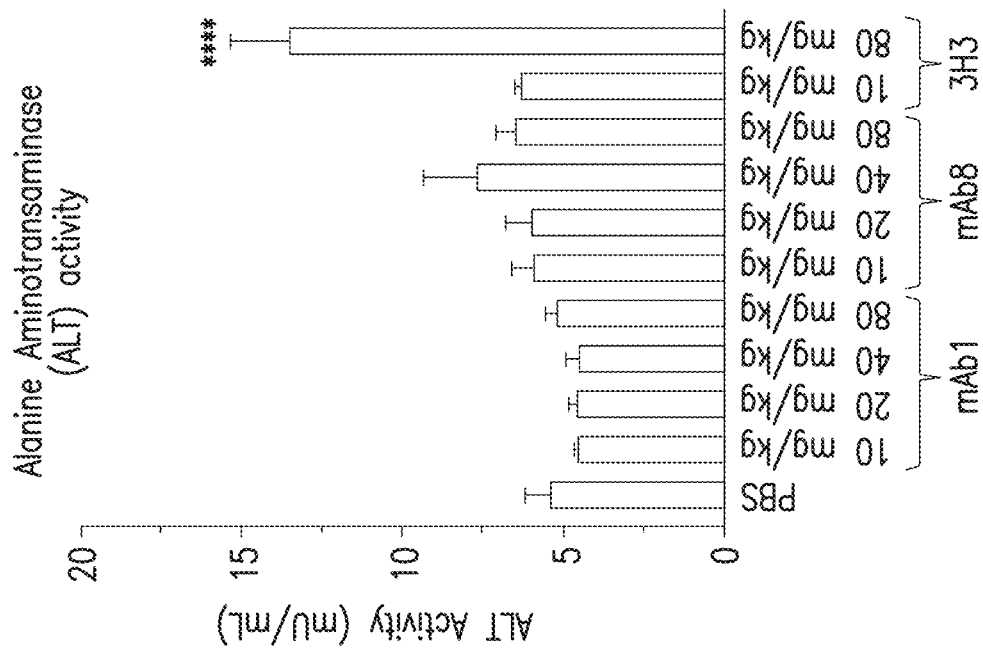
FIGS. 20A-20C provide graphs of in vivo indicators of toxicity resulting from multiple administrations of anti-CD137 antibodies mAb1, mAb8 or 3H3 at varying doses.
Figure 20A:
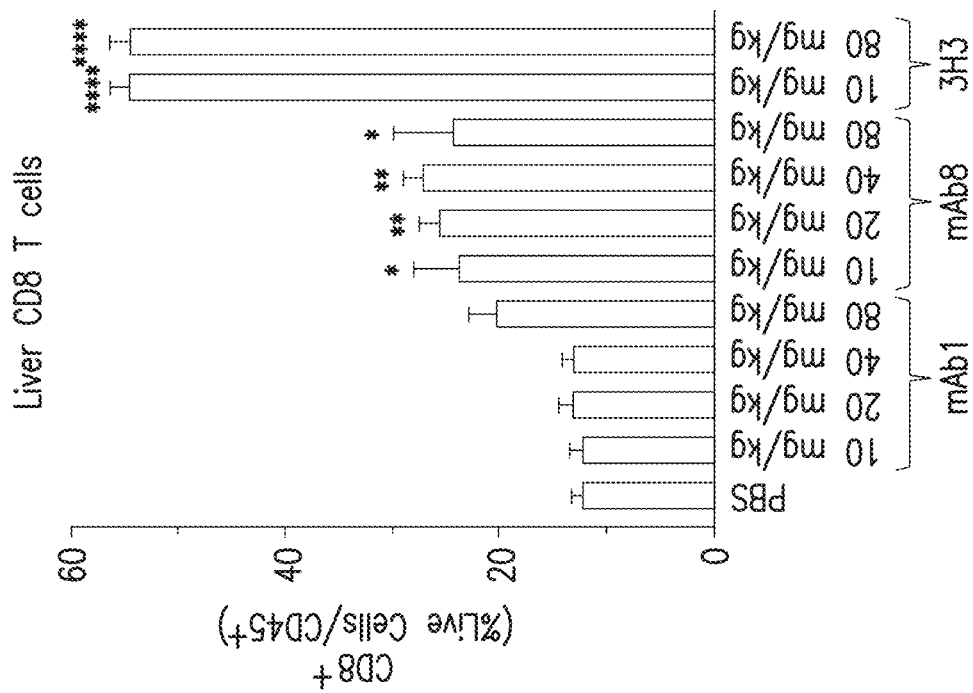
Figure 20C:
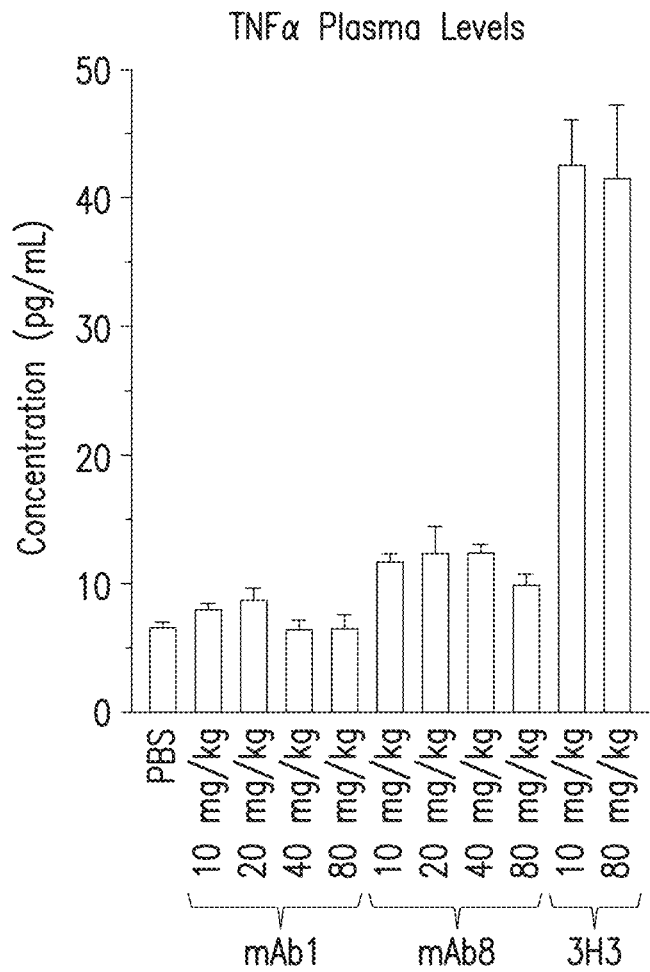

FIG. 20A shows low levels of CD8+ T cells in the livers of mice administered mAb1 and mAb8 at all 4 doses, whereas 3H3 induced high levels of CD8+ T cells at both the low (10 mg/kg) and high (80 mg/kg) doses. FIG. 20B shows low levels of ALT activity in the plasma of mice administered mAb1 and mAb8 at all 4 doses, whereas 3H3 induced high levels of ALT at the 80 mg/kg dose. FIG. 20C shows low levels of TNFα in the plasma of mice administered mAb1 mAb8 at both low (10 mg/kg) and high (80 mg/kg) doses, whereas 3H3 induced high levels of TNFα at both low (10 mg/kg) and high (80 mg/kg) doses.

Figure 21:
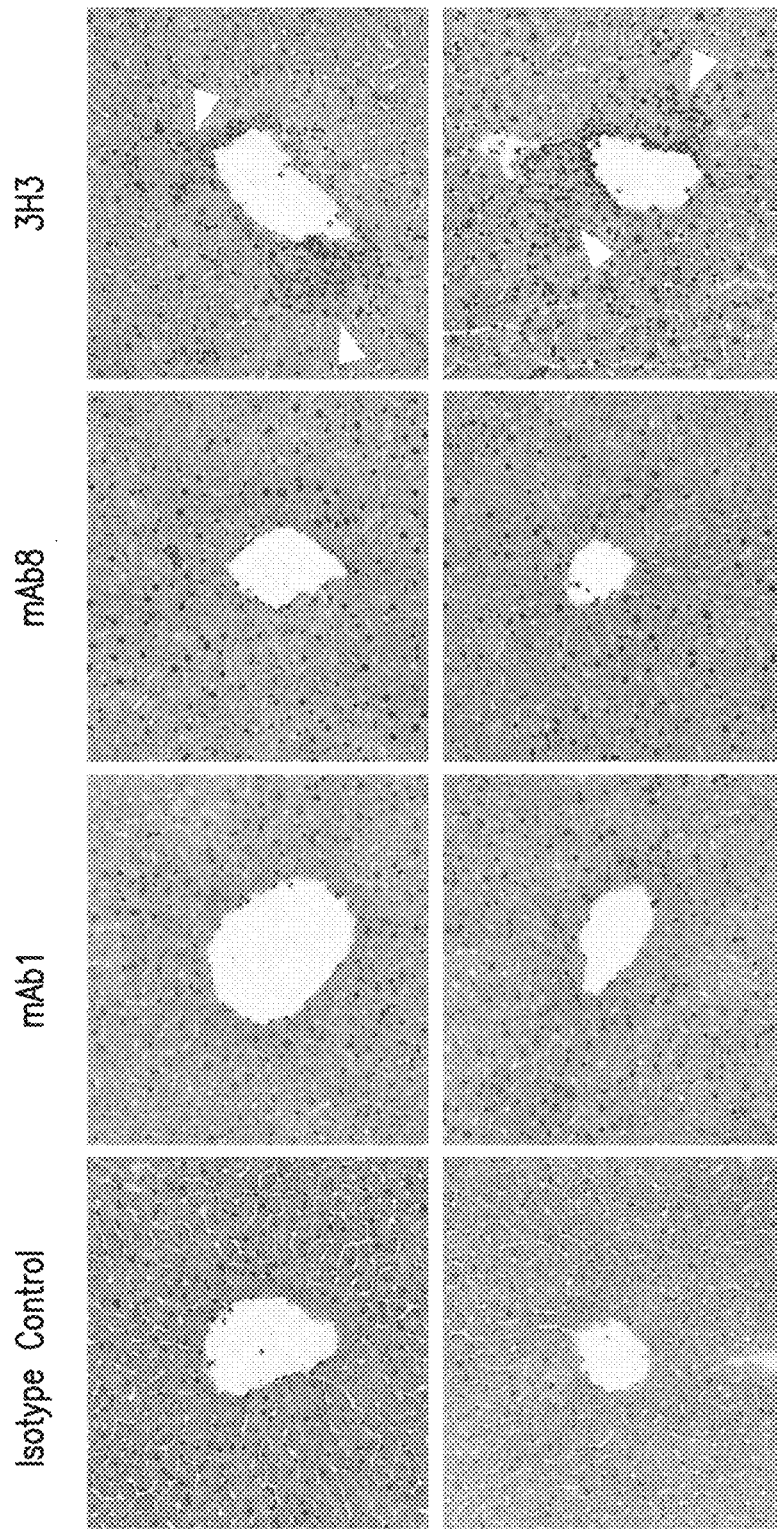
FIG. 21 provides representative images of sectioned livers stained with hematoxylin and eosin (H&E) from mice treated with mAb1, mAb8, 3H3 or isotype control as described in FIGS. 20A-20C. Arrows indicate infiltration of immune cells.

In addition, livers from treated mice that received 80 mg/kg of the anti-CD137 agonistic antibodies were sectioned and stained with H&E. From each animal, half of a liver lobe was embedded in OCT and fresh frozen in liquid nitrogen. Sectioning and H&E staining was performed by a histopathology laboratory (Mass Histology Service, Inc.) according to standard procedures. FIG. 21 provides the results, which show inflammatory centrilobular foci in mice that received 3H3 (see arrows), but not mAb1 or affinity-matured mAb1.

Example 19: Immune Reprogramming with Anti-CD137 Antibodies

To determine the role of anti-CD137 antibodies on immune cells in the tumor microenvironment, the CT26 tumor model was utilized. Specifically, CT26 tumors were established as described in Example 7. mAb8 was administered to mice on days 0, 3, 6 and 9 at a dose of 25 ug. Tumors were analyzed on day 11 as described in Example 16.

Figure 22A:
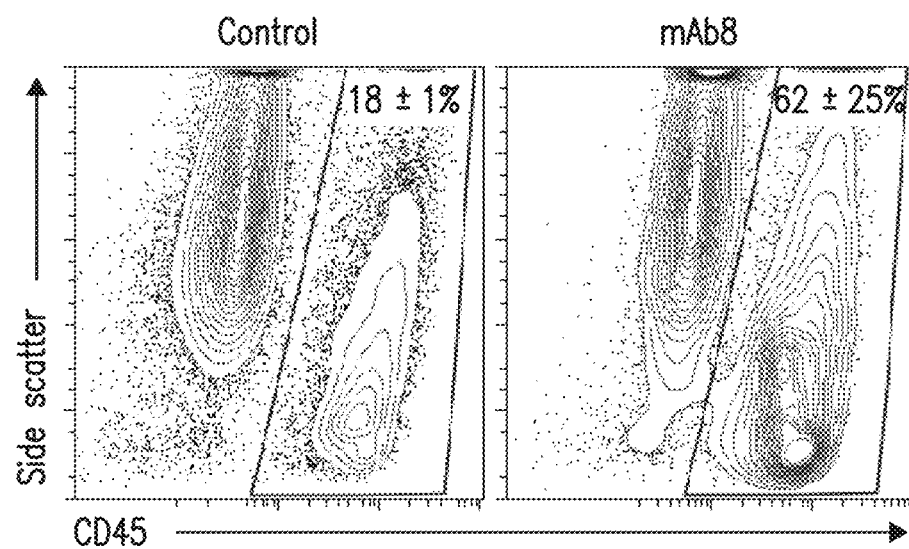
FIGS. 22A-22D provide representative FACS plots showing immune cell reprogramming in the tumor microenvironment. Mice having CT26 tumors were administered multiple doses of mAb8 or isotype control (days 0, 3, 6 and 9).

Overall infiltration of immune cells into the tumor microenvironment was determined by measuring the quantity of CD45+ live cells. As shown in FIG. 22A, mAb8 significantly increased infiltration of immune cells into the tumor microenvironment.

Figure 22B:
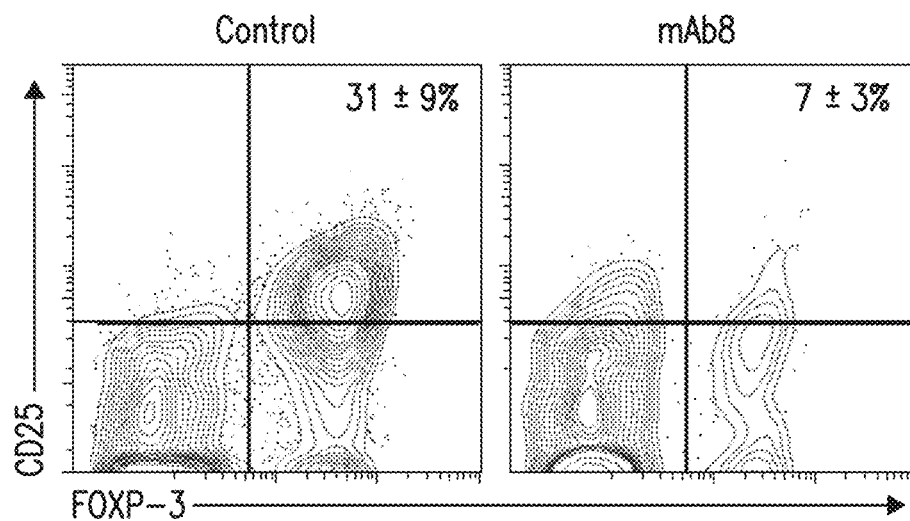

The level of Treg cells in the tumor microenvironment was determined by measuring the quantity of CD25+ FOXP-3+ CD4+ tumor infiltrating lymphocytes. As shown in FIG. 22B, mAb8 significantly reduced the level of Tregs in the tumor microenvironment.

Figure 22C:
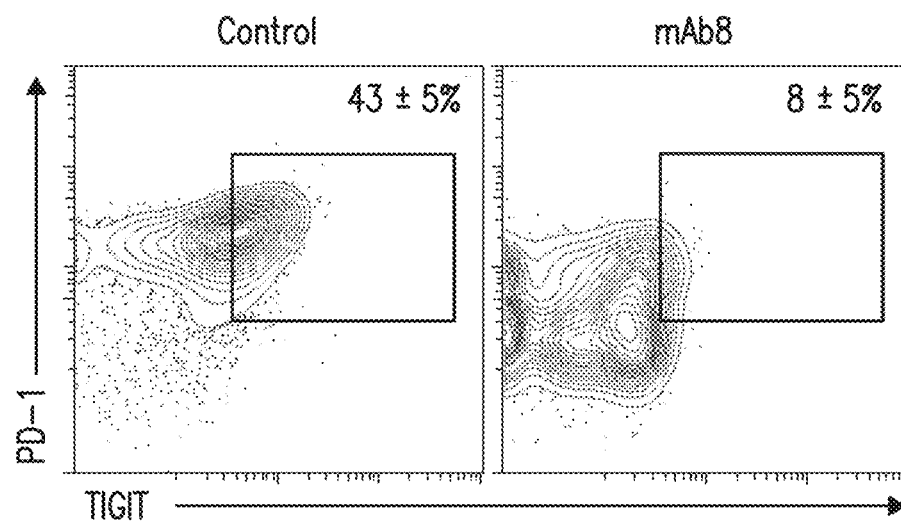
Figure 22D:
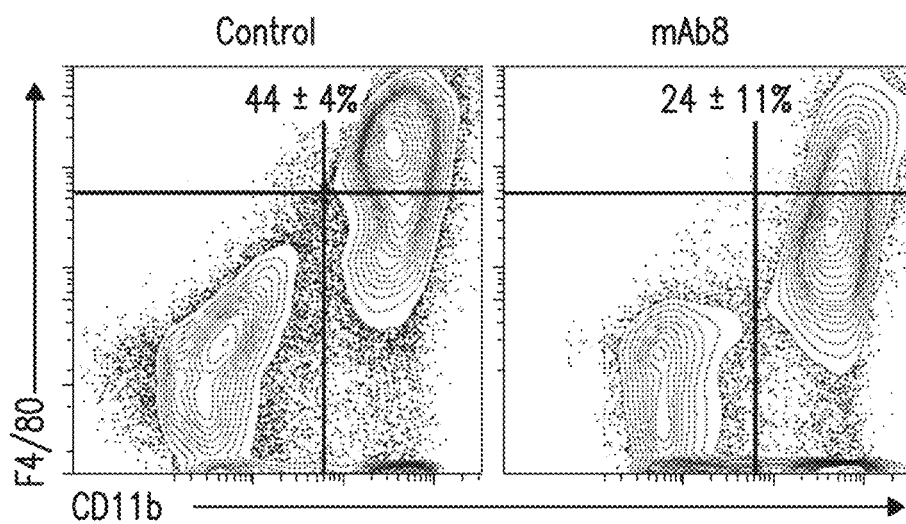

The effect of mAb8 on T-cell exhaustion was determined by measuring the level of PD-1+TIGIT+expression on CD8+ or CD4+ tumor infiltrating lymphocytes (TILs). FIG. 22C shows the results for CD8+ TILs, wherein PD-1+ TIGIT+ cells were reduced in the tumor microenvironment when mAb8 was administered. Similar results were observed for CD4+ TILs (data not shown). These results indicate mAb8 protects and/or reverses T-cell exhaustion.

In addition, the effect of mAb8 on tumor-associated macrophages was analyzed. Specifically, F4/80+CD11b+ CD45+ cells were measured and a reduction in tumor-associated macrophages was observed with treatment of mAb8.

Figure 23:
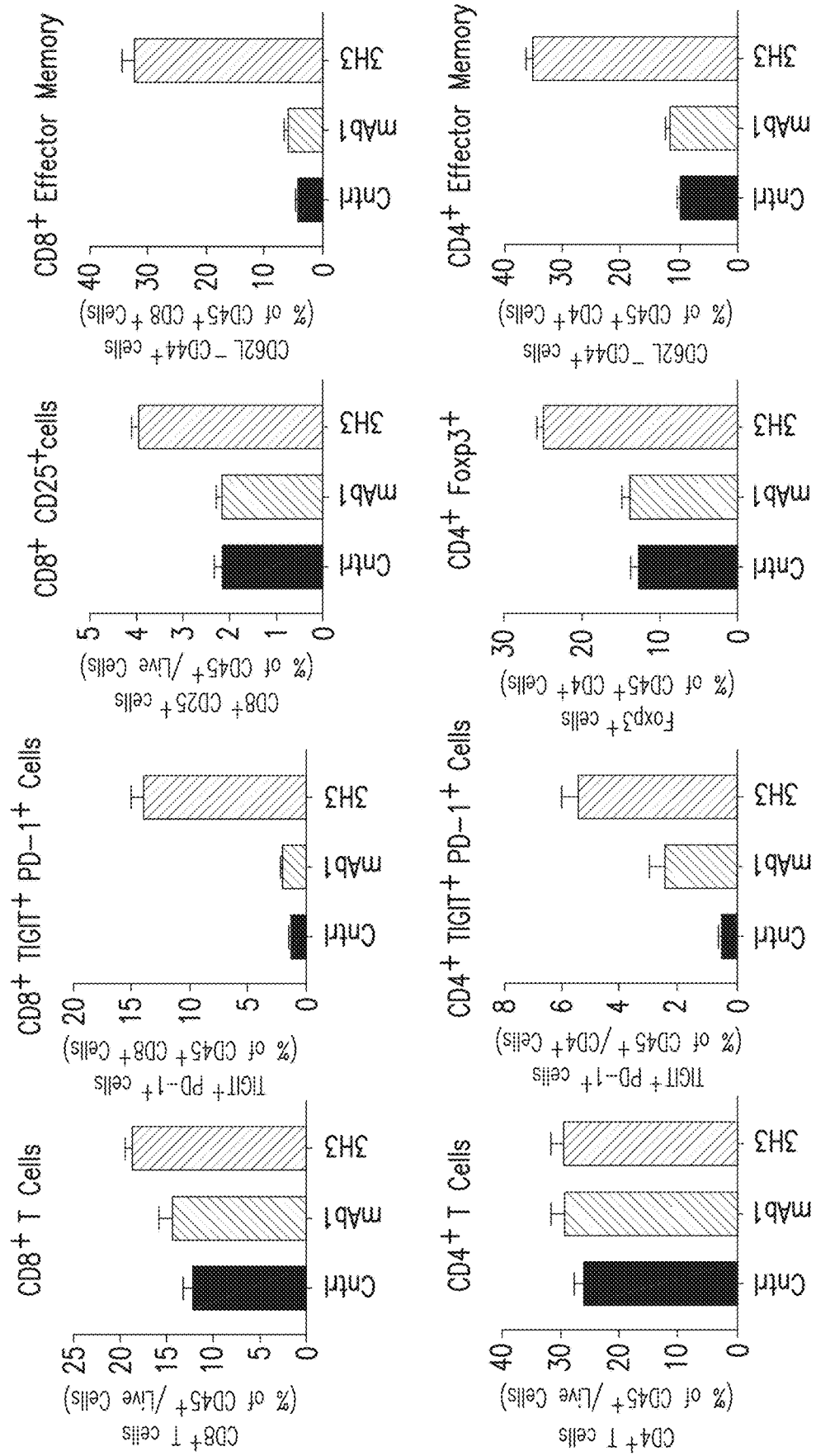
FIG. 23 shows immunophenotyping analysis of spleens from mice having CT26 tumors and treated with either anti-CD137 antibodies mAb1 and 3H3, or isotype control.

In a separate study, the effect of anti-CD137 antibodies (i.e., mAb1 and 3H3) on peripheral immune cells was assessed. Specifically, spleens from CT26 tumor-bearing mice treated with mAb1 or 3H3 on days 0 and 3 at a dose of 150 ug, were analyzed on day 7. As shown in FIG. 23, anti-CD137 antibody 3H3 induced TIGIT and PD-1 expression on CD8+ and CD4+ T cells, as well as increased CD8+CD25+ and CD4+Foxp3+ cells. In addition, 3H3 induced both CD8+ and CD4+ effector memory cells. In contrast, anti-CD137 antibody mAb1 did not significantly induce CD8+ TIGIT+PD-1+, CD8+CD25+, and CD4+ Foxp3+ T cells. Further, mAb1 did not induce CD8+ or CD4+ effector memory cells.

Overall, these results indicate anti-CD137 antibodies mAb1 and mAb8 induce dramatic immune reprogramming within the tumor microenvironment and has less of an effect, if any, on peripheral immune cells.

Example 20: Enhancement of Murine T Cell Activation by Anti-CD137 Antibodies

The agonistic activity of the anti-CD137 antibodies was further analyzed by assessing the stimulation of IL-2 production in a murine ovalbumin stimulation assay. In a 96-well plate, JAWS-II dendritic cell-like cells were plated at $10^4$ cells/well and incubated overnight in the presence of murine IFNγ (10 ng/mL). Cells were incubated with 2 g/mL OVA/A2 peptide and incubated for 2 hours at 37° C., followed by incubation with 105 CD8+ T cells isolated from OT-I mouse spleen, which express OVA. Antibodies were added simultaneously. Atezolizumab (anti-PD-L1 antibody) and a mouse anti-PD-1 antibody (RMP1-14), along with an IgG4 isotype control, were used as comparators. IL-2 concentration was determined by Meso Scale Discovery (MSD).

Figure 24:
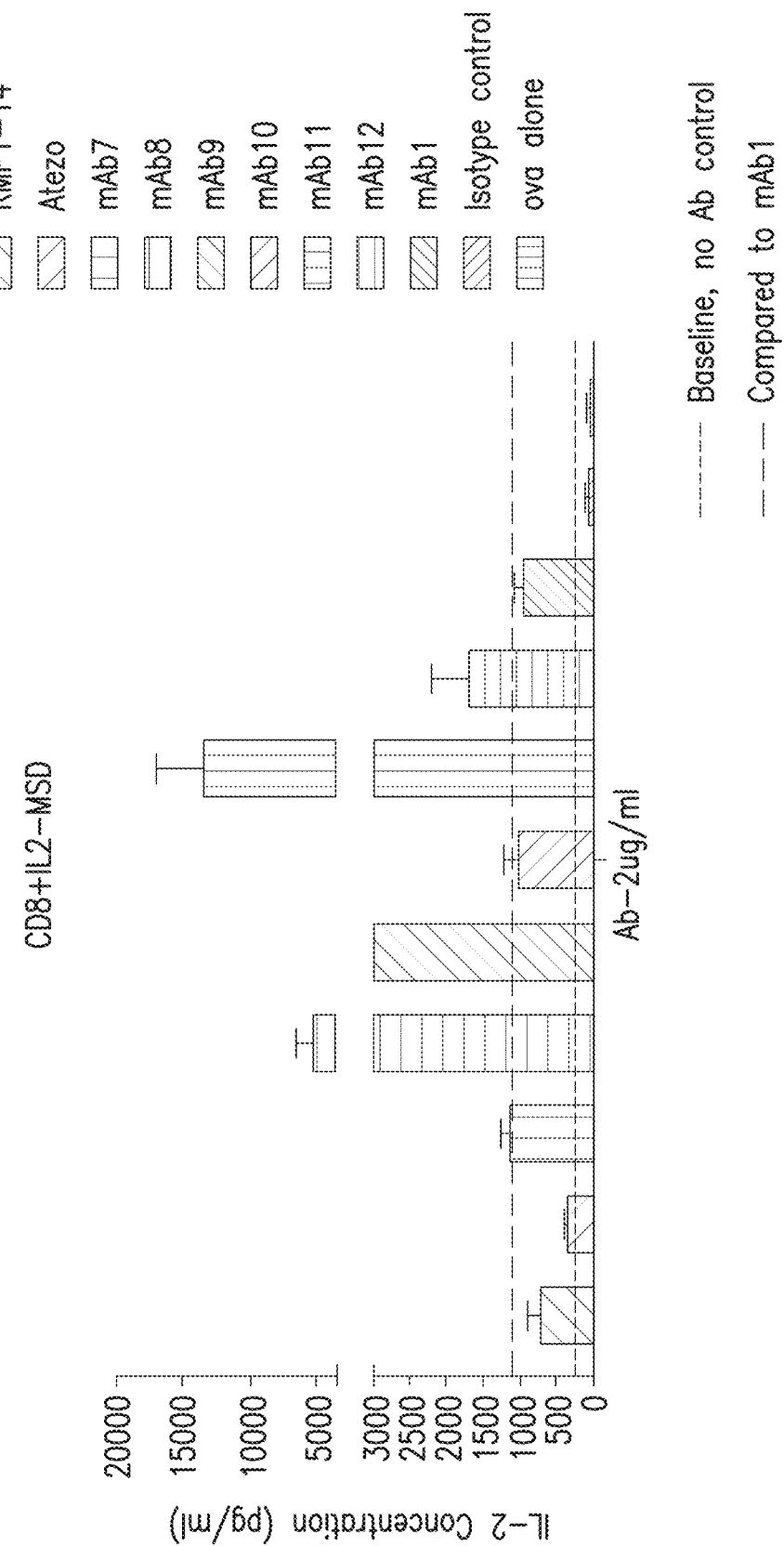
FIG. 24 is a graph showing the concentration of IL-2 (pg/ml) produced by murine T cells in an OVA stimulation assay, when stimulated with the anti-CD137 antibodies indicated. Along with Atezolizumab (anti-PD-L1 antibody), a murine anti-PD-1 (RMP1-14) was used as a comparator.

As shown in FIG. 24, mAb8 and mAb10 significantly enhanced IL-2 production.

Figures 25A, 25B:
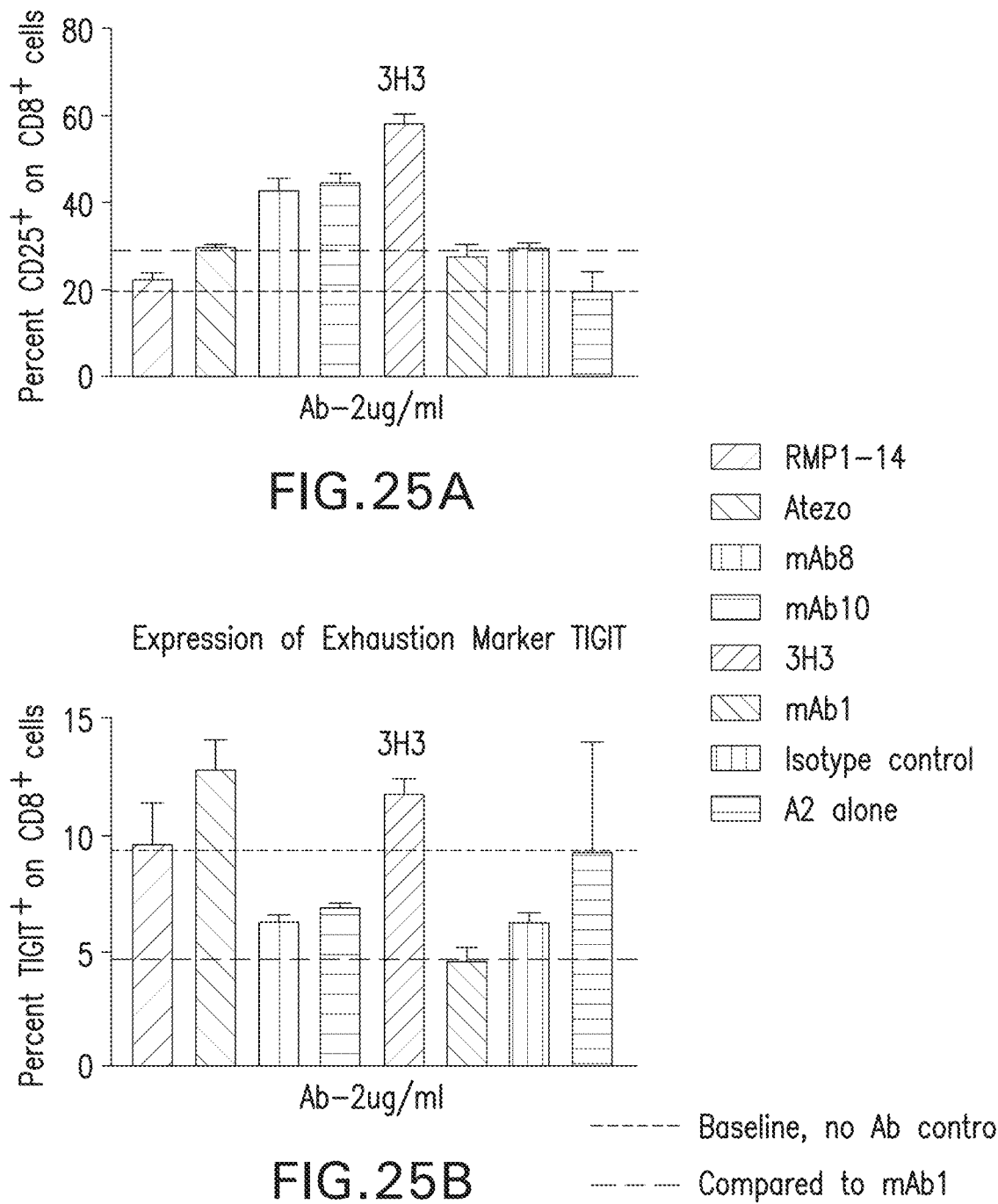
FIGS. 25A and 25B are graphs showing the percentage of murine CD8+ T cells expressing either CD25 (25A) or TIGIT (25B) when stimulated with the anti-CD137 antibodies indicated, in an OVA stimulation assay. Along with Atezolizumab (anti-PD-L1 antibody), a murine anti-PD-1 (RMP1-14) and murine anti-CD137 (3H3) were used as comparators.

In addition to measuring IL-2 production, the percentages of CD25+CD8+ T cells and TIGIT+CD8+ T cells were analyzed using the same murine ovalbumin stimulation assay. Antibody 3H3 was included as a comparator. FIGS. 25A and 25B show that mAb8 and mAb10 enhanced the expression of CD25, an activation marker, and spared the induction of TIGIT, an exhaustion marker. In contrast, 3H3 enhanced the expression of TIGIT.

Example 21: Effect of Anti-CD137 Antibodies on Cytokine Induction

To determine the effect of anti-CD137 antibodies on cytokine induction by T cells, plate-bound antibodies were utilized. Three antibodies were used as comparators: mAb4, corresponding to urelumab (Bristol-Myers Squibb; CAS Number: 934823-49-1), a fully human IgG4-S228P agonistic antibody that targets the extracellular domain of CD137, but does not block ligand binding; mAb5, corresponding to utomilumab (Pfizer; CAS Number: 1417318-27-4), a fully human IgG2-S228P agonistic antibody that targets the extracellular domain of CD137 and blocks ligand binding; and mAb6, a fully human IgG4-S228P agonistic antibody selected from the same library as mAb1 and targets the extracellular domain of CD137. The mAb6 antibody does not block ligand binding.

Human CD3+ T cells were isolated via negative selection and added to plates bound with anti-CD137 antibodies and 1 µg/ml of anti-CD3. Anti-CD137 antibodies were added at either 1 nM, 10 nM, 50 nM or 100 nM. Antibodies were coated overnight at 4° C.

Figure 26:
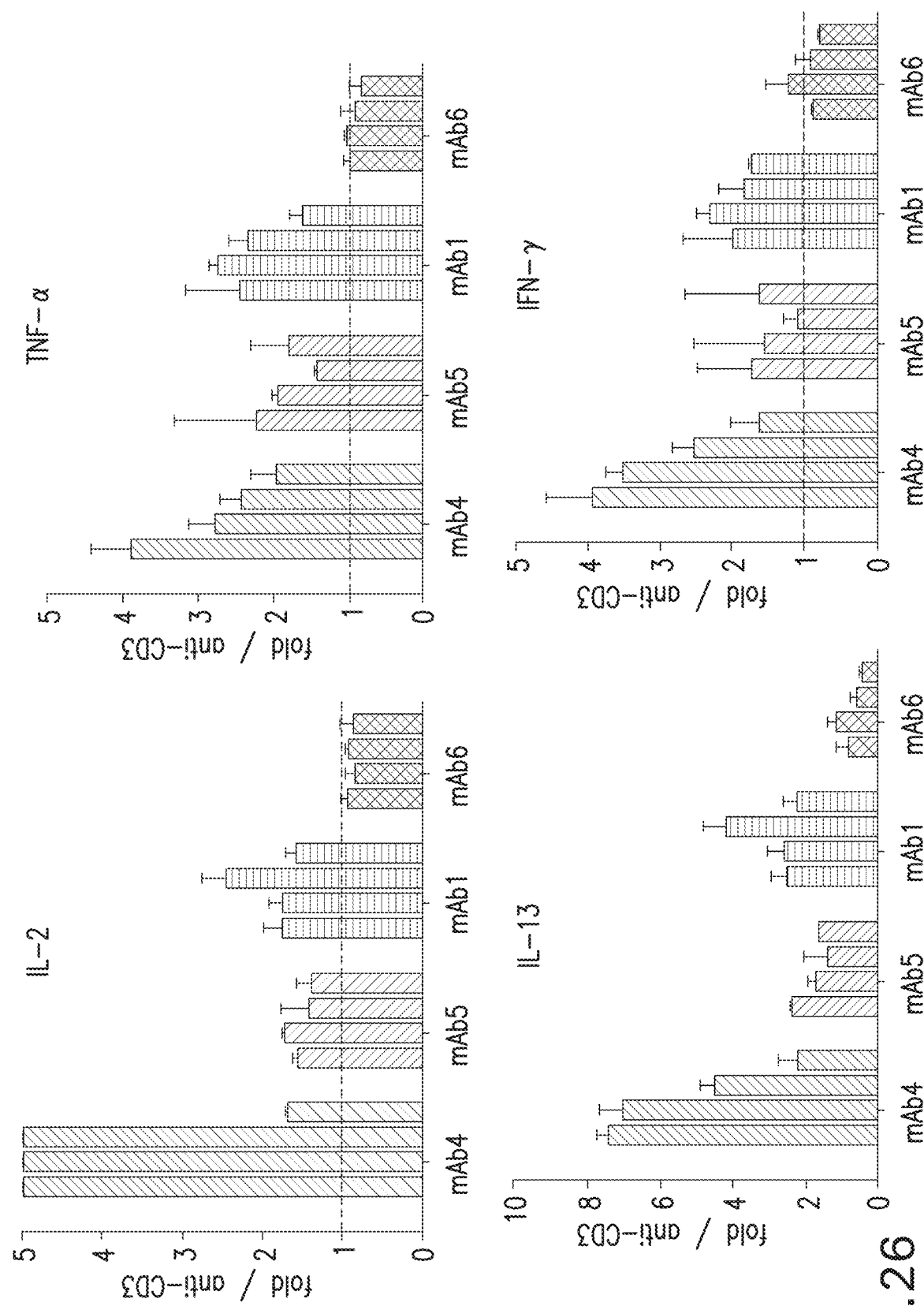
FIG. 26 provides bar graphs depicting the quantification of cytokines (IL-2, TNFα, IL-13, and IFNγ) produced by CD3+ T cells following incubation with plate-bound anti-CD137 antibodies. Cytokine levels are shown as fold increase over baseline activation by an anti-CD3 antibody.

72 hours after addition of the T cells, levels of IL-2, IFNγ, TNFα and IL-13 were assessed by Luminex kits (Luminex Corporation, Austin, Tex.) following the manufacturer's instructions. Soluble anti-CD28 (2 µg/mL) was used as a T cell activation control and the activation baseline was set using the plate bound anti-CD3. FIG. 26 shows the fold change in each cytokine level as it relates to the activation baseline. mAb4 (urelumab) showed the highest level of induction of each cytokine, with mAb1 showing a lower level of induction but higher relative to mAb5 (utomilumab) and mAb6. These results indicate mAb1 agonizes CD137 less than mAb4 (urelumab) at the same concentrations.

Example 22: Induction of Interferon-gamma (IFNγ) by Anti-CD137 Antibodies

To further assess the agonistic activity of the anti-CD137 antibodies, IFNγ production was analyzed in a mixed lymphocyte reaction (MLR). mAb2, mAb4 (urelumab), mAb5 (utomilumab) and KEYTRUDA, a humanized antibody that blocks PD-1 (Merck) and is known to induce IFNγ production, were used as comparators.

Figures 27A, 27B:
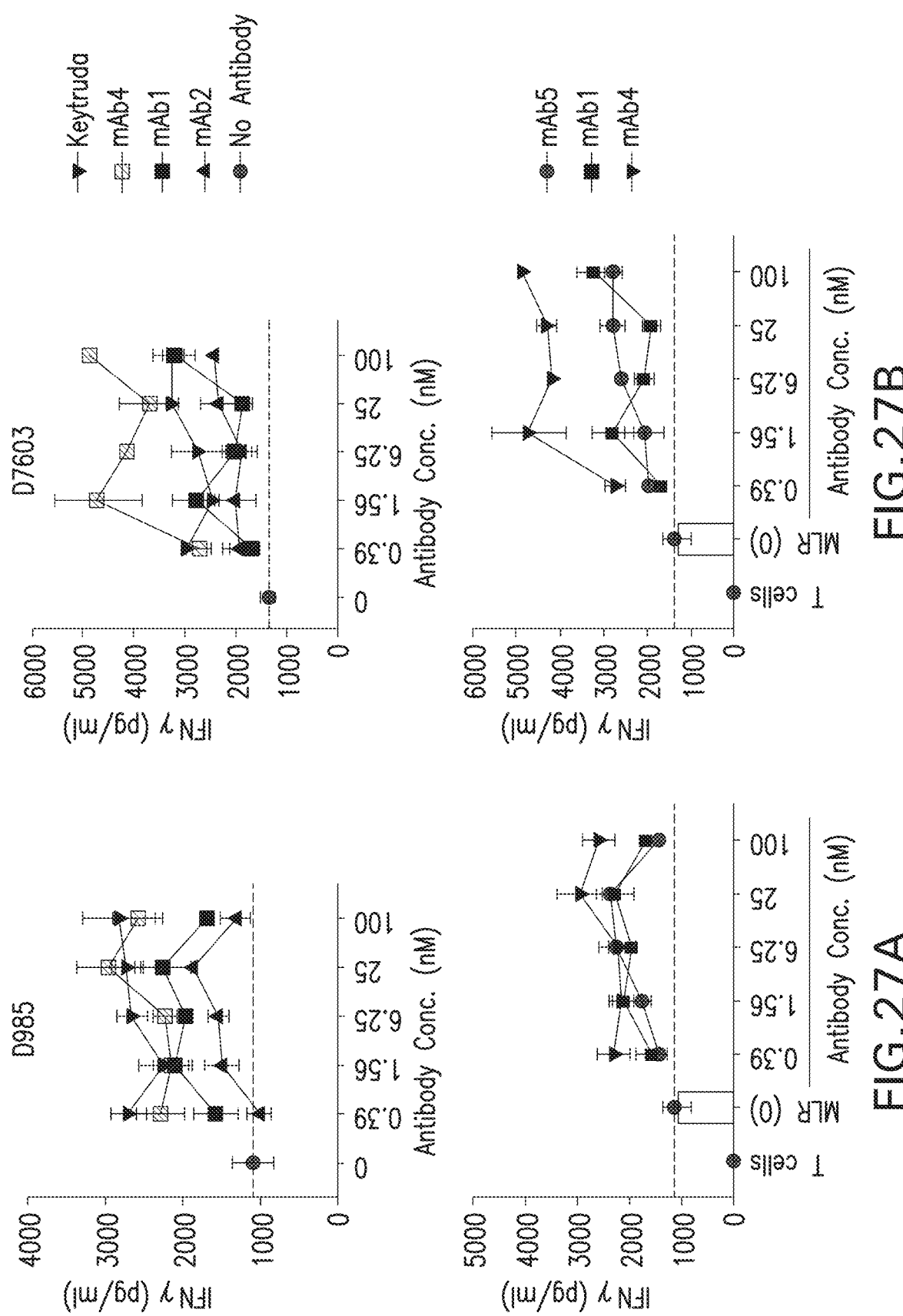

Peripheral blood mononuclear cells (PBMCs) were isolated from leukopaks (HemaCare, Van Nuys, CA) derived from three independent human donors (D985, D7603, and D5004). Total T cells were enriched from PBMC by negative selection using immunomagnetic cell separation (EASYSEP™; Stemcell Technologies, Vancouver BC). Monocytes were isolated from PBMCs using immunomagnetic cell separation (EASYSEP™; Stemcell Technologies, Vancouver BC). T cells were resuspended in complete RPMI at $1\times10^6$ cells/ml concentration and monocytes were adjusted to $5\times10^5$ cells/ml respectively. In a 96-well plate, 100 µl of media containing T cells were plated at $1\times10^5$ cells/well density followed by adding 100 µl of monocyte cell suspension (E:T ratio 2:1). Next, 50 µl of media containing various dilutions of CD137 antibodies was added. Plates were incubated at 37° C. in a $CO_2$ incubator for five days. At the end of incubation period, culture supernatants were collected and IFNγ levels were analyzed by MSD assay (Mesoscale Diagnostics, Rockville, Md.). FIGS. 27A-27C show the concentration of IFNγ as pg/mL at the final concentrations of antibodies tested, as indicated. These results indicated mAb1 agonizes CD137 less than mAb4 (urelumab), but to a similar extent as mAb5 (utomilumab) at the same concentrations.

In a separate study, IFNγ induction was measured by utilizing CHO cells engineered to express CD32 (FCγRIIb) (CHO-CD32 cells). Specifically, CHO-CD32 cells were co-cultured with human T cells in the presence of soluble anti-CD3 and anti-CD137 antibodies mAb1, mAb8, mAb4 and mAb5.

Frozen PBMCs were thawed and rested overnight in T cell media (TCM) in a humidified 37° C. 5% $CO_2$ incubator. The following day, CD3+ T cells were isolated with an untouched CD3 T cell isolation kit (Stemcell #17951) before being mixed together with CHO cells (Gibco #A29127) transduced to express human CD32 (CHO-CD32), 250 ng/ml anti-CD3 (clone OKT3), and the anti-CD137 or control antibodies. 100,000 T cells were mixed together with 50,000 CHO-CD32 cells. After incubation at 37° C. for 3 days, supernatants were collected for analysis of secreted interferon-gamma (IFNγ) via MesoScale Discovery (MSD).

Figure 28:
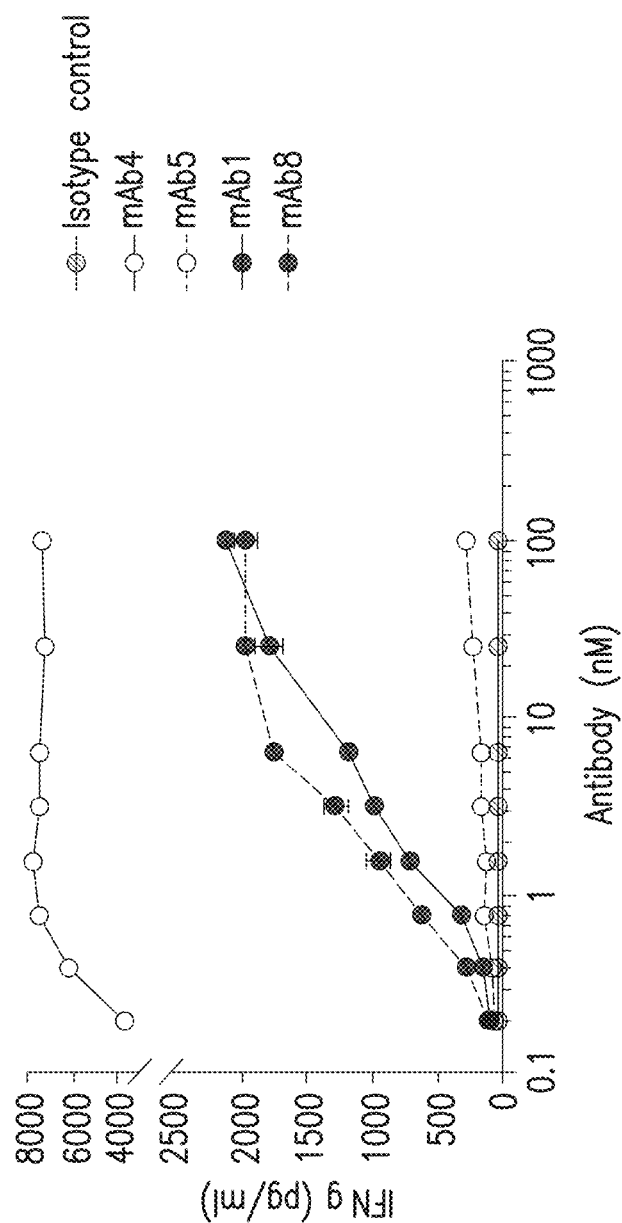
FIG. 28 is a graph showing IFNγ production from human T cells co-cultured with CHO cells engineered to express CD32 (CHO-CD32 cells) in the presence of anti-CD137 antibodies mAb1, mAb8, mAb4 or mAb5, or isotype control.

FIG. 28 provides the results, showing mAb4 induced IFNγ to the highest level and at low doses. In contrast, mAb5 induced almost no product of IFNγ. Notably, mAb1 and mAb8 provided a dose-dependent response and induced IFNγ production between the levels induced by mAb4 and mAb5. Overall, these results indicate that mAb4 has superagonist activity, mAb5 has weaker activity, and mAb1 and mAb8 have an intermediate activity compared to mAb4 and mAb5.

Example 23: Effect of Anti-CD137 Antibodies on Treg Cells

To further characterize the mechanism of action for anti-CD137 antibodies, the effect of the antibodies on Treg cells was determined. Human Tregs were isolated using EASYSEP™ Human CD4+CD127lowCD25+ Regulatory T Cell Isolation Kit (Stemcell Technologies, Cat #18063) and expanded for 13 days by immunocult anti-CD3/28 (Stemcell #10971) in complete T cell media with 10% FBS. Specifically, the CHO-CD32 cells described in Example 21 were co-cultured with expanded human Treg cells, which were labeled with Cell-trace violet dye (Thermo Fisher, Cat #C34557) in the presence of soluble anti-CD3 (clone OKT3) and anti-CD137 antibodies mAb1, mAb8, mAb4, mAb5 and isotype control. Proliferation of Treg cells was determined on Day 4.

Figure 29:
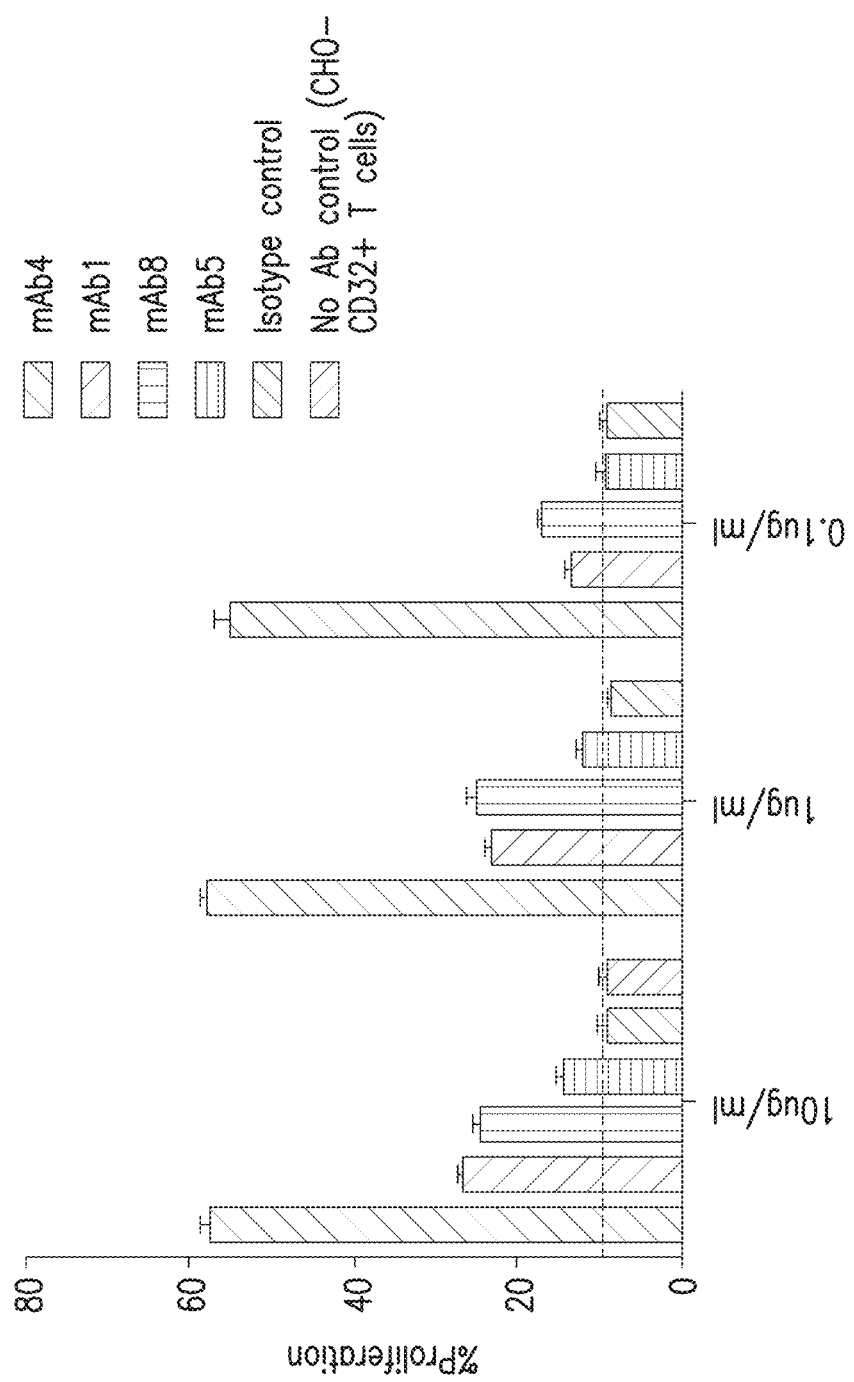
FIG. 29 is a graph showing proliferation of Treg cells when co-cultured with CHO cells engineered to express CD32 (CHO-CD32 cells) in the presence or absence of anti-CD137 antibodies mAb1, mAb8, mAb4 or mAb5, isotype control.

FIG. 29 provides the results, showing mAb4 strongly induced Treg proliferation, even at low concentrations. In contrast, mAb5 had a very weak effect on Treg proliferation. Notably, mAb1 and mAb8 showed moderate increases in Treg proliferation. Overall, these results confirm that mAb4 has superagonist activity, mAb5 has weak activity, and mAb1 and mAb8 have an intermediate activity.

Example 24: Effect of Anti-CD137 Antibodies on Intracellular Signaling

To further assess the differences between anti-CD137 agonistic antibodies, intracellular signaling was assessed in vitro. Specifically, CCL-119 T cells (ATCC; Cat #ATCC CCL-119) lentifected with NFkβ (Qiagen; Cat #CLS-013L-1) or SRF (Qiagen; Cat #CLS-010L-1) were stimulated with 250 ng/mL of plate-bound anti-CD3 (clone OKT3) in conjunction with varying concentrations of plate-bound mAb1, mAb8, mAb4, mAb5 and isotype control. After stimulation for 16 hours in RPMI media without additives, cells were lysed in luciferase buffer (Promega; Cat #E263B) and relative light units (RLUs) were acquired on a BioTek Synergy H1 microplate reader (Cat #11-120-533). Raw RLU data was then exported to Microsoft Excel and fold-induction was calculated by dividing RLUs from stimulated conditions over unstimulated controls.

Figure 30:
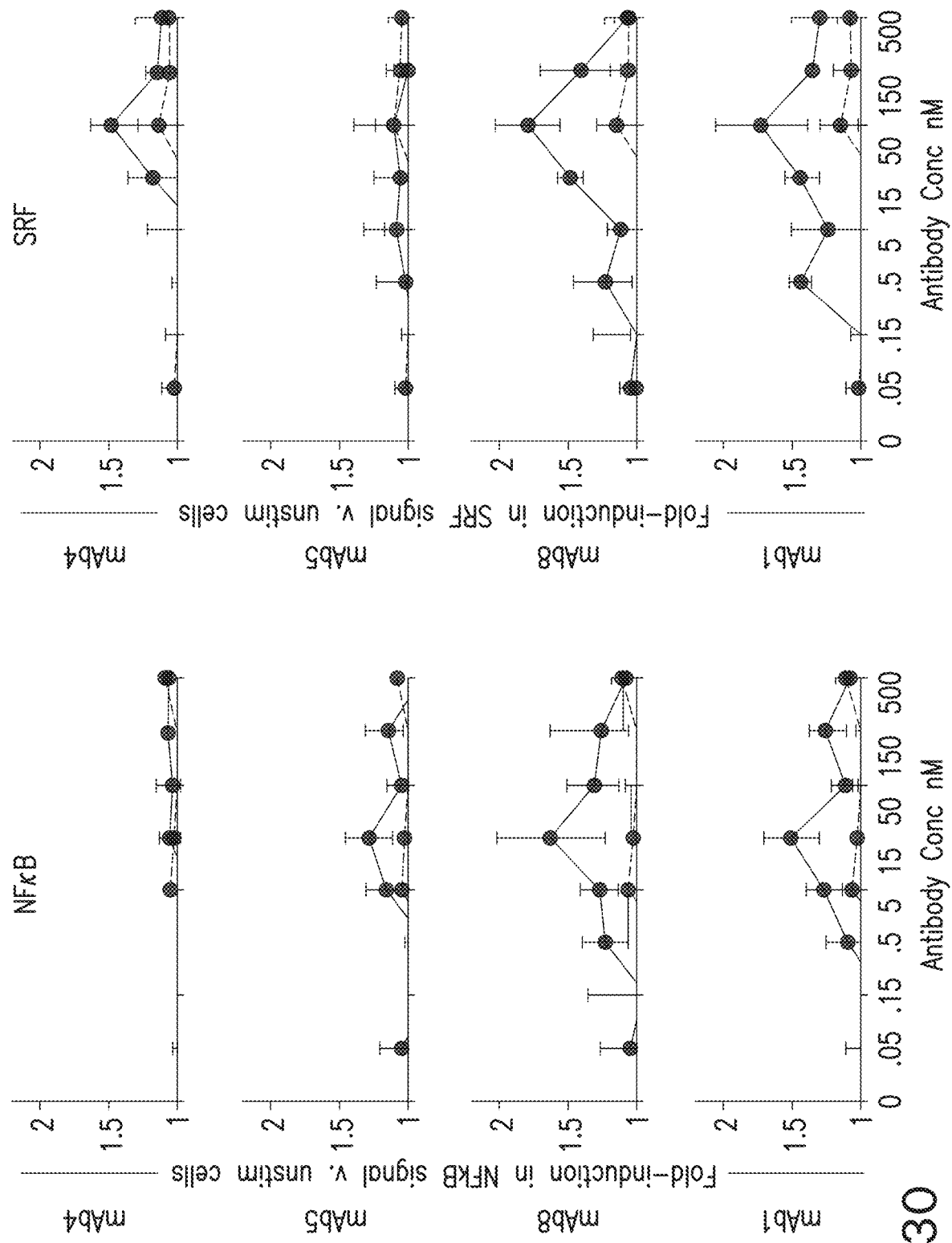
FIG. 30 provides graphs showing NFκβ and SRF signaling in CCL-119 cells transduced with luciferase reporters for NFκβ or SRF in the presence of mAb1, mAB8, mAb4 or mAb5 at varying concentrations.

FIG. 30 provides the results, showing minimal NFkβ and SRF activity of mAb4 and mAb5 relative to mAb1 and its affinity-matured variant, mAb8. Overall, these results indicate mAb1 induces intracellular signaling differently than mAb4 and mAb5.

Example 25: Effect of Anti-CD137 Antibodies on Macrophage Activation and Differentiation It has previously been shown the hepatotoxicity induced by anti-mCD137 agonistic antibody 3H3 was associated with expansion of macrophages and CD8+ T cells in the livers, and increased cytokine levels and ALT activity in the serum. Further, antibody 3H3 has been characterized as having similar properties as urelumab. As described herein, mAb1 does not induce hepatotoxicity. Accordingly, anti-CD137 agonistic antibodies were analyzed for their effect on macrophage activation in vitro.

Figure 31:
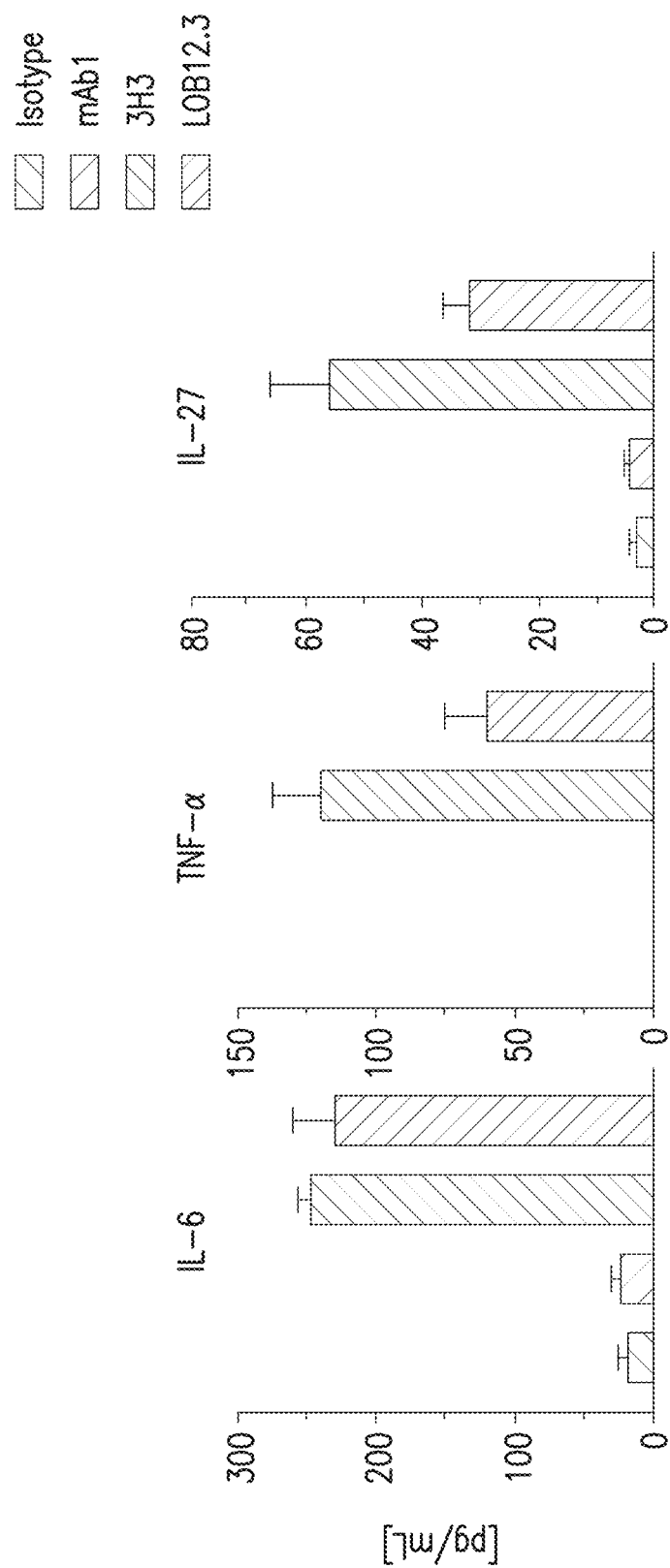
FIG. 31 provides graphs showing induction of IL-6, TNFα, or IL-27 by bone marrow-derived mouse macrophages stimulated with TLR9 agonist CpG in the presence of anti-CD137 antibodies mAb1, 3H3 or LOB12.3, or isotype control.

Specifically, murine bone marrow-derived mouse macrophages were established from 10-week old female C57BL/6 mice (Charles River Laboratories). The femur and tibia bones were extracted from the musculature of the mice and bone marrow was flushed with PBS into 15 mL conical tubes on ice. The cells were centrifuged at 1500 rpm for 5 minutes and the supernatant was discarded. The cell pellet was broken and culture media (RPMI, 20% FBS, 50 µg/mL M-CSF (Shenandoah Biotechnology, Inc.; Cat #200-08-100), and pen/strep) was added. Cells were filtered on 40-micron mesh filter and plated into non-tissue culture treated petri dishes. After 3 days 10 mL of media was added to each petri dish. On day 7 of culture, media was removed and cells were washed with PBS (10 mL) twice. MACS buffer (PBS, 2 µM EDTA, and 0.5% FBS) was added to each dish and incubated at 37° C. for 10 minutes. Cells were collected from the petri dishes and centrifuged at 1500 rpm for 5 minutes. These bone marrow derived macrophages were then stimulated with TLR9 agonist CpG in the presence of 50 nm of anti-CD137 antibodies mAb1, 3H3, or LOB12.3 (mouse specific CD137 agonist antibody). Production of IL-6, TNFα and IL-27 by murine bone marrow-derived macrophages was assessed from culture supernatants after 48 hours using an electrochemiluminscence assay (Meso Scale Discovery, custom kit) according to manufacturer's instructions. FIG. 31 provides the results, which indicate mAb1 did not induce secretion of proinflammatory cytokines by macrophages, whereas antibodies 3H3 and LOB12.3 did.

Figure 32:
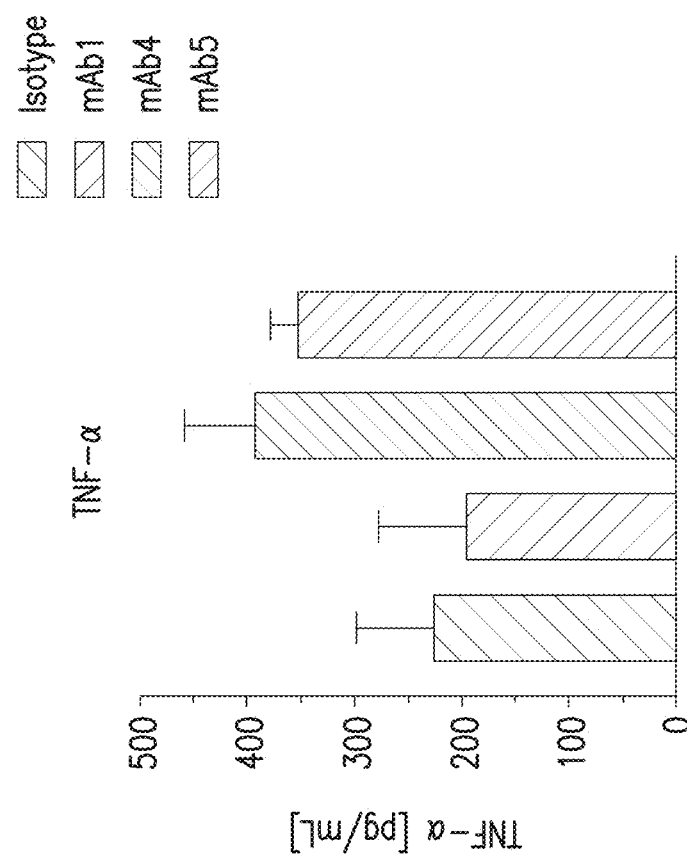
FIG. 32 provides a graph showing induction of TNFα by human monocyte derived macrophages stimulated with LPS in the presence of anti-CD137 antibodies mAb1, mAb4 or mAb5, or isotype control.

The human monocyte-derived macrophages were generated by magnetically separating CD14+ cells using anti-CD14 microbeads (Miltenyi Biotech, Cat #130-050-201) and maturing 7 days in the presence of 50 ng/mL m-CSF. Human monocyte-derived macrophages were then stimulated with 10 ng/mL LPS in the presence of 5 nm of anti-CD137 antibodies mAb1, mAb4, or mAb5. Production of TNFα was assessed after 48 hours using an electrochemiluminscence assay (Meso Scale Discovery, custom kit) according to manufacturer's instructions. FIG. 32 provides the results, which indicate mAb4 and mAb5 induced macrophage activation significantly more than mAb1.

Figure 33:
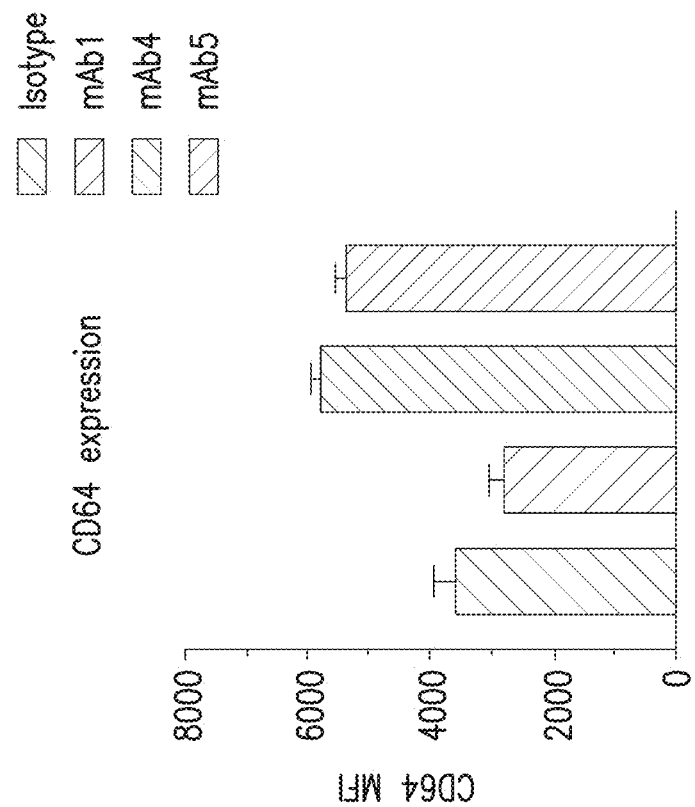
FIG. 33 provides a graph showing effect of anti-CD137 antibodies on macrophage differentiation as determined by CD64 expression of THP1 monocytes cultured with PMA in the presence of anti-CD137 antibodies mAb1, mAb4 or mAb5, or isotype control.

Further, THP1 monocytes were differentiated to macrophages with 2 µM phorbol 12-myristate 13-acetate (PMA; Sigma; P1585) overnight. The macrophages were than cultured in the presence of 50 nm of anti-CD137 antibodies mAb1, mAb4 or mAb5 and CD64 expression was measured 48 hours later using flow cytometry (APC anti-human CD64 antibody clone 10.1; BioLegend; Cat #305013). FIG. 33 provides the results, which indicate mAb4 and mAb5 induced macrophage differentiation significantly more than mAb1.

While the disclosure is not bound or limited by any particular theory or mechanism of action, overall, these results suggest mAb1 spares hepatic toxicity due to reduced potential for macrophage activation.

Example 26: Expansion of Human CD8+ T Cells In Vivo by Anti-CD137 Agonistic Antibodies To test the effect of CD137 agonistic antibodies on human cells in vivo, human PBMCs ($7 \times 10^6$) were intravenously injected to immunocompromised NSG mice (NOD.Cg-Prkdc$^{scid}$ Il2rg$^{tm1Wjl}$/SzJ; Jackson Laboratory; Cat #005557). The mice were randomized to groups of 8 and received CD137 antibodies (200 µg/mouse) or vehicle control on days 0, 7 and 14. Peripheral blood from each mouse was collected on days 10, 20 and 29 for determination of human CD45+(FITC anti-human CD45 clone 11130; BioLegend; Cat #304038), CD8+(ALEXA FLUOR® 647 anti-human CD8a clone HIT8a; BioLegend; Cat #300918), and CD4+ (APC-Cy7 anti-human CD4 clone RPA-T4; Bd; Cat #557871) engraftment using flow cytometry.

Figure 34A:
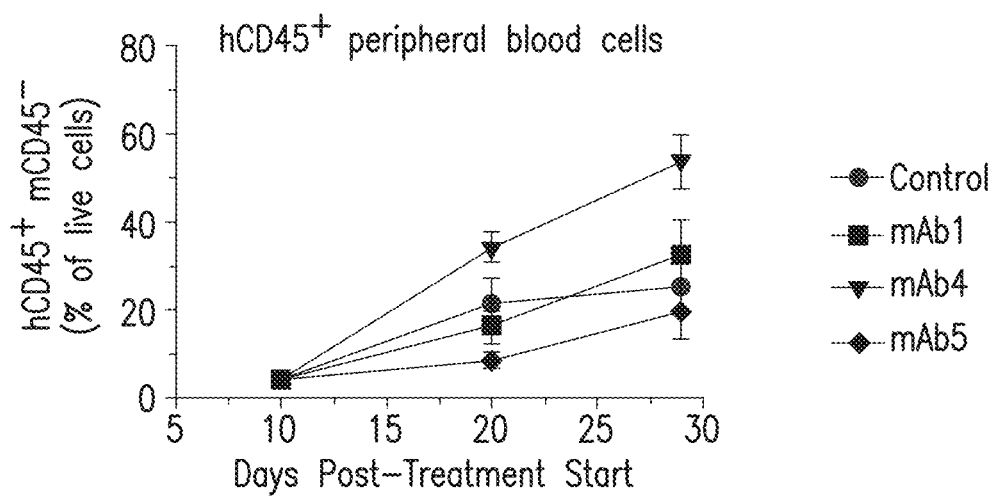
FIGS. 34A-34C provides graphs showing percentage of hCD45+, hCD8+ or hCD4+ from immunocompetent mice that received human PBMCs and anti-CD137 antibodies mAb1, mAb4 or mAb5, or isotype control.
Figure 34B:
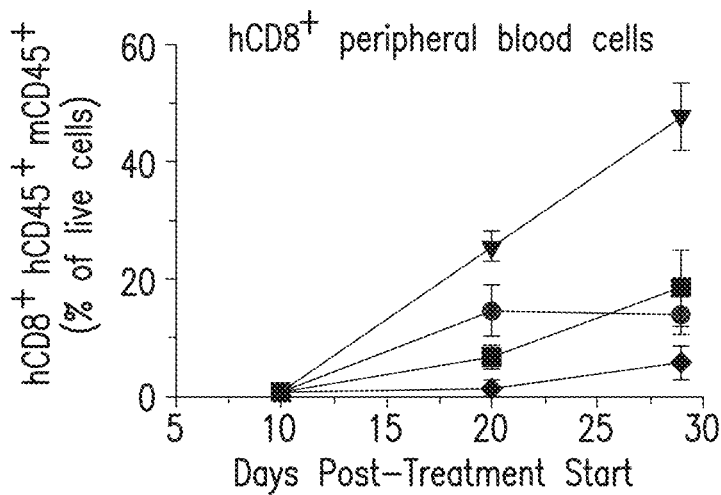
Figure 34C:
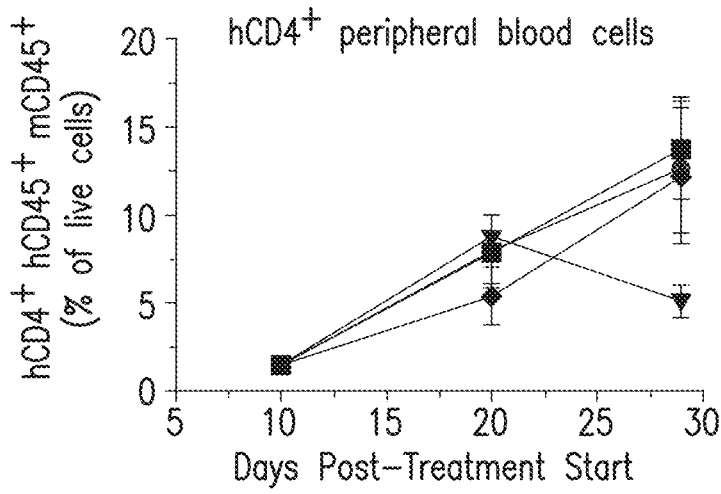

FIGS. 34A-34C show overall increase in numbers of hCD45+ cells and systemic hyper expansion of human CD8+ T cells in mice that received mAb4 at the expense of human CD4+ T cells. Notably, mAb1 did not induce over activation of human T cells. Reduced potential of mAb1 to activate human T cells in the periphery might contribute to reduced potential for toxicity.

Example 27: In Vitro Effects of Anti-CD137 Antibodies and Anti-PD-L1 Antibody Combination To further assess the agonistic activity of the anti-CD137 antibodies, IFNγ production was analyzed in an antigen-recall assay. Specifically, PBMCs were harvested from a CMV-specific donor and plated in a 96-well plate at $2 \times 10^5$ cells/well. CMV antigens (2 µg/mL) and antibodies were added to a final concentration of 50 nM. Anti-CD137 antibodies were added in combination with Atezolizumab, an anti-PD-L1 antibody, to determine the ability of the anti-CD137 antibodies to enhance T cell activation. KEYTRUDA®, an anti-PD-1 antibody, along with an IgG4 isotype control were used as comparators. The concentration of IFNγ was determined by Meso Scale Discovery (MSD).

Figure 35:
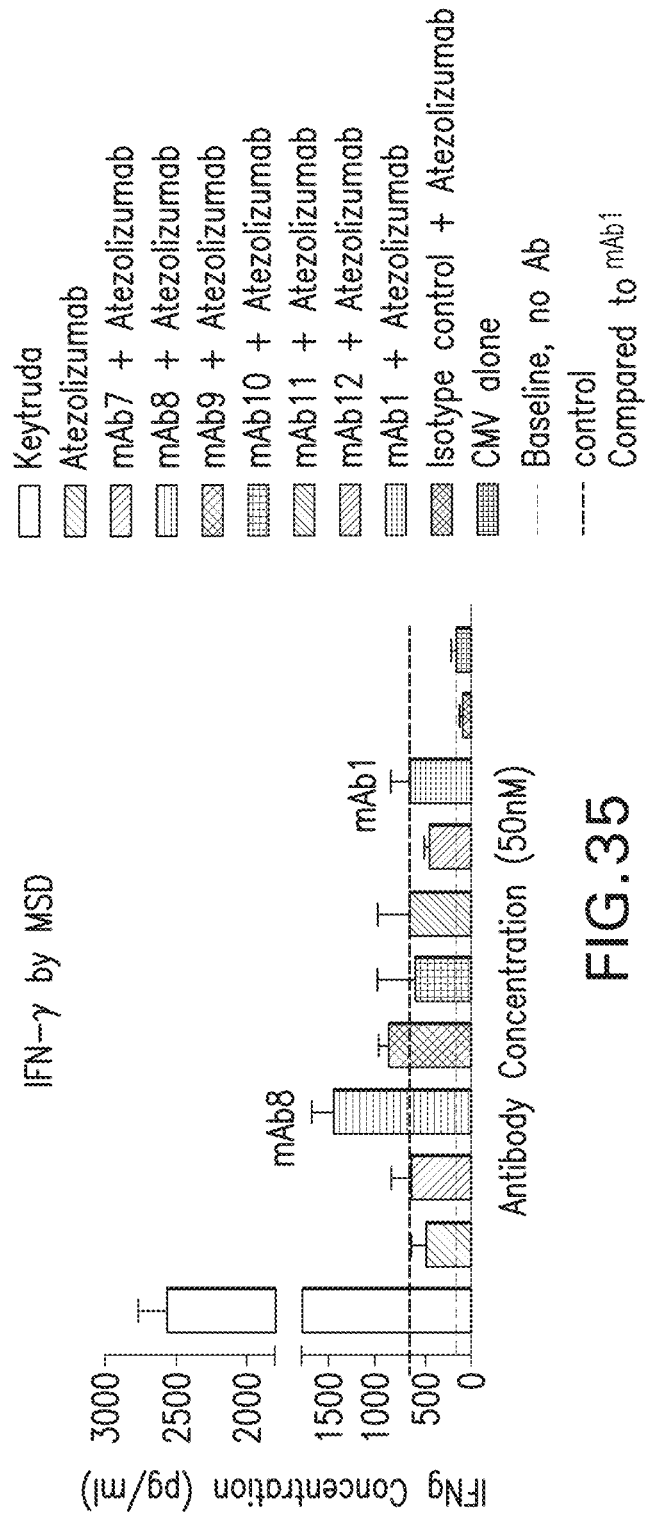
FIG. 35 provides a graph showing the induction of IFNγ by human PBMCs isolated from a CMV-specific donor, stimulated with CMV antigen, and incubated the presence of anti-CD137 antibodies mAb1, mAb7, mAb8, mAb9, mAb10, mAb11, mAb12, or an isotype control in combination with an anti-PD-L1 antibody (Atezolizumab). KEYTRUDA®, an anti-PD-1 antibody, along with an IgG4 isotype control were used as comparators.

As shown in FIG. 35, mAb8 significantly enhanced IFNγ compared to the parental mAb1. These results indicated this affinity-matured anti-CD137 antibody enhanced T cell activation induced by an anti-PD-L1 antibody.

Example 28: Synergistic Effect of Anti-CD137 Antibody and Anti-PD-1 Antibody in Mouse Tumor Model Based on the results of Example 27, mAb8v (a variant of mAb8 lacking GT amino acids at the N-terminus) was further assessed for synergy with an anti-PD-1 antibody. To assess this effect, Balb/c mice with tumors derived from injection of orthotopic EMT6 breast cancer cells were generated. Specifically, 200,000 EMT6 cells were injected into the mammary fat pads of mice. Treatment was initiated 7 days after injection. mAb8v was intraperitoneally injected alone or in combination with a murine anti-PD-1 antibody (RMP1-14) following a staggered dosing regimen. Specifically, mice received 25 g of mAb8v on days 0, 3, 6 and 9, and 200 µg RMP1-14 on days 10, 13 and 16.

Figure 36A:
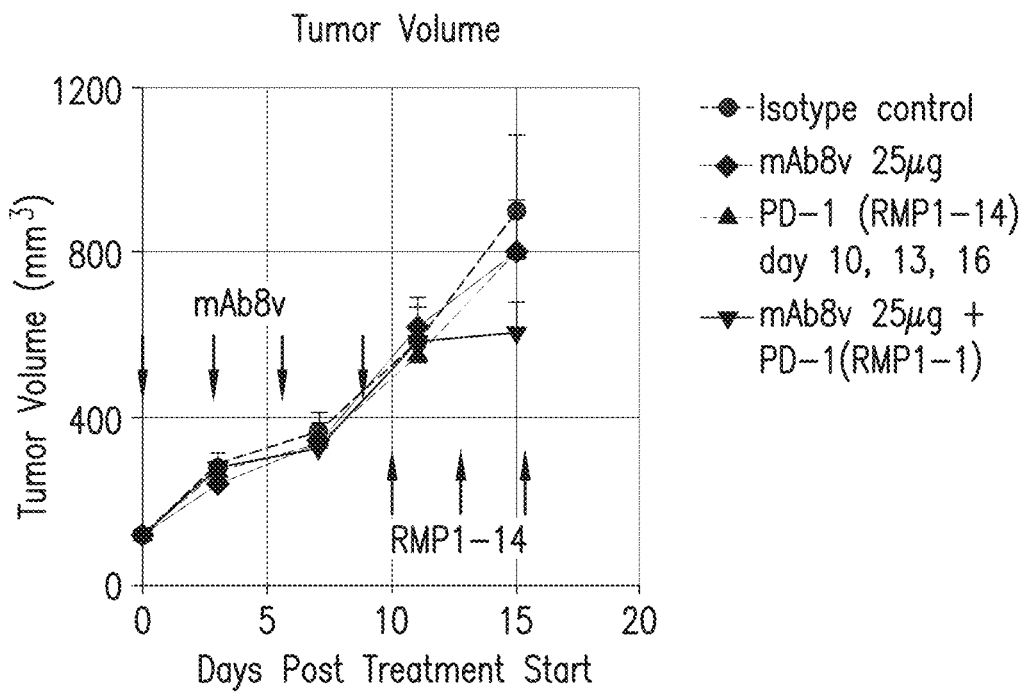
FIGS. 36A-36C provide graphs depicting the in vivo anti-tumor efficacy of an anti-CD137 antibody (mAb8v) in combination with an immune checkpoint-targeting antibody (anti-PD-1; RMP1-14) in mice with tumors derived from mouse EMT6 mammary (breast) cancer cells. Mean tumor volumes are shown in 36A, percent survival is shown in 36B, and individual tumor volumes are shown in 36C.
Figure 36B:
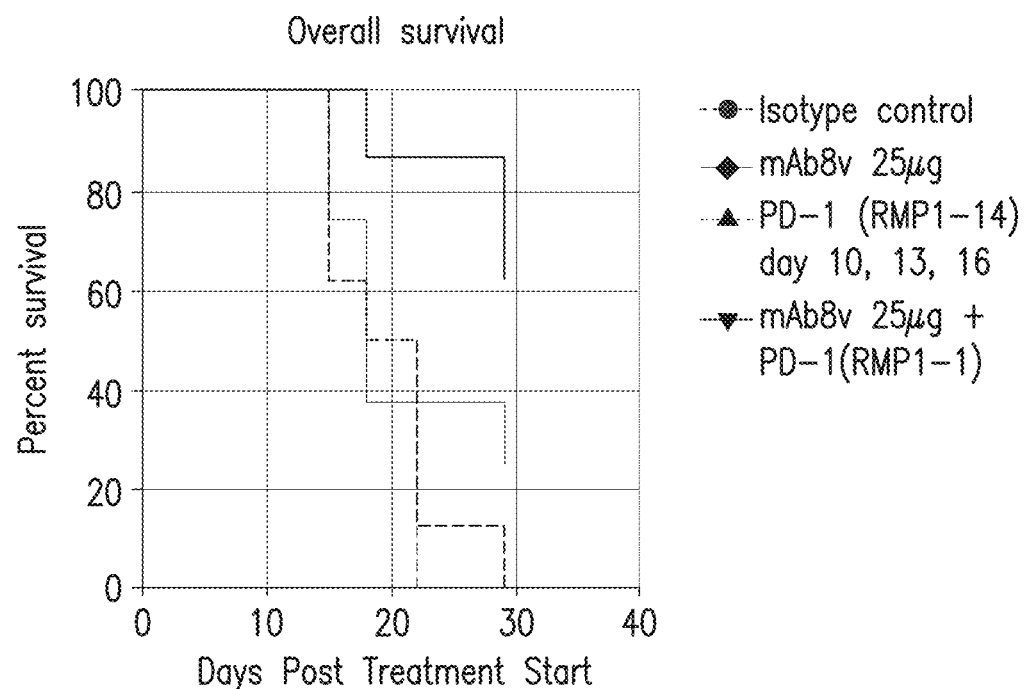
Figure 36C:
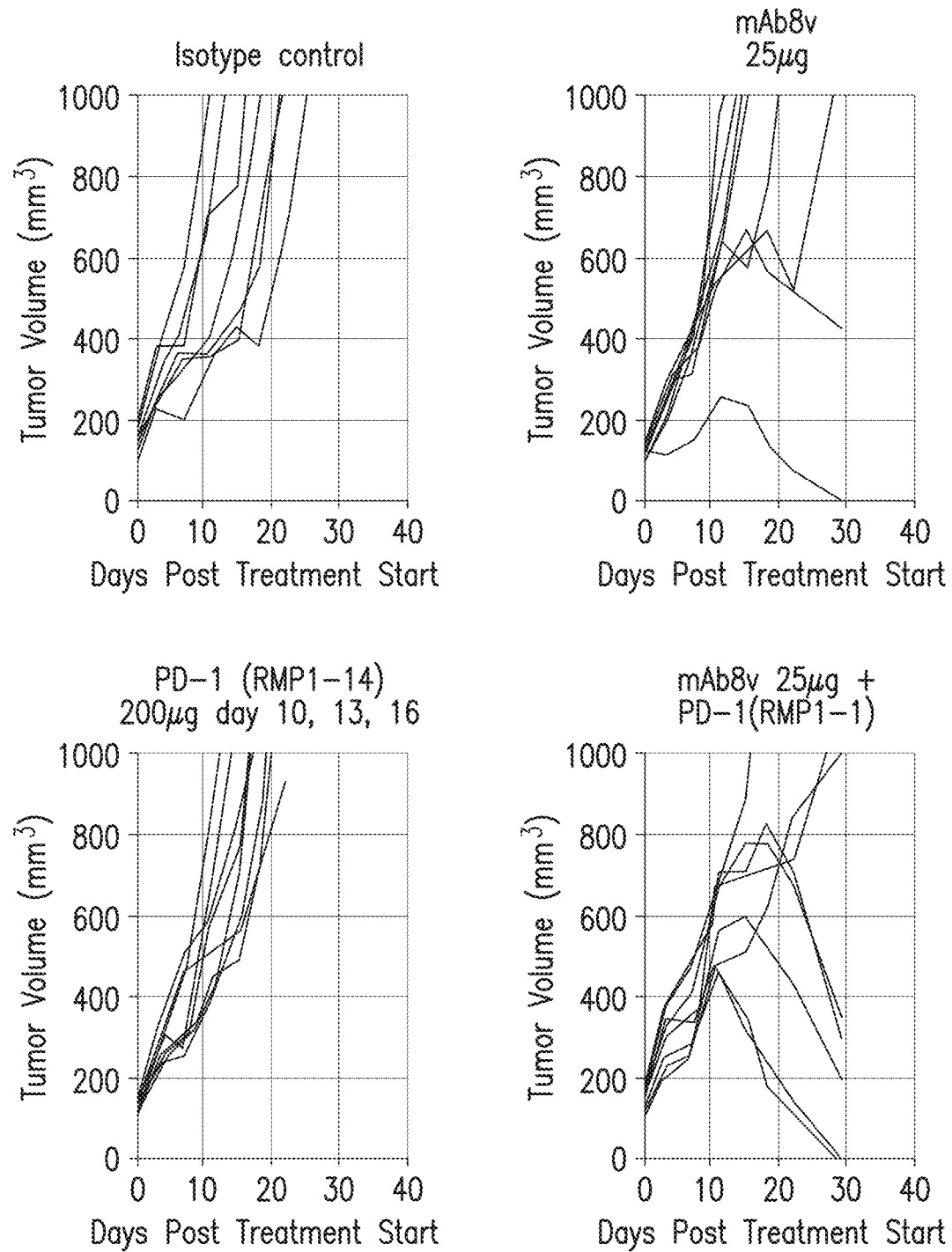

Mean tumor volume, percent survival, and individual tumor volumes of treated mice are shown in FIG. 36A, FIG. 36B, and FIG. 36C, respectively. These results indicated that treatment with an agonistic anti-CD137 antibody (mAb8v) in combination with an antagonistic anti-PD-1 antibody (RMP1-14) resulted in a synergistic anti-tumor effect, reducing tumor volume and increasing mouse survival to a greater extent than either treatment with mAb8v or RMP1-14 alone.

Figure 38A:
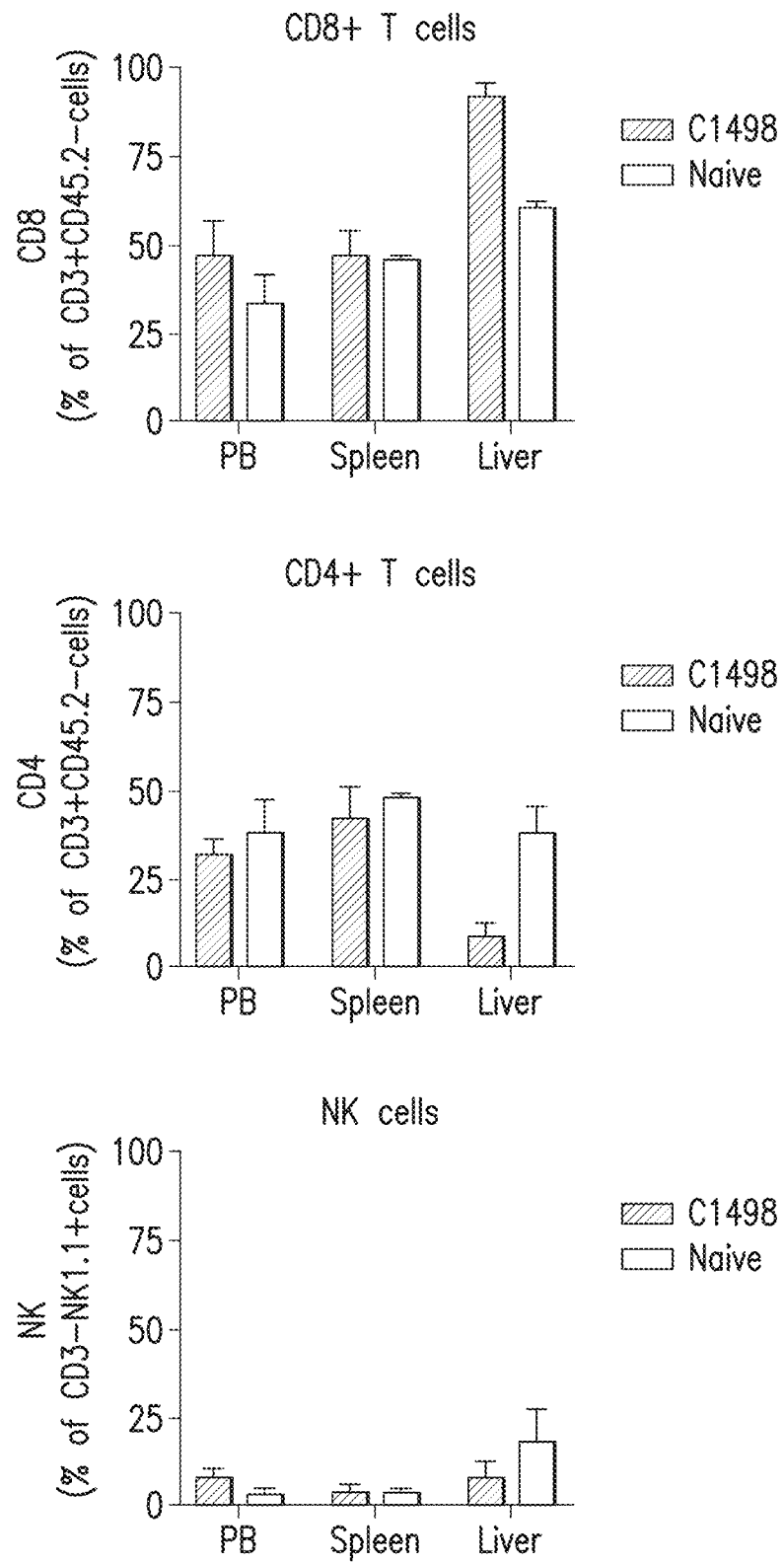
FIGS. 38A-38B shows graphs depicting cellular immunophenotyping analyses of peripheral blood, spleens, and livers from mice having C1488 tumors or from tumor-free (naïve) mice.

Example 29: Synergistic Effect of Anti-CD137 Antibody and Anti-PD-L1 Antibody in Mouse AML Systemic Disease Tumor Model Based on the results of Examples 27 and 28, mAb8v was further assessed for synergy with an anti-PD-L1 antibody. To assess this effect, C57BL/6-CD45.1 mice (C57BL/7 congenic strain carrying the pan leukocyte marker Ptprc$^a$) were injected with C1498 acute myeloid leukemia (AML) cells (ATCC #TIB-49). Specifically, 1×10$^6$ C1498 cells were injected intravenously into mice. Treatment was initiated 7 days after injection of C1498 cells. After 8 days post-cell injection, blood samples were collected for immunophenotyping analyses shown in FIGS. 38A and 38B. mAb8 was injected intraperitoneally alone or in combination with an anti-PD-L1 antibody. Specifically, mice received 25 µg mAb8 on days 0, 7, 14, 21 and 28 and 200 µg anti-PD-L1 antibody either on days 0, 3 and 6, or on days 7, 10 and 13.

Figure 37A:
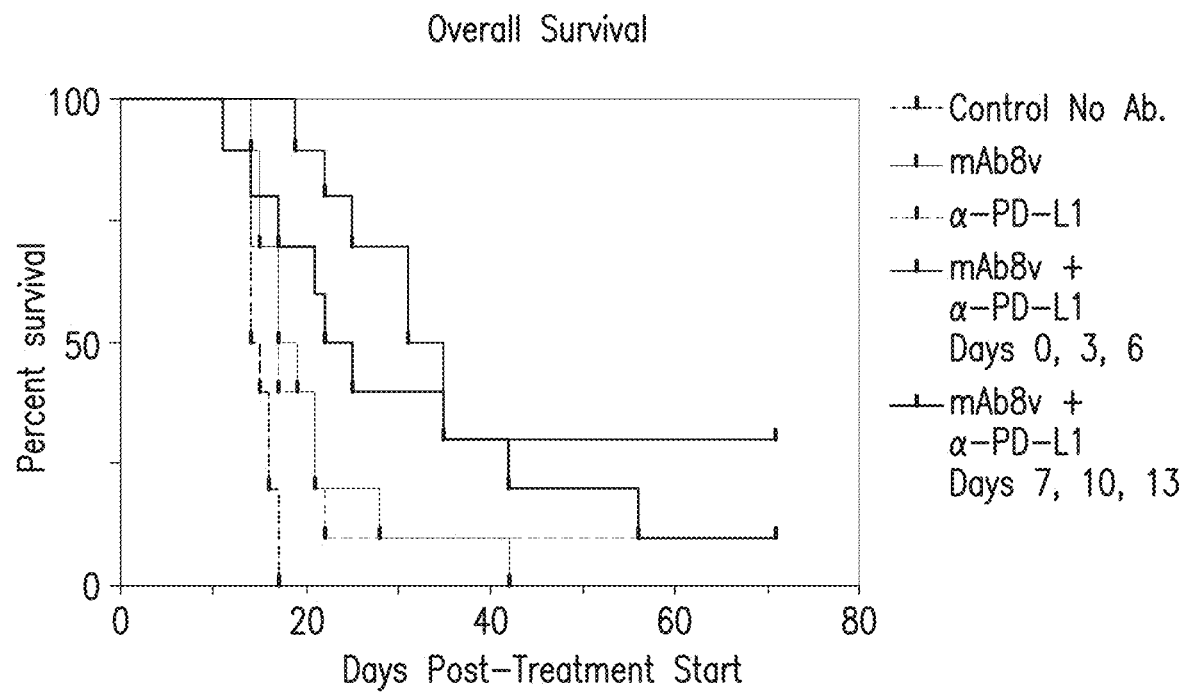
FIGS. 37A-37B provide graphs depicting the in vivo anti-tumor efficacy of an anti-CD137 antibody (mAb1) in combination with an immune checkpoint-targeting antibody (anti-PD-L1) in mice with tumors derived from C1498 acute myeloid leukemia (AML) cells. Percent survival is shown in 37A, and percent survival after re-challenge of surviving mice from FIG. 37A with C1498 cells is shown 37B.
Figure 37B:
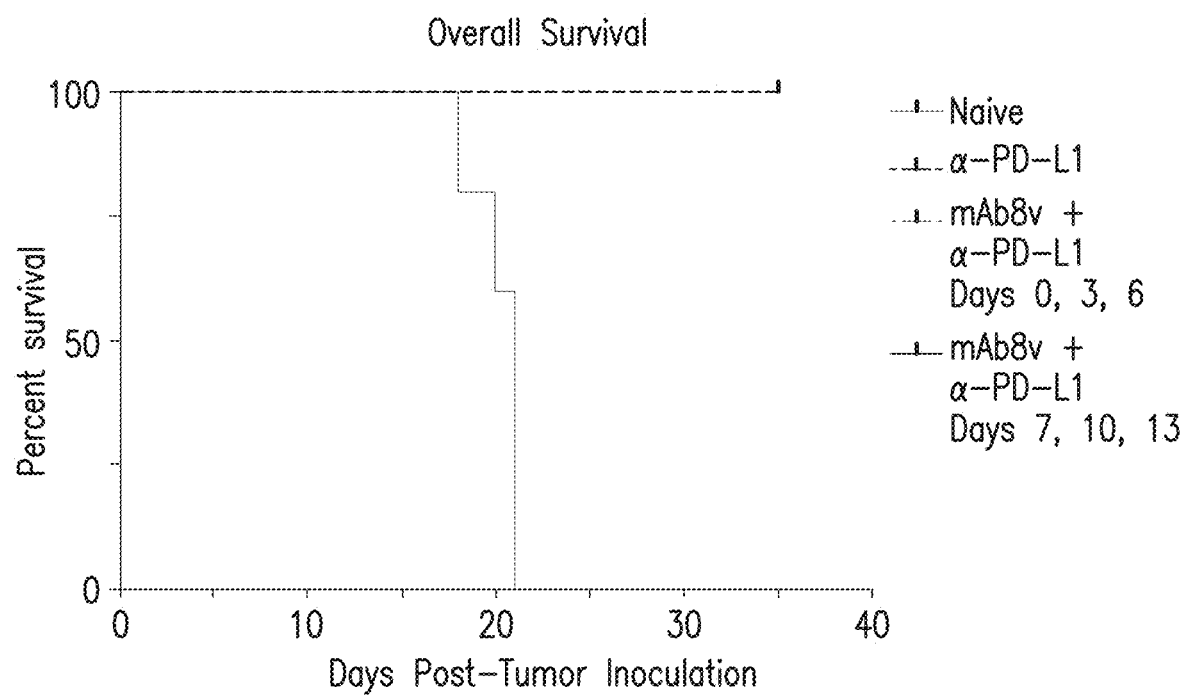

Overall survival (percent survival) of mice in each treatment group is shown in FIG. 37A. Mice with no detectable circulating C1498 cells at day 70 were considered cured and subsequently re-challenged with C1498 cells. Specifically, cured mice and naïve C57BL/6 mice were injected intravenously with 1×10$^6$ C1498 cells. After 35 days post-injection of C1498 cells, none of the previously cured mice formed tumors and survived re-challenge. In contrast, all of the naïve mice that were injected with the same cells progressively formed tumors, resulting in death of all naïve mice around 20 days post-cell injection (FIG. 37B). Therefore, all mice that were considered cured rejected C1498 tumors, indicating that mAb8 can induce long-term protective memory immunity.

Figure 38B:
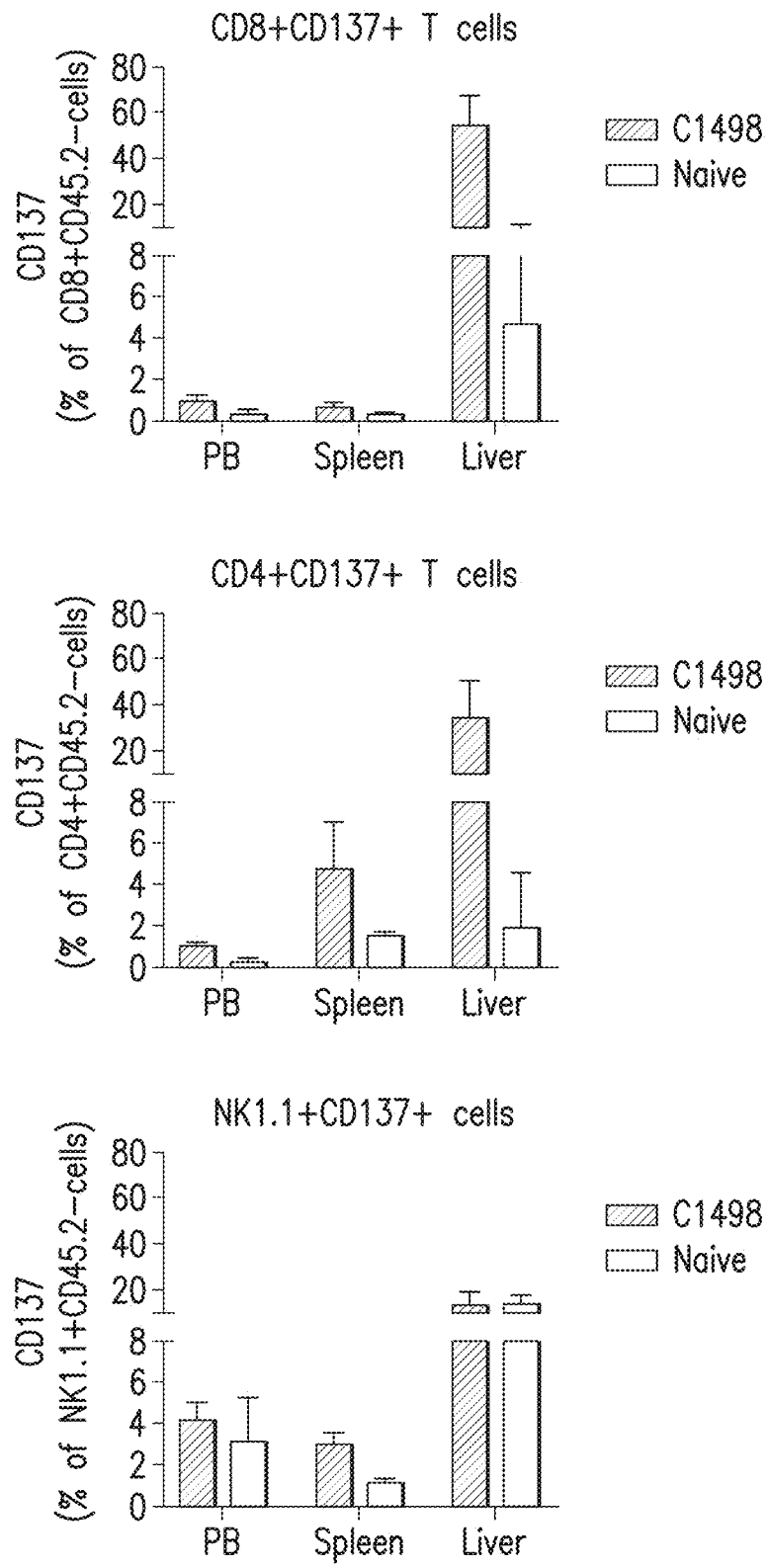

C1498 AML manifests itself as a systemic disease involving multiple tissues including liver, bone marrow, peripheral blood and to a much lesser extent spleen and kidneys. The number of CD8+, CD4+ T cells and NK cells expressing CD137 in naïve mice or mice injected with C1498 cells was determined to better understand the expression of the target in tissues with high tumor burden (liver) vs low or no tumor burden (spleen). As shown in FIG. 38B, the number of CD8+CD137+ and CD4+CD137+ T cells in the liver of mice injected with C1498 cells was higher than in naïve mice and higher than spleens indicating that activated T cells in the tumor microenvironment upregulate CD137 expression. No change in the number of CD137+ NK cells was observed in the livers of injected vs. naïve mice.

Example 30: Synergistic Effect of Anti-CD137 Antibody and Anti-PD-1 Antibody in Mouse Pancreatic Tumor Model Based on the results of Examples 27-29, the ability of an anti-CD137 antibody to synergize with an anti-PD-1 antibody was further assessed in a mouse pancreatic tumor model. To assess this effect, the pancreas of C57BL/6 mice were orthotopically injected with Panc02 mouse pancreatic ductal adenocarcinoma cells. Treatment was initiated 7 days after injection. mAb8v (a variant of mAb8 lacking GT amino acids at the N-terminus) was intraperitoneally injected alone or in combination with a murine anti-PD-1 antibody (RMP1-14) following either a simultaneous or a staggered dosing regimen. Specifically, for the staggered dosing regimen, mice received 25 µg of mAb8v on days 0, 3, 6 and 9, and 200 µg RMP1-14 on days 10, 13 and 16.

Figure 39A:
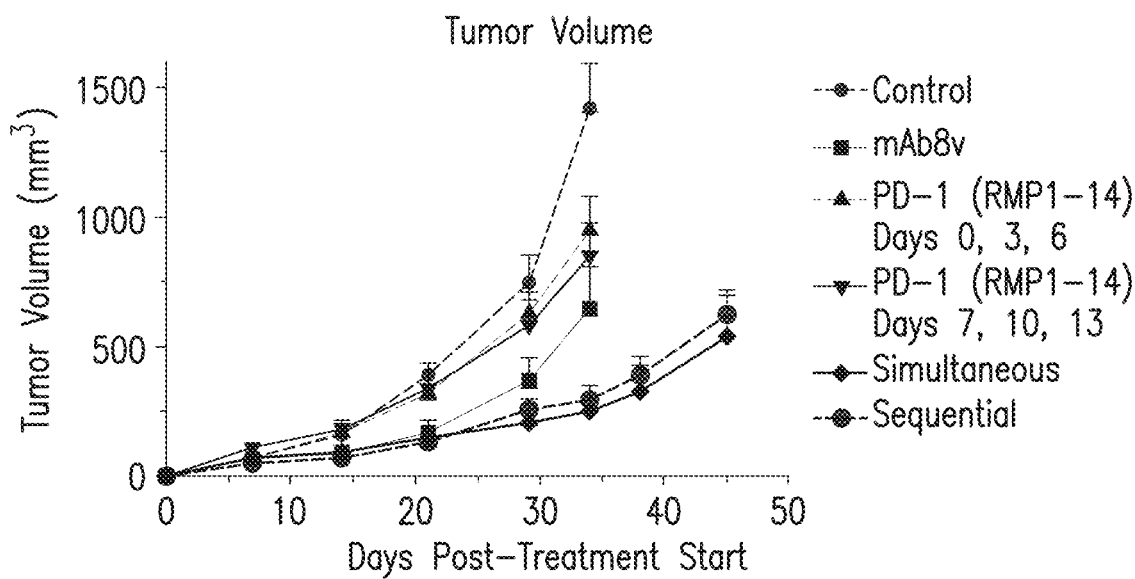
FIGS. 39A-39C provide graphs depicting the in vivo anti-tumor efficacy of an anti-CD137 antibody (mAb8v) in combination with an immune checkpoint-targeting antibody (anti-PD-1; RMP1-14) in mice with tumors derived from mouse Panc02 pancreatic ductal adenocarcinoma cells. Mean tumor volumes are shown in 39A, percent survival is shown in 39B, and individual tumor volumes are shown in 39C.
Figure 39B:
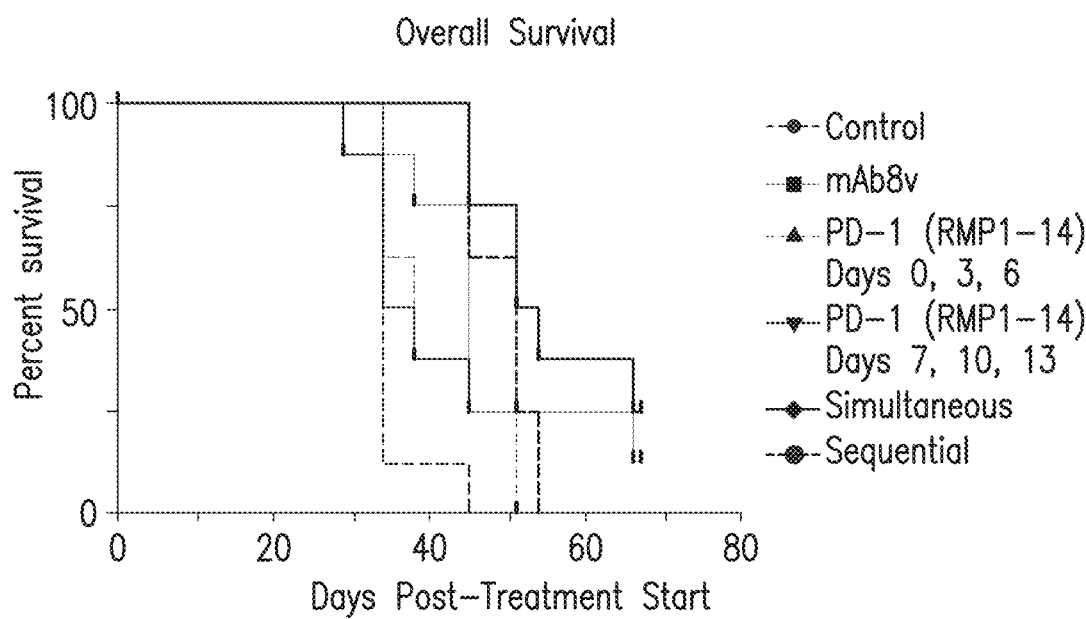
Figures 1, 39C:
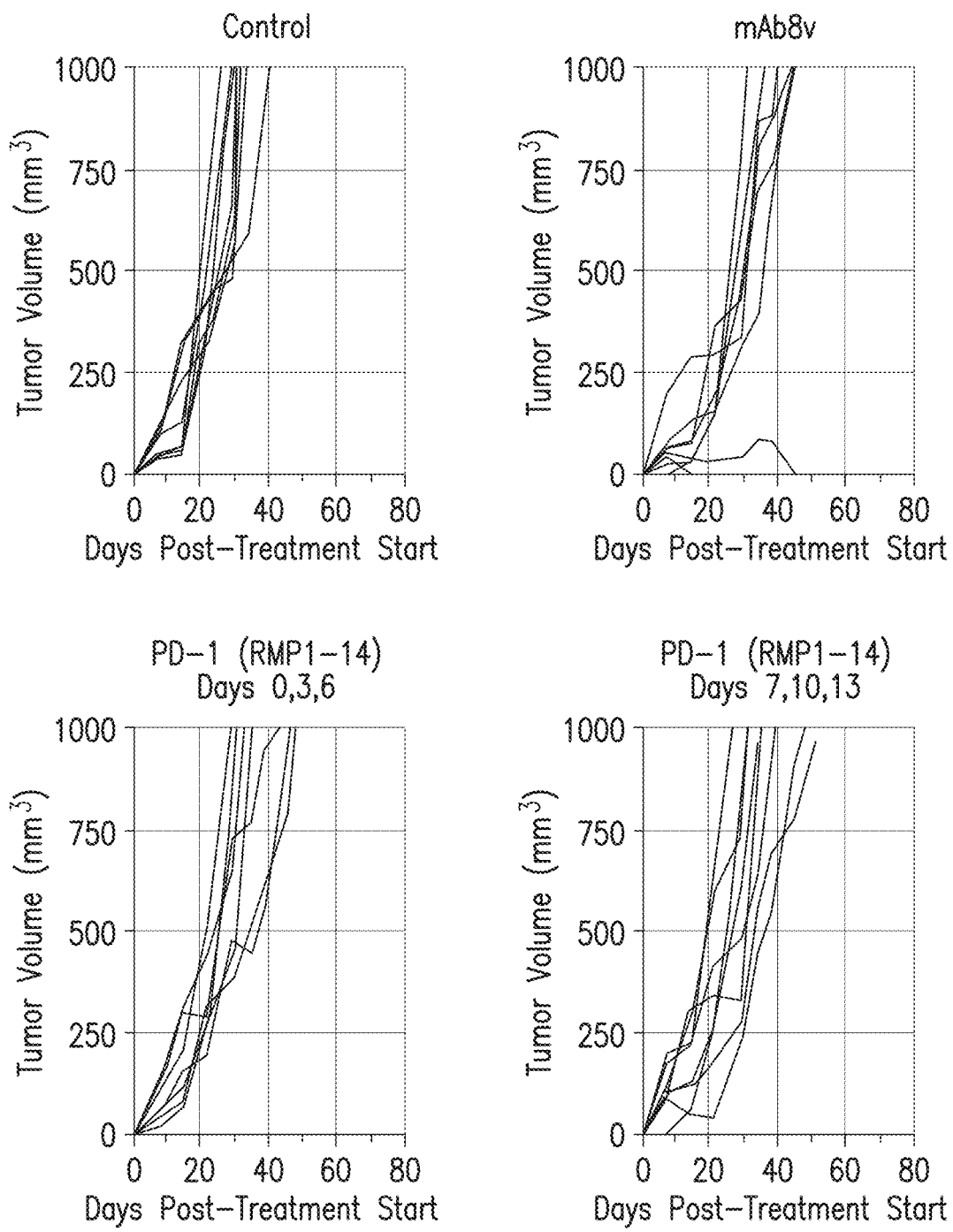
Figures 2, 39C:
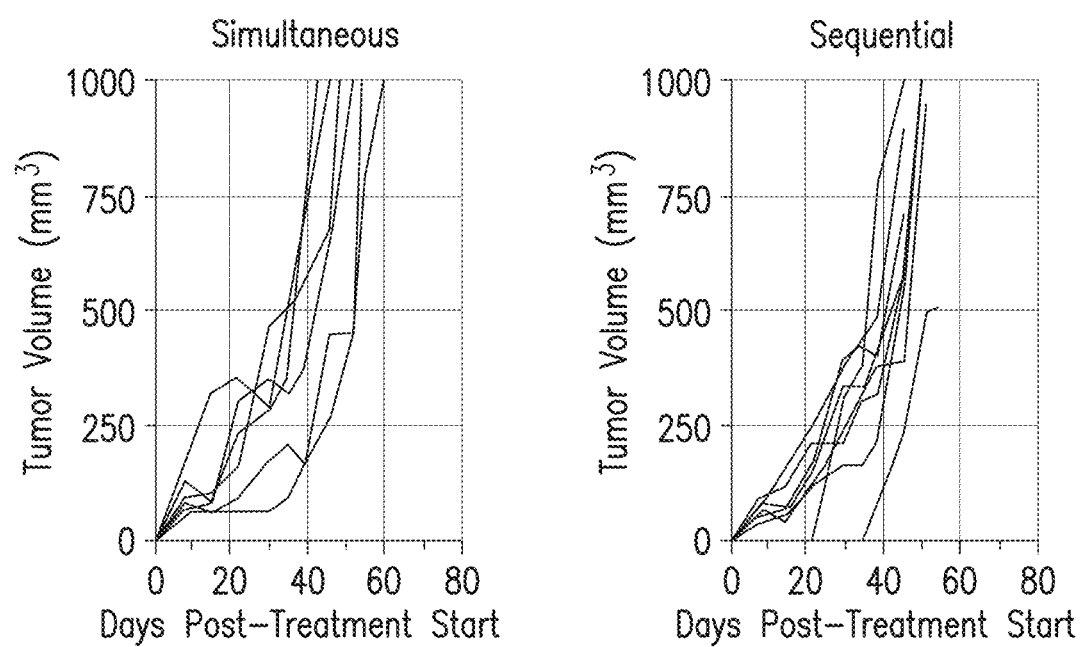
FIG. 2 provides a schematic showing the results of mAb1 CDRH3 alanine scanning, as measured by binding affinity ($K_D$) to human or mouse CD137.

Mean tumor volume, percent survival, and individual tumor volumes of treated mice are shown in FIG. 39A, FIG. 39B, and FIG. 39C, respectively. These results indicated that treatment with an agonistic anti-CD137 antibody (mAb8v) in combination with an antagonistic anti-PD-1 antibody (RMP1-14) resulted in a synergistic anti-tumor effect, reducing tumor volume and increasing mouse survival to a greater extent than either treatment with mAb8v or RMP1-14 alone.

Example 31: Effect of Anti-CD137 Antibody and Anti-PD-1 Antibody Combination on Cytokine Induction In Vivo Based on the results from Example 21, the effect of anti-CD137 antibody alone and in combination with anti-PD-1 antibody on cytokine induction in vivo was determined.

Figure 40A:
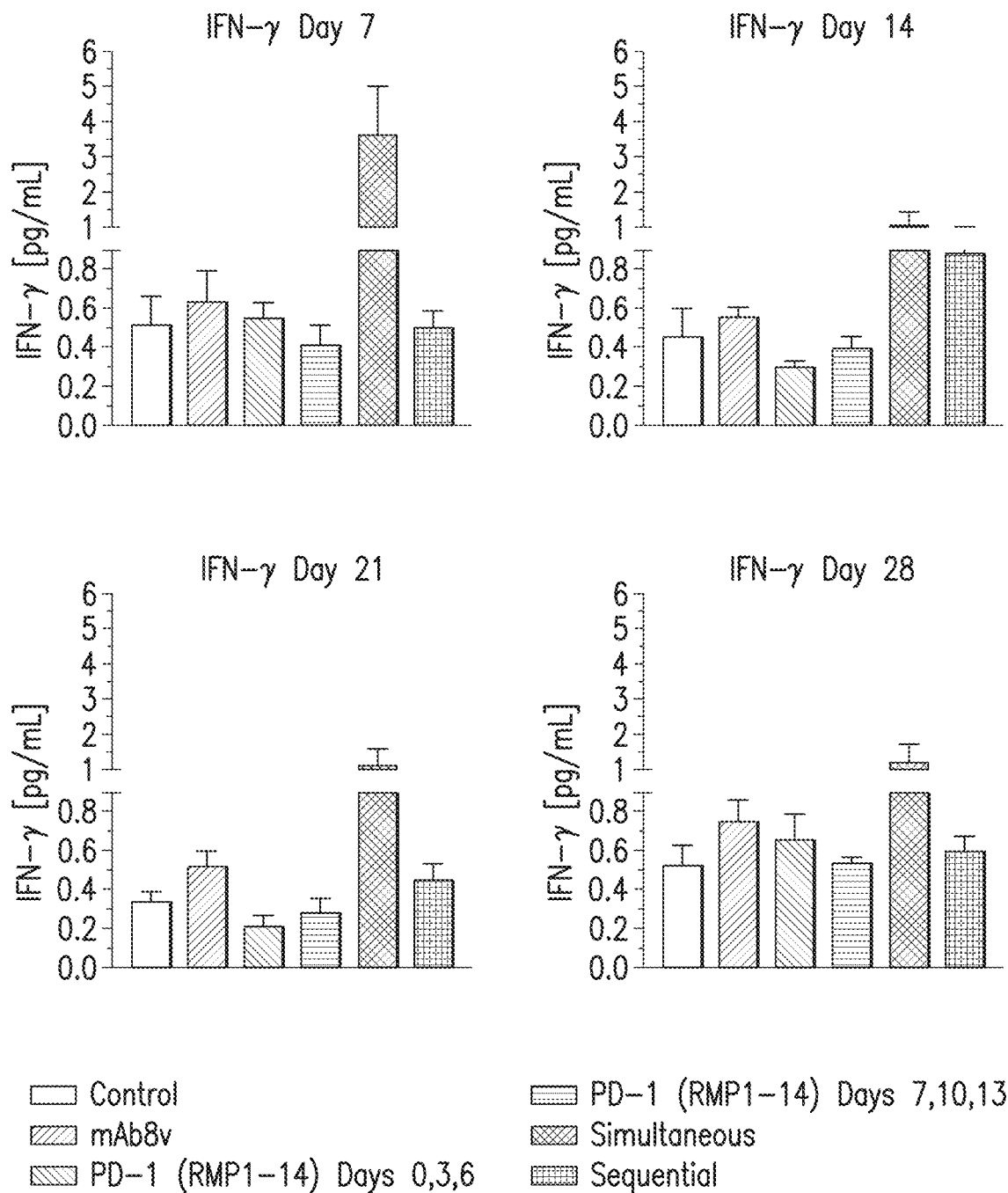
FIGS. 40A-40C provide bar graphs depicting the quantification of cytokines IFNγ (FIG. 40A), TNFα (FIG. 40B) and IL-2 (FIG. 40C) produced in vivo over time following administration of an anti-CD137 antibody (mAb8v) alone or in combination with an immune checkpoint-targeting antibody (anti-PD-1; RMP1-14). Cytokine concentrations are shown as amount (pg) of cytokine per mL of mouse blood.
Figure 40B:
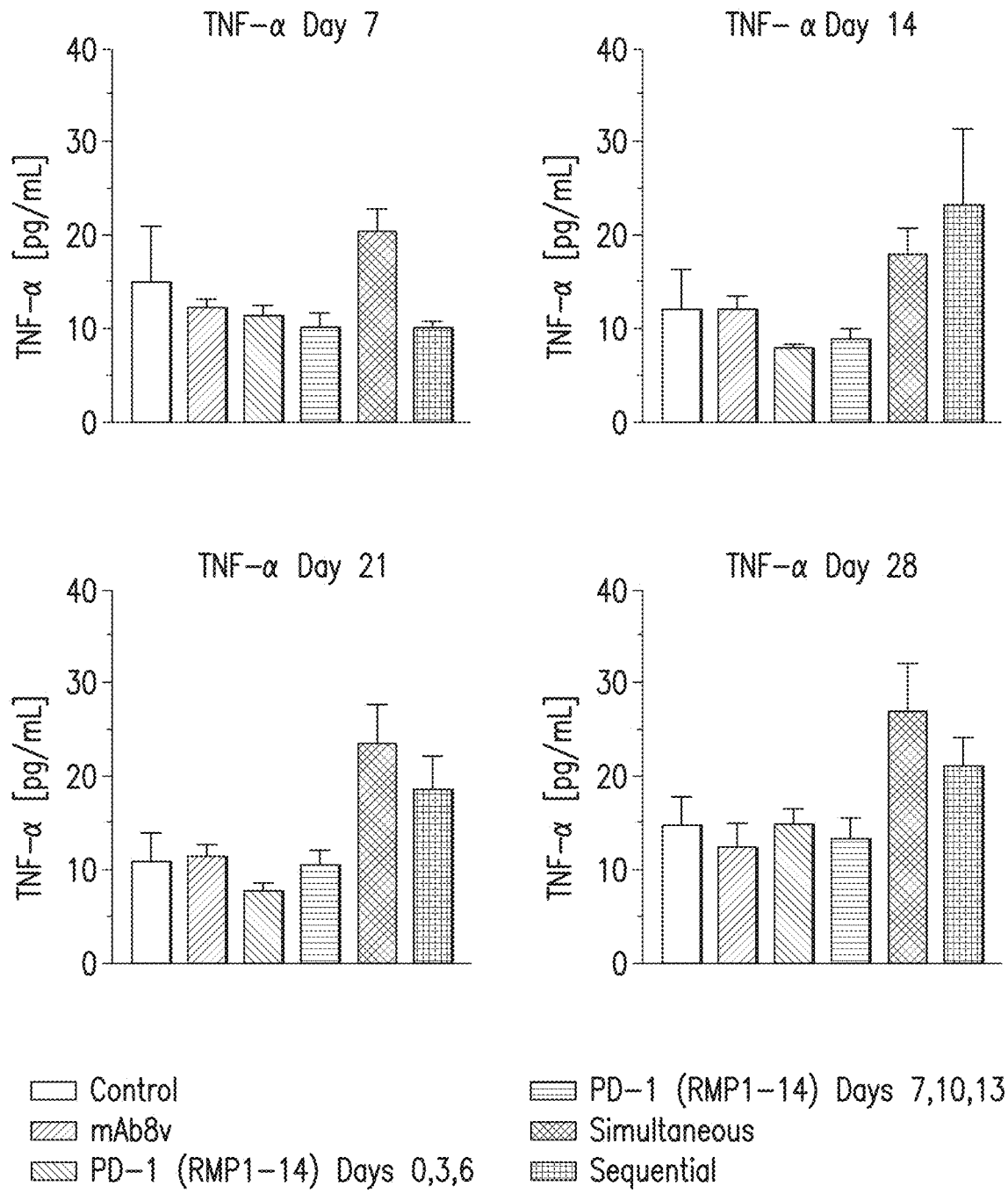
Figure 40C:
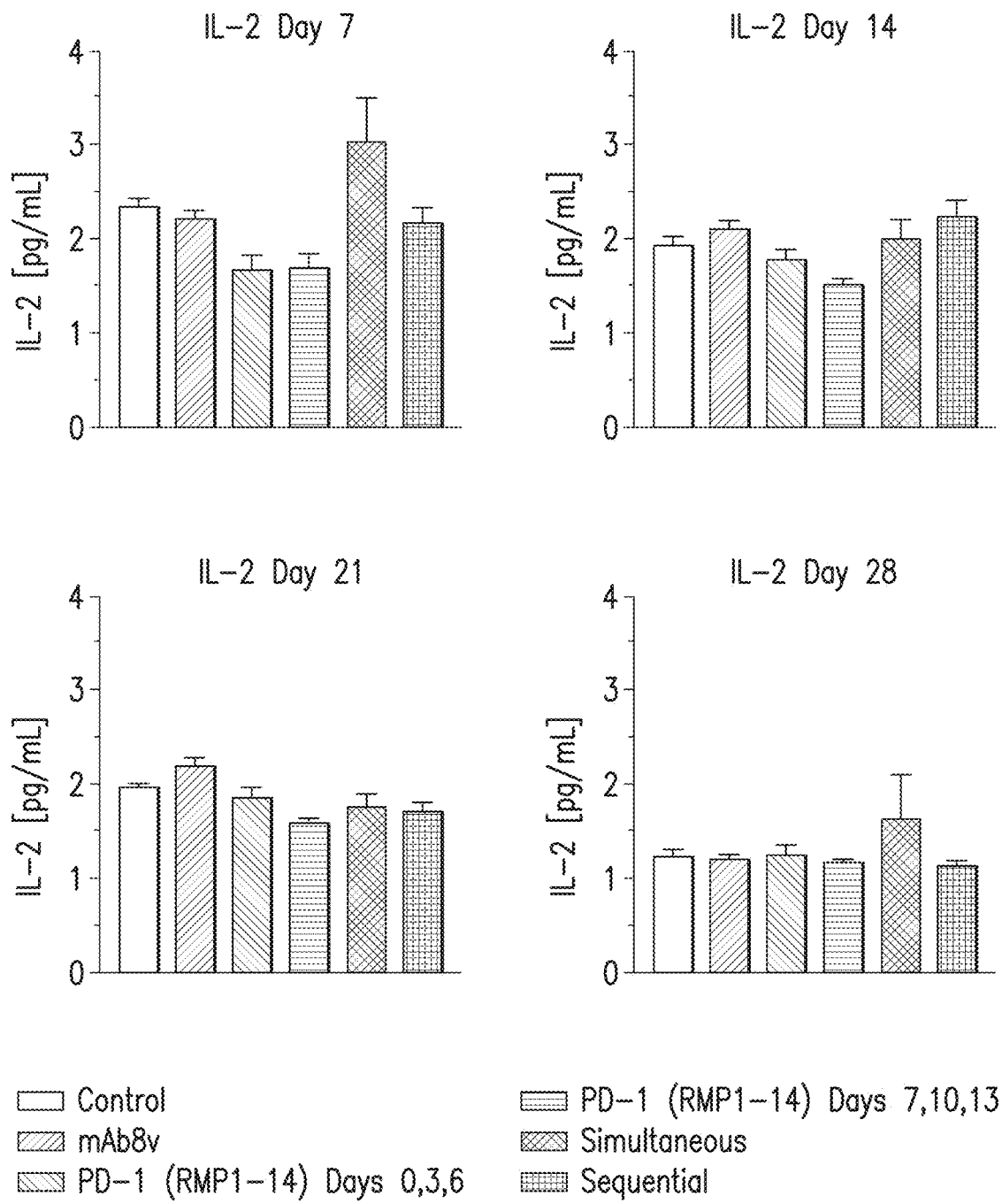

Briefly, mice were treated with mAb8v alone or in combination (simultaneously or sequentially) with anti-PD-1 (RMP1-14) as described in Example 30. The amount of circulating IL-2, IFNγ, and TNFα from the plasma of treated mice was assessed by Luminex kits (Luminex Corporation, Austin, Tex.) following the manufacturer's instructions. FIGS. 40A-40C show the amount of each cytokine level 7, 14, 21 and 28 days after treatment with mAb8v alone, RMP1-14 alone, or in combination. These results show that the administration of mAb8v and RMP1-14 in combination increase induction of IFNγ and TNFα to a greater extent than the administration of either antibody alone. These results indicated that treatment with an agonistic anti-CD137 antibody (mAb8v) in combination with an antagonistic anti-PD-1 antibody (RMP1-14) resulted in a synergistic effect on the induction of cytokines in mice, thereby indicating, without being bound or limited by theory, that agonism of CD137 combined with blockade of the PD-1/PD-L1/PD-L2 synergistically enhances a component of the protective anti-tumor response.

TABLE 3

ANTIBODY COMBINATION TABLE

| | | $V_H$ CDR | | | $V_L$ CDR | | |
|---|---|---|---|---|---|---|---|
| $V_H$ | $V_L$ | CDR1 | CDR2 | CDR3 | CDR1 | CDR2 | CDR3 |
| 4 | 6 | 48 | 56 | 68 | 69 | 78 | 89 |
| 4 | 28 | 48 | 56 | 68 | 70 | 79 | 90 |
| 4 | 30 | 48 | 56 | 68 | 71 | 80 | 91 |
| 4 | 32 | 48 | 56 | 68 | 72 | 81 | 92 |
| 4 | 34 | 48 | 56 | 68 | 73 | 82 | 91 |

TABLE 3-continued

ANTIBODY COMBINATION TABLE

| | | V_H CDR | | | V_L CDR | | |
|---|---|---|---|---|---|---|---|
| V_H | V_L | CDR1 | CDR2 | CDR3 | CDR1 | CDR2 | CDR3 |
| 4 | 36 | 48 | 56 | 68 | 74 | 83 | 93 |
| 4 | 38 | 48 | 56 | 68 | 75 | 84 | 91 |
| 4 | 40 | 48 | 56 | 68 | 74 | 85 | 94 |
| 4 | 42 | 48 | 56 | 68 | 76 | 86 | 95 |
| 4 | 44 | 48 | 56 | 68 | 77 | 87 | 93 |
| 4 | 46 | 48 | 56 | 68 | 69 | 88 | 90 |
| 4 | 105 | 48 | 56 | 68 | 109 | 110 | 92 |
| 8 | 6 | 49 | 57 | 68 | 69 | 78 | 89 |
| 10 | 6 | 49 | 58 | 68 | 69 | 78 | 89 |
| 12 | 6 | 49 | 59 | 68 | 69 | 78 | 89 |
| 14 | 6 | 49 | 60 | 68 | 69 | 78 | 89 |
| 16 | 6 | 50 | 61 | 68 | 69 | 78 | 89 |
| 18 | 6 | 50 | 58 | 68 | 69 | 78 | 89 |
| 20 | 6 | 51 | 62 | 68 | 69 | 78 | 89 |
| 22 | 6 | 52 | 63 | 68 | 69 | 78 | 89 |
| 24 | 6 | 50 | 64 | 68 | 69 | 78 | 89 |
| 26 | 6 | 50 | 65 | 68 | 69 | 78 | 89 |
| 101 | 6 | 51 | 108 | 68 | 69 | 78 | 89 |
| 103 | 6 | 107 | 56 | 68 | 69 | 78 | 89 |
| 8 | 28 | 49 | 57 | 68 | 70 | 79 | 90 |
| 8 | 30 | 49 | 57 | 68 | 71 | 80 | 91 |
| 8 | 32 | 49 | 57 | 68 | 72 | 81 | 92 |
| 8 | 34 | 49 | 57 | 68 | 73 | 82 | 91 |
| 8 | 36 | 49 | 57 | 68 | 74 | 83 | 93 |
| 8 | 38 | 49 | 57 | 68 | 75 | 84 | 91 |
| 8 | 40 | 49 | 57 | 68 | 74 | 85 | 94 |
| 8 | 42 | 49 | 57 | 68 | 76 | 86 | 95 |
| 8 | 44 | 49 | 57 | 68 | 77 | 87 | 93 |
| 8 | 46 | 49 | 57 | 68 | 69 | 88 | 90 |
| 8 | 105 | 49 | 57 | 68 | 109 | 110 | 92 |
| 10 | 28 | 49 | 58 | 68 | 70 | 79 | 90 |
| 10 | 30 | 49 | 58 | 68 | 71 | 80 | 91 |
| 10 | 32 | 49 | 58 | 68 | 72 | 81 | 92 |
| 10 | 34 | 49 | 58 | 68 | 73 | 82 | 91 |
| 10 | 36 | 49 | 58 | 68 | 74 | 83 | 93 |
| 10 | 38 | 49 | 58 | 68 | 75 | 84 | 91 |
| 10 | 40 | 49 | 58 | 68 | 74 | 85 | 94 |
| 10 | 42 | 49 | 58 | 68 | 76 | 86 | 95 |
| 10 | 44 | 49 | 58 | 68 | 77 | 87 | 93 |
| 10 | 46 | 49 | 58 | 68 | 69 | 88 | 90 |
| 10 | 105 | 49 | 58 | 68 | 109 | 110 | 92 |
| 12 | 28 | 49 | 59 | 68 | 70 | 79 | 90 |
| 12 | 30 | 49 | 59 | 68 | 71 | 80 | 91 |
| 12 | 32 | 49 | 59 | 68 | 72 | 81 | 92 |
| 12 | 34 | 49 | 59 | 68 | 73 | 82 | 91 |
| 12 | 36 | 49 | 59 | 68 | 74 | 83 | 93 |
| 12 | 38 | 49 | 59 | 68 | 75 | 84 | 91 |
| 12 | 40 | 49 | 59 | 68 | 74 | 85 | 94 |
| 12 | 42 | 49 | 59 | 68 | 76 | 86 | 95 |
| 12 | 44 | 49 | 59 | 68 | 77 | 87 | 93 |
| 12 | 46 | 49 | 59 | 68 | 69 | 88 | 90 |
| 12 | 105 | 49 | 59 | 68 | 109 | 110 | 92 |
| 14 | 28 | 49 | 60 | 68 | 70 | 79 | 90 |
| 14 | 30 | 49 | 60 | 68 | 71 | 80 | 91 |
| 14 | 32 | 49 | 60 | 68 | 72 | 81 | 92 |
| 14 | 34 | 49 | 60 | 68 | 73 | 82 | 91 |
| 14 | 36 | 49 | 60 | 68 | 74 | 83 | 93 |
| 14 | 38 | 49 | 60 | 68 | 75 | 84 | 91 |
| 14 | 40 | 49 | 60 | 68 | 74 | 85 | 94 |
| 14 | 42 | 49 | 60 | 68 | 76 | 86 | 95 |
| 14 | 44 | 49 | 60 | 68 | 77 | 87 | 93 |
| 14 | 46 | 49 | 60 | 68 | 69 | 88 | 90 |
| 14 | 105 | 49 | 60 | 68 | 109 | 110 | 92 |
| 16 | 28 | 50 | 61 | 68 | 70 | 79 | 90 |
| 16 | 30 | 50 | 61 | 68 | 71 | 80 | 91 |
| 16 | 32 | 50 | 61 | 68 | 72 | 81 | 92 |
| 16 | 34 | 50 | 61 | 68 | 73 | 82 | 91 |
| 16 | 36 | 50 | 61 | 68 | 74 | 83 | 93 |
| 16 | 38 | 50 | 61 | 68 | 75 | 84 | 91 |
| 16 | 40 | 50 | 61 | 68 | 74 | 85 | 94 |
| 16 | 42 | 50 | 61 | 68 | 76 | 86 | 95 |
| 16 | 44 | 50 | 61 | 68 | 77 | 87 | 93 |
| 16 | 46 | 50 | 61 | 68 | 69 | 88 | 90 |
| 16 | 105 | 50 | 61 | 68 | 109 | 110 | 92 |
| 18 | 28 | 50 | 58 | 68 | 70 | 79 | 90 |
| 18 | 30 | 50 | 58 | 68 | 71 | 80 | 91 |
| 18 | 32 | 50 | 58 | 68 | 72 | 81 | 92 |
| 18 | 34 | 50 | 58 | 68 | 73 | 82 | 91 |
| 18 | 36 | 50 | 58 | 68 | 74 | 83 | 93 |
| 18 | 38 | 50 | 58 | 68 | 75 | 84 | 91 |
| 18 | 40 | 50 | 58 | 68 | 74 | 85 | 94 |
| 18 | 42 | 50 | 58 | 68 | 76 | 86 | 95 |
| 18 | 44 | 50 | 58 | 68 | 77 | 87 | 93 |
| 18 | 46 | 50 | 58 | 68 | 69 | 88 | 90 |
| 18 | 105 | 50 | 58 | 68 | 109 | 110 | 92 |
| 20 | 28 | 51 | 62 | 68 | 70 | 79 | 90 |
| 20 | 30 | 51 | 62 | 68 | 71 | 80 | 91 |
| 20 | 32 | 51 | 62 | 68 | 72 | 81 | 92 |
| 20 | 34 | 51 | 62 | 68 | 73 | 82 | 91 |
| 20 | 36 | 51 | 62 | 68 | 74 | 83 | 93 |
| 20 | 38 | 51 | 62 | 68 | 75 | 84 | 91 |
| 20 | 40 | 51 | 62 | 68 | 74 | 85 | 94 |
| 20 | 42 | 51 | 62 | 68 | 76 | 86 | 95 |
| 20 | 44 | 51 | 62 | 68 | 77 | 87 | 93 |
| 20 | 46 | 51 | 62 | 68 | 69 | 88 | 90 |
| 20 | 105 | 51 | 62 | 68 | 109 | 110 | 92 |
| 22 | 28 | 52 | 63 | 68 | 70 | 79 | 90 |
| 22 | 30 | 52 | 63 | 68 | 71 | 80 | 91 |
| 22 | 32 | 52 | 63 | 68 | 72 | 81 | 92 |
| 22 | 34 | 52 | 63 | 68 | 73 | 82 | 91 |
| 22 | 36 | 52 | 63 | 68 | 74 | 83 | 93 |
| 22 | 38 | 52 | 63 | 68 | 75 | 84 | 91 |
| 22 | 40 | 52 | 63 | 68 | 74 | 85 | 94 |
| 22 | 42 | 52 | 63 | 68 | 76 | 86 | 95 |
| 22 | 44 | 52 | 63 | 68 | 77 | 87 | 93 |
| 22 | 46 | 52 | 63 | 68 | 69 | 88 | 90 |
| 22 | 105 | 52 | 63 | 68 | 109 | 110 | 92 |
| 24 | 28 | 50 | 64 | 68 | 70 | 79 | 90 |
| 24 | 30 | 50 | 64 | 68 | 71 | 80 | 91 |
| 24 | 32 | 50 | 64 | 68 | 72 | 81 | 92 |
| 24 | 34 | 50 | 64 | 68 | 73 | 82 | 91 |
| 24 | 36 | 50 | 64 | 68 | 74 | 83 | 93 |
| 24 | 38 | 50 | 64 | 68 | 75 | 84 | 91 |
| 24 | 40 | 50 | 64 | 68 | 74 | 85 | 94 |
| 24 | 42 | 50 | 64 | 68 | 76 | 86 | 95 |
| 24 | 44 | 50 | 64 | 68 | 77 | 87 | 93 |
| 24 | 46 | 50 | 64 | 68 | 69 | 88 | 90 |
| 24 | 105 | 50 | 64 | 68 | 109 | 110 | 92 |
| 26 | 28 | 50 | 65 | 68 | 70 | 79 | 90 |
| 26 | 30 | 50 | 65 | 68 | 71 | 80 | 91 |
| 26 | 32 | 50 | 65 | 68 | 72 | 81 | 92 |
| 26 | 34 | 50 | 65 | 68 | 73 | 82 | 91 |
| 26 | 36 | 50 | 65 | 68 | 74 | 83 | 93 |
| 26 | 38 | 50 | 65 | 68 | 75 | 84 | 91 |
| 26 | 40 | 50 | 65 | 68 | 74 | 85 | 94 |
| 26 | 42 | 50 | 65 | 68 | 76 | 86 | 95 |
| 26 | 44 | 50 | 65 | 68 | 77 | 87 | 93 |
| 26 | 46 | 50 | 65 | 68 | 69 | 88 | 90 |
| 26 | 105 | 50 | 65 | 68 | 109 | 110 | 92 |
| 101 | 28 | 51 | 108 | 68 | 70 | 79 | 90 |
| 101 | 30 | 51 | 108 | 68 | 71 | 80 | 91 |
| 101 | 32 | 51 | 108 | 68 | 72 | 81 | 92 |
| 101 | 34 | 51 | 108 | 68 | 73 | 82 | 91 |
| 101 | 36 | 51 | 108 | 68 | 74 | 83 | 93 |
| 101 | 38 | 51 | 108 | 68 | 75 | 84 | 91 |
| 101 | 40 | 51 | 108 | 68 | 74 | 85 | 94 |
| 101 | 42 | 51 | 108 | 68 | 76 | 86 | 95 |
| 101 | 44 | 51 | 108 | 68 | 77 | 87 | 93 |
| 101 | 46 | 51 | 108 | 68 | 69 | 88 | 90 |
| 101 | 105 | 51 | 108 | 68 | 109 | 110 | 92 |
| 103 | 28 | 107 | 56 | 68 | 70 | 79 | 90 |
| 103 | 30 | 107 | 56 | 68 | 71 | 80 | 91 |
| 103 | 32 | 107 | 56 | 68 | 72 | 81 | 92 |
| 103 | 34 | 107 | 56 | 68 | 73 | 82 | 91 |
| 103 | 36 | 107 | 56 | 68 | 74 | 83 | 93 |

TABLE 3-continued

ANTIBODY COMBINATION TABLE

| | | V_H CDR | | | V_L CDR | | |
|---|---|---|---|---|---|---|---|
| V_H | V_L | CDR1 | CDR2 | CDR3 | CDR1 | CDR2 | CDR3 |
| 103 | 38 | 107 | 56 | 68 | 75 | 84 | 91 |
| 103 | 40 | 107 | 56 | 68 | 74 | 85 | 94 |
| 103 | 42 | 107 | 56 | 68 | 76 | 86 | 95 |
| 103 | 44 | 107 | 56 | 68 | 77 | 87 | 93 |
| 103 | 46 | 107 | 56 | 68 | 69 | 88 | 90 |
| 103 | 105 | 107 | 56 | 68 | 109 | 110 | 92 |

TABLE 4

SEQUENCE LISTING

| SEQ ID NO | Description | Sequence |
|---|---|---|
| 1 | Human IgG1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 2 | Human IgG4 mutant (S228P/C-terminal K truncation) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| 3 | Human CD137 (Accession # NP_001552) | MGNSCYNIVATLLLVLNFERTRSLQDPCSNCPAGTFCDNNRNQICSPCPPNSFSSAGGQRTCDICRQCKGVFRTRKECSSTSNAECDCTPGFHCLGAGCSMCEQDCKQGQELTKKGCKDCCFGTFNDQKRGICRPWTNCSLDGKSVLVNGTKERDVVCGPSPADLSPGASSVTPPAPAREPGHSPQIISFFLALTSTALLFLLFFLTLRFSVVKRGRKKLLYIFKQPFMRPVQTTQEEDGCSCRFPEEEEGGCEL |
| 4 | V_H1 amino acid sequence | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKDSPFLLDDYYYYYMDVWGKGTTVTVSS |
| 5 | V_H1 nucleic acid sequence | GAAGTGCAATTATTGGAATCCGGCGGCGGTTTAGTTCAGCCAGGTGGCTCTTTGAGGCTGAGTTGCGCAGCCTCTGGATTCACTTTTAGTTCGTATGCAATGTCGTGGGTTCGCCAGGCGCCCGGTAAGGGTCTGGAGTGGGTGAGTGCTATTTCCGGCTCTGGCGGATCTACCTATTACGCCGACTCTGTGAAAGGTCGTTTTACCATAAGCCGCGACAATTCTAAGAATACTTTATATCTTCAAATGAATTCGCTGCGGGCAGAAGACACGGCCGTCTATTACTGCGCAAAGGACTCACCTTTTCTATTAGACGACTACTACTACTACTACTACATGGACGTATGGGGCAAGGGTACAACTGTCACCGTCTCCTCAGCTAGC |
| 6 | V_L1 amino acid sequence | DIQMTQSPSSVSASVGDRVTITCRASQGISSWLAWYQQKPGKAPKLLIYAASSLQSGVPSRFSGSGSGTDFTLTISSLQPEDFATYYCQQGHLFPITFGGGTKVEIK |
| 7 | V_L1 nucleic acid sequence | GATATTCAGATGACACAGAGCCCGTCATCAGTAAGTGCAAGCGTCGGAGATCGGGTTACAATAACATGTCGTGCCTCGCAAGGAATTTCCTCCTGGTTGGCCTGGTATCAGCAGAAACCTGGCAAAGCCCCCAAATTACTAATTTATGCCGCAAGCTCTCTGCAATCGGGTGTTCCTTCGCGGTTTTCTGGCTCTGGAAGTGGCACCGACTTCACGCTTACTATCTCTAGCCTTCAGCGGAGGATTTTGCTACCTACTACTGCCAACAAGGCCATTTATTCCCTATTACCTTTGGGGGCGGTACAAAAGTCGAGATCAAGCGTACG |
| 8 | V_H2 amino acid sequence | EVQLLESGGGLVQPGGSLRLSCAASGFTFNYYAMSWVRQAPGKGLEWVSAIDGSGDNTTYADSVKGRFTISRDNSKNTLYLQMNSLRAEDTAVYYCAKDSPFLLDDYYYYYMDVWGKGTTVTVSS |

TABLE 4-continued

SEQUENCE LISTING

| SEQ ID NO | Description | Sequence |
|---|---|---|
| 9 | V$_H$2 nucleic acid sequence | GAAGTGCAATTATTGGAATCCGGCGGCGGTTTAGTTCAGCC<br>AGGTGGCTCTTTGAGGCTGAGTTGCGCAGCCTCTGGATTCA<br>CCTTTAACTATTACGCAATGTCTTGGGTTCGCCAGGCGCCC<br>GGTAAGGGTCTGGAGTGGGTGTCTGCAATCGATGGTTCTGG<br>TGATAACACTACTTACGCCGACTCTGTGAAAGGTCGTTTTA<br>CCATAAGCCGCGACAATTCTAAGAATACTTTATATCTTCAA<br>ATGAATTCGCTGCGGGCAGAAGACACGGCCGTCTATTACTG<br>CGCAAAGGACTCACCTTTTCTATTAGACGACTACTACTACT<br>ACTACTACATGGACGTATGGGGCAAGGGTACAACTGTCACC<br>GTCTCCTCAGCTAGC |
| 10 | V$_H$3 amino acid sequence | EVQLLESGGGLVQPGGSLRLSCAASGFTFNYYAMSWVRQAP<br>GKGLEWVAAISGSGDGTYYADSVKGRFTISRDNSKNTLYLQ<br>MNSLRAEDTAVYYCAKDSPFLLDDYYYYYMDVWGKGTTVT<br>VSS |
| 11 | V$_H$3 nucleic acid sequence | GAAGTGCAATTATTGGAATCCGGCGGCGGTTTAGTTCAGCC<br>AGGTGGCTCTTTGAGGCTGAGTTGCGCAGCCTCTGGATTCA<br>CCTTTAACTATTACGCAATGTCTTGGGTTCGCCAGGCGCCC<br>GGTAAGGGTCTGGAGTGGGTGGCAGCAATCTCTGGTTCTGG<br>TGATGGTACTTACTACGCCGACTCTGTGAAAGGTCGTTTTA<br>CCATAAGCCGCGACAATTCTAAGAATACTTTATATCTTCAA<br>ATGAATTCGCTGCGGGCAGAAGACACGGCCGTCTATTACTG<br>CGCAAAGGACTCACCTTTTCTATTAGACGACTACTACTACT<br>ACTACTACATGGACGTATGGGGCAAGGGTACAACTGTCACC<br>GTCTCCTCAGCTAGC |
| 12 | V$_H$4 amino acid sequence | EVQLLESGGGLVQPGGSLRLSCAASGFTFNYYAMSWVRQAP<br>GKGLEWVSAISGSGDSTYYADSVKGRFTISRDNSKNTLYLQ<br>MNSLRAEDTAVYYCAKDSPFLLDDYYYYYMDVWGKGTTVT<br>VSS |
| 13 | V$_H$4 nucleic acid sequence | GAAGTGCAATTATTGGAATCCGGCGGCGGTTTAGTTCAGCC<br>AGGTGGCTCTTTGAGGCTGAGTTGCGCAGCCTCTGGATTCA<br>CCTTTAACTATTACGCAATGTCTTGGGTTCGCCAGGCGCCC<br>GGTAAGGGTCTGGAGTGGGTGTCTGCAATCTCTGGTTCTGG<br>TGATTCTACTTACTACGCCGACTCTGTGAAAGGTCGTTTTA<br>CCATAAGCCGCGACAATTCTAAGAATACTTTATATCTTCAA<br>ATGAATTCGCTGCGGGCAGAAGACACGGCCGTCTATTACTG<br>CGCAAAGGACTCACCTTTTCTATTAGACGACTACTACTACT<br>ACTACTACATGGACGTATGGGGCAAGGGTACAACTGTCACC<br>GTCTCCTCAGCTAGC |
| 14 | V$_H$5 amino acid sequence | EVQLLESGGGLVQPGGSLRLSCAASGFTFNYYAMSWVRQAP<br>GKGLEWVAAISGGGDATYYADSVKGRFTISRDNSKNTLYLQ<br>MNSLRAEDTAVYYCAKDSPFLLDDYYYYYMDVWGKGTTVT<br>VSS |
| 15 | V$_H$5 nucleic acid sequence | GAAGTGCAATTATTGGAATCCGGCGGCGGTTTAGTTCAGCC<br>AGGTGGCTCTTTGAGGCTGAGTTGCGCAGCCTCTGGATTCA<br>CCTTTAACTATTACGCAATGTCTTGGGTTCGCCAGGCGCCC<br>GGTAAGGGTCTGGAGTGGGTGGCAGCAATCTCTGGTGGTGG<br>TGATGCAACTTACTACGCCGACTCTGTGAAAGGTCGTTTTA<br>CCATAAGCCGCGACAATTCTAAGAATACTTTATATCTTCAA<br>ATGAATTCGCTGCGGGCAGAAGACACGGCCGTCTATTACTG<br>CGCAAAGGACTCACCTTTTCTATTAGACGACTACTACTACT<br>ACTACTACATGGACGTATGGGGCAAGGGTACAACTGTCACC<br>GTCTCCTCAGCTAGC |
| 16 | V$_H$6 amino acid sequence | EVQLLESGGGLVQPGGSLRLSCAASGFTFYGYAMSWVRQAP<br>GKGLEWVSSISGSGDVTYYADSVKGRFTISRDNSKNTLYLQ<br>MNSLRAEDTAVYYCAKDSPFLLDDYYYYYMDVWGKGTTVT<br>VSS |
| 17 | V$_H$6 nucleic acid sequence | GAAGTGCAATTATTGGAATCCGGCGGCGGTTTAGTTCAGCC<br>AGGTGGCTCTTTGAGGCTGAGTTGCGCAGCCTCTGGATTCA<br>CCTTTTATGGTTACGCAATGTCTTGGGTTCGCCAGGCGCCC<br>GGTAAGGGTCTGGAGTGGGTGTCTTCTATCTCTGGTTCTGG<br>TGATGTTACTTACTACGCCGACTCTGTGAAAGGTCGTTTTA<br>CCATAAGCCGCGACAATTCTAAGAATACTTTATATCTTCAA<br>ATGAATTCGCTGCGGGCAGAAGACACGGCCGTCTATTACTG<br>CGCAAAGGACTCACCTTTTCTATTAGACGACTACTACTACT<br>ACTACTACATGGACGTATGGGGCAAGGGTACAACTGTCACC<br>GTCTCCTCAGCTAGC |

TABLE 4-continued

SEQUENCE LISTING

| SEQ ID NO | Description | Sequence |
|---|---|---|
| 18 | $V_H7$ amino acid sequence | EVQLLESGGGLVQPGGSLRLSCAASGFTFYGYAMSWVRQAP GKGLEWVAAISGSGDGTYYADSVKGRFTISRDNSKNTLYLQ MNSLRAEDTAVYYCAKDSPFLLDDYYYYYMDVWGKGTTVT VSS |
| 19 | $V_H7$ nucleic acid sequence | GAAGTGCAATTATTGGAATCCGGCGGCGGTTTAGTTCAGCC AGGTGGCTCTTTGAGGCTGAGTTGCGCAGCCTCTGGATTCA CCTTTTATGGTTACGCAATGTCTTGGGTTCGCCAGGCGCCC GGTAAGGGTCTGGAGTGGGTGGCAGCAATCTCTGGTTCTGG TGATGGTACTTACTACGCCGACTCTGTGAAAGGTCGTTTTA CCATAAGCCGCGACAATTCTAAGAATACTTTATATCTTCAA ATGAATTCGCTGCGGGCAGAAGACACGGCCGTCTATTACTG CGCAAAGGACTCACCTTTTCTATTAGACGACTACTACTACT ACTACTACATGGACGTATGGGGCAAGGGTACAACTGTCACC GTCTCCTCAGCTAGC |
| 20 | $V_H8$ amino acid sequence | EVQLLESGGGLVQPGGSLRLSCAASGFTFRNYAMSWVRQAP GKGLEWVSAISGFGESTYYADSVKGRFTISRDNSKNTLYLQ MNSLRAEDTAVYYCAKDSPFLLDDYYYYYMDVWGKGTTVT VSS |
| 21 | $V_H8$ nucleic acid sequence | GAAGTGCAATTATTGGAATCCGGCGGCGGTTTAGTTCAGCC AGGTGGCTCTTTGAGGCTGAGTTGCGCAGCCTCTGGATTCA CCTTTTAGAAACTACGCAATGTCTTGGGTTCGCCAGGCGCCC GGTAAGGGTCTGGAGTGGGTGTCTGCAATCTCTGGTTTTGG TGAATCTACTTACTACGCCGACTCTGTGAAAGGTCGTTTTA CCATAAGCCGCGACAATTCTAAGAATACTTTATATCTTCAA ATGAATTCGCTGCGGGCAGAAGACACGGCCGTCTATTACTG CGCAAAGGACTCACCTTTTCTATTAGACGACTACTACTACT ACTACTACATGGACGTATGGGGCAAGGGTACAACTGTCACC GTCTCCTCAGCTAGC |
| 22 | $V_H9$ amino acid sequence | EVQLLESGGGLVQPGGSLRLSCAASGFTFNYYAMNWVRQAP GKGLEWVAAISGSGGRTYYADSVKGRFTISRDNSKNTLYLQ MNSLRAEDTAVYYCAKDSPFLLDDYYYYYMDVWGKGTTVT VSS |
| 23 | $V_H9$ nucleic acid sequence | GAAGTGCAATTATTGGAATCCGGCGGCGGTTTAGTTCAGCC AGGTGGCTCTTTGAGGCTGAGTTGCGCAGCCTCTGGATTCA CCTTTTAACTATTACGCAATGAACTGGGTTCGCCAGGCGCCC GGTAAGGGTCTGGAGTGGGTGGCAGCAATCTCTGGTTCTGG TGGTAGAACTTACTACGCCGACTCTGTGAAAGGTCGTTTTA CCATAAGCCGCGACAATTCTAAGAATACTTTATATCTTCAA ATGAATTCGCTGCGGGCAGAAGACACGGCCGTCTATTACTG CGCAAAGGACTCACCTTTTCTATTAGACGACTACTACTACT ACTACTACATGGACGTATGGGGCAAGGGTACAACTGTCACC GTCTCCTCAGCTAGC |
| 24 | $V_H10$ amino acid sequence | EVQLLESGGGLVQPGGSLRLSCAASGFTFYGYAMSWVRQAP GKGLEWVSAISGSGGNTSYADSVKGRFTISRDNSKNTLYLQ MNSLRAEDTAVYYCAKDSPFLLDDYYYYYMDVWGKGTTVT VSS |
| 25 | $V_H10$ nucleic acid sequence | GAAGTGCAATTATTGGAATCCGGCGGCGGTTTAGTTCAGCC AGGTGGCTCTTTGAGGCTGAGTTGCGCAGCCTCTGGATTCA CCTTTTATGGTTACGCAATGTCTTGGGTTCGCCAGGCGCCC GGTAAGGGTCTGGAGTGGGTGTCTGCAATCTCTGGTTCTGG TGGTAACACTTCTTACGCCGACTCTGTGAAAGGTCGTTTTA CCATAAGCCGCGACAATTCTAAGAATACTTTATATCTTCAA ATGAATTCGCTGCGGGCAGAAGACACGGCCGTCTATTACTG CGCAAAGGACTCACCTTTTCTATTAGACGACTACTACTACT ACTACTACATGGACGTATGGGGCAAGGGTACAACTGTCACC GTCTCCTCAGCTAGC |
| 26 | $V_H11$ amino acid sequence | EVQLLESGGGLVQPGGSLRLSCAASGFTFYGYAMSWVRQAP GKGLEWVAAISGSGDSTYYADSVKGRFTISRDNSKNTLYLQ MNSLRAEDTAVYYCAKDSPFLLDDYYYYYMDVWGKGTTVT VSS |
| 27 | $V_H11$ nucleic acid sequence | GAAGTGCAATTATTGGAATCCGGCGGCGGTTTAGTTCAGCC AGGTGGCTCTTTGAGGCTGAGTTGCGCAGCCTCTGGATTCA CCTTTTATGGTTACGCAATGTCTTGGGTTCGCCAGGCGCCC GGTAAGGGTCTGGAGTGGGTGGCAGCAATCTCTGGTTCTGG TGATTCTACTTACTACGCCGACTCTGTGAAAGGTCGTTTTA |

TABLE 4-continued

SEQUENCE LISTING

| SEQ ID NO | Description | Sequence |
|---|---|---|
| | | CCATAAGCCGCGACAATTCTAAGAATACTTTATATCTTCAA ATGAATTCGCTGCGGGCAGAAGACACGGCCGTCTATTACTG CGCAAAGGACTCACCTTTTCTATTAGACGACTACTACTACT ACTACTACATGGACGTATGGGGCAAGGGTACAACTGTCACC GTCTCCTCAGCTAGC |
| 28 | V$_L$2 amino acid sequence | DIQMTQSPSTLSASVGDRVTITCRASQNIHNWLAWYQQKPG KAPKLLIYKASGLESGVPSRFSGSGSGTEFTLTISSLQPDD FATYYCQQGDRFPLTFGGGTKVEIK |
| 29 | V$_L$2 nucleic acid sequence | GACATCCAGATGACCCAGTCTCCTTCCACCCTGTCTGCATC TGTAGGAGACAGAGTCACCATCACTTGCCGGGCCAGTCAGA ATATTCATAACTGGTTGGCCTGGTATCAGCAAAAACCAGGG AAAGCCCCTAAGCTCCTGATCTATAAGGCGTCTGGTTTGGA AAGTGGGGTCCCATCAAGATTCAGCGGCAGTGGATCTGGGA CAGAGTTCACTCTCACCATCAGCAGCCTGCAACCTGATGAT TTTGCAACTTACTACTGTCAACAGGGTGACAGATTCCCTCT CACTTTCGGCGGAGGGACCAAGGTGGAGATCAAACGTACG |
| 30 | V$_L$3 amino acid sequence | DIQMTQSPSILSASVGDRVTITCRASQSISRWLAWYQQKPG KPPKLLIFKASALESGVPSRFSGSGYGTDFTLTISNLQPED FATYFCQQGNSFPLTFGGGTKVDIK |
| 31 | V$_L$3 nucleic acid sequence | GACATCCAGATGACCCAGTCTCCTTCCATCCTGTCTGCATC TGTAGGAGACAGAGTCACTATCACTTGCCGGGCCAGTCAGA GTATCAGTAGGTGGTTGGCCTGGTATCAGCAGAAGCCAGGG AAACCCCCTAAACTCCTGATCTTTAAGGCGTCTGCTTTAGA AAGTGGGGTCCCATCGAGGTTCAGCGGCAGTGGATATGGGA CAGATTTCACTCTCACCATCAGCAACCTGCAGCCTGAAGAC TTTGCAACTTACTTCTGTCAACAGGGTAATAGTTTCCCTCT CACTTTCGGCGGAGGGACCAAAGTGGATATCAAACGTACG |
| 32 | V$_L$4 amino acid sequence | DIQMTQSPSTLSASVGDRVTITCRASQNIDIWLAWYQWKPG KAPKLLIYKASGLETGVPSRFSGSGSGTEFTLTISSLQPED FATYYCQQGNQFPLTFGQGTRLEIK |
| 33 | V$_L$4 nucleic acid sequence | GACATCCAGATGACCCAGTCTCCTTCCACCCTGTCTGCATC TGTAGGAGACAGAGTCACCATCACTTGCCGGGCCAGTCAGA ATATTGATATCTGGTTGGCCTGGTATCAGTGGAAACCAGGG AAGGCCCCTAAACTCCTGATCTATAAGGCGTCTGGTTTAGA AACTGGGGTCCCTTCAAGGTTCAGCGGCAGTGGATCTGGGA CAGAATTCACTCTCACTATCAGCAGCCTGCAGCCAGAGGAT TTTGCGACTTACTATTGTCAACAGGGTAACCAGTTCCCGCT CACCTTCGGCCAAGGGACACGACTGGAGATTAAACGTACG |
| 34 | V$_L$5 amino acid sequence | DIQMTQSPSSLSASVGDRVTITCRASQSIGRWLAWYQQKPG KAPKLLIFKASALEVGVPSRFSGSGSGTDFTLTISSLQPED FATYYCQQGNSFPLTFGGGTKVDIK |
| 35 | V$_L$5 nucleic acid sequence | GACATCCAGATGACCCAGTCTCCTTCCTCCCTGTCTGCATC TGTAGGAGACAGAGTCACCATCACTTGCCGGGCCAGTCAGA GTATCGGTAGGTGGTTGCCTGGTATCAGCAGAAACCAGGG AAAGCCCCTAAACTCCTGATCTTTAAGGCGTCTGCTTTAGA AGTTGGGGTCCCATCAAGGTTCAGCGGCAGTGGGTCTGGGA CAGATTTCACTCTCACCATCAGCAGCCTGCAGCCTGAAGAT TTTGCAACTTACTATTGTCAACAGGGTAACAGTTTCCCGCT CACTTTCGGCGGAGGGACCAAAGTGGATATCAAACGTACG |
| 36 | V$_L$6 amino acid sequence | DIQLTQSPSTLSASVGDRVTITCRASQSISSWLAWYQQKPG KAPKLLIYAASALQSGVPSRFSGSGSGTDFTLTISSLQPED FATYYCQQGDSFPLTFGGGTKVEIK |
| 37 | V$_L$6 nucleic acid sequence | GACATCCAGTTGACCCAGTCTCCTTCCACCCTGTCTGCATC TGTAGGAGACAGAGTCACCATCACTTGCCGGGCCAGTCAGA GTATTAGTAGCTGGTTGGCCTGGTATCAGCAGAAACCAGGG AAAGCCCCTAAACTCCTGATCTATGCTGCATCCGCTTTGCA AAGTGGGGTCCCATCAAGGTTCAGCGGCAGCGGATCTGGGA CAGATTTCACTCTCACTATCAGCAGCCTGCAGCCCGAAGAT TTTGCAACTTACTATTGTCAACAGGGTGACAGTTTCCCTCT CACTTTCGGCGGAGGGACCAAGGTGGAGATCAAACGTACG |
| 38 | V$_L$7 amino acid sequence | DIQMTQSPSTLSASVGDTVTFSCRASQSINTWLAWYQQKPG KAPKLLIYKASALENGVPSRFSGSGSGTEFTLTISSLQPED FATYYCQQGNSFPLTFGGGTKVEIK |

TABLE 4-continued

SEQUENCE LISTING

| SEQ ID NO | Description | Sequence |
|---|---|---|
| 39 | V<sub>L</sub>7 nucleic acid sequence | GACATCCAGATGACCCAGTCTCCTTCCACCCTGTCTGCATC TGTAGGAGACACAGTCACCTTCAGTTGCCGGGCCAGTCAGA GTATTAACACCTGGTTGGCCTGGTATCAGCAAAAGCCAGGG AAAGCCCCTAAACTCCTTATCTATAAGGCGTCTGCTTTAGA AAATGGGGTCCCATCAAGGTTCAGCGGCAGTGGATCTGGGA CAGAGTTCACTCTCACAATCAGCAGCCTGCAGCCTGAAGAT TTTGCAACTTACTATTGTCAACAGGGGAACAGTTTCCCTCT CACTTTCGGCGGAGGGACCAAGGTGGAGATCAAACGTACG |
| 40 | V<sub>L</sub>8 amino acid sequence | DIQMTQSPSSLSASVGDRVTITCRASQSISSWLAWYQQKPG KAPKLLIYKASALESGVPSRFSGGGSGTEFTLTISSLQPED FATYYCQQGHSFPLTFGGGTKLEIK |
| 41 | V<sub>L</sub>8 nucleic acid sequence | GACATCCAGATGACCCAGTCTCCATCCTCCCTGTCTGCATC TGTAGGAGACAGAGTCACCATCACTTGCCGGGCCAGTCAGA GTATTAGTAGCTGGTTGGCCTGGTATCAGCAGAAACCAGGG AAAGCCCCTAAACTCCTCATCTATAAGGCGTCTGCTTTAGA AAGTGGGGTCCCATCAAGGTTCAGCGGCGGTGGATCTGGGA CAGAATTCACTCTCACCATCAGCAGCCTGCAGCCTGAAGAT TTTGCAACTTACTATTGTCAACAGGGTCACAGTTTCCCTCT CACTTTCGGCGGAGGGACCAAGCTGGAGATCAAACGTACG |
| 42 | V<sub>L</sub>9 amino acid sequence | DIQLTQSPSSLSASVGDRVTITCRASQSISDWLAWYQQKPG KAPKLLIFKASALEGGVPSRFSGSGSGTDFTLTISSLQPED FATYYCQQGNSFPITFGQGTRLEIK |
| 43 | V<sub>L</sub>9 nucleic acid sequence | GACATCCAGTTGACCCAGTCTCCATCCTCCCTGTCTGCATC TGTAGGAGACAGAGTCACCATCACTTGCCGGGCCAGTCAGA GTATTAGTGACTGGTTGGCCTGGTATCAGCAGAAGCCAGGT AAAGCCCCTAAACTCCTGATCTTTAAGGCTTCTGCTTTAGA AGGTGGGGTCCCATCAAGGTTCAGCGGCAGTGGATCTGGGA CAGATTTCACTCTCACCATCAGCAGCCTGCAGCCTGAAGAT TTTGCAACTTACTATTGTCAACAGGGTAACAGTTTCCCGAT CACCTTCGGCCAAGGGACACGACTGGAGATTAAACGTACG |
| 44 | V<sub>L</sub>10 amino acid sequence | DIQMTQSPATLSASVGDRVTITCRASQSVDRWLAWYQQKPG KAPNLLIYEASALQGGVPSRFSGSGSGTDFTLTISSLQPED FATYYCQQGDSFPLTFGGGTKVEIK |
| 45 | V<sub>L</sub>10 nucleic acid sequence | GACATCCAGATGACCCAGTCTCCAGCCACCCTGTCTGCATC TGTTGGAGACAGGGTCACCATCACTTGCCGGGCCAGTCAGA GTGTTGATAGGTGGTTGGCCTGGTACCAGCAGAAACCAGGG AAAGCCCCTAACCTCCTAATCTATGAGGCGTCTGCCTTACA AGGTGGGGTCCCGTCAAGGTTCAGCGGCAGTGGATCTGGGA CAGATTTCACTCTCACCATCAGCAGCCTGCAGCCTGAAGAT TTTGCAACTTACTATTGTCAACAGGGTGATAGTTTCCCTCT CACTTTCGGCGGAGGGACCAAGGTGGAGATCAAACGTACG |
| 46 | V<sub>L</sub>11 amino acid sequence | DIQLTQSPSSVSASVGDRVTITCRASQGISSWLAWYQQKPG KAPKLLIYAASGLQNGVPSRFSGSGSGTDFTLTISSLQPED FATYYCQQGDRFPLTFGGGTKVEIK |
| 47 | V<sub>L</sub>11 nucleic acid sequence | GACATCCAGTTGACCCAGTCTCCATCTTCCGTGTCTGCATC TGTAGGAGACAGAGTCACCATCACTTGTCGGGCGAGTCAGG GTATTAGCAGCTGGTTAGCCTGGTATCAGCAGAAACCAGGG AAAGCCCCTAAGCTCCTGATCTATGCTGCATCCGGTTTGCA AAATGGGGTCCCATCAAGGTTCAGCGGCAGTGGATCTGGGA CAGATTTCACTCTCACCATCAGCAGCCTGCAGCCTGAAGAT TTTGCAACTTACTATTGTCAACAGGGTGACAGGTTCCCGCT CACTTTCGGCGGAGGGACCAAGGTGGAGATCAAACGTACG |
| 48 | V<sub>H</sub> CDR1 | FTFSSYAMS |
| 49 | V<sub>H</sub> CDR1.1 | FTFNYYAMS |
| 50 | V<sub>H</sub> CDR1.2 | FTFYGYAMS |
| 51 | V<sub>H</sub> CDR1.3 | FTFRNYAMS |
| 52 | V<sub>H</sub> CDR1.4 | FTFNYYAMN |
| 53 | V<sub>H</sub> CDR1.5 | FTFNYYAMXaa$_1$, wherein Xaa$_1$ = S or N |
| 54 | V<sub>H</sub> CDR1.6 | FTFXaa$_1$Xaa$_2$YAMS, wherein Xaa1 = S, N, Y, R; Xaa2 = S, N, Y, G |

TABLE 4-continued

SEQUENCE LISTING

| SEQ ID NO | Description | Sequence |
|---|---|---|
| 55 | $V_H$ CDR1.7 | FTFXaa$_1$Xaa$_2$YAMXaa$_3$, wherein Xaa1 = S, N, Y, R; Xaa2 = S, N, Y, G; Xaa3 = S or N. |
| 56 | $V_H$ CDR2 | SAISGSGGSTYY |
| 57 | $V_H$ CDR2.1 | SAIDGSGDNTTY |
| 58 | $V_H$ CDR2.2 | AAISGSGDGTYY |
| 59 | $V_H$ CDR2.3 | SAISGSGDSTYY |
| 60 | $V_H$ CDR2.4 | AAISGGGDATYY |
| 61 | $V_H$ CDR2.5 | SSISGSGDVTYY |
| 62 | $V_H$ CDR2.6 | SAISGFGESTYY |
| 63 | $V_H$ CDR2.7 | AAISGSGGRTYY |
| 64 | $V_H$ CDR2.8 | SAISGSGGNTSY |
| 65 | $V_H$ CDR2.9 | AAISGSGDSTYY |
| 66 | $V_H$ CDR2.10 | AAISGXaa1GXaa2Xaa3TYY, wherein Xaa1 = S or G; Xaa2 = D or G, Xaa3 = S, R, G, A |
| 67 | $V_H$ CDR2.11 | Xaa$_1$Xaa$_2$IXaa$_3$GXaa$_4$GXaa$_5$Xaa$_6$TXaa$_7$Y |
| 68 | $V_H$ CDR3 | AKDSPFLLDDYYYYYMD |
| 69 | $V_L$ CDR1 | RASQGISSWLAW |
| 70 | $V_L$ CDR1.1 | RASQNIHNWLAW |
| 71 | $V_L$ CDR1.2 | RASQSISRWLAW |
| 72 | $V_L$ CDR1.3 | RASQNIDIWLAW |
| 73 | $V_L$ CDR1.4 | RASQSIGRWLAW |
| 74 | $V_L$ CDR1.5 | RASQSISSWLAW |
| 75 | $V_L$ CDR1.6 | RASQSINTWLAW |
| 76 | $V_L$ CDR1.7 | RASQSISDWLAW |
| 77 | $V_L$ CDR1.8 | RASQSVDRWLAW |
| 78 | $V_L$ CDR2 | YAASSLQS |
| 79 | $V_L$ CDR2.1 | YKASGLES |
| 80 | $V_L$ CDR2.2 | FKASALES |
| 00 | $V_L$ CDR2.3 | YKASGLET |
| 82 | $V_L$ CDR2.4 | FKASALEV |
| 33 | $V_L$ CDR2.5 | YAASALQS |
| 84 | $V_L$ CDR2.6 | YKASALEN |
| 85 | $V_L$ CDR2.7 | YKASALES |
| 86 | $V_L$ CDR2.8 | FKASALEG |
| 87 | $V_L$ CDR2.9 | YEASALQG |
| 88 | $V_L$ CDR2.10 | YAASGLQN |
| 89 | $V_L$ CDR3 | QQGHLFPITF |
| 90 | $V_L$ CDR3.1 | QQGDRFPLTF |

TABLE 4-continued

SEQUENCE LISTING

| SEQ ID NO | Description | Sequence |
|---|---|---|
| 91 | $V_L$ CDR3.2 | QQGNSFPLTF |
| 92 | $V_L$ CDR3.3 | QQGNQFPLTF |
| 93 | $V_L$ CDR3.4 | QQGDSFPLTF |
| 94 | $V_L$ CDR3.5 | QQGHSFPLTF |
| 95 | $V_L$ CDR3.6 | QQGNSFPITF |
| 96 | $V_L$ CDR3.7 | QQGXaa$_1$Xaa$_2$FPXaa$_3$TF |
| 97 | Human CD137L Uniprot ID - P41273 | MEYASDASLDPEAPWPPAPRARACRVLPWALVAGLLLLLLL AAACAVFLACPWAVSGARASPGSAASPRLREGPELSPDDPA GLLDLRQGMFAQLVAQNVLLIDGPLSWYSDPGLAGVSLTGG LSYKEDTKELVVAKAGVYYVFFQLELRRVVAGEGSGSVSLA LHLQPLRSAAGAAALALTVDLPPASSEARNSAFGFQGRLLH LSAGQRLGVHLHTEARARHAWQLTQGATVLGLFRVTPEIPA GLPSPRSE |
| 98 | FLAG | DYKDDDDK |
| 99 | 6-His | HHHHHH |
| 100 | HA | YPYDVPDYA |
| 101 | $V_H$12 amino acid sequence | EVQLLESGGGLVQPGGSLRLSCAASGFTFRNYAMSWVRQAP GKGLEWVSAISGSGDTTYYADSVKGRFTISRDNSKNTLYLQ MNSLRAEDTAVYYCAKDSPFLLDDYYYYYMDVWGKGTTVT VSS |
| 102 | $V_H$12 nucleic acid sequence | GAAGTGCAATTATTGGAATCCGGCGGCGGTTTAGTTCAGCC AGGTGGCTCTTTGAGGCTGAGTTGCGCAGCCTCTGGATTCA CCTTTAGAAACTACGCAATGTCTTGGGTTCGCCAGGCGCCC GGTAAGGGTCTGGAGTGGGTGTCTGCAATCTCTGGTTCTGG TGATACTACTTACTACGCCGACTCTGTGAAAGGTCGTTTTA CCATAAGCCGCGACAATTCTAAGAATACTTTATATCTTCAA ATGAATTCGCTGCGGGCAGAAGACACGGCCGTCTATTACTG CGCAAAGGACTCACCTTTTCTATTAGACGACTACTACTACT ACTACTACATGGACGTATGGGGCAAGGGTACAACTGTCACC GTCTCCTCAGCTAGC |
| 103 | $V_H$13 amino acid sequence | EVQLLESGGGLVQPGGSLRLSCAASGFTFGSYAMSWVRQAP GKGLEWVSAISGSGGSTYYADSVKGRFTISRDNSKNTLYLQ MNSLRAEDTAVYYCAKDSPFLLDDYYYYYMDVWGKGTTVT VSS |
| 104 | $V_H$13 nucleic acid sequence | GAAGTGCAATTATTGGAATCCGGCGGCGGTTTAGTTCAGCC AGGTGGCTCTTTGAGGCTGAGTTGCGCAGCCTCTGGATTCA CCTTTGGTTCTTACGCAATGTCTTGGGTTCGCCAGGCGCCC GGTAAGGGTCTGGAGTGGGTGTCTGCAATCTCTGGTTCTGG TGGTTCTACTTACTACGCCGACTCTGTGAAAGGTCGTTTTA CCATAAGCCGCGACAATTCTAAGAATACTTTATATCTTCAA ATGAATTCGCTGCGGGCAGAAGACACGGCCGTCTATTACTG CGCAAAGGACTCACCTTTTCTATTAGACGACTACTACTACT ACTACTACATGGACGTATGGGGCAAGGGTACAACTGTCACC GTCTCCTCAGCTAGC |
| 105 | $V_L$12 amino acid sequence | DIQLTQSPSSLSASVGDRVTITCRASQDIGDWLAWYQQKPG KAPKLLIYKASGLQSGVPSRFSGSGSGTEFTLTISNLQPED FATYYCQQGNQFPLTFGQGTRLE |
| 106 | $V_L$12 nucleic acid sequence | GACATCCAGTTGACCCAGTCTCCATCCTCCCTGTCTGCATC TGTAGGAGACAGAGTAACCATCACTTGCCGGGCAAGTCAGG ATATTGGTGACTGGTTGGCCTGGTATCAGCAGAAGCCTGGG AAAGCCCCTAAGCTCCTGATCTATAAGGCGTCTGGTTTACA AAGTGGGGTCCCATCAAGATTCAGTGGCAGTGGATCTGGGA CAGAATTCACTCTCACTATCAGCAACCTGCAGCCAGAGGAT TTTGCGACTTACTATTGTCAACAGGGTAACCAGTTCCCGCT CACCTTCGGCCAAGGGACACGACTGGAG |
| 107 | $V_H$ CDR1.8 | FTFGWYAMS |
| 108 | $V_H$ CDR2.12 | SAISGSGDTTYY |

TABLE 4-continued

SEQUENCE LISTING

| SEQ ID NO | Description | Sequence |
|---|---|---|
| 109 | $V_L$ CDR1.9 | RASQDIGDWLAW |
| 110 | $V_L$ CDR2.11 | YKASGLQS |
| 111 | $V_H$ CDR3.1 | AKASPFLLDDYYYYYMD |
| 112 | $V_H$ CDR3.2 | AKDAPFLLDDYYYYYMD |
| 113 | $V_H$ CDR3.3 | AKDSAFLLDDYYYYYMD |
| 114 | $V_H$ CDR3.4 | AKDSPALLDDYYYYYMD |
| 115 | $V_H$ CDR3.5 | AKDSPFALDDYYYYYMD |
| 116 | $V_H$ CDR3.6 | AKDSPFLADDYYYYYMD |
| 117 | $V_H$ CDR3.7 | AKDSPFLLADYYYYYMD |
| 118 | $V_H$ CDR3.8 | AKDSPFLLDAYYYYYMD |
| 119 | $V_H$ CDR3.9 | AKDSPFLLDDAYYYYMD |
| 120 | $V_H$ CDR3.10 | AKDSPFLLDDYAYYYMD |
| 121 | $V_H$ CDR3.11 | AKDSPFLLDDYYAYYMD |
| 122 | $V_H$ CDR3.12 | AKDSPFLLDDYYYAYMD |
| 123 | $V_H$ CDR3.13 | AKDSPFLLDDYYYYAMD |
| 124 | $V_H$ CDR3.14 | AKDSPFLLDDYYYYYAD |
| 125 | $V_H$ CDR3.15 | AKDSPFLLDDYYYYYAD |
| 126 | $V_H$ CDR3.16 | DXXXXLXXXXYXYYX |
| 127 | $V_H$ CDR3.17 | DXPFXLDXXYYYYYX |
| 128 | $V_H$ CDR3.18 | $DX_1X_2X_3X_4LX_5X_6X_7X_8YX_9YYX_{10}$ |
| 129 | mAb1 heavy chain | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKDSPFLLDDYYYYYMDVWGKGTTVT VSSASTKGPSVFPLAPCSRSTSESTAALGCLVKDYFPEPVT VSWNSGALTSGVHTFPAVLQSSGLYSLSSVVTVPSSSLGTK TYTCNVDHKPSNTKVDKRVESKYGPPCPPCPAPEFLGGPSV FLFPPKPKDTLMISRTPEVTCVVVDVSQEDPEVQFNWYVDG VEVHNAKTKPREEQFNSTYRVVSVLTVLHQDWLNGKEYKCK VSNKGLPSSIEKTISKAKGQPREPQVYTLPPSQEEMTKNQV SLTCLVKGFYPSDIAVEWESNGQPENNYKTTPPVLDSDGSF FLYSRLTVDKSRWQEGNVFSCSVMHEALHNHYTQKSLSLSL G |
| 130 | mAb8 heavy chain V1 | GTEVQLLESGGGLVQPGGSLRLSCAASGFTFRNYAMSWVRQ APGKGLEWVSAISGSGDTTYYADSVKGRFTISRDNSKNTLY LQMNSLRAEDTAVYYCAKDSPFLLDDYYYYYMDVWGKGTT VTVSSASTKGPSVFPLAPCSRSTSESTAALGCLVKDYFPEP VTVSWNSGALTSGVHTFPAVLQSSGLYSLSSVVTVPSSSLG TKTYTCNVDHKPSNTKVDKRVESKYGPPCPPCPAPEFLGGP SVFLFPPKPKDTLMISRTPEVTCVVVDVSQEDPEVQFNWYV DGVEVHNAKTKPREEQFNSTYRVVSVLTVLHQDWLNGKEYK CKVSNKGLPSSIEKTISKAKGQPREPQVYTLPPSQEEMTKN QVSLTCLVKGFYPSDIAVEWESNGQPENNYKTTPPVLDSDG SFFLYSRLTVDKSRWQEGNVFSCSVMHEALHNHYTQKSLSL SLG |
| 131 | mAb8 heavy chain V2 | EVQLLESGGGLVQPGGSLRLSCAASGFTFRNYAMSWVRQAP GKGLEWVSAISGSGDTTYYADSVKGRFTISRDNSKNTLYLQ MNSLRAEDTAVYYCAKDSPFLLDDYYYYYMDVWGKGTTVT VSSASTKGPSVFPLAPCSRSTSESTAALGCLVKDYFPEPVT VSWNSGALTSGVHTFPAVLQSSGLYSLSSVVTVPSSSLGTK TYTCNVDHKPSNTKVDKRVESKYGPPCPPCPAPEFLGGPSV FLFPPKPKDTLMISRTPEVTCVVVDVSQEDPEVQFNWYVDG VEVHNAKTKPREEQFNSTYRVVSVLTVLHQDWLNGKEYKCK VSNKGLPSSIEKTISKAKGQPREPQVYTLPPSQEEMTKNQV |

TABLE 4-continued

SEQUENCE LISTING

| SEQ ID NO | Description | Sequence |
|---|---|---|
| | | SLTCLVKGFYPSDIAVEWESNGQPENNYKTTPPVLDSDGSF FLYSRLTVDKSRWQEGNVFSCSVMHEALHNHYTQKSLSLSL G |
| 132 | mAb10 heavy chain | EVQLLESGGGLVQPGGSLRLSCAASGFTFYGYAMSWVRQAP GKGLEWVAAISGSGDSTYYADSVKGRFTISRDNSKNTLYLQ MNSLRAEDTAVYYCAKDSPFLLDDYYYYYMDVWGKGTTVT VSSASTKGPSVFPLAPCSRSTSESTAALGCLVKDYFPEPVT VSWNSGALTSGVHTFPAVLQSSGLYSLSSVVTVPSSSLGTK TYTCNVDHKPSNTKVDKRVESKYGPPCPPCPAPEFLGGPSV FLFPPKPKDTLMISRTPEVTCVVVDVSQEDPEVQFNWYVDG VEVHNAKTKPREEQFNSTYRVVSVLTVLHQDWLNGKEYKCK VSNKGLPSSIEKTISKAKGQPREPQVYTLPPSQEEMTKNQV SLTCLVKGFYPSDIAVEWESNGQPENNYKTTPPVLDSDGSF FLYSRLTVDKSRWQEGNVFSCSVMHEALHNHYTQKSLSLSL G |
| 133 | mAb1, mAb8 and mAb10 light chain | DIQMTQSPSSVSASVGDRVTITCRASQGISSWLAWYQQKPG KAPKLLIYAASSLQSGVPSRFSGSGSGTDFTLTISSLQPED FATYYCQQGHLFPITFGGGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| 134 | Human PD-1 Amino Acid Sequence | MQIPQAPWPVVWAVLQLGWRPGWFLDSPDRPWNPPTFFPAL LVVTEGDNATFTCSFSNTSESFVLNWYRMSPSNQTDKLAAF PEDRSQPGQDCRFRVTQLPNGRDFHMSVVRARRNDSGTYLC GAISLAPKAQIKESLRAELRVTERRAEVPTAHPSPSPRPAG QFQTLVVGVVGGLLGSLVLLVWVLAVICSRAARGTIGARRT GQPLKEDPSAVPVFSVDYGELDFQW REKTPEPPVPCVPEQTEYATIVFPSGMGTSSPARRGSADGP RSAQPLRPEDGHCSWPL |
| 135 | Human PD-L1 Amino Acid Sequence | MRIFAVFIFMTYWHLLNAFTVTVPKDLYVVEYGSNMTIECK FPVEKQLDLAALIVYWEMEDKNIIQFVHGEEDLKVQHSSYR QRARLLKDQLSLGNAALQITDVKLQDAGVYRCMISYGGADY KRITVKVNAPYNKINQRILVVDPVTSEHELTCQAEGYPKAE VIWTSSDHQVLSGKTTTTNSKREEKLFNVTSTLRINTTTNE IFYCTFRRLDPEENHTAELVIPELP LAHPPNERTHLVILGAILLCLGVALTFIFRLRKGRMMDVKK CGIQDINSKKQSDTHLEET |
| 136 | Human IgG4 | ASTKGPSVFPLAPCSRSTSESTAALGCLVKDYFPEPVTVSW NSGALTSGVHTFPAVLQSSGLYSLSSVVTVPSSSLGTKTYT CNVDHKPSNTKVDKRVESKYGPPCPSCPAPEFLGGPSVFLF PPKPKDTLMISRTPEVTCVVVDVSQEDPEVQFNWYVDGVEV HNAKTKPREEQFNSTYRVVSVLTVLHQDWLNGKEYKCKVSN KGLPSSIEKTISKAKGQPREPQVYTLPPSQEEMTKNQVSLT CLVKGFYPSDIAVEWESNGQPENNYKTTPPVLDSDGSFFLY SRLTVDKSRWQEGNVFSCSVMHEALHNHYTQKSLSLSLGK |

The invention claimed is:

1. A method for treating cancer in a subject, the method comprising: administering to the subject an effective amount of:
   (i) an isolated agonistic monoclonal antibody that specifically binds to human CD137 with an affinity ($K_D$) of about 30-100 nM, or that binds to an epitope on human CD137 comprising K114 of SEQ ID NO: 3, or both, or an antigen-binding fragment thereof; and
   (ii) a PD-1 antagonist,
   wherein the agonistic monoclonal antibody or antigen-binding fragment thereof is administered to the subject prior to administration of the PD-1 antagonist, thereby treating the subject, and
   wherein the isolated agonistic monoclonal antibody or antigen-binding fragment thereof comprises heavy and light chain CDRs comprising heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively.

2. The method of claim 1, wherein administration of (ii) occurs after at least one or more doses of (i) and prior to a subsequent dose of (i).

3. The method of claim 2, wherein administration of (ii) occurs after at least 2 doses of (i).

4. The method of claim 1, wherein treatment comprises delaying cancer progression in the subject.

5. The method of claim 1, wherein treatment comprises enhancing a cancer-specific immune response in the subject.

6. The method of claim 5, wherein the cancer-specific immune response is a T cell response.

7. The method of claim 6, wherein the T cell response comprises:
   (i) the production of IFNγ by one or both of CD4+ T cells and CD8+ T cells;
   (ii) the production of IL-2 by one or both of CD4+ T cells and CD8+ T cells; or
   (iii) proliferation of one or both of CD4+ T cells and CD8+ T cells.

8. The method of claim 1, wherein the subject comprises a tumor expressing or overexpressing PD-L1.

9. The method of claim 1, wherein the PD-1 antagonist is an isolated monoclonal antibody or an antigen-binding fragment thereof, that specifically binds to human PD-L1 or human PD-1.

10. The method of claim 1, wherein the isolated agonistic monoclonal antibody or antigen-binding fragment thereof comprises heavy and light chain variable regions, wherein the heavy chain variable region comprises the amino acid sequence of SEQ ID NO: 4; and wherein the light chain variable region comprises the amino acid sequence of SEQ ID NO: 6.

11. The method of claim 1, wherein the isolated agonistic monoclonal antibody or antigen-binding fragment thereof comprises heavy and light chain variable regions encoded by the nucleotide sequences of
   SEQ ID NOs: 5 and 7, respectively.

12. The method of claim 1, wherein the isolated agonistic monoclonal antibody or antigen-binding fragment thereof comprises heavy and light chain variable regions comprising or at least 90% identical to the amino acid sequences of:
   SEQ ID NOs: 4 and 6, respectively.

13. The method of claim 1, wherein the isolated agonistic monoclonal antibody or antigen-binding fragment thereof comprises heavy and light chain variable regions, wherein the heavy chain variable region comprises an amino acid sequence which is at least 90% identical to the amino acid sequence of SEQ ID NO: 4; and wherein the light chain variable region comprises an amino acid sequence which is at least 90% identical to the amino acid sequence of SEQ ID NO: 6.

14. The method of claim 1, wherein the isolated agonistic monoclonal antibody or antigen-binding fragment thereof exhibits at least one of the following properties selected from the group consisting of:
   (a) induces or enhances dimerization of CD137 trimers;
   (b) induces or enhances multimerization of CD137 trimers;
   (c) induces or enhances T cell activation;
   (d) induces or enhances a cytotoxic T cell response;
   (e) induces or enhances T cell proliferation;
   (f) induces or enhances immune cell cytokine production; and
   (g) any combination of properties (a)-(f).

15. The method of claim 14, wherein the isolated agonistic monoclonal antibody or antigen-binding fragment thereof induces or enhances T cell activation in the subject, and wherein the T cell activation occurs in a tumor microenvironment.

16. The method of claim 14, wherein the isolated agonistic monoclonal antibody or antigen-binding fragment thereof induces or enhances a cytotoxic T cell response in the subject, and wherein the cytotoxic T cell response occurs in a tumor microenvironment.

17. The method of claim 14, wherein the isolated agonistic monoclonal antibody or antigen-binding fragment thereof induces or enhances cytokine production of an immune cell in the subject, wherein the cytokine produced is IL-2, TNFα, IL-13, IFNγ, or combinations thereof, and wherein the cytokine production occurs in a tumor microenvironment.

18. The method of claim 14, wherein the isolated agonistic monoclonal antibody or antigen-binding fragment thereof induces or enhances T cell proliferation in the subject, and wherein the T cell proliferation occurs in a tumor microenvironment.

19. The method of claim 14, wherein the isolated agonistic monoclonal antibody or antigen-binding fragment thereof reduces or inhibits tumor growth in the subject.

20. The method of claim 14, wherein the cancer is selected from the group consisting of melanoma, glioma, renal, breast, hematological, and head and neck cancer.

21. A composition comprising an isolated agonistic monoclonal antibody that specifically binds CD137 with an affinity ($K_D$) of about 30-100 nM, or that binds to an epitope on human CD137 comprising K114 of SEQ ID NO: 3, or both, or an antigen-binding fragment thereof, and an optional pharmaceutically acceptable carrier, for use in treating cancer, delaying cancer progression, or enhancing a cancer-specific immune response in a subject in need thereof, wherein the agonistic monoclonal antibody, or antigen-binding fragment thereof, is administered in combination with a second composition comprising a PD-1 antagonist, and optionally a pharmaceutically acceptable carrier, and wherein the isolated agonistic monoclonal antibody or antigen-binding fragment thereof comprises heavy and light chain variable regions encoded by nucleotide sequences comprising SEQ ID NO: 5 and 7, respectively.

22. The composition of claim 21, wherein the isolated agonistic monoclonal antibody or antigen-binding fragment comprises heavy and light chain CDRs, wherein heavy chain CDR3 comprises the amino acid sequence set forth in SEQ ID NO: 68.

23. The composition of claim 21, wherein the isolated agonistic monoclonal antibody or antigen-binding fragment thereof comprises
heavy chain CDR1, CDR2 and CDR3 sequences set forth in SEQ ID NOs: 48, 56 and 68, respectively, and light chain CDR1, CDR2 and CDR3 sequences set forth in SEQ ID NOs: 69, 78 and 89, respectively.

24. The composition of claim 21, wherein the isolated agonistic monoclonal antibody or antigen-binding fragment thereof comprises heavy and light chain variable regions, wherein the heavy chain variable region comprises the amino acid sequence of SEQ ID NO: 4; and wherein the light chain variable region comprises the amino acid sequence of SEQ ID NO: 6.

25. The composition of claim 21, wherein the isolated agonistic monoclonal antibody or antigen-binding fragment thereof comprises heavy and light chain variable regions comprising or at least 90% identical to the amino acid sequences of
SEQ ID NOs: 4 and 6, respectively.

26. The composition of claim 21, wherein the isolated agonistic monoclonal antibody or antigen-binding fragment thereof comprises heavy and light chain variable regions, wherein the heavy chain variable region comprises an amino acid sequence which is at least 90% identical to the amino acid sequence of SEQ ID NO: 4; and wherein the light chain variable region comprises an amino acid sequence which is at least 90% identical to the amino acid sequence of SEQ ID NO: 6.

27. The composition of claim 21, wherein the PD-1 antagonist is an isolated monoclonal antibody that specifically binds to human PD-L1, human PD-1, or an antigen-binding fragment thereof.

28. Use of the composition of claim 21, and an optional pharmaceutically acceptable carrier, for treating cancer, delaying cancer progression, or enhancing a cancer-specific immune response in a subject in need thereof, wherein a first medicament comprises the agonistic monoclonal antibody that specifically binds human CD137 and an optional pharmaceutically acceptable carrier, and wherein the first medicament is administered in combination with a second medicament comprising the PD-1 antagonist, and optionally a pharmaceutically acceptable carrier.

* * * * *

UNITED STATES PATENT AND TRADEMARK OFFICE
CERTIFICATE OF CORRECTION

Page 1 of 1

PATENT NO. : 11,718,679 B2
APPLICATION NO. : 16/760600
DATED : August 8, 2023
INVENTOR(S) : Eskiocak et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 309 days.

Signed and Sealed this
Twelfth Day of August, 2025

Coke Morgan Stewart
*Acting Director of the United States Patent and Trademark Office*